United States Patent
Park et al.

(10) Patent No.: US 12,295,259 B2
(45) Date of Patent: May 6, 2025

(54) ORGANIC COMPOUND AND ORGANIC ELECTROLUMINESCENT DEVICE USING SAME

(71) Applicant: SOLUS ADVANCED MATERIALS CO., LTD., Iksan-si (KR)

(72) Inventors: Woojae Park, Yongin-si (KR); Minsik Eum, Yongin-si (KR); Jaeyi Sim, Yongin-si (KR)

(73) Assignee: SOLUS ADVANCED MATERIALS CO., LTD., Iksan-si (KR)

( * ) Notice: Subject to any disclaimer, the term of this patent is extended or adjusted under 35 U.S.C. 154(b) by 724 days.

(21) Appl. No.: 17/312,788

(22) PCT Filed: Dec. 12, 2019

(86) PCT No.: PCT/KR2019/017596
§ 371 (c)(1),
(2) Date: Jun. 10, 2021

(87) PCT Pub. No.: WO2020/122637
PCT Pub. Date: Jun. 18, 2020

(65) Prior Publication Data
US 2022/0052270 A1    Feb. 17, 2022

(30) Foreign Application Priority Data
Dec. 13, 2018    (KR) .................. 10-2018-0161355

(51) Int. Cl.
| | |
|---|---|
| *H10K 85/60* | (2023.01) |
| *C07D 239/26* | (2006.01) |
| *C07D 251/24* | (2006.01) |
| *C09K 11/06* | (2006.01) |
| *H10K 50/11* | (2023.01) |
| *H10K 50/15* | (2023.01) |
| *H10K 50/16* | (2023.01) |
| *H10K 50/17* | (2023.01) |
| *H10K 101/10* | (2023.01) |

(52) U.S. Cl.
CPC ......... *H10K 85/654* (2023.02); *C07D 239/26* (2013.01); *C07D 251/24* (2013.01); *C09K 11/06* (2013.01); *H10K 85/615* (2023.02); *H10K 85/624* (2023.02); *H10K 85/626* (2023.02); *C09K 2211/1018* (2013.01); *H10K 50/11* (2023.02); *H10K 50/15* (2023.02); *H10K 50/16* (2023.02); *H10K 50/17* (2023.02); *H10K 50/171* (2023.02); *H10K 2101/10* (2023.02)

(58) Field of Classification Search
None
See application file for complete search history.

(56) References Cited

U.S. PATENT DOCUMENTS

| | | | |
|---|---|---|---|
| 2019/0214571 A1* | 7/2019 | Huh | C07D 405/10 |
| 2020/0131138 A1* | 4/2020 | Han | H10K 85/615 |
| 2020/0287142 A1* | 9/2020 | Huh | H10K 85/615 |

FOREIGN PATENT DOCUMENTS

| | | |
|---|---|---|
| CN | 108349913 A | 7/2018 |
| CN | 109096217 A | 12/2018 |
| CN | 111095587 A | 5/2020 |
| EP | 3351537 A1 | 7/2018 |
| EP | 3418272 A1 | 12/2018 |
| KR | 10-2014-0012598 A | 2/2014 |
| KR | 10-2016-0126862 A | 11/2016 |
| KR | 10-2018-0111558 A | 10/2018 |
| KR | 10-2018-0127835 A | 11/2018 |
| KR | 10-2018-0130329 A | 12/2018 |
| WO | 2019/245160 A1 | 12/2019 |

OTHER PUBLICATIONS

Datasheet from National Library of Medicine for 9H-xanthene, no date given, 55 pages. (Year: NONE).*
International Searching Authority, International Search Report for PCT/KR2019/017596 dated Mar. 24, 2020 (PCT/ISA/210).
Office Action dated Mar. 24, 2023 from the Chinese Patent Office in Application No. 201980082540.X.
Extended European Search Report dated Oct. 18, 2022, in European Application No. 19896852.1.

* cited by examiner

*Primary Examiner* — Robert S Loewe
(74) *Attorney, Agent, or Firm* — Sughrue Mion, PLLC

(57) ABSTRACT

A novel compound having excellent heat resistance, electron transport ability and luminescence is disclosed. An organic EL device which includes the novel compound in one or more organic layers, has improved characteristics, such as luminous efficiency, driving voltage, and lifespan.

12 Claims, No Drawings

ORGANIC COMPOUND AND ORGANIC ELECTROLUMINESCENT DEVICE USING SAME

CROSS REFERENCE TO RELATED APPLICATIONS

This application is a National Stage of International Application No. PCT/KR2019/017596 filed Dec. 12, 2019, claiming priority based on Korean Patent Application No. 10-2018-0161355 filed Dec. 13, 2018.

TECHNICAL FIELD

The present invention relates to a novel organic compound and an organic electroluminescent device including the same, and more particularly, to a compound having excellent heat resistance, electron transport ability and luminescence characteristics and to an organic electroluminescent device having improved characteristics such as luminous efficiency, driving voltage, lifespan, and the like by including the compound in one or more organic layers.

DISCUSSION OF RELATED ART

Starting from Bernanose's observation of light emission from organic thin films in the 1950s, the study of organic electroluminescent devices (hereinafter, "EL devices") led to blue electroluminescence using anthracene monocrystals in 1965, and Tang suggested in 1987 an organic EL device in a stack structure which may be divided into functional layers of hole layers and light emitting layers. Then, in order to develop high efficiency, long lifespan organic EL devices, organic layers each having distinctive characteristics have been introduced in the EL devices, leading to the development of specialized materials used therein.

In organic EL devices, upon application of voltage between two electrodes, holes are injected from an anode (e.g., positive electrode) to an organic layer and electrons are injected from a cathode (e.g., negative electrode) into the organic layer. Injected holes and electrons meet each other to form excitons, and light emission occurs when the excitons fall to a ground state. In this case, materials used for the organic layer may be classified into, for example, luminescent materials, hole injection materials, hole transport materials, electron transport materials and electron injection materials depending on their function.

The material for forming the light emitting layer of the organic EL device may be classified into blue, green, and red light emitting materials according to the emission color. In addition, yellow and orange light emitting materials are also used as light emitting materials for realizing better natural colors. In addition, a host/dopant system may be employed in the luminescent material to increase color purity and luminous efficiency through energy transition. Dopant materials may be classified into fluorescent dopants using organic materials and phosphorescent dopants using metal complex compounds which include heavy atoms such as Ir and Pt. In such a case, the developed phosphorescent materials may improve the luminous efficiency theoretically up to four times as compared to fluorescent materials, so attention is given to phosphorescent dopants as well as phosphorescent host materials.

To date, NPB, BCP and $Alq_3$, shown below, are widely known as materials used in the hole injection layer, the hole transport layer, the hole blocking layer and the electron transport layer, and anthracene derivatives have been reported as luminescent materials. Particularly, metal complex compounds including Ir, such as FIrpic, $Ir(ppy)_3$, and $(acac)Ir(btp)_2$, which are known to have advantages in terms of efficiency improvement among luminescent materials, are used as blue, green and red phosphorescent dopant materials. In addition, to date, CBP has shown excellent properties as a phosphorescent host material.

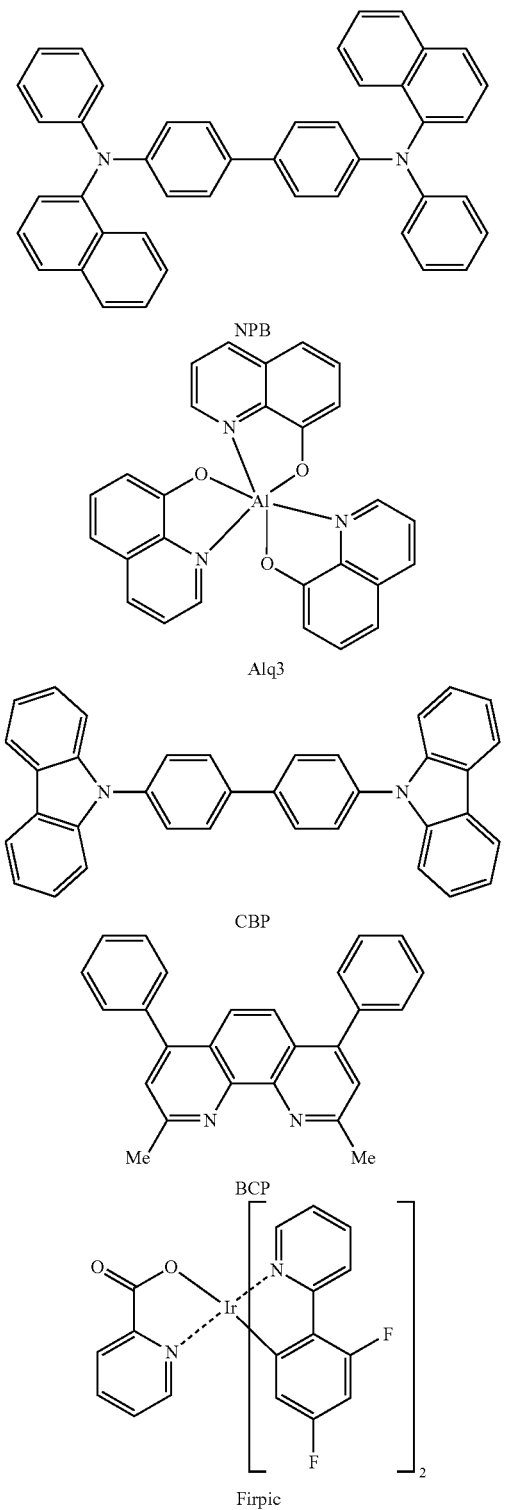

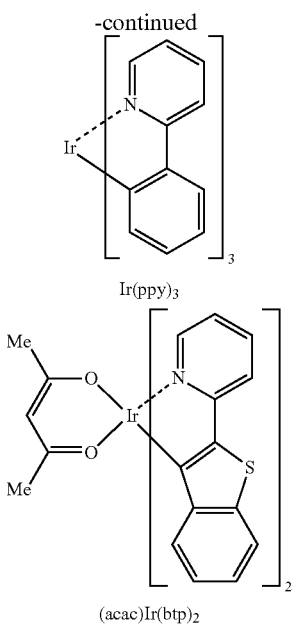

Ir(ppy)₃

(acac)Ir(btp)₂

However, although conventional materials for organic layers are advantages in terms of luminescence properties, they have low glass transition temperatures, thus having poor thermal stability, and thus organic EL devices in which such conventional materials are used do not exhibit satisfactory lifespan characteristics.

DESCRIPTION OF THE INVENTION

Technical Objectives

The present invention is directed to a novel compound having excellent heat resistance, electron transport ability and luminescent characteristics to be applicable to an organic layer material of an organic EL device, specifically, a light emitting layer material, a life-improvement layer, a light emitting auxiliary layer, or an electron transport layer material.

In addition, the present invention is also directed to an organic EL device including the aforementioned novel compound, thereby having low driving voltage, high luminous efficiency, and improved lifespan.

Technical Solution to the Problem

According to an embodiment of the present invention, a compound is represented by the following Chemical Formula 1,

[Chemical Formula 1]

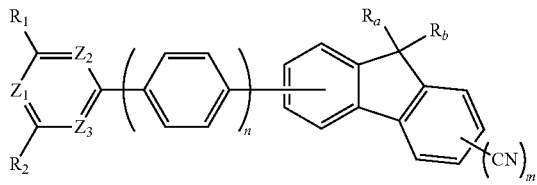

wherein in Chemical Formula 1, $R_a$ and $R_b$ are the same as or different from each other, and are each independently a $C_1$ to $C_{40}$ alkyl group or a $C_6$ to $C_{60}$ aryl group, or combine with each other to form a fused ring, $Z_1$ to $Z_3$ are the same as or different from each other, and are each independently N or $C(R_3)$, provided that $Z_1$ to $Z_3$ include at least one N, $R_1$ to $R_3$ are the same as or different from each other, each independently being selected from the group consisting of: hydrogen, deuterium, a halogen group, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and m and n are each independently an integer of 1 or 2, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_1$ to $R_3$ are each independently substituted or unsubstituted with one or more kinds of substituents selected from the group consisting of deuterium, a halogen group, a cyano group, a nitro group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_1$ to $C_{40}$ alkyl group, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other.

According to another embodiment, an electroluminescent device includes: an anode, a cathode, and one or more organic layers disposed between the anode and the cathode, wherein at least one of the one or more organic layers includes the compound represented by Chemical Formula 1.

In some embodiments, the organic layer including the compound represented by Chemical Formula 1 is selected from the group consisting of: a light emitting layer, a light emitting auxiliary layer, a hole injection layer, a hole transport layer, an electron injection layer, an electron transport layer, and an electron transport auxiliary layer.

Effects of the Invention

The compound represented by Chemical Formula 1 according to one or more embodiments of the present invention has excellent heat resistance, electron transport ability and luminescent characteristics to be applicable as an organic layer material of an organic EL device.

In addition, an organic EL device including the aforementioned compound may be improved in terms of luminescent characteristics, driving voltage, life span, and efficiency to be effectively applicable to a full-color display panel and the like.

DETAILED DESCRIPTION OF THE INVENTION

Hereinafter, the present invention will be described in detail.

<Novel Organic Compounds>

A compound represented by Chemical Formula 1 according to the present invention has a base skeleton structure in which fluorene and a nitrogen-containing heteroaromatic ring (e.g., azine) are respectively positioned at opposite ends of a molecule, and a phenylene or biphenylene group is linked therebetween as a linker (e.g., linker) (L), and at least one cyano group (—CN) is directly bonded to the fluorene group.

Specifically, the compound of Chemical Formula 1 has a dual EWG-type (e.g., EWG1-L-EWG2) structure by including a fluorene group, which is an electron donating group (EDG), and a nitrogen-containing aromatic ring (e.g., pyridine, pyrazine, or triazine), which is an electron withdrawing group (EWG1), at opposite sides of the molecule, and further including a cyano group (—CN) which is a strong electron withdrawing group (EWG2) directly bonded to a phenyl ring on one side of the fluorene group. As described above, by introducing at least two functional groups with strong electron withdrawing capability (EWG), e.g., the azine group and the cyano group, it is possible to improve electron mobile speed and have physicochemical properties more suitable for electron injection and electron transportation. When the compound of Chemical Formula 1 is applied as a material for an electron transport layer or an electron transport auxiliary layer, it may well receive electrons from a cathode (e.g., negative electrode), so that electrons may be smoothly transferred to a light emitting layer, thereby lowering a driving voltage of the device, improving high efficiency and leading to long lifespan. Accordingly, such an organic EL device may substantially maximize the performance of a full color organic light emitting panel.

In addition, the compound of Chemical Formula 1 not only has a high triplet energy but also has a significantly increased molecular weight as compared to a conventional compound where two 6-membered mono-heterocyclic compounds (e.g., two azine groups) are introduced, and accordingly, may have an improved glass transition degree (Tg) and high thermal stability. Accordingly, in an organic EL device including the compound, durability and lifespan characteristics may be greatly improved.

In addition, since the compound of Chemical Formula 1 is a bipolar compound, recombination of holes and electrons is high, so that hole injection/transport capability, luminous efficiency, driving voltage, lifespan characteristics, durability, etc. may be improved. In addition, the electron transport ability and the like may also be improved depending on the type of the introduced substituent. Accordingly, the compound of Chemical Formula 1 may be used as an organic material layer material of an organic EL device, preferably an electron transport layer material, an electron transport auxiliary layer material, and a light emitting layer material.

In addition, the compound represented by Chemical Formula 1 is not only significantly advantageous for electron transport but also shows low driving voltage, high efficiency, and long lifespan characteristics. The excellent electron transport ability of these compounds may achieve high efficiency and high mobility (e.g., rapid) in an organic EL device, and it is easy to control HOMO and LUMO energy levels according to direction or position of a substituent. Accordingly, it is possible to exhibit high electron transport properties in an organic EL device using such a compound.

With the above-described characteristics, when the compound of Chemical Formula 1 is applied as an organic layer material of an organic EL device, preferably a light emitting layer material (blue, green and/or red phosphorescent host material), an electron transport/injection layer material, and a light emitting auxiliary layer material, the performance and lifespan characteristics of the organic EL device may be greatly improved. Accordingly, such an organic EL device may maximize the performance of a full-color organic EL panel.

Meanwhile, red and green light emitting layers of the organic EL device may each use phosphorescent materials, and currently, technology maturity for the red and green light emitting layers is relatively high. On the other hand, a blue light emitting layer may use a fluorescent material and a phosphorescent material, of which the fluorescent material needs further performance improvement, and the blue phosphorescent material is still under development, so the entry barrier is relatively high. That is, while the blue light emitting layer has a high possibility of development, the technical difficulty is relatively high, so there is a limit to improving the performance (e.g., driving voltage, efficiency, lifespan, etc.) of a blue organic light emitting device including such a blue light emitting layer. Accordingly, in the present invention, the compound of Chemical Formula 1 may be applied as a material for an electron transport layer (ETL) or an electron transport auxiliary layer, in addition to the light emitting layer (EML). In such a way, by changing the material of the electron transport layer or the electron transport auxiliary layer which are used as a common layer in the organic EL device, the performance of the light emitting layer, specifically the blue light emitting layer, and the performance of the organic EL device including the light emitting layer may be improved.

Specifically, the compound represented by Chemical Formula 1 according to the present invention has a base skeleton structure in which fluorene and a nitrogen-containing heteroaromatic ring (e.g., azine), which is a type of an azine group, respectively positioned at opposite ends of the molecule are linked through an aromatic linker, and at least one cyano group (—CN) is directly bonded to a phenyl ring on one side of the fluorene.

In Chemical Formula 1, the nitrogen-containing heteroaromatic ring may be a monocyclic heteroaryl group (e.g., azine) including at least one nitrogen atom. As an embodiment of such a nitrogen-containing heteroaromatic ring (e.g., $Z_1$ to $Z_3$-containing heterocycle), $Z_1$ to $Z_3$ are the same as or different from each other, and are each independently N or $C(R_3)$ provided that at least one of $Z_1$ to $Z_3$ is N. As a specific example, the plurality of $Z_1$ to $Z_3$ include one to three nitrogens (N), and preferably include two or three nitrogens (N). As such, by including a heterocyclic ring containing two or three nitrogens, more excellent electron withdrawing properties are exhibited, which is advantageous for electron injection and transport.

In such an embodiment, $R_3$ may preferably be selected from the group consisting of: hydrogen, deuterium, a halogen group, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ phosphine group, a $C_1$ to $C_{40}$ phosphine oxide group and a $C_6$ to $C_{60}$ arylamine group. Specifically, $R_3$ is preferably selected from the group consisting of: hydrogen, deuterium, a halogen group, a cyano group, a $C_1$ to $C_{40}$ alkyl group, a $C_6$ to $C_{60}$ aryl group, a heteroaryl group having 5 to 60 nuclear atoms.

The heterocyclic ring containing $Z_1$ to $Z_3$ according to the present invention may each be substituted with $R_1$ and $R_2$ as various substituents.

$R_1$ and $R_2$ may be the same as or different from each other and may each independently be selected from the group consisting of: hydrogen, deuterium, a halogen group, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group. Specifically, it is preferable that $R_1$ and $R_2$ are each independently selected from the group consisting of: a $C_1$ to $C_{40}$ alkyl group, a $C_6$ to $C_{60}$ aryl group, a heteroaryl group having 5 to 60 nuclear atoms, a $C_6$ to $C_{60}$ aryloxy group, a $C_6$ to $C_{60}$ arylphosphine oxide group and a $C_6$ to $C_{60}$ arylamine group. As a more preferred example, $R_1$ and $R_2$ are each independently selected from the group consisting of: a $C_6$ to $C_{60}$ aryl group or a heteroaryl group having 5 to 60 nuclear atoms, and the case where $R_1$ and $R_2$ are the same as each other is excluded.

In Chemical Formula 1, the fluorene group includes at least one cyano group (—CN). Specifically, a phenyl group on one side of the fluorene group is linked to phenylene or biphenylene, which is an aromatic linker, and at least one cyano group (—CN) is directly bonded to a phenyl group on another side of the fluorene group. In such an embodiment, the number of cyano groups (—CN) substituted in the fluorene group is not particularly limited, and may be, for example, at least one.

$R_a$ and $R_b$ included in the fluorene group may be the same as or different from each other and may each independently be a $C_1$ to $C_{40}$ alkyl group or a $C_6$ to $C_{60}$ aryl group, or may combine with each other to form a monocyclic or polycyclic condensed or fused ring. The fluorene group-derived condensed ring may each be a monocyclic or polycyclic alicyclic ring, a monocyclic or polycyclic heteroalicyclic ring, a monocyclic or polycyclic aromatic ring, or a monocyclic or polycyclic heteroaromatic ring, and for example, it may be a monocyclic or polycyclic aromatic ring having 6 to 18 carbon atoms, or a monocyclic or polycyclic heteroaromatic ring having 5 to 18 nuclear atoms.

According to an embodiment of the present invention, a cyano group-containing fluorene group or a condensed ring derived therefrom may be embodied as any one selected from the following structural formulas. However, the present invention is not limited thereto.

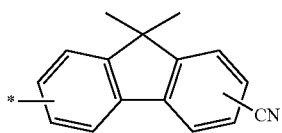

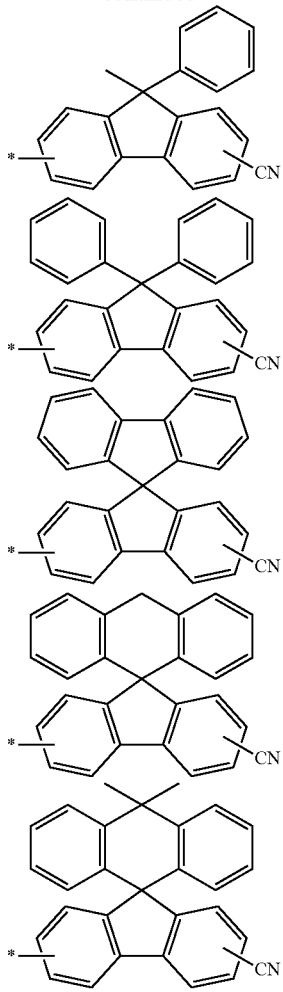

In the above structural formulas,
* represents a site where a bond is made with the compound represented by Chemical Formula 1, and although not illustrated in the above structural formulas, the above-described structural formulas may each be substituted with at least one substituent known in the art (e.g., the same as the description of $R_3$).

The nitrogen-containing heterocyclic ring and the fluorene group introduced with the cyano group, described above, are linked to each other through an aromatic linker. Such an aromatic linker is a divalent linker, and specific examples thereof may be phenylene or biphenylene.

In Chemical Formula 1, the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_1$ to $R_3$ may each independently be substituted or unsubstituted with one or more kinds of substituents selected from the group consisting of: deuterium, a halogen group, a cyano group, a nitro group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_1$ to $C_{40}$ alkyl group, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents may be the same as or different from each other.

The compound represented by Chemical Formula 1, when the type of the aromatic ring introduced as a linker and the bonding position thereof are further specified, may be embodied as a compound represented by any one of the following Chemical Formula 2 to Chemical Formula 6:

[Chemical Formula 2]

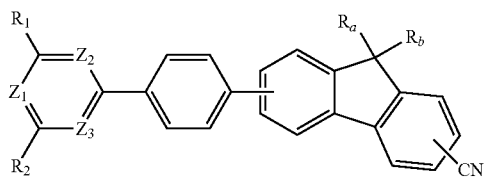

[Chemical Formula 3]

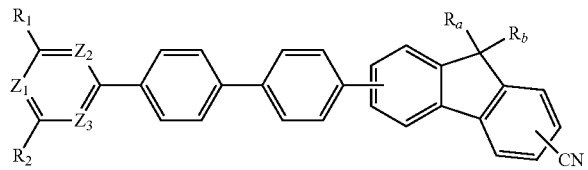

[Chemical Formula 4]

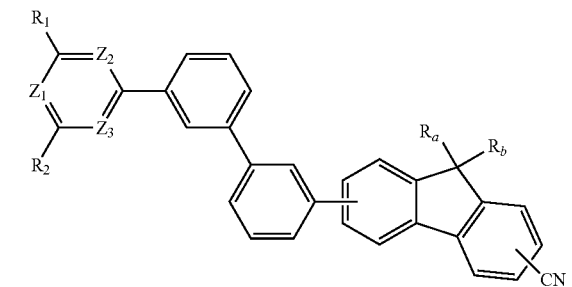

[Chemical Formula 5]

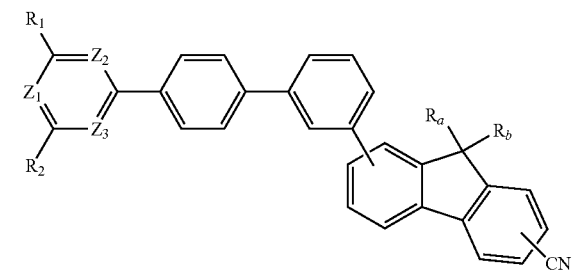

[Chemical Formula 6]

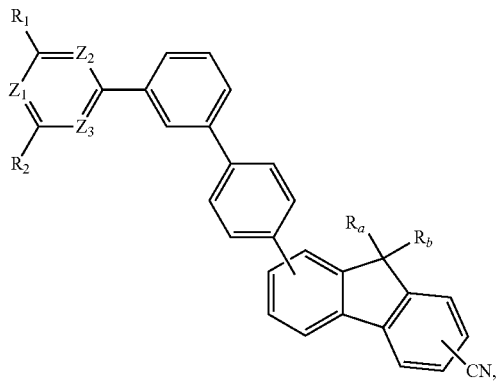

wherein in Chemical Formulas 2 to 6, $Z_1$ to $Z_3$, $R_a$ and $R_b$, and $R_1$ and $R_2$ are as defined in Chemical Formula 1, respectively.

In Chemical Formula 3, the biphenylene linker is linked in a para-para (p,p-) bonding position, and the biphenylene linker of Chemical Formula 4 is linked in a meta-meta (m,m-) bonding position. In addition, in Chemical Formulas 5 and 6, with respect to one phenylene group (e.g., a first phenylene group) of the biphenylene linker, an adjacent nitrogen-containing heterocycle (e.g., an $Z_1$- to $Z_3$-containing ring in Chemical Formula 1) and another phenylene group (e.g., a second phenylene group) are bonded in a para-position, and with respect to the another phenylene group (e.g., the second phenylene group), an adjacent cyano group-substituted fluorene group and the phenylene group (e.g., the first phenylene group) are bonded in a meta-position. As such, the para-meta (p,m-) linked biphenylene linker extends a distance between the two EWG moieties, thereby minimizing interaction between these EWG moieties, and increasing the stability of the compound itself. In addition, the compound of Chemical Formula 1 including the biphenylene linker linked in para-meta exhibits an effect of inhibiting crystallization of an organic layer, as compared to the compound containing a biphenylene linker linked in para-para or meta-meta. Accordingly, an organic EL device employing the compound of Chemical Formula 1 may exhibit excellent driving voltage and current efficiency and may greatly improve durability and lifespan characteristics.

In addition, the compound represented by Chemical Formula 1 according to the present invention may be further specified into any one of the following Chemical Formulas 7 to 10 according to the bonding position of the cyano group (—CN) introduced into the fluorene group. However, the present invention is not limited thereto.

[Chemical Formula 7]

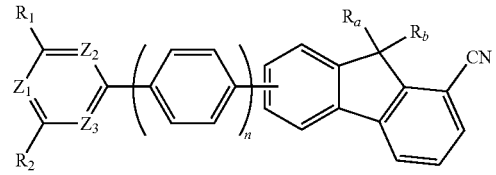

[Chemical Formula 8]

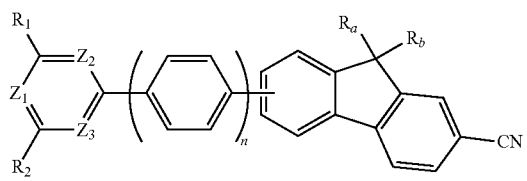

[Chemical Formula 9]

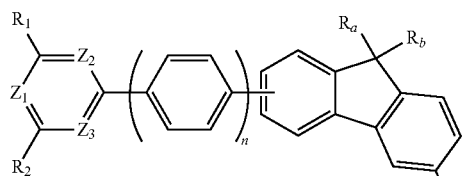

[Chemical Formula 10]

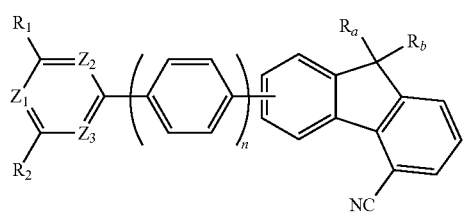

wherein in Chemical Formulas 7 to 10, $Z_1$ to $Z_3$, $R_a$ and $R_b$, $R_1$ and $R_2$, and n are as defined in Chemical Formula 1, respectively.

In an embodiment, since an active site of the fluorene group is at position 2, a structure in which the cyano group (—CN) is bonded to the position 2 of the fluorene group is chemically most stable. Accordingly, among the aforementioned Chemical Formulas 7 to 10, the chemical structure represented by Chemical Formula 8 is preferable.

For a preferred example of the compound represented by any one of Chemical Formulas 2 to 10, $Z_1$ to $Z_3$ are the same as or different from each other, and each independently represent N or $C(R_3)$, provided that two or three of $Z_1$ to $Z_3$ are N, $R_1$ and $R_2$ are different from each other and are each independently a $C_6$ to $C_{60}$ aryl group or a heteroaryl group having 5 to 60 nuclear atoms, $R_3$ is selected from the group consisting of hydrogen, a $C_1$ to $C_{40}$ alkyl group, a $C_6$ to $C_{60}$ aryl group, and a heteroaryl group having 5 to 60 nuclear atoms, $R_a$ and $R_b$ are each independently a $C_1$ to $C_{40}$ alkyl group or a $C_6$ to $C_{60}$ aryl group, or combine with each other to form a fused ring, provided that the $R_a$ and $R_b$-containing ring includes at least one cyano group (—CN).

The compound represented by Chemical Formula 1 according to the present invention described above may be further embodied as a compound represented by any one of the compounds 1 to 800 exemplified below. However, the compound represented by Chemical Formula 1 of the present invention is not limited by those exemplified below.

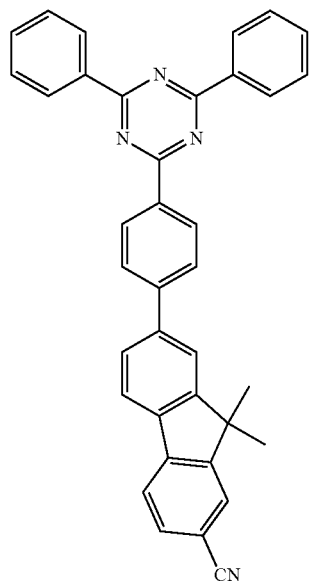

1

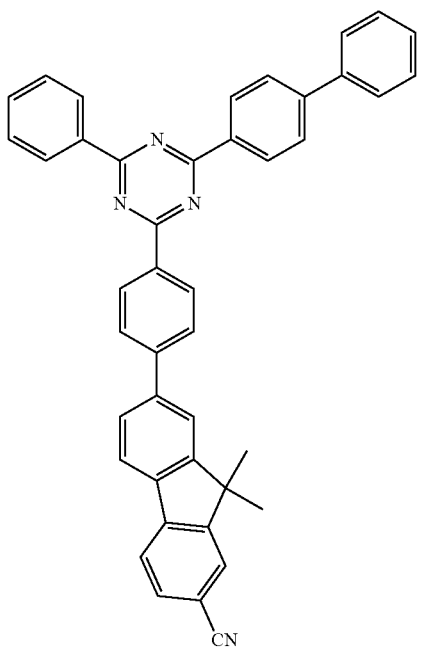

2

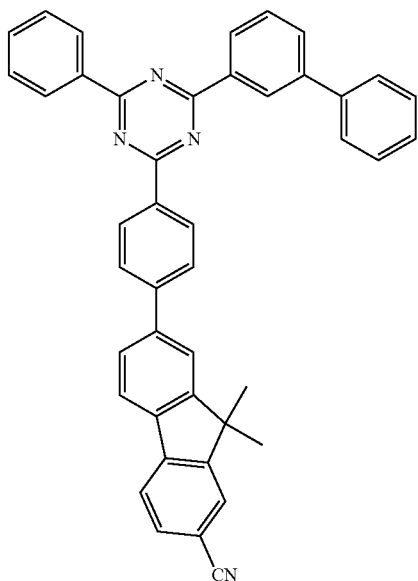
3
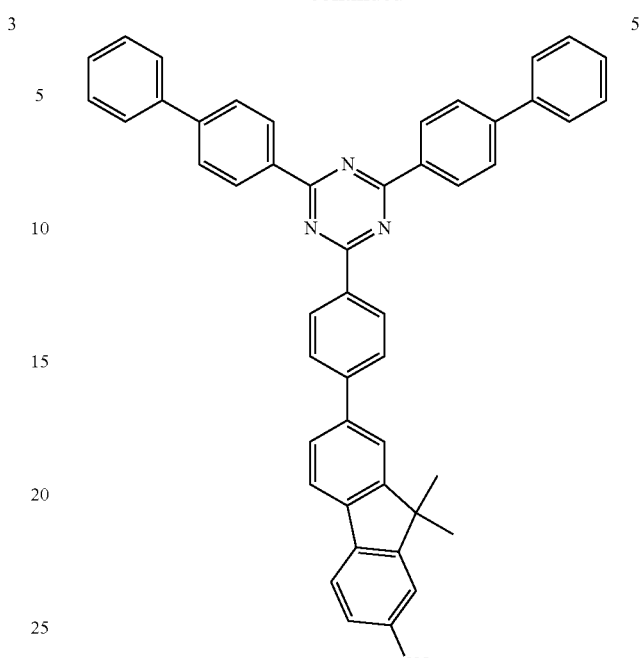
5
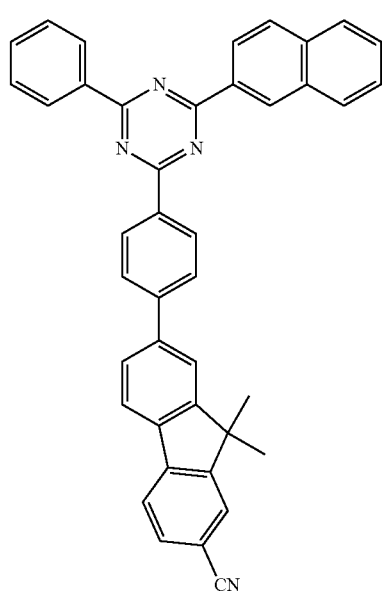
4
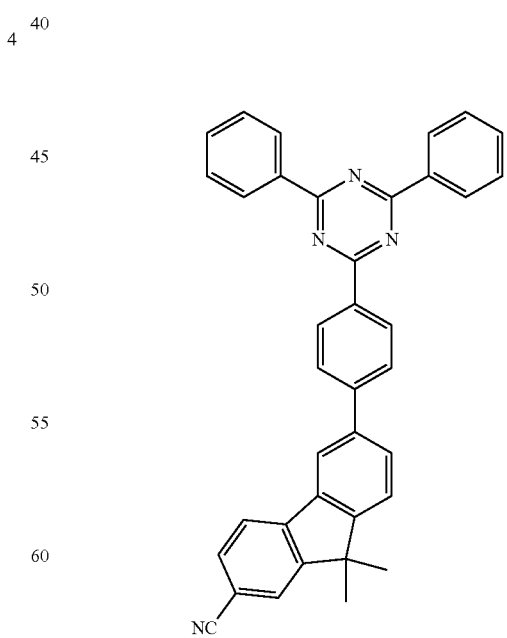
6

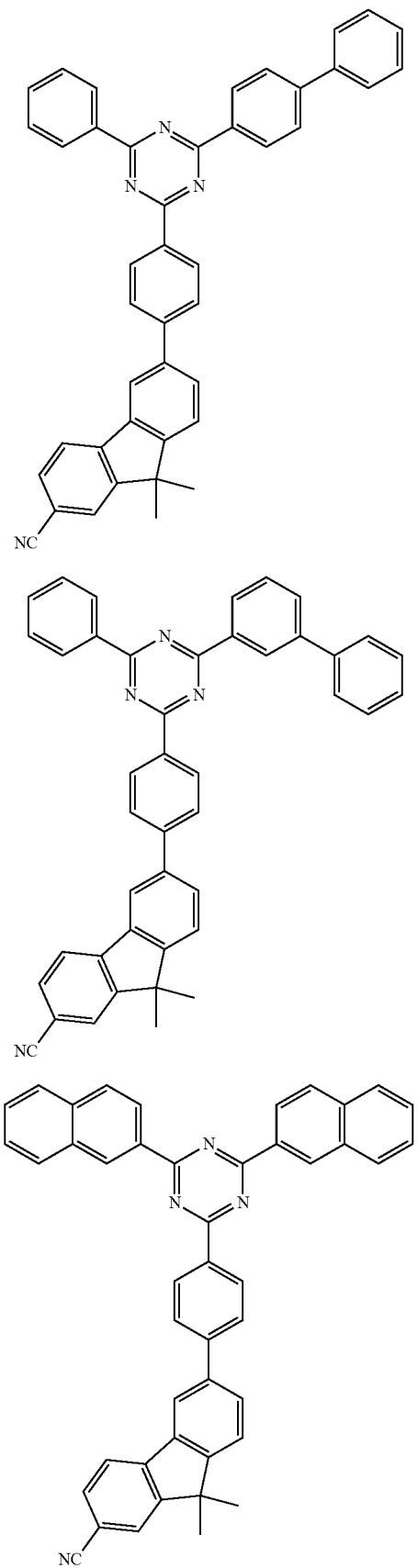
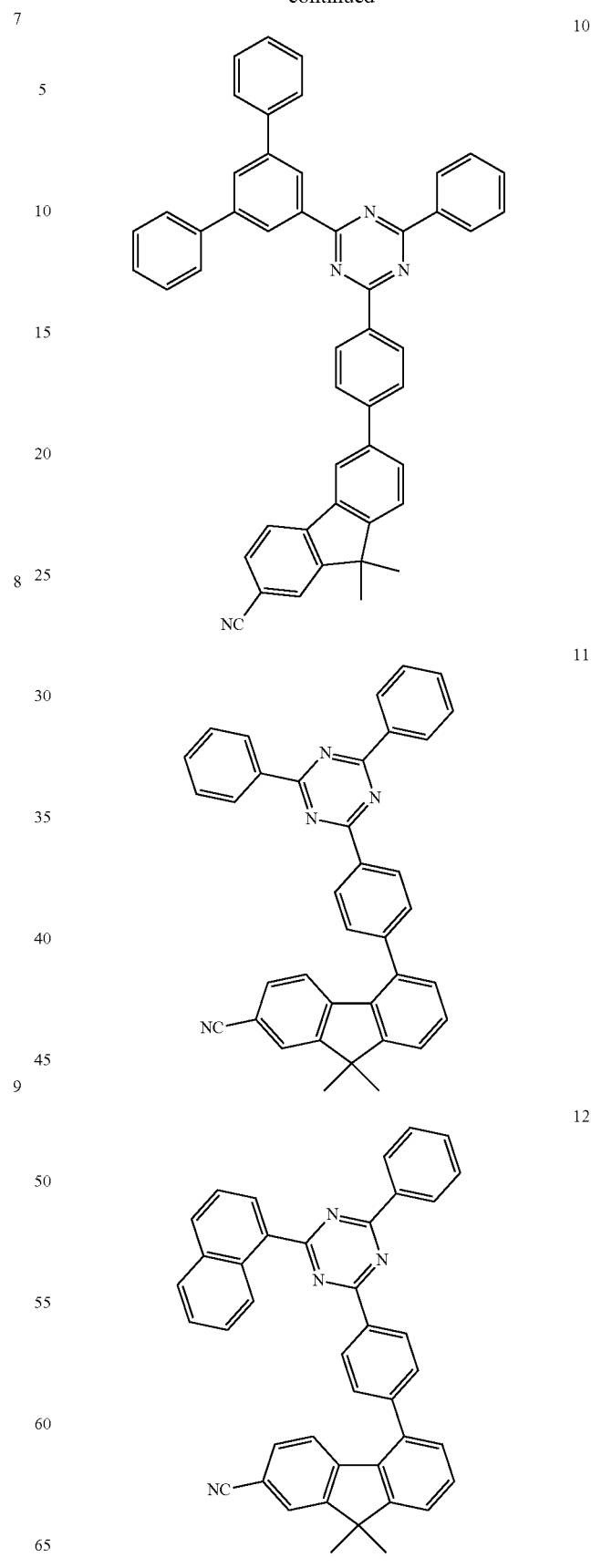

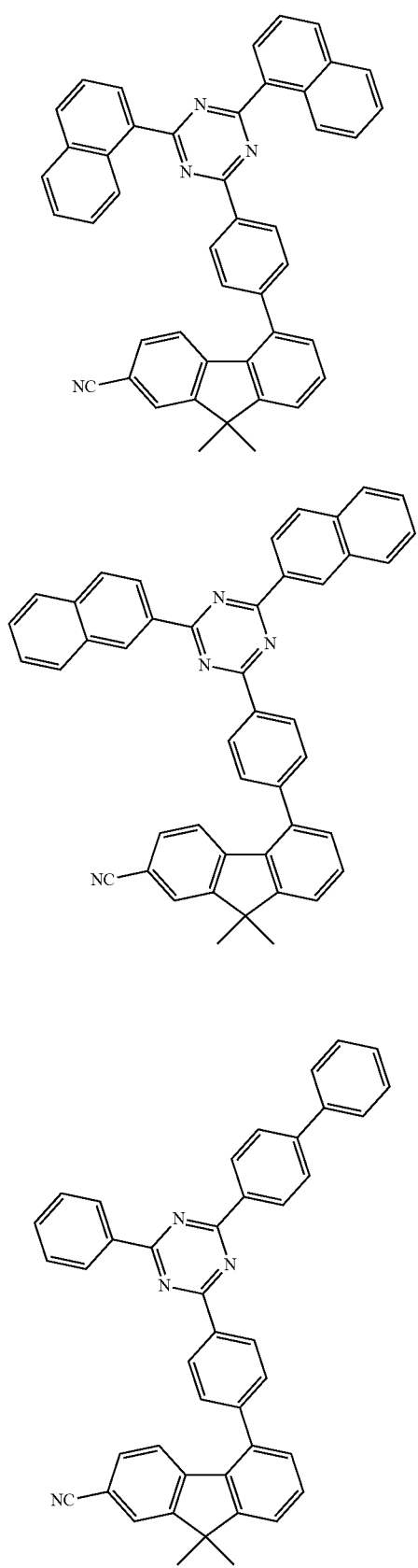
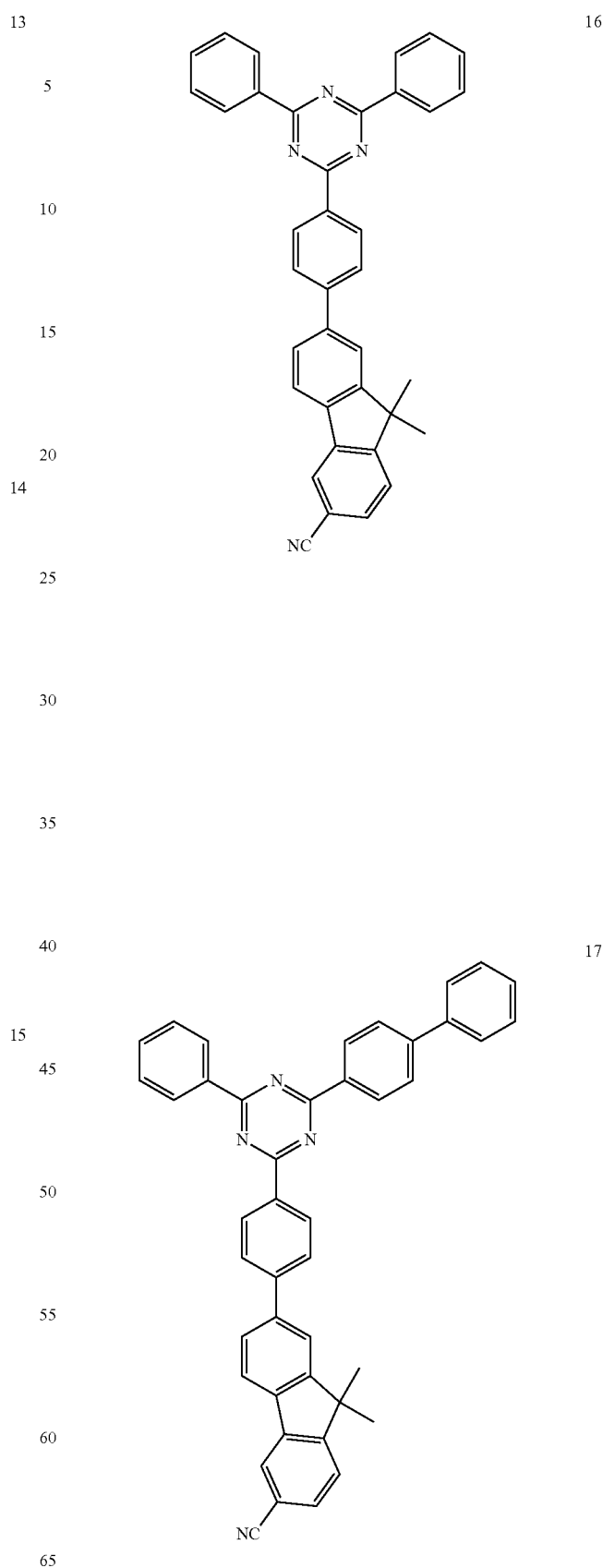

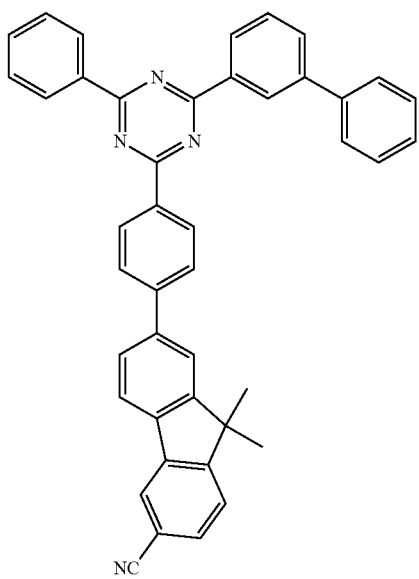
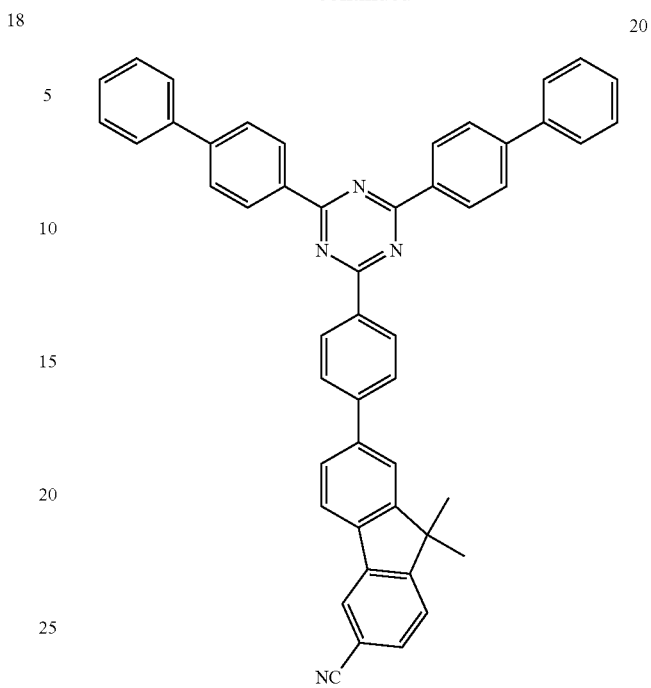
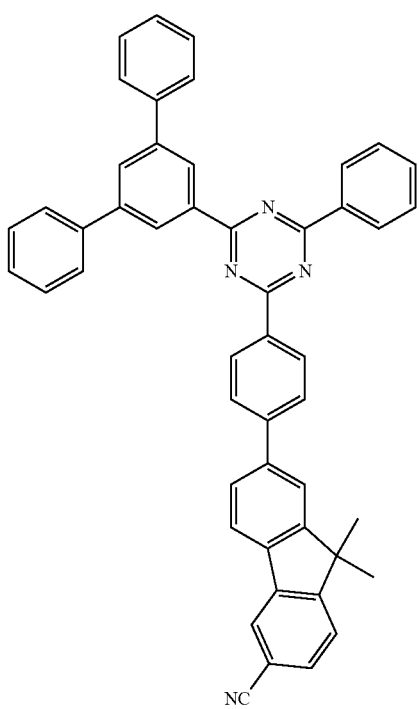
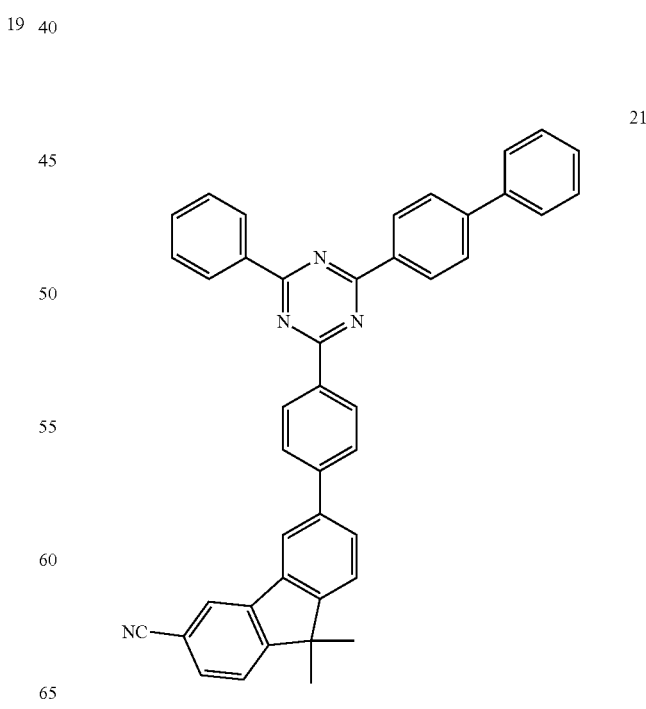

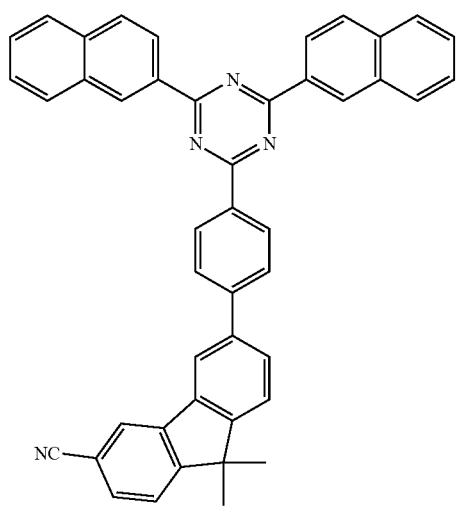
22
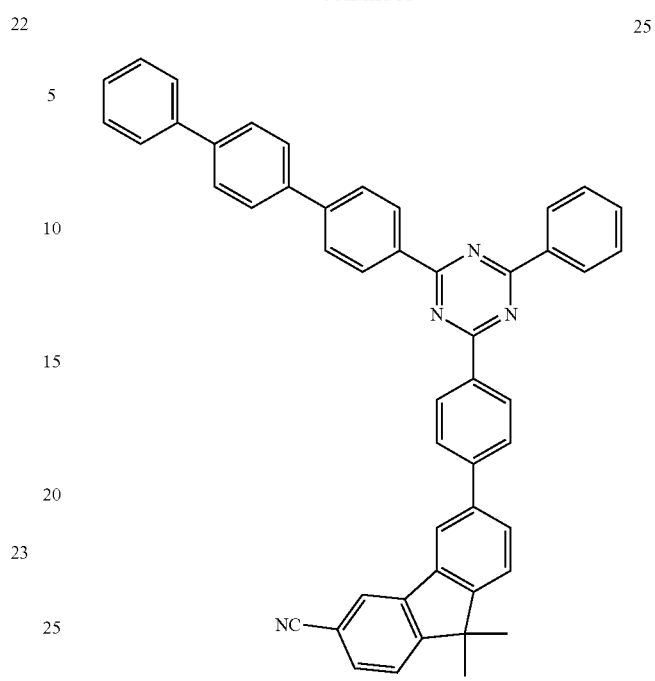
25
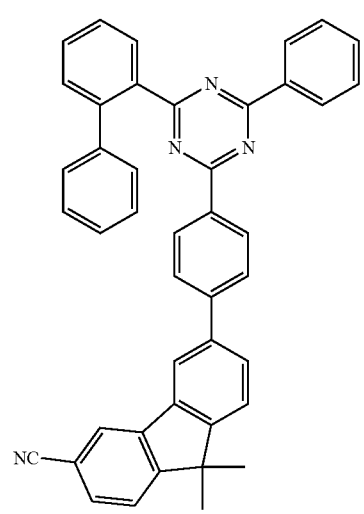
23
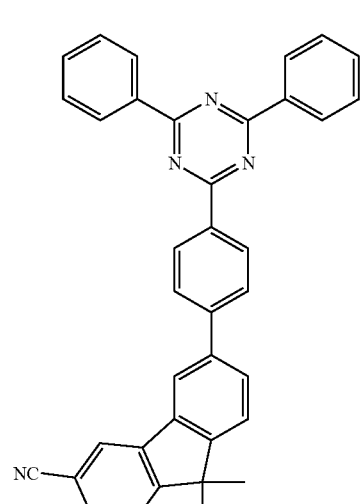
24
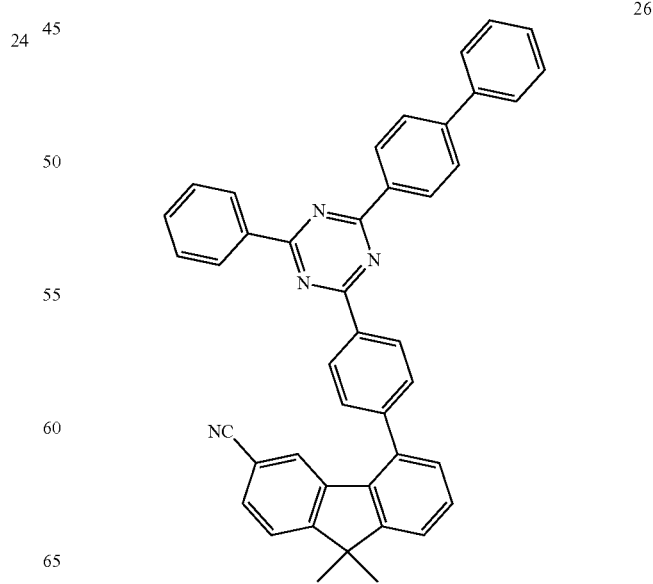
26

27
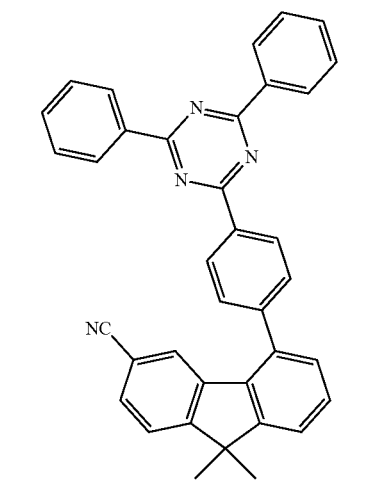
28
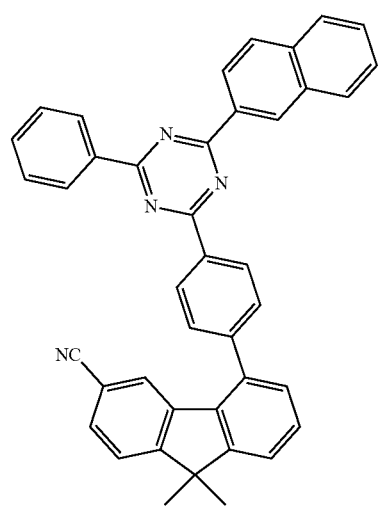
29
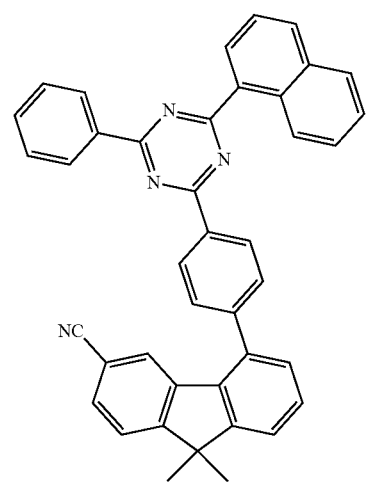
30
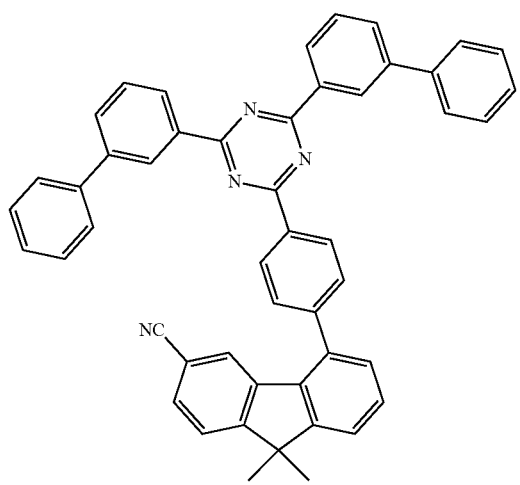
31
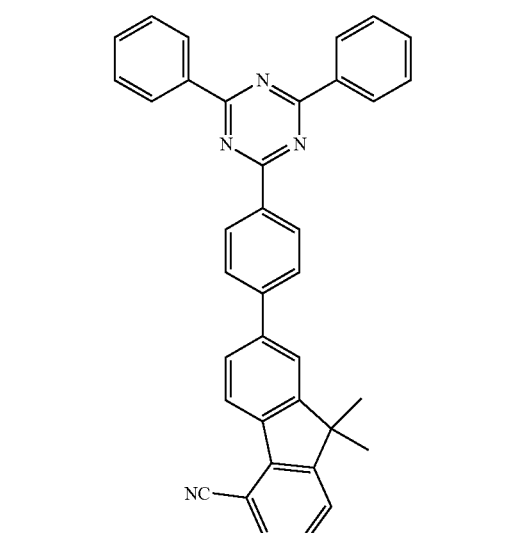
32
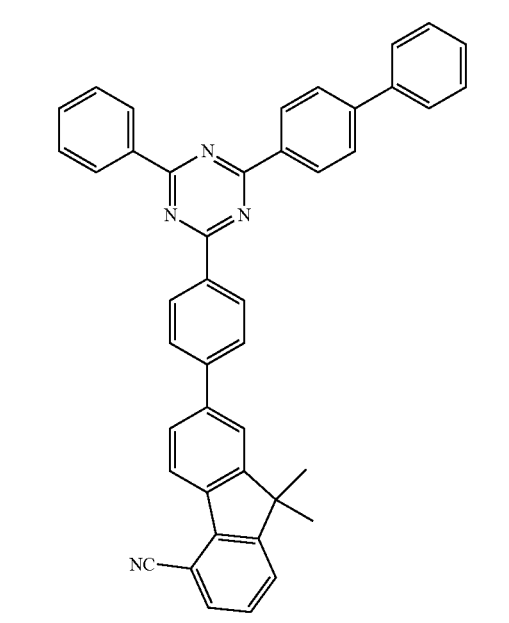

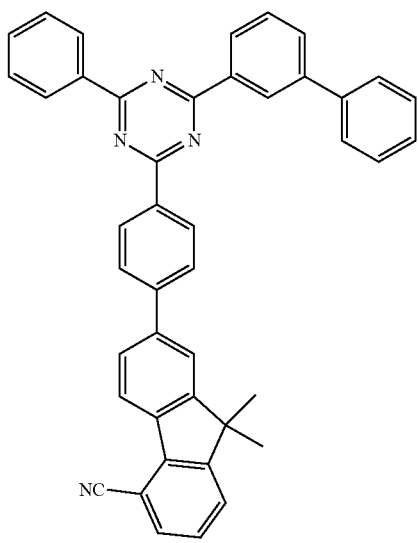
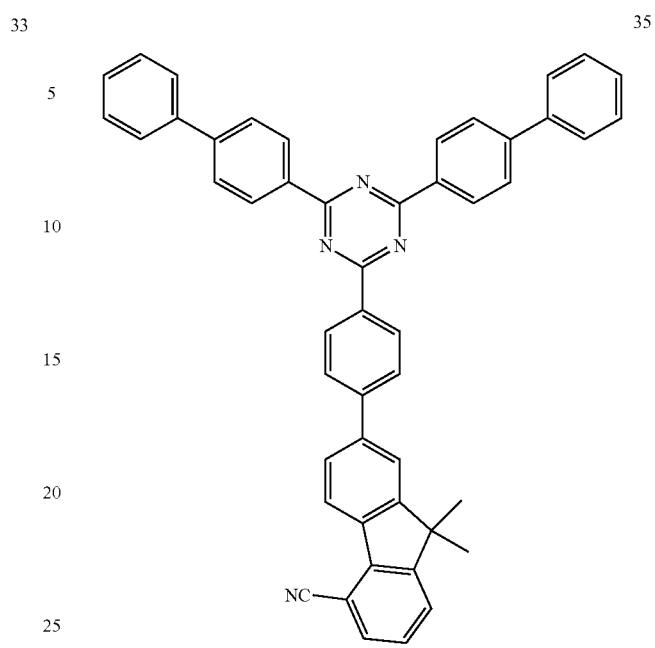

37
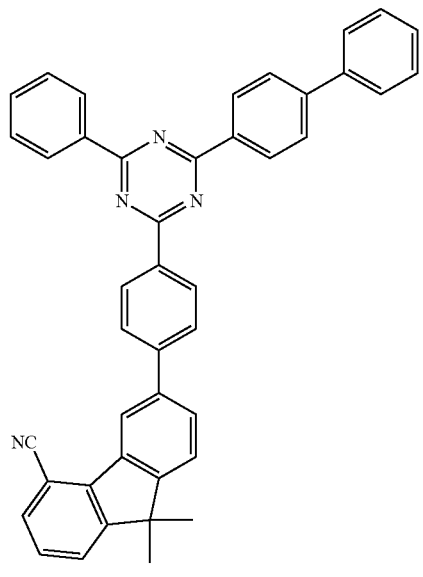
38
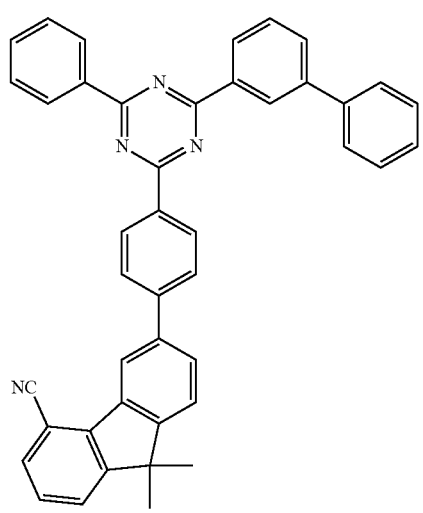
39
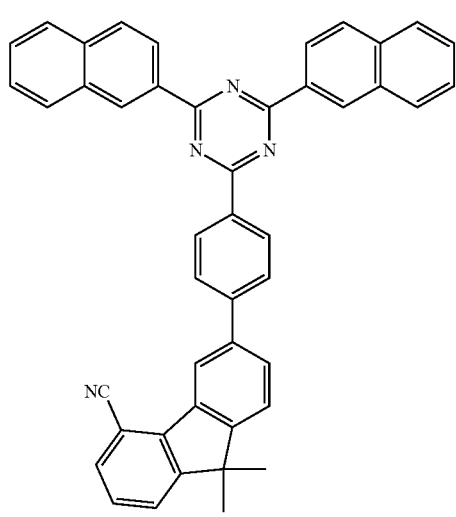
40
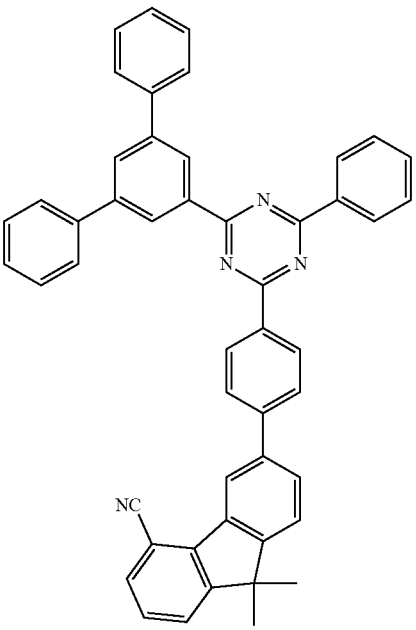
41
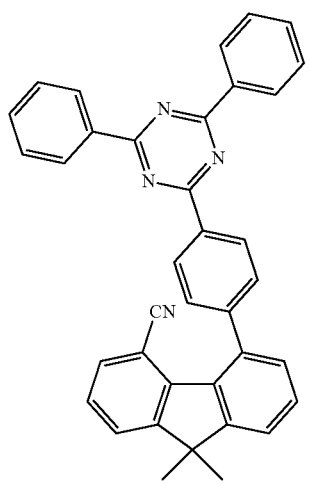
42
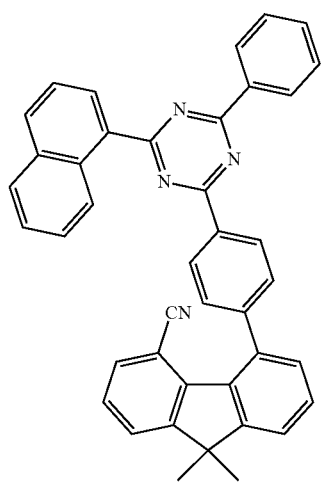

43
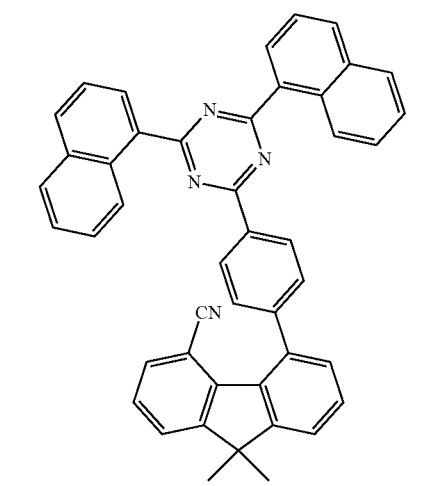
44
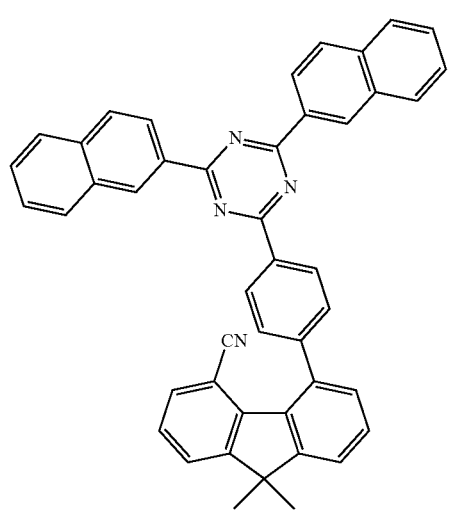
45
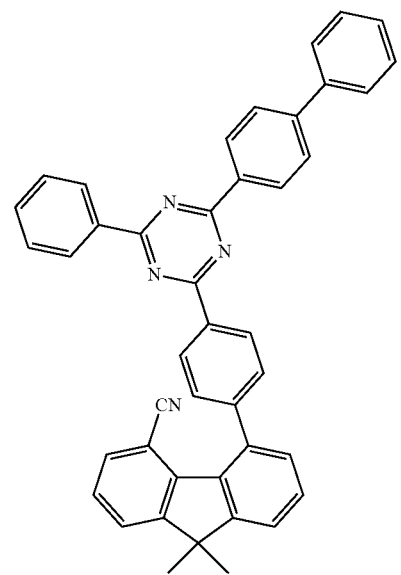
46
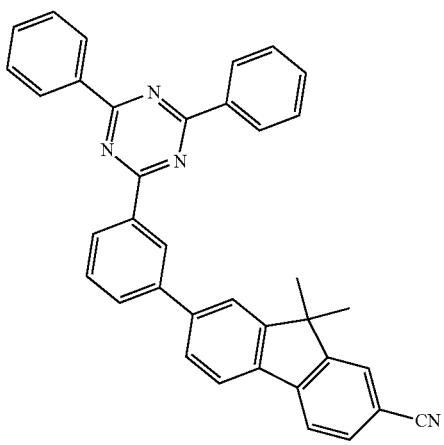
47
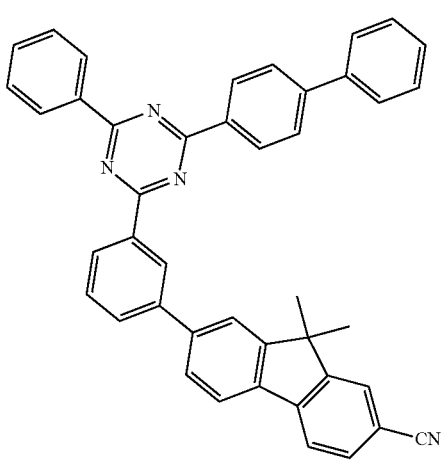
48
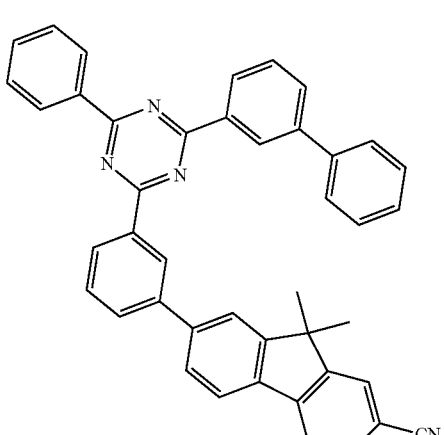

49
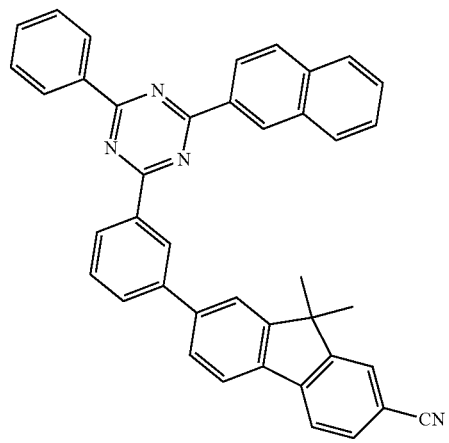
50
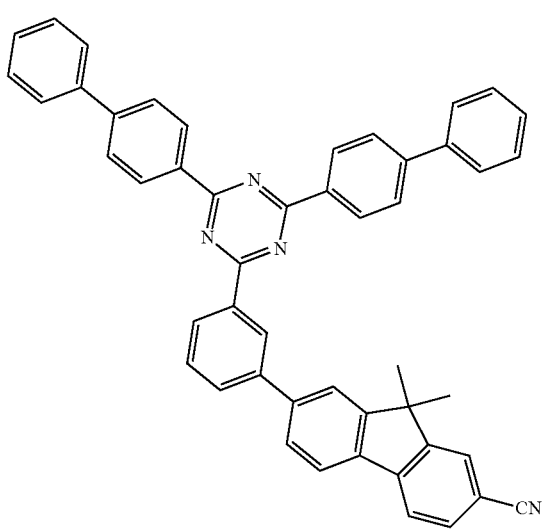
51
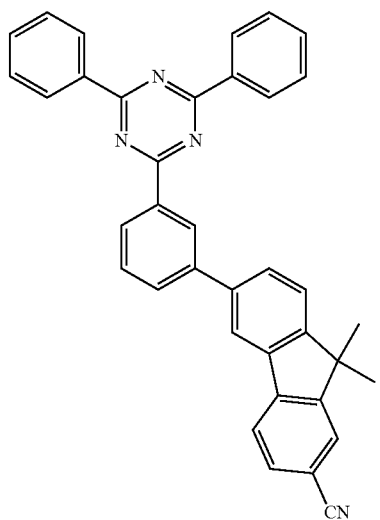
52
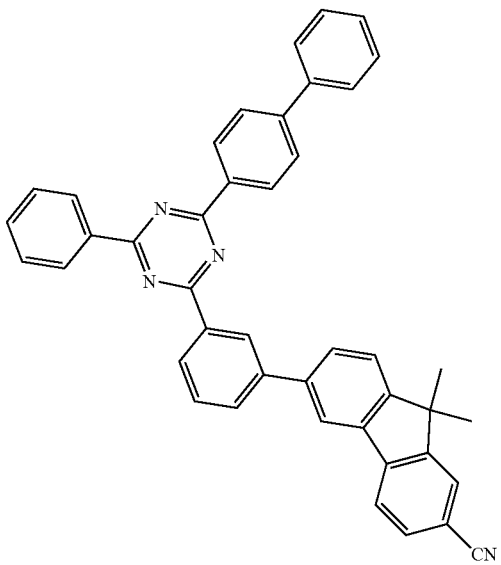
53
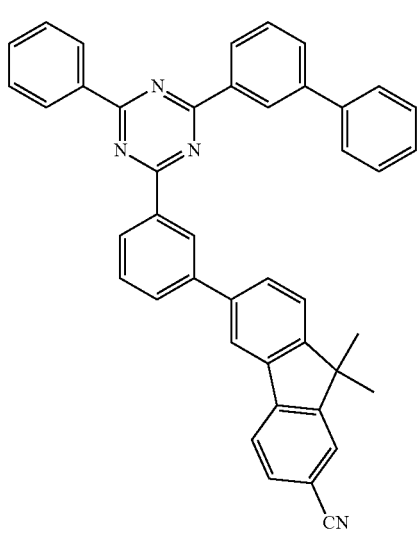
54
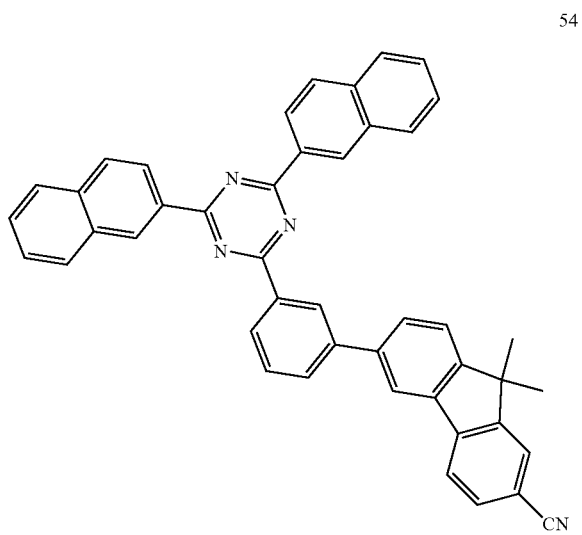

33
-continued
55
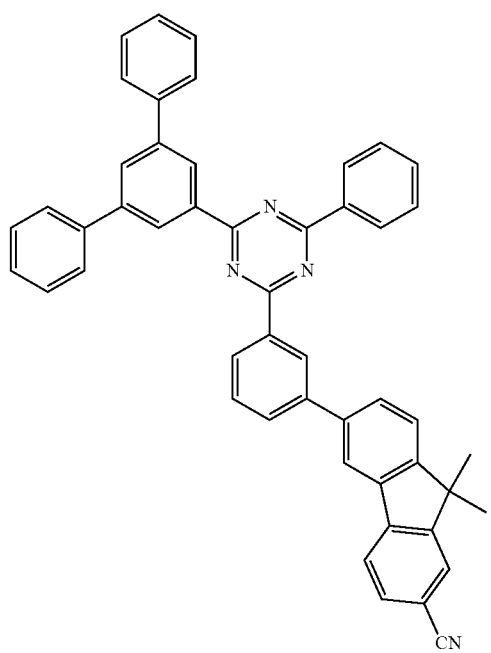
56
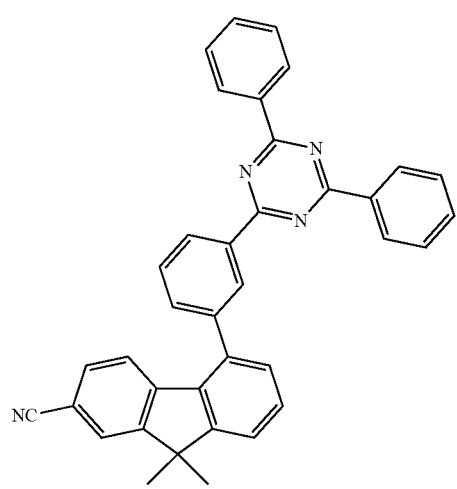
57
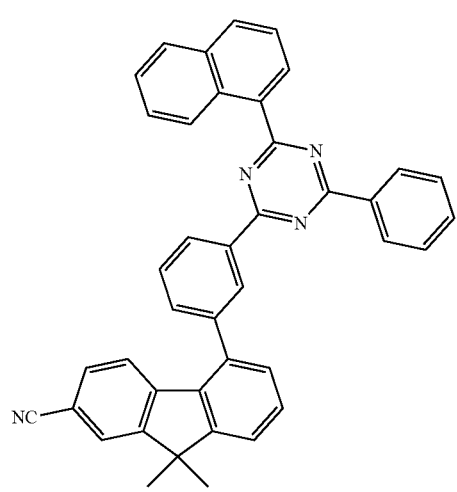
34
-continued
58
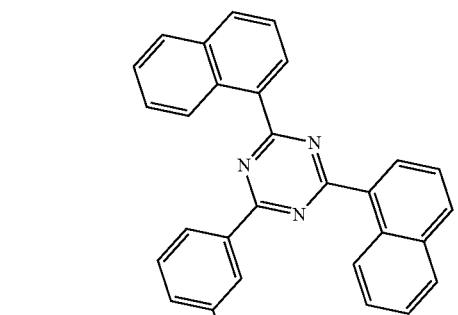
59
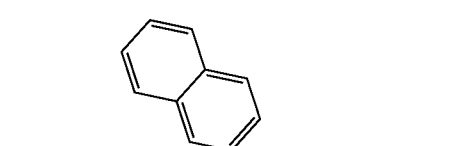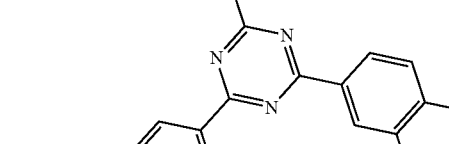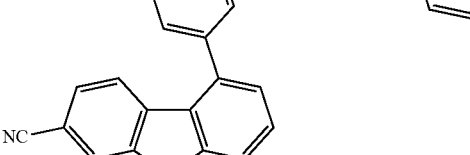
60
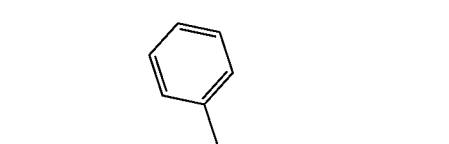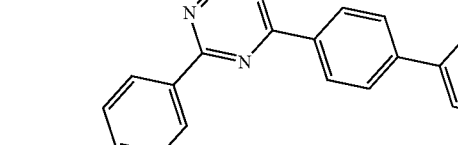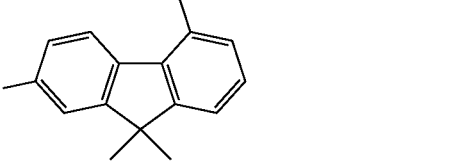

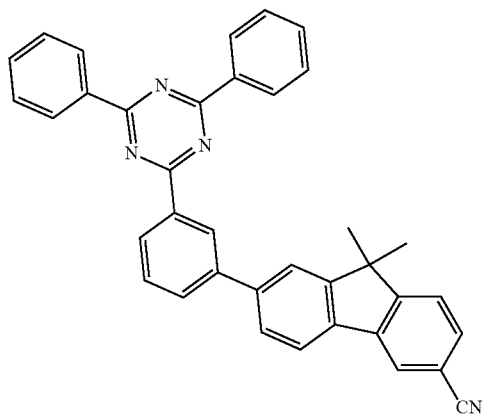
61
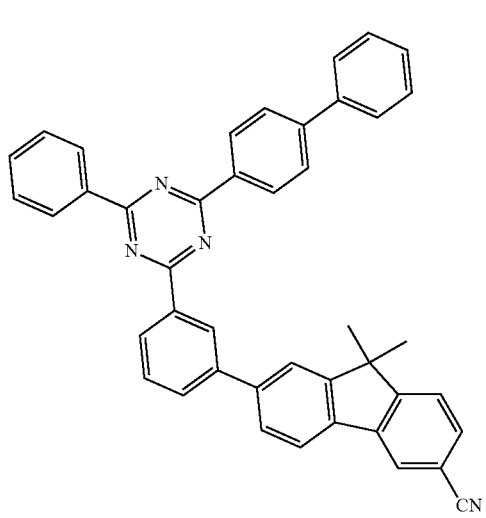
62
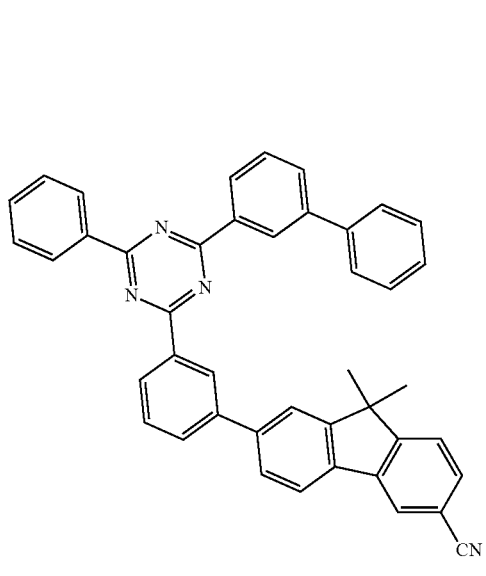
63
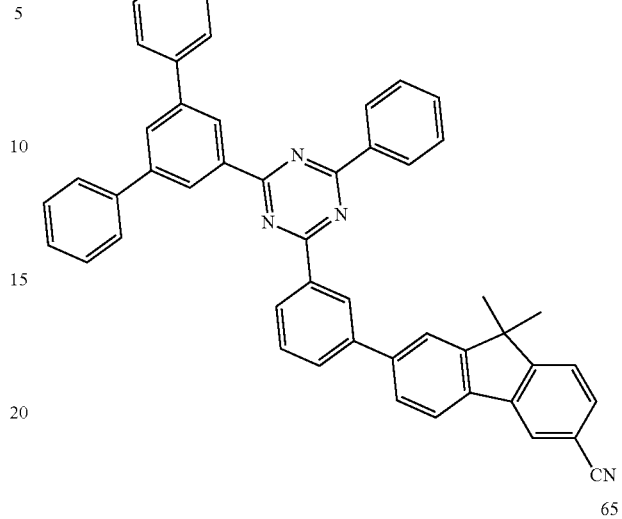
64
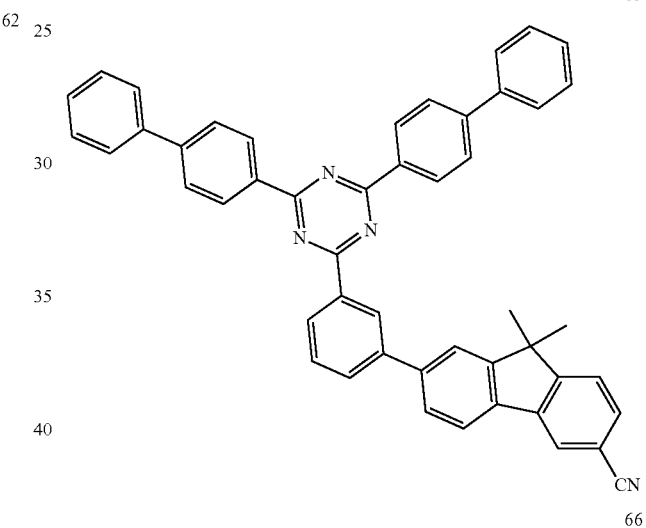
65
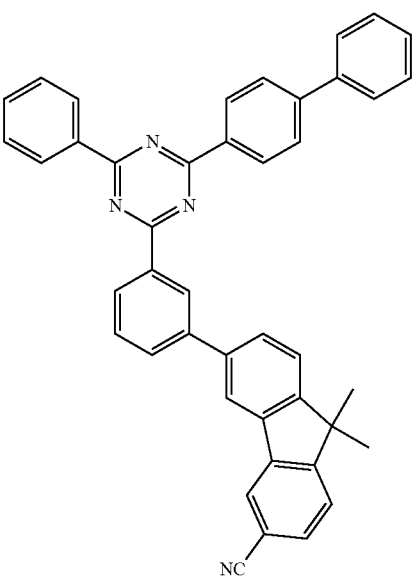
66

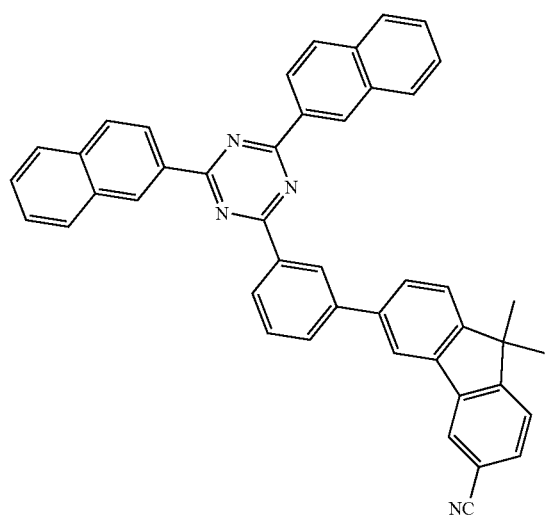
67
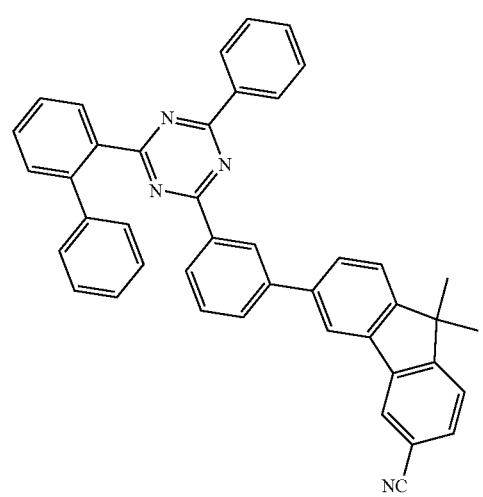
68
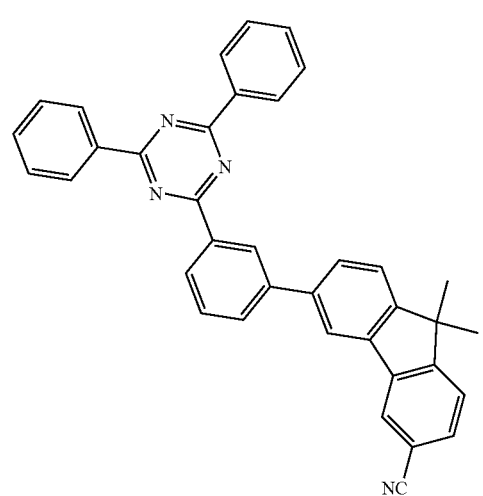
69
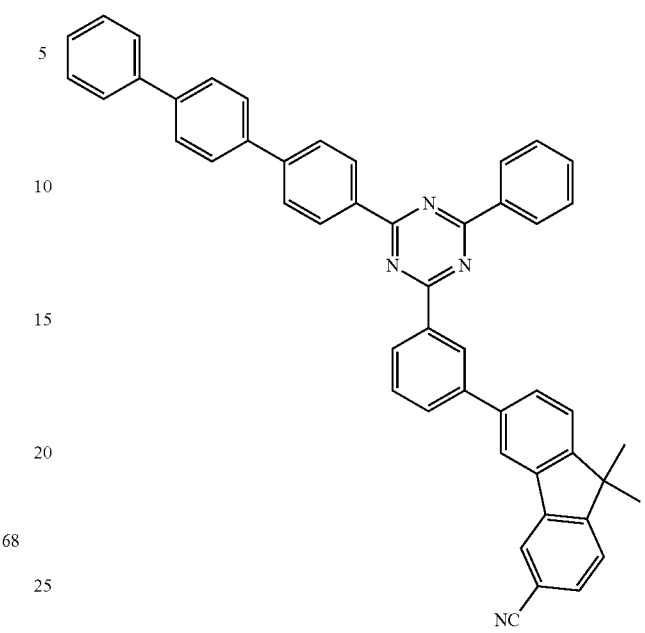
70
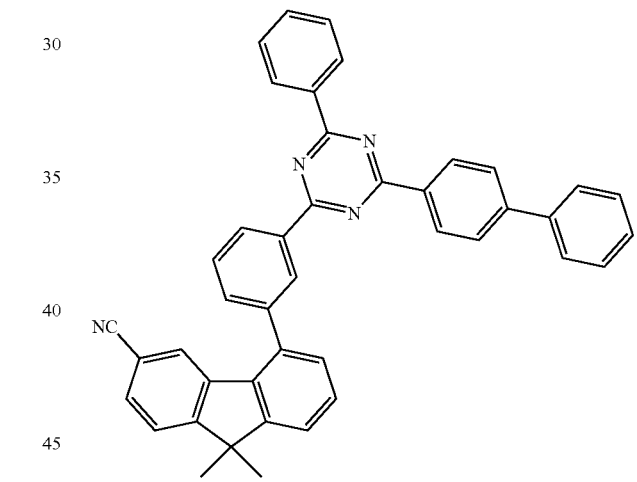
71
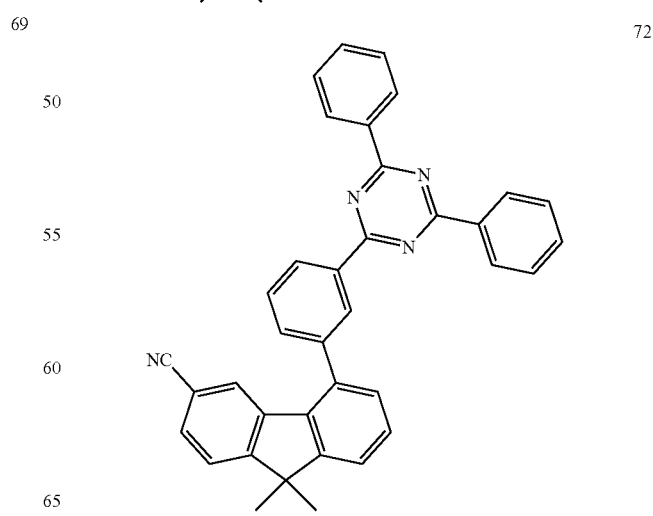
72

73
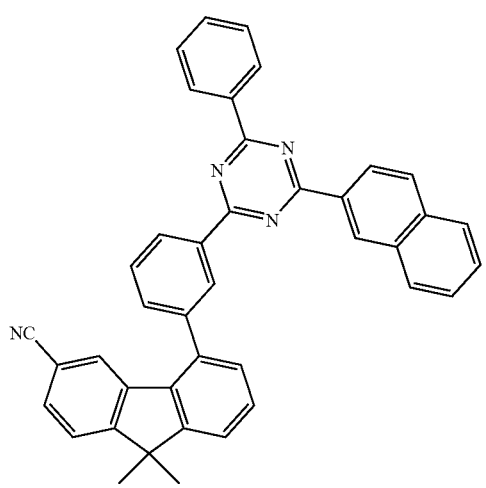
74
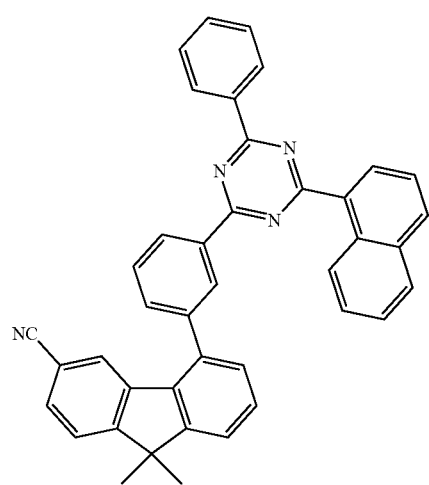
75
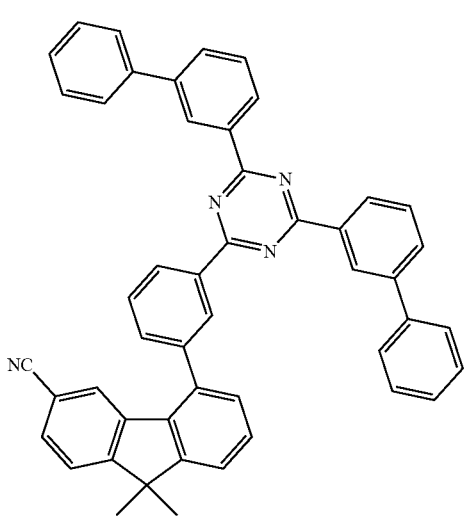
76
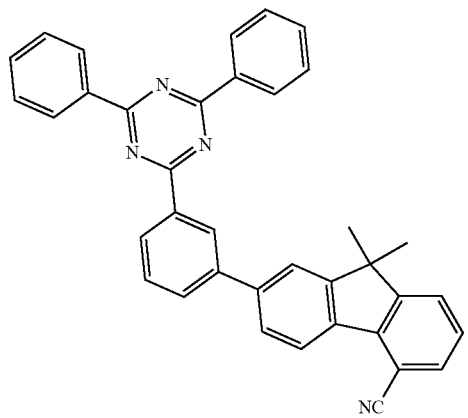
77
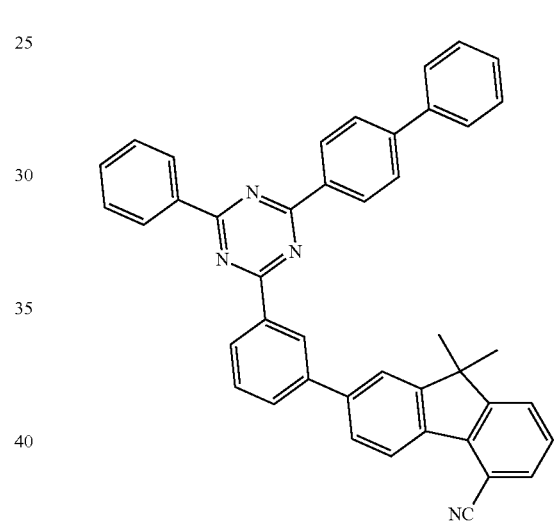
78
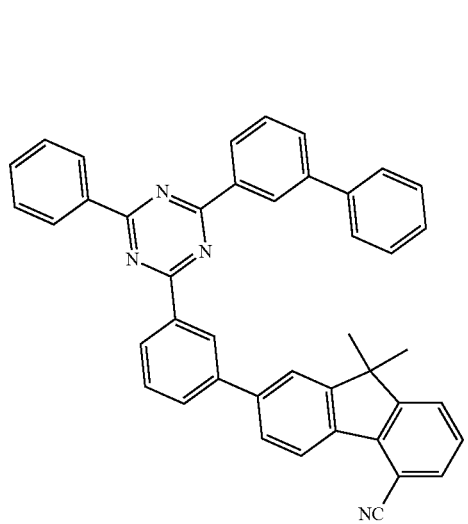

79
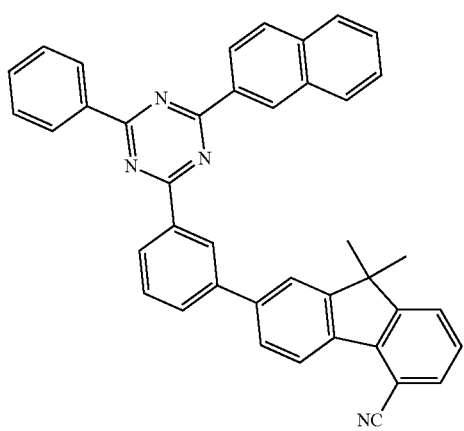
80
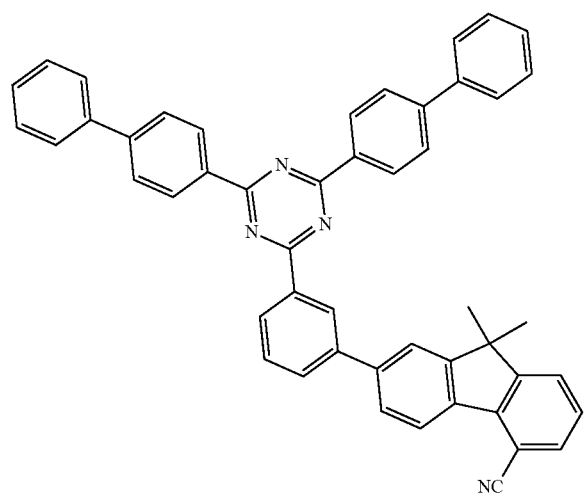
81
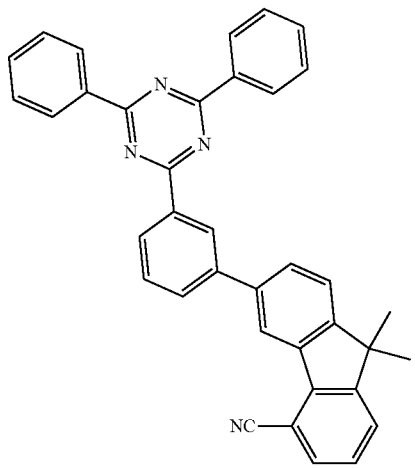
82
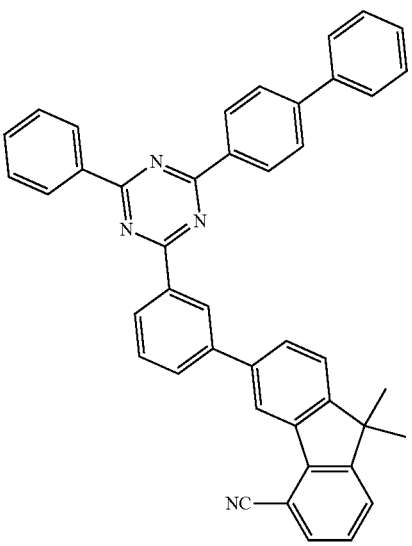
83
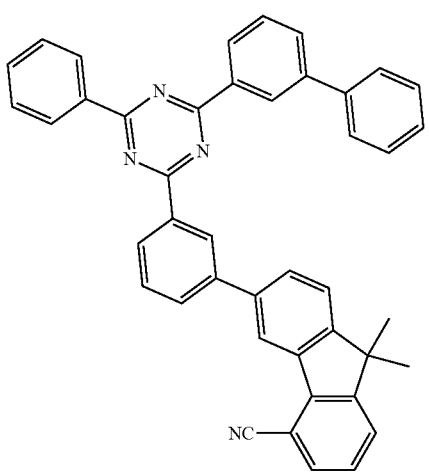
84
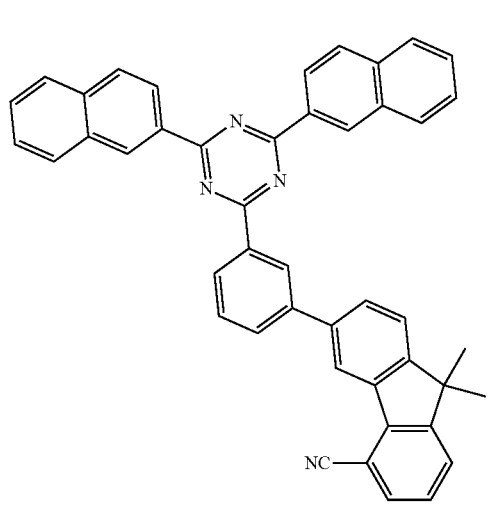

85
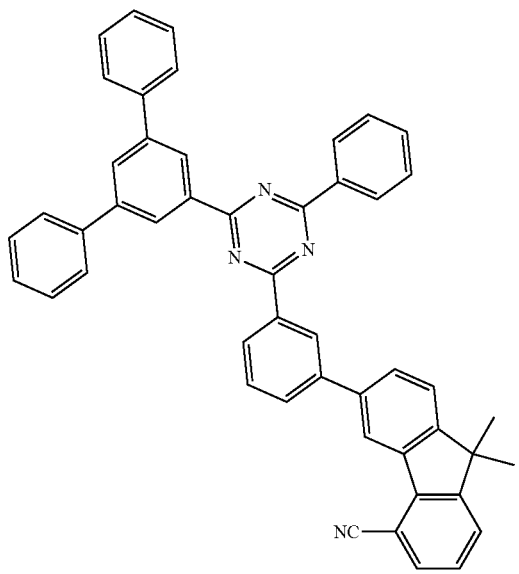
86
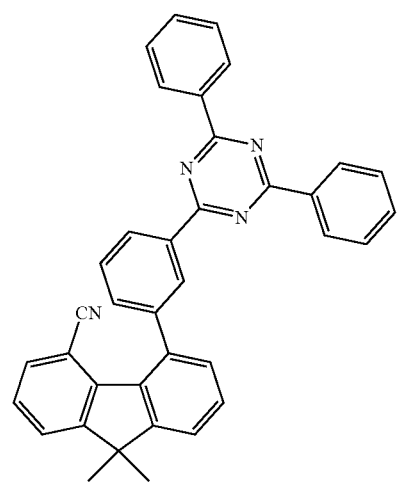
87
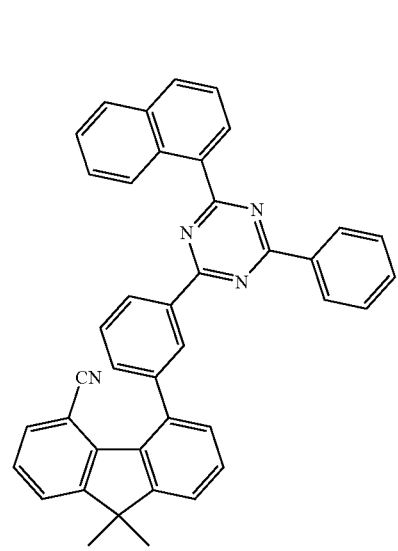
88
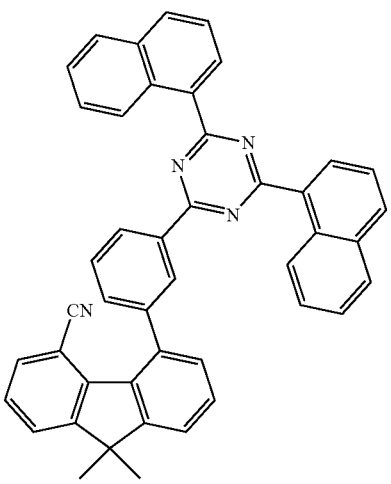
89
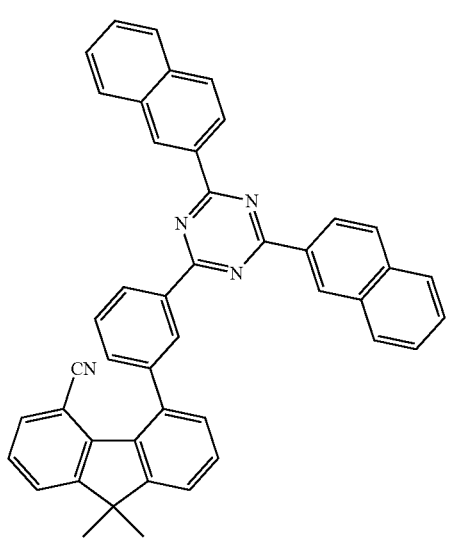
90
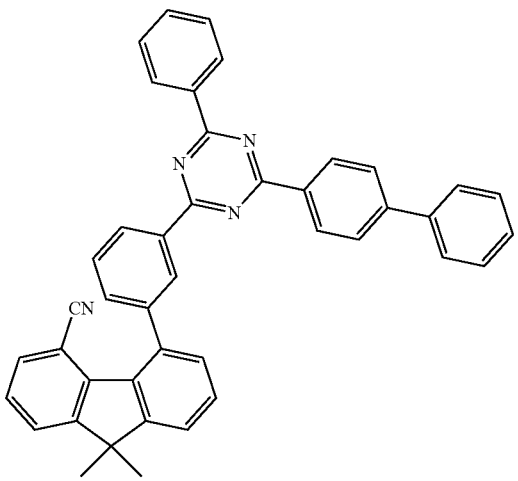

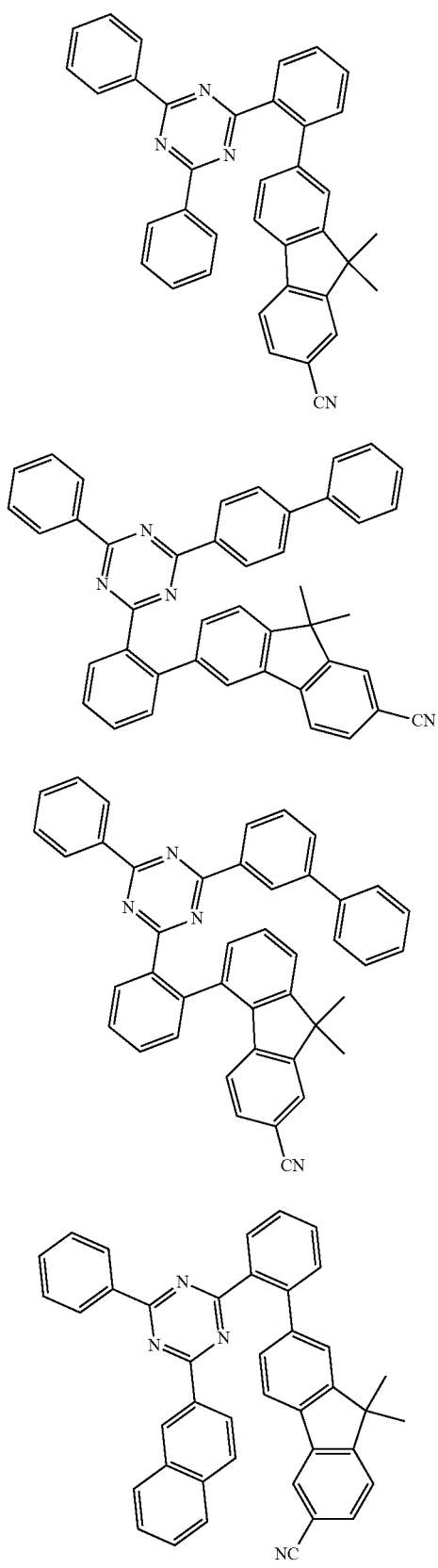
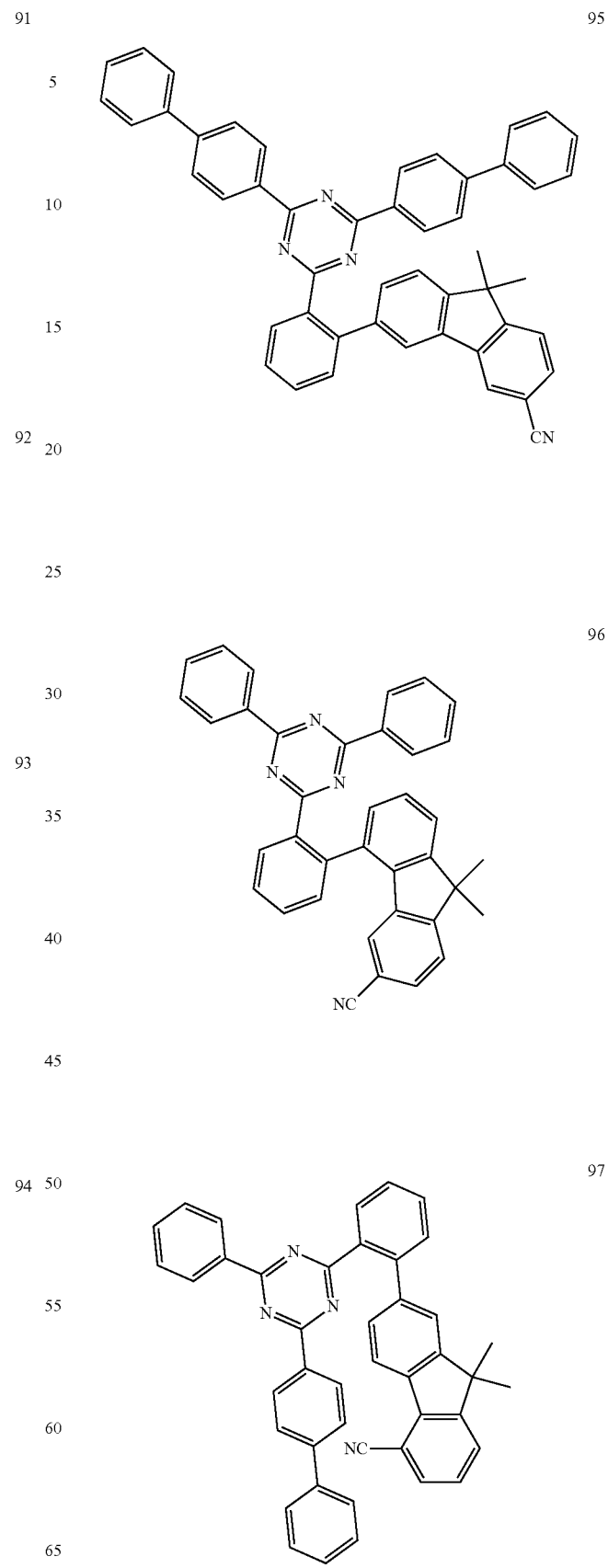

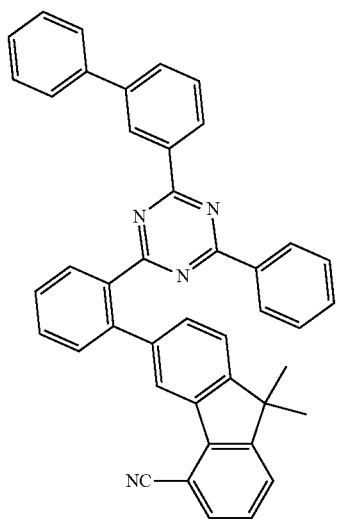
98
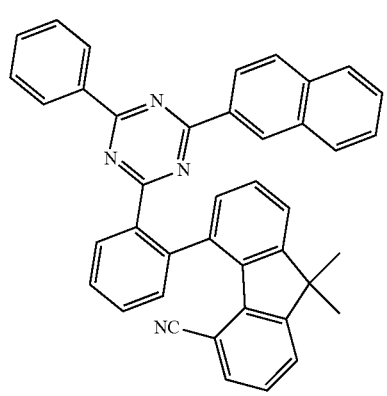
99
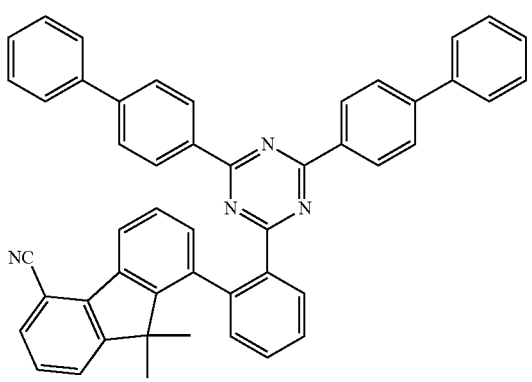
100
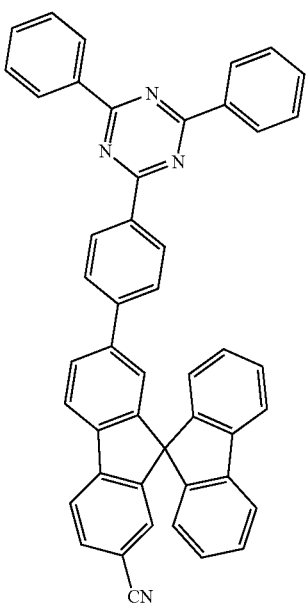
101
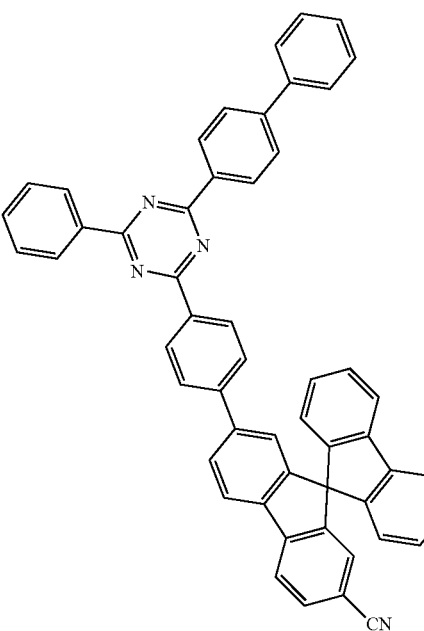
102

103
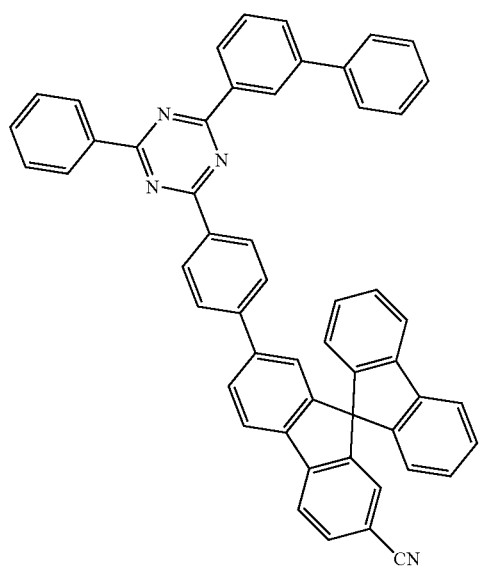
104
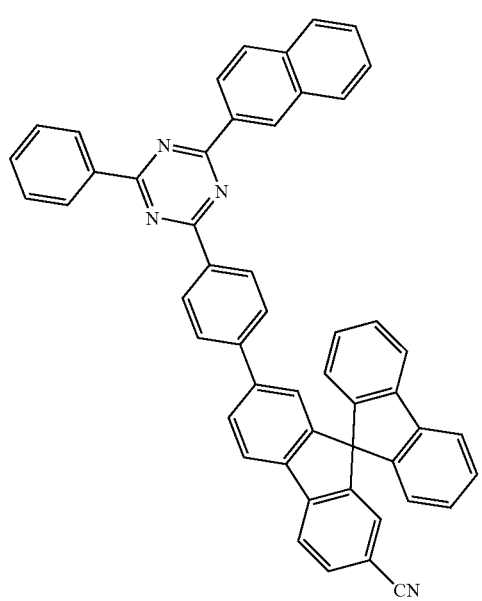
105
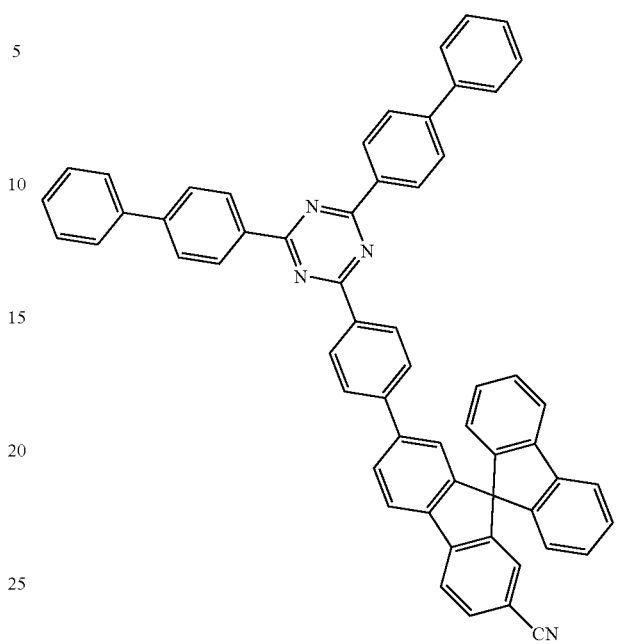
106
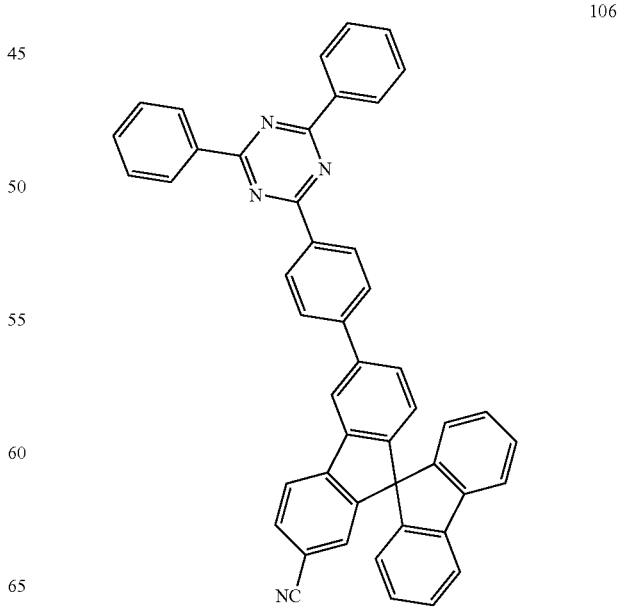

107
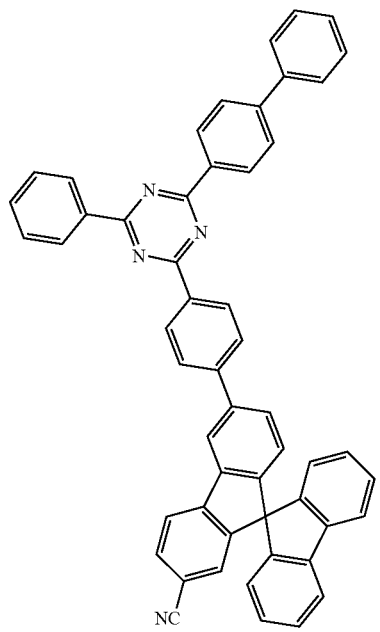
108
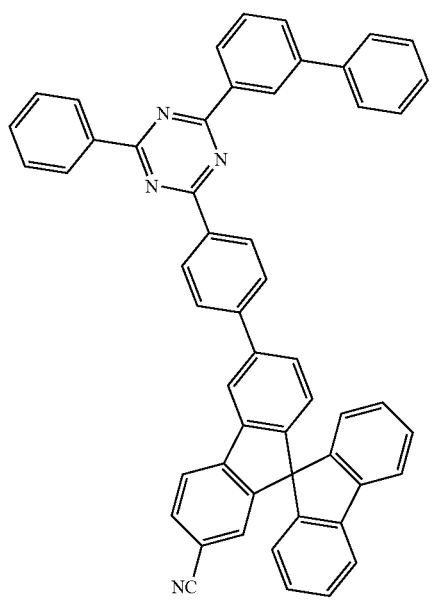
109
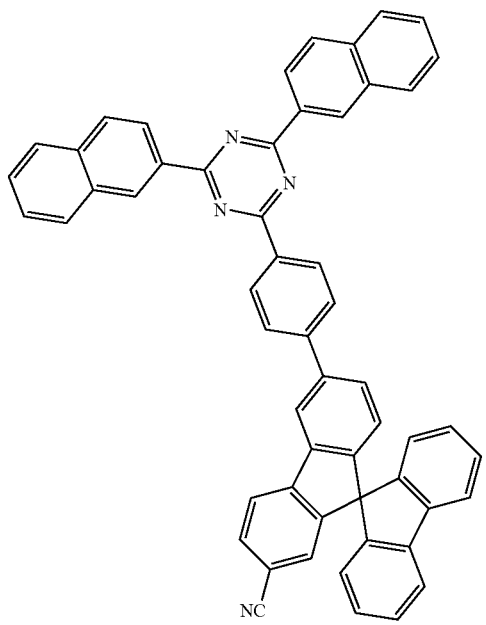
110
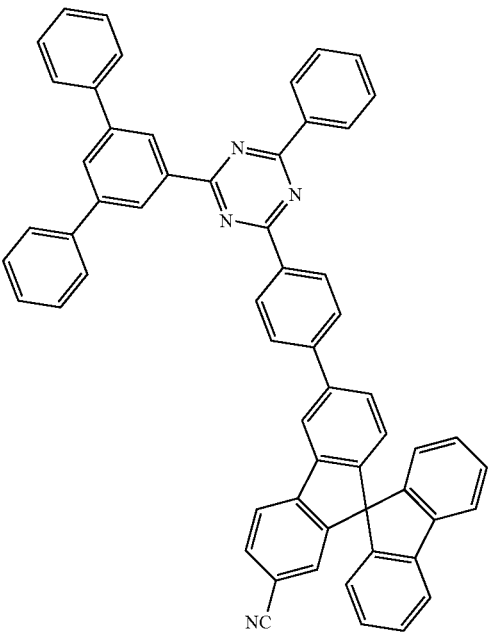

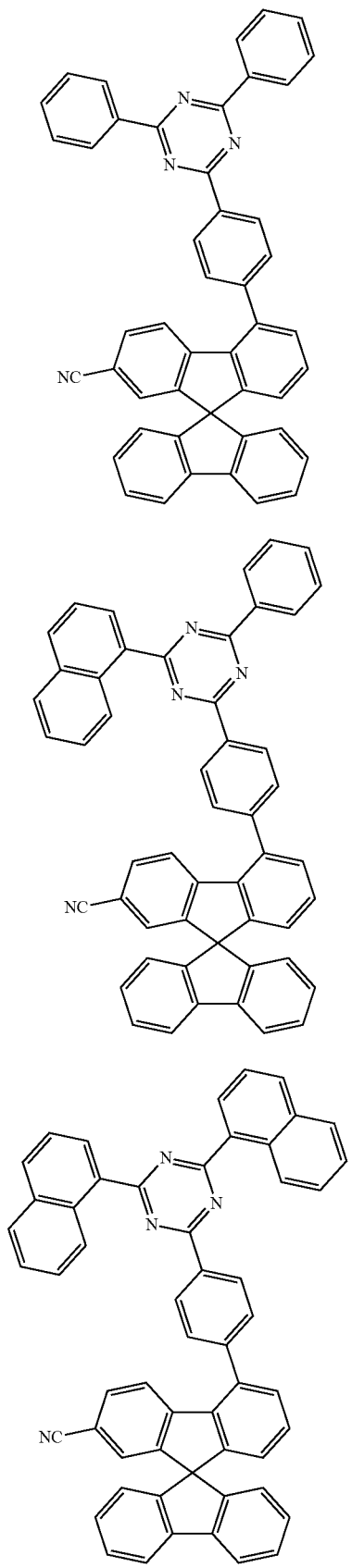
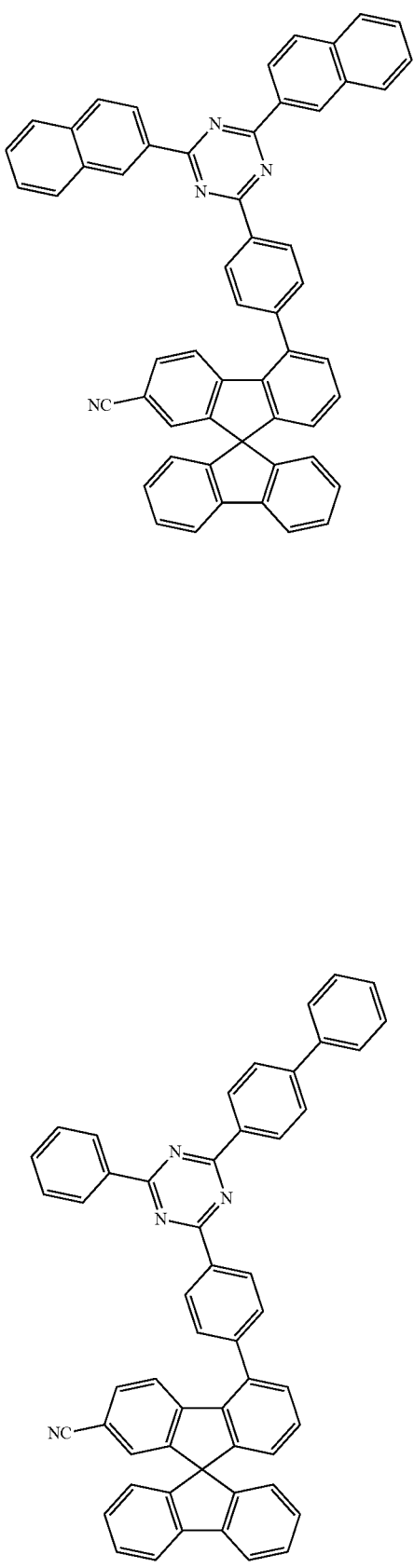

116
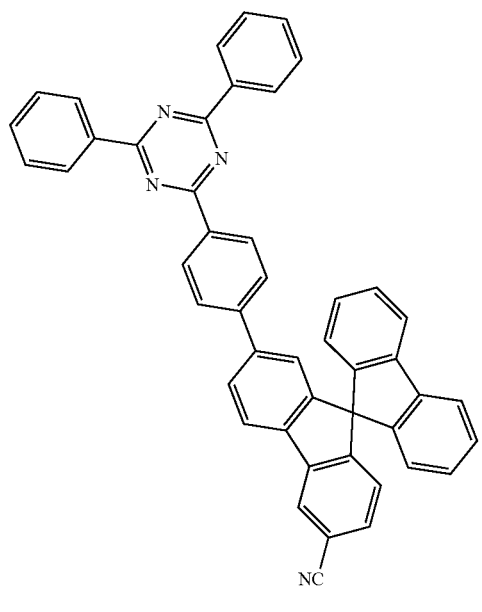
117
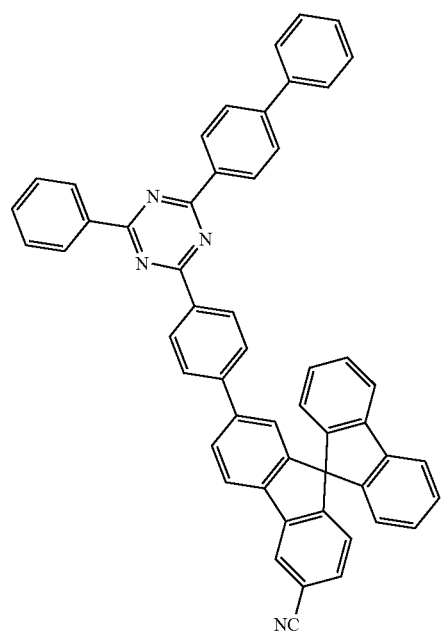
118
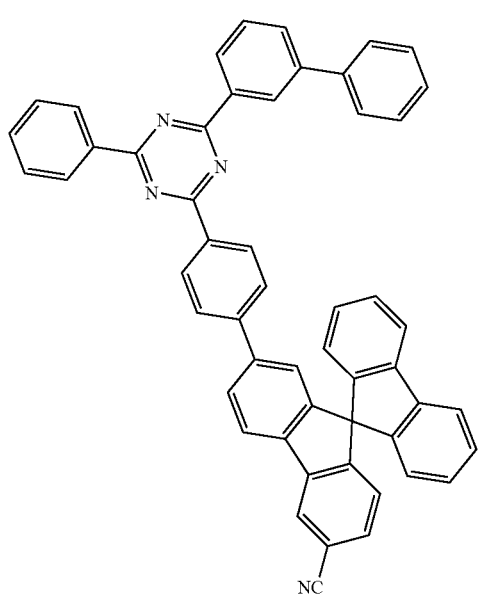
119

120
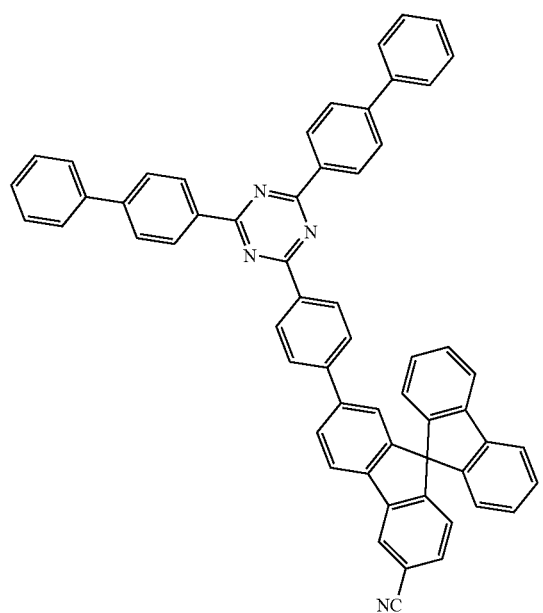
121
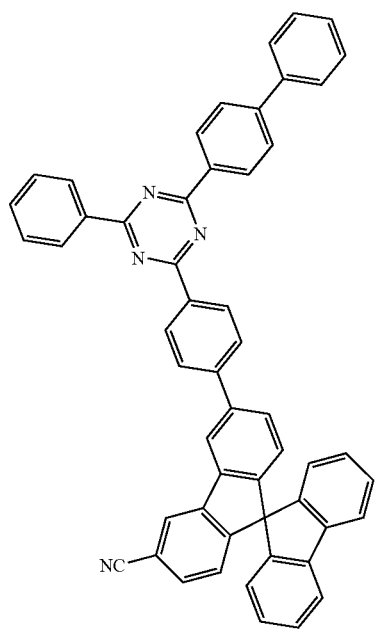
122
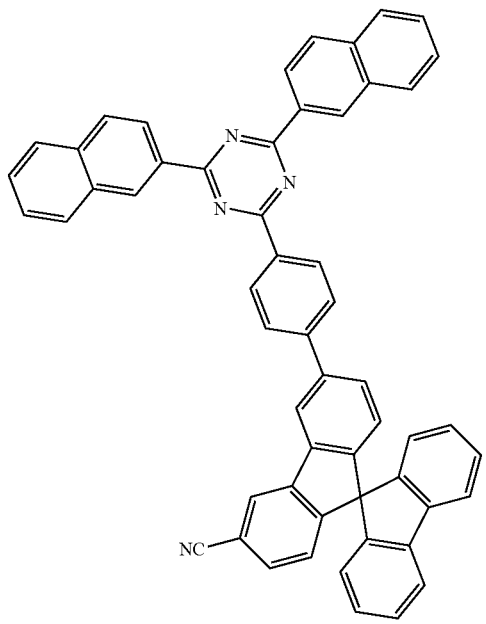
123
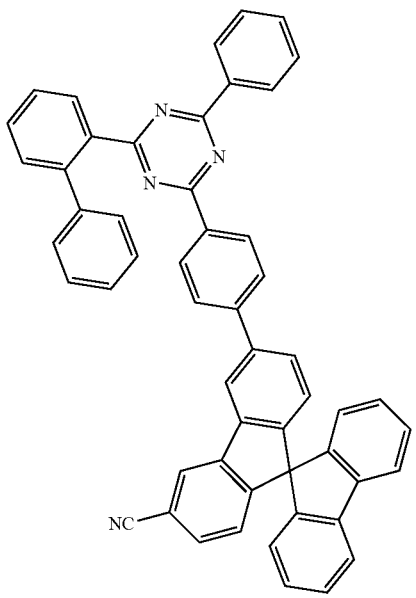

124
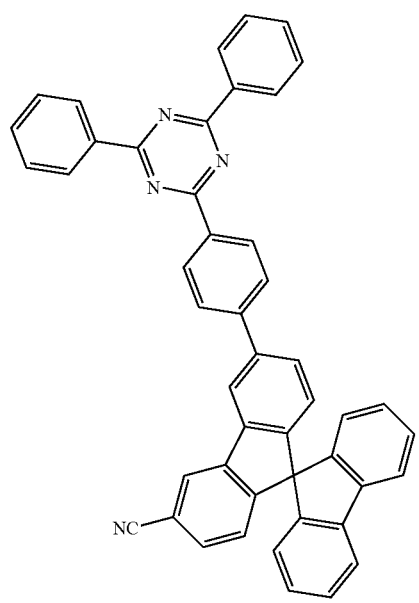
125
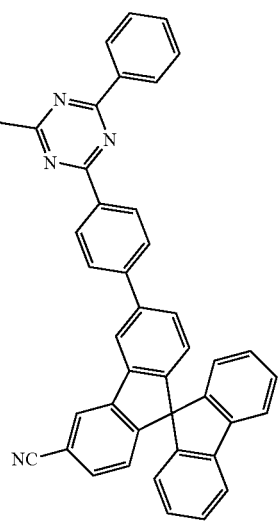
126
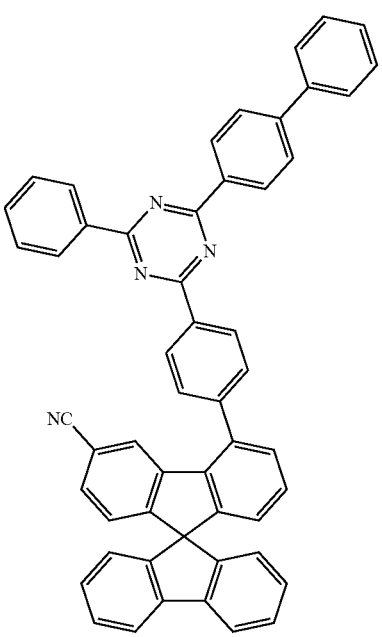
127
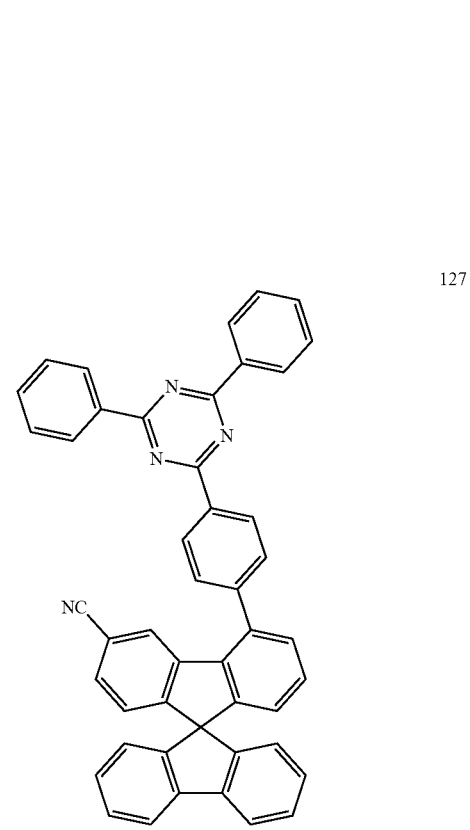

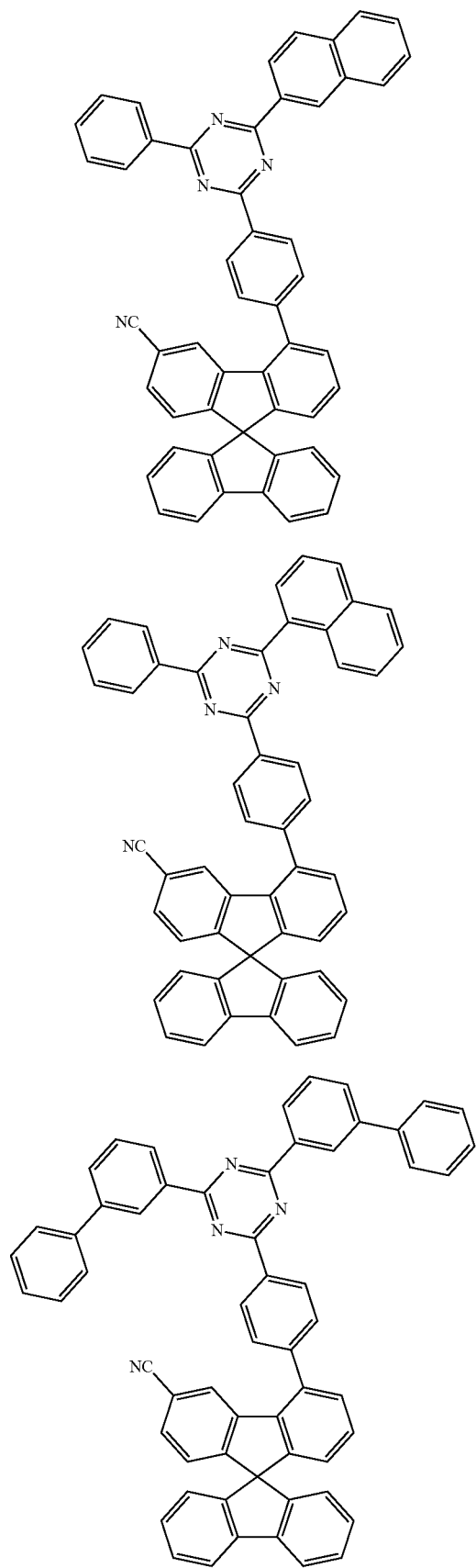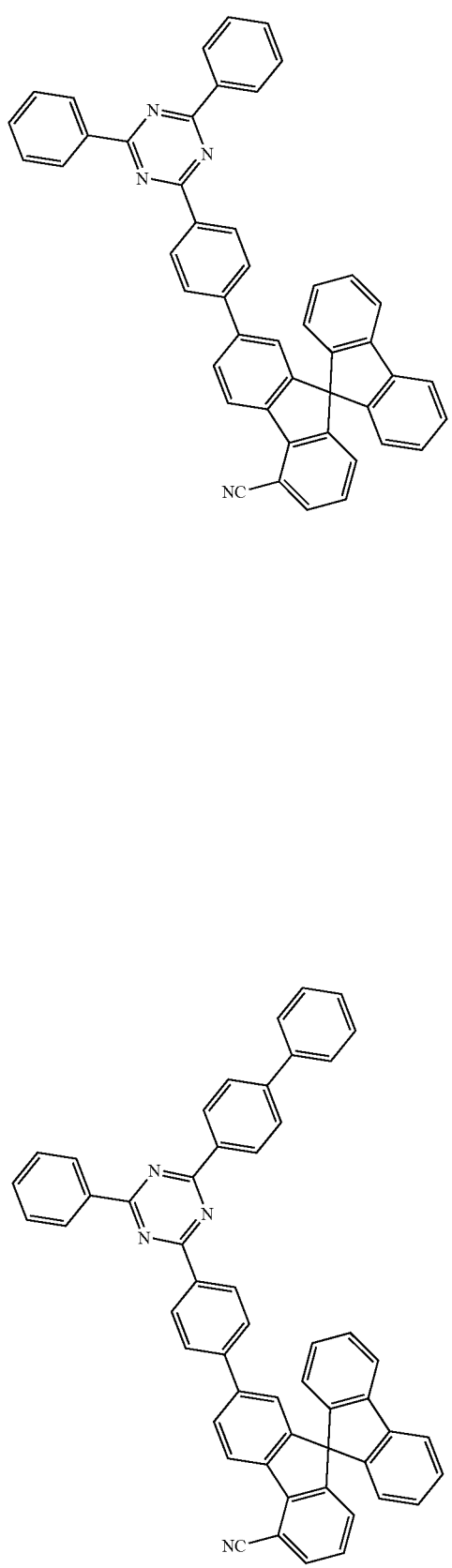

133
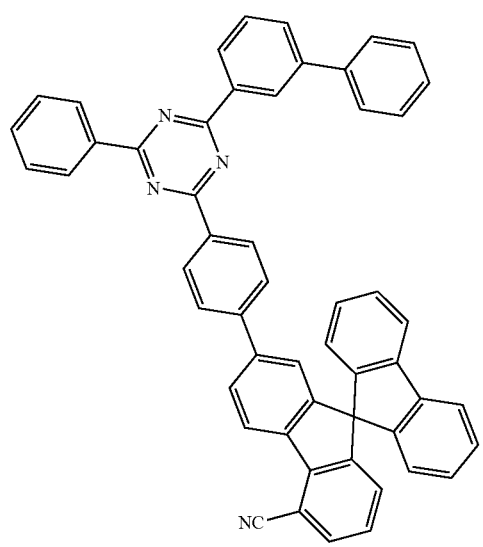
134
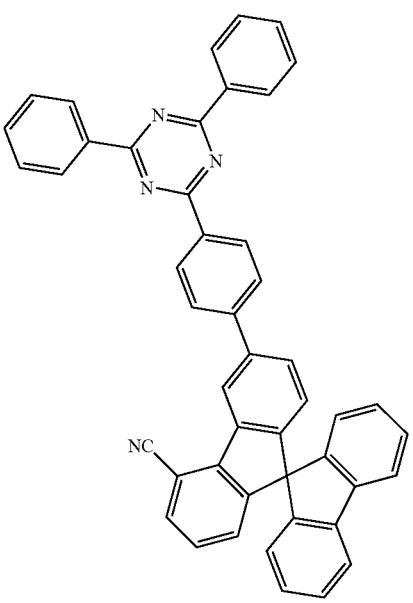
135
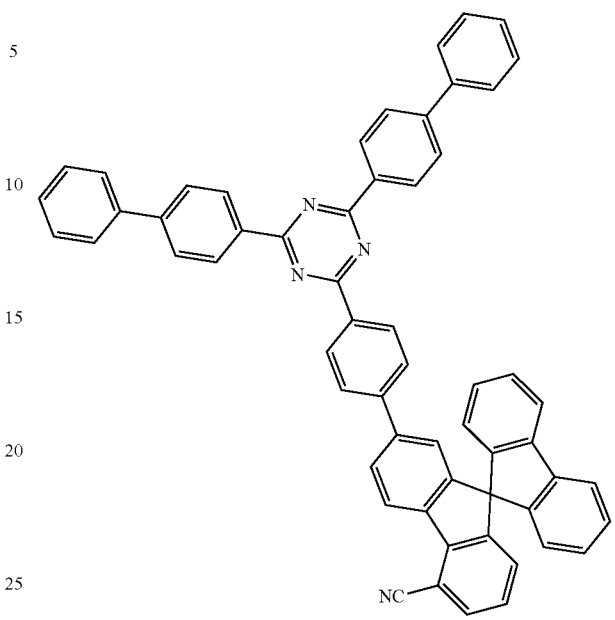
136

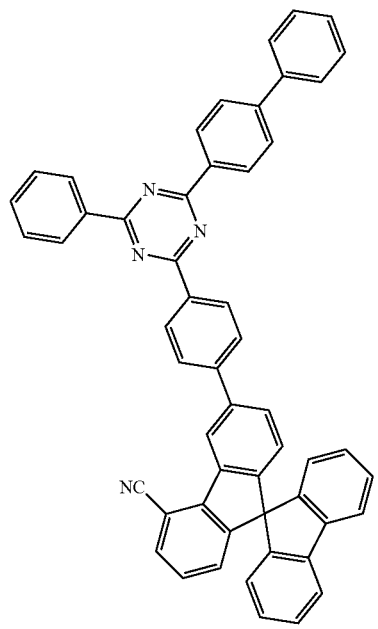
137
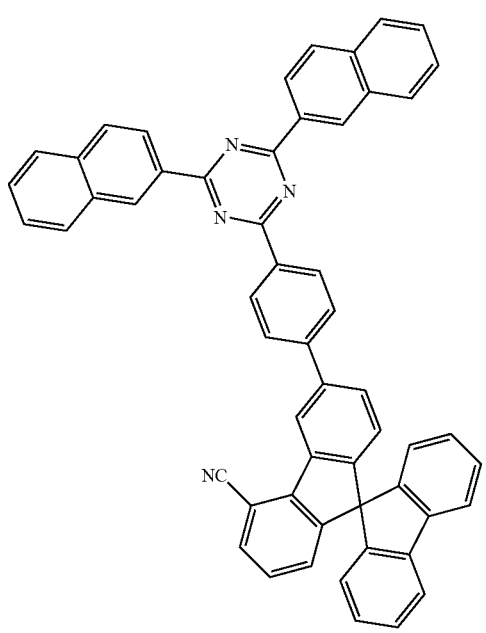
139
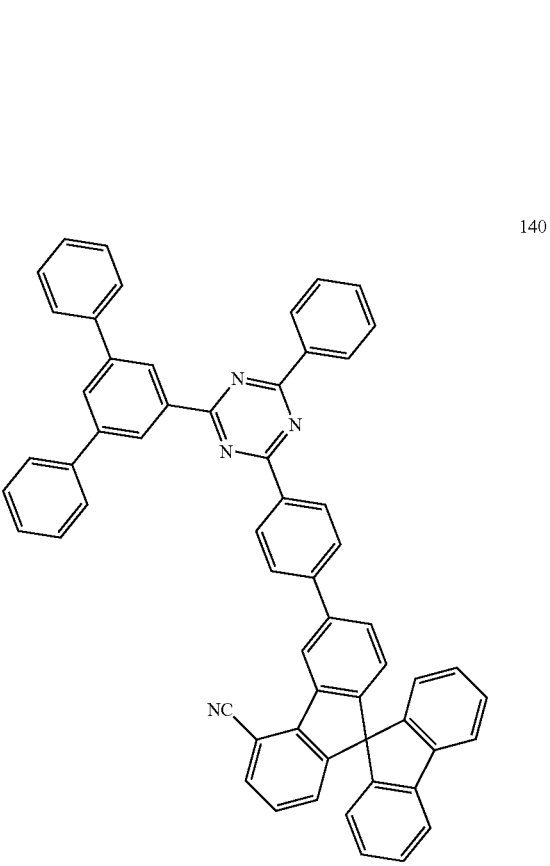
138
140

141
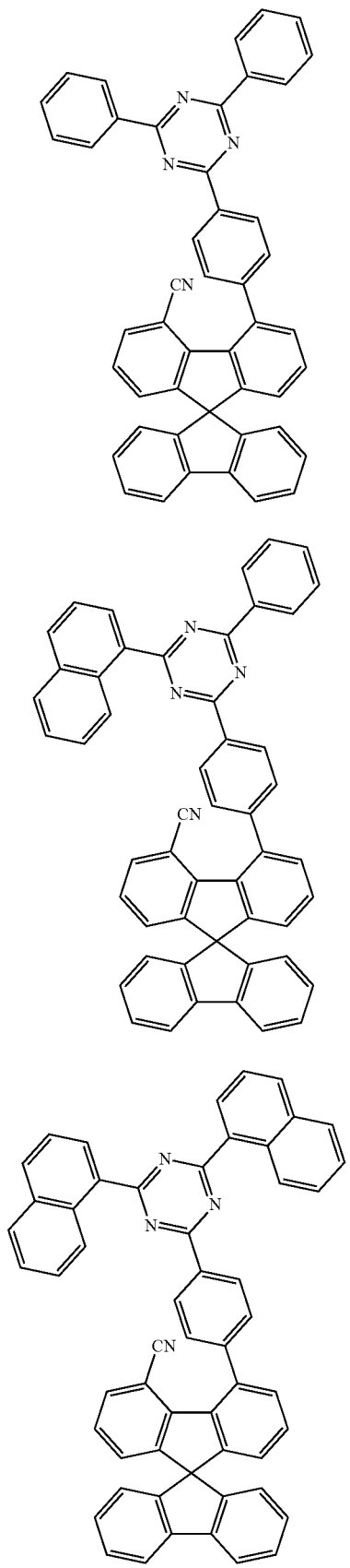
142
143
144
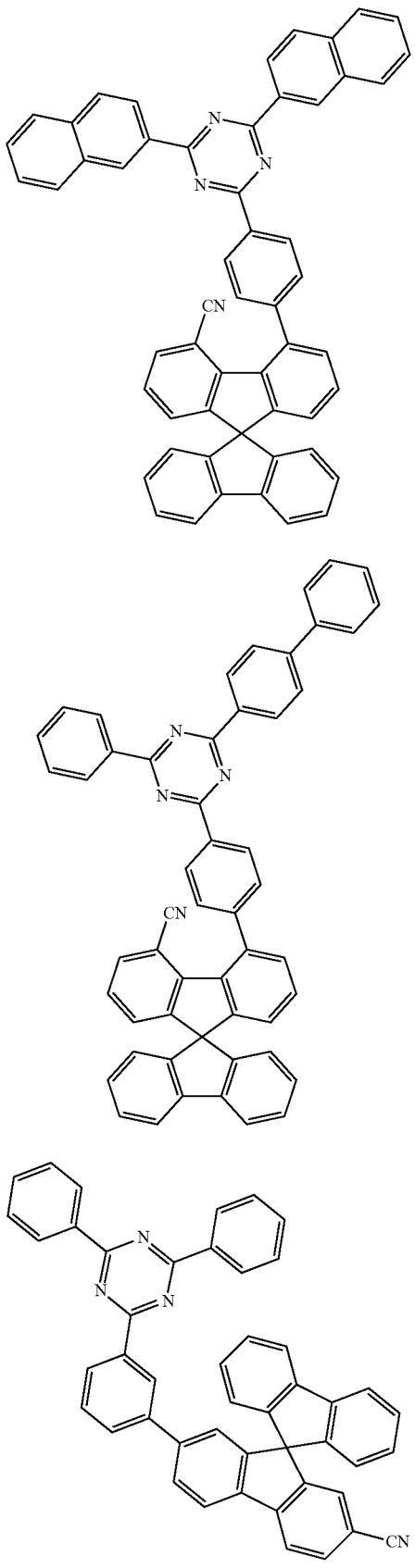
145
146

-continued
147
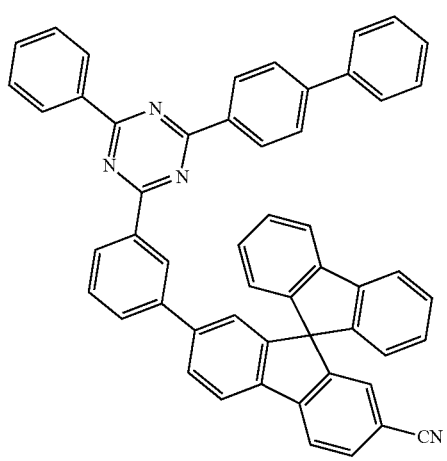
148
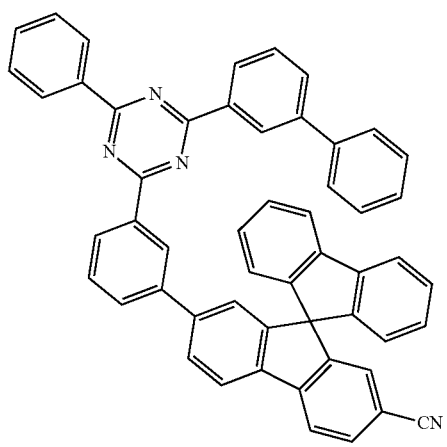
149
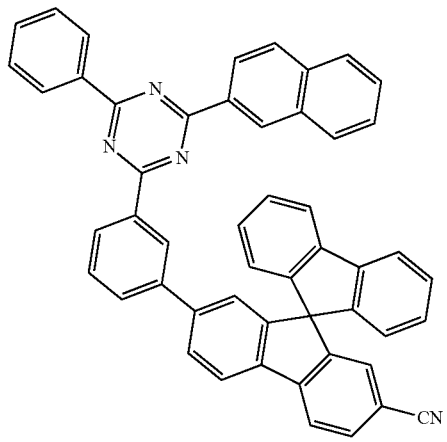
-continued
150
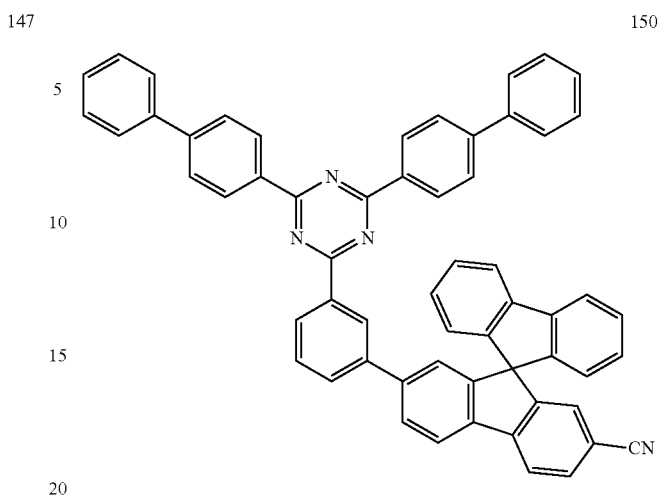
151
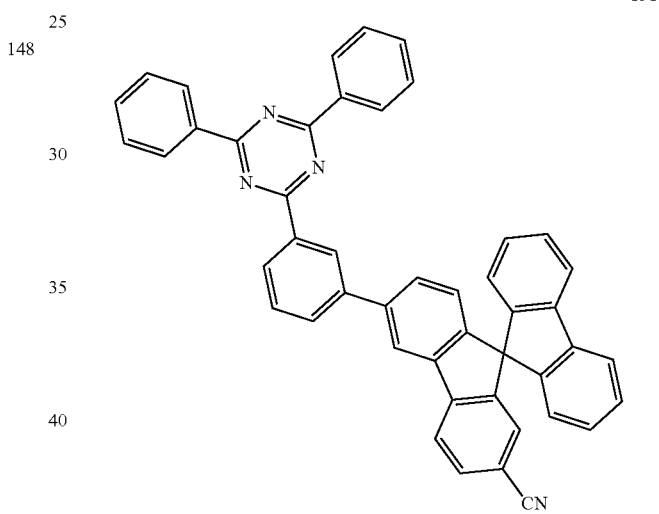
152
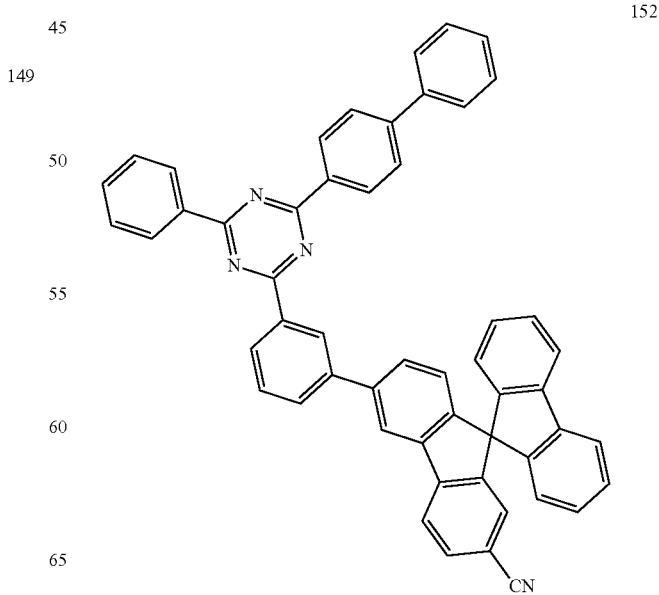

-continued
153
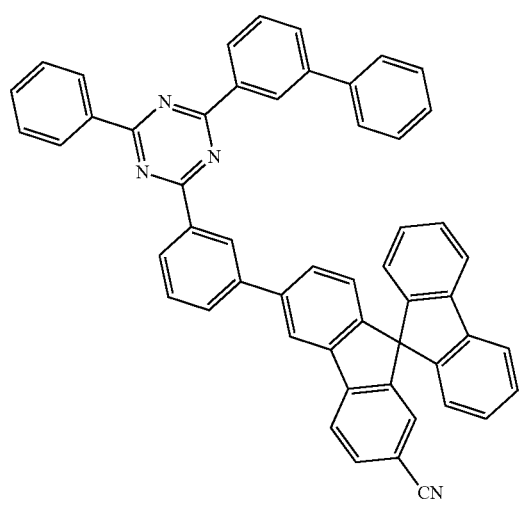
154
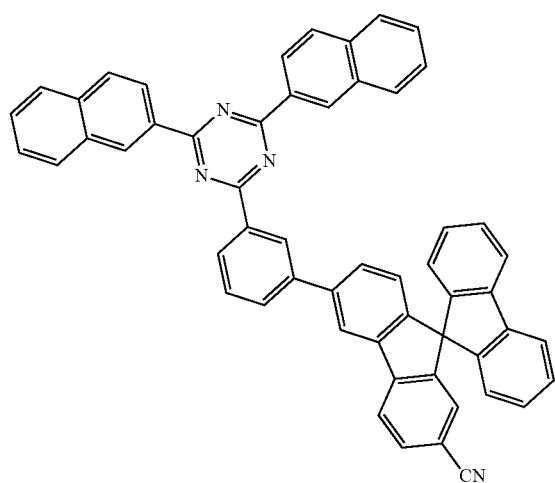
155
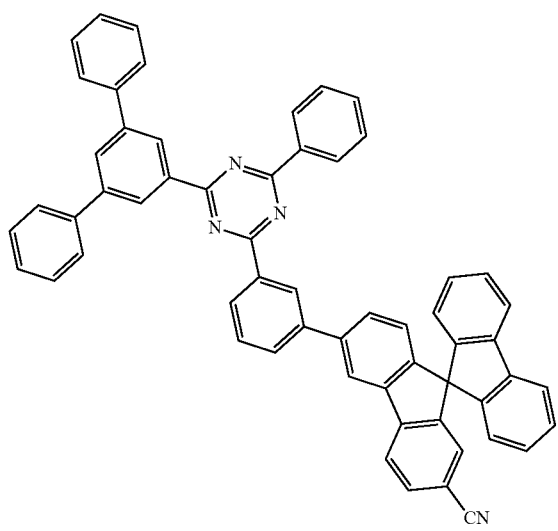
-continued
156
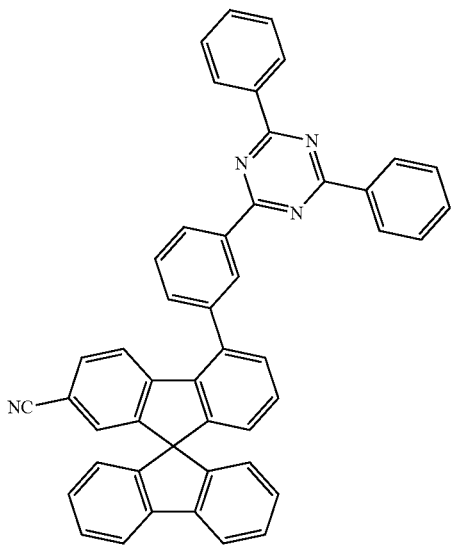
157
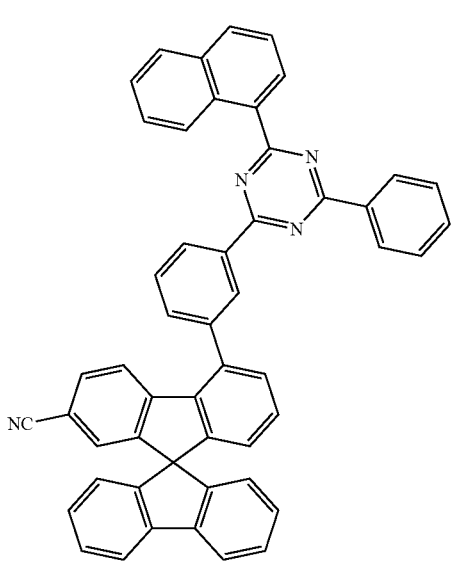
158
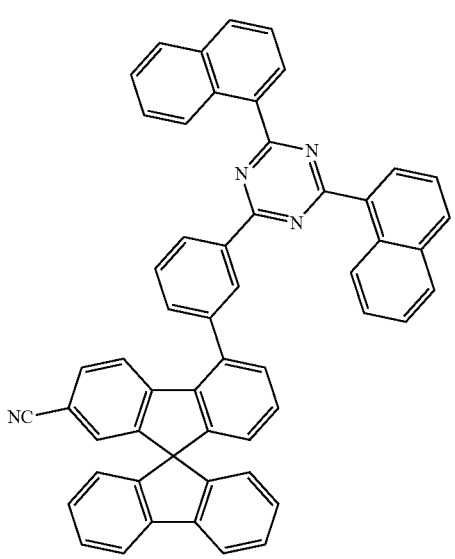

-continued
159
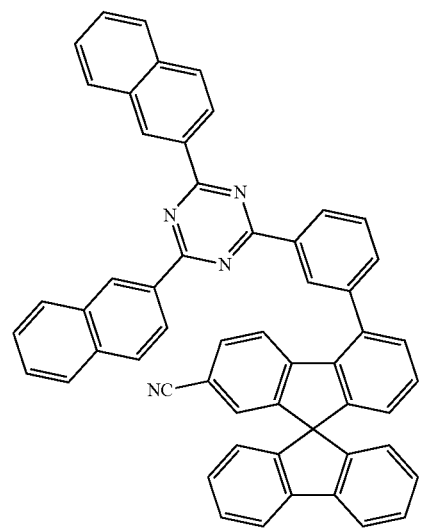
160
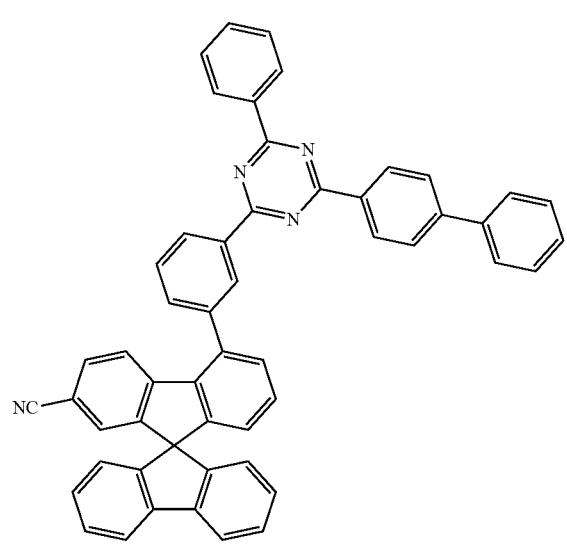
161
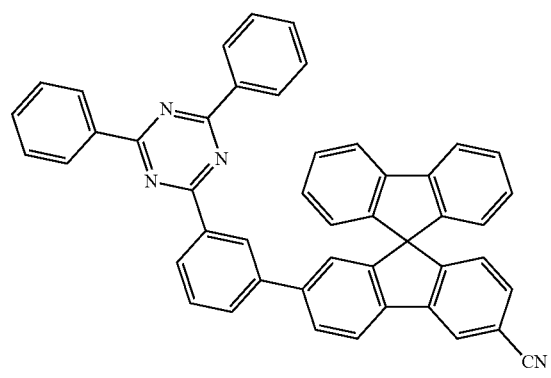
-continued
162
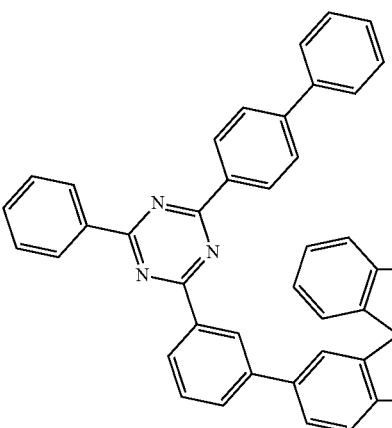
163
164
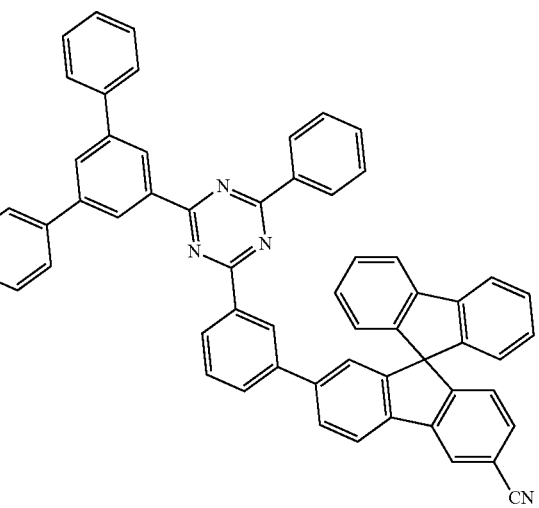

165
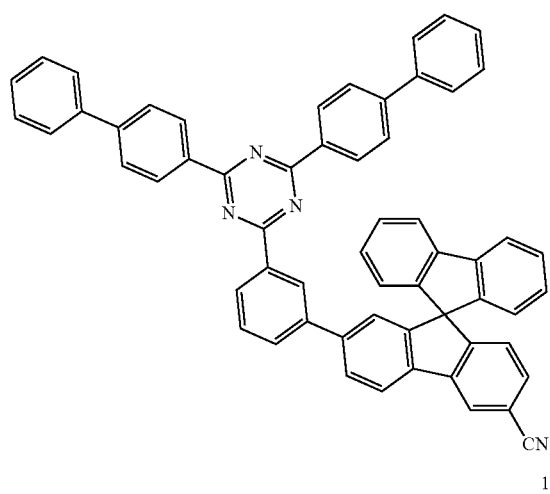
166
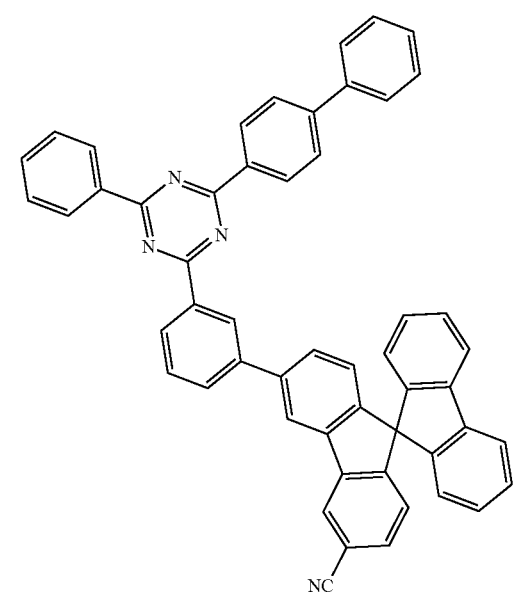
167
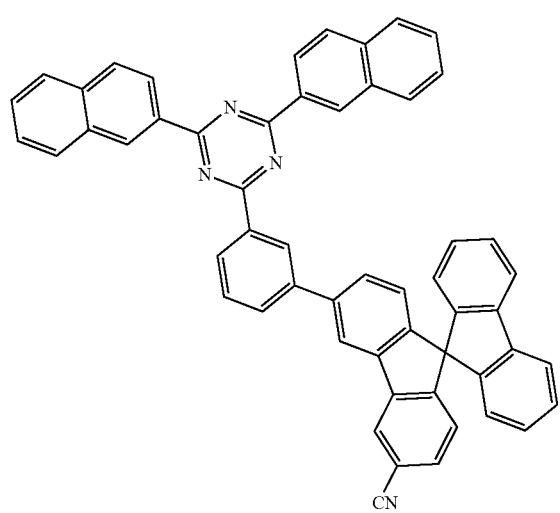
168
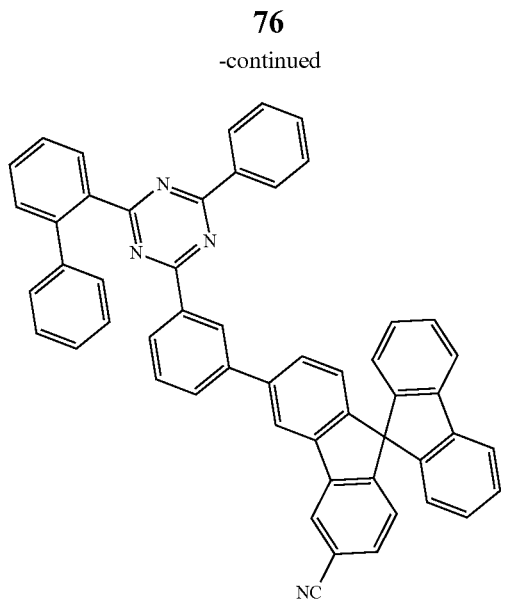
169
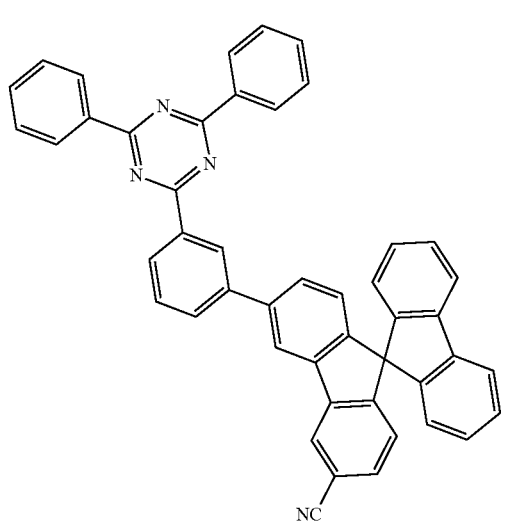
170
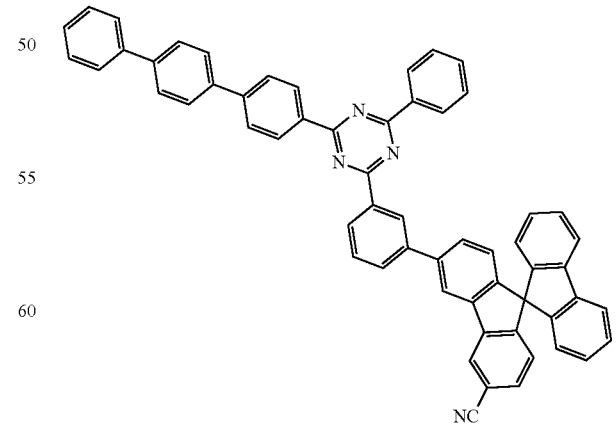

171
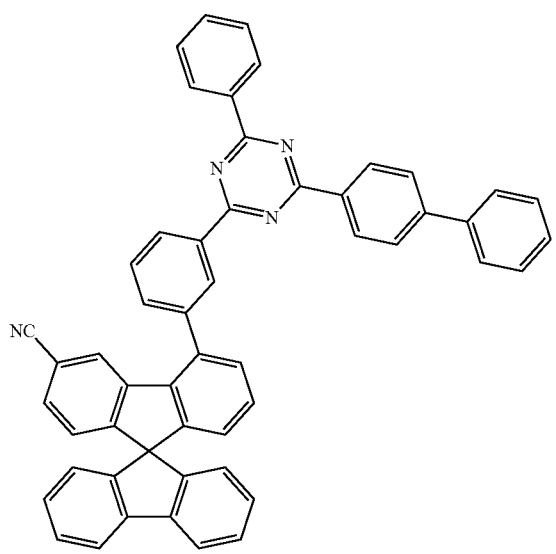
172
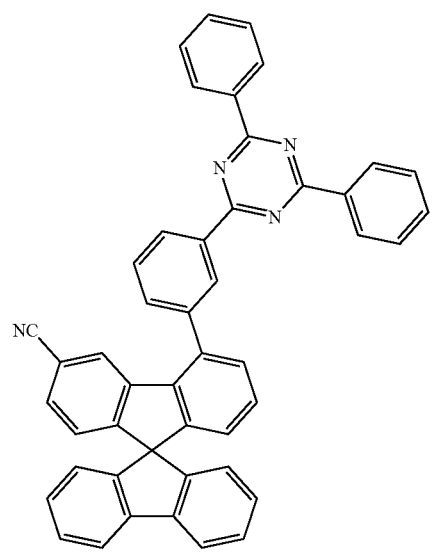
173
174
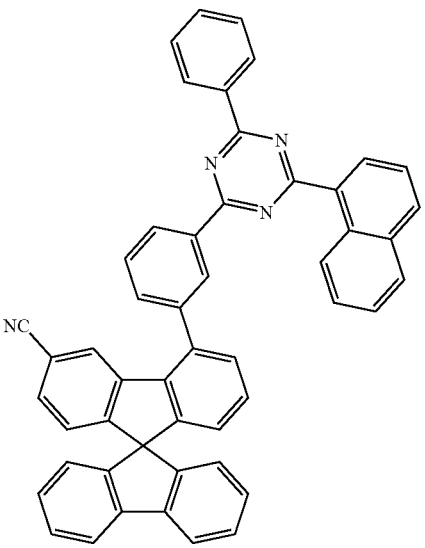
175
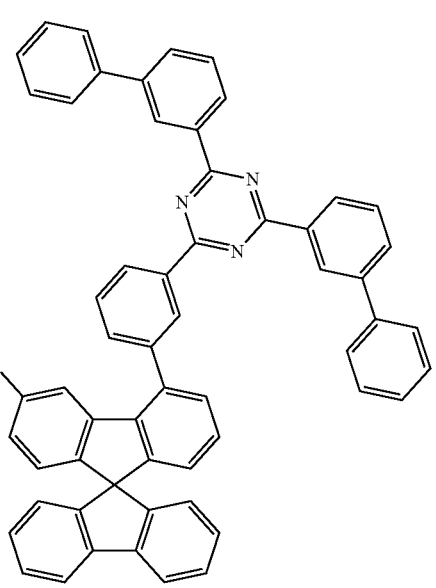
176
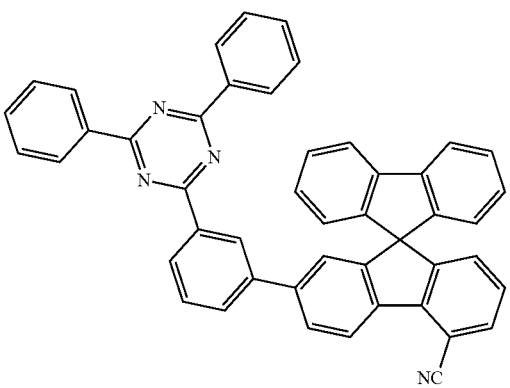

177
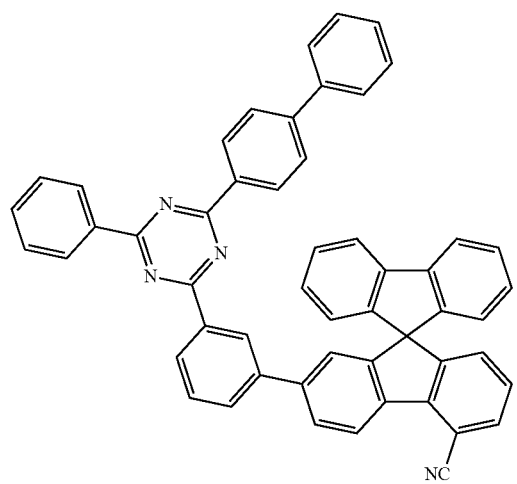
178
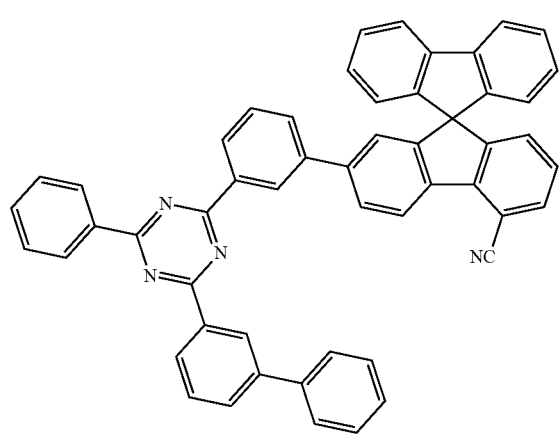
179
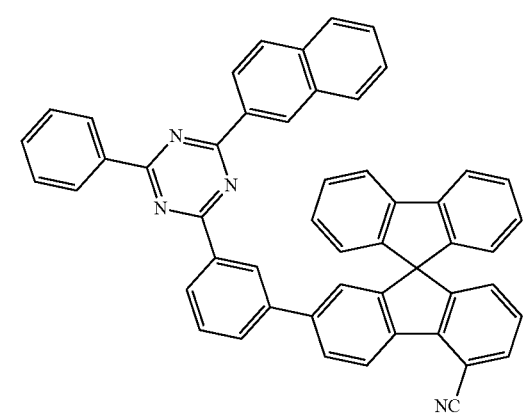
180
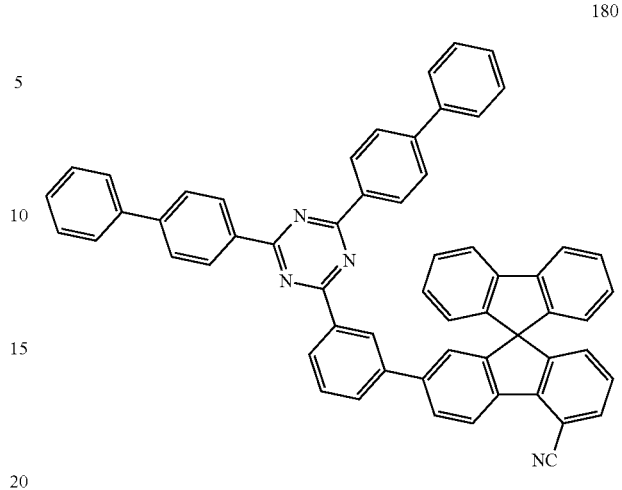
181
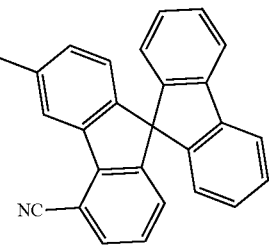
182
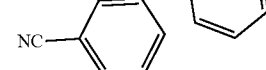

183
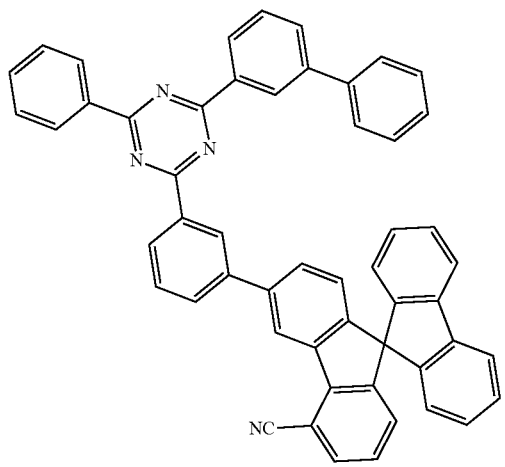
184
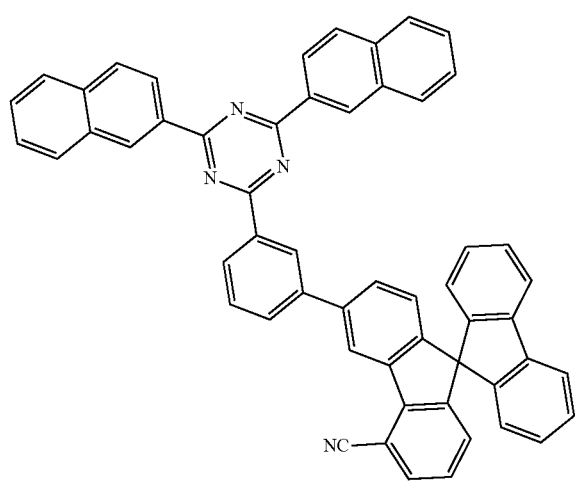
185
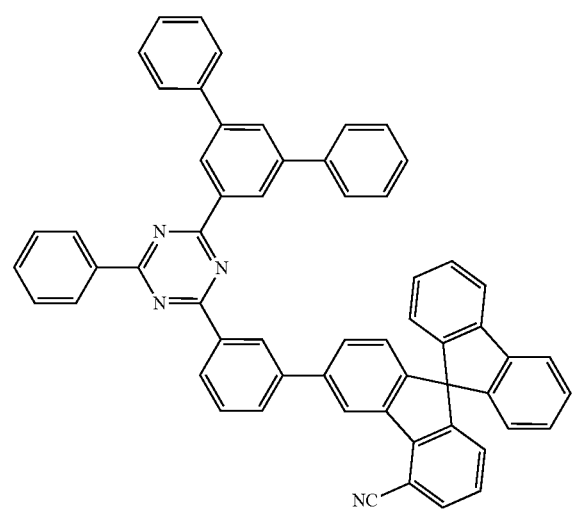
186
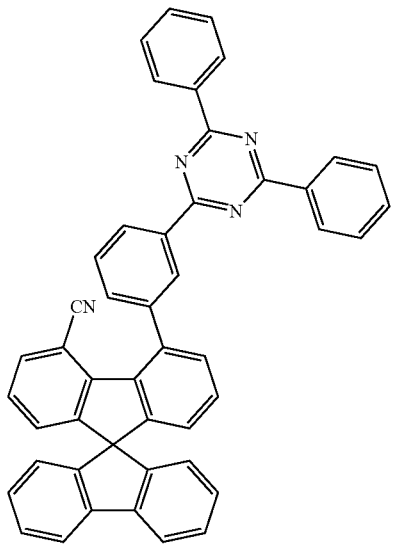
187
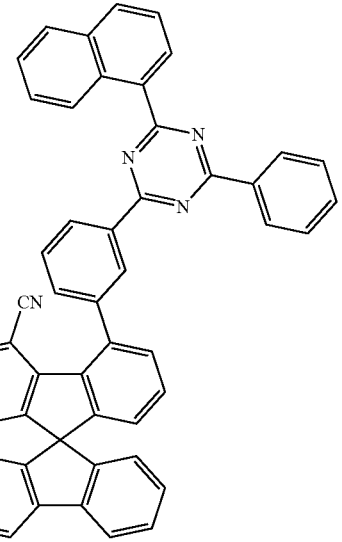
188
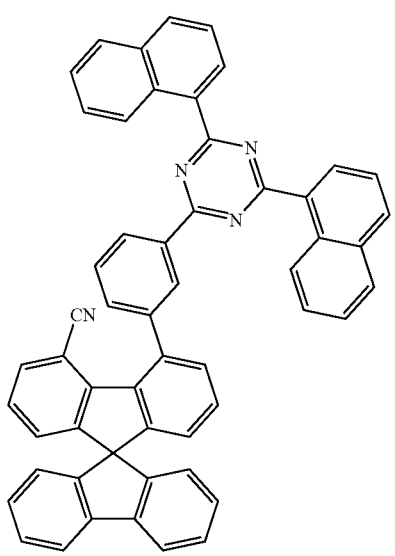

-continued
189
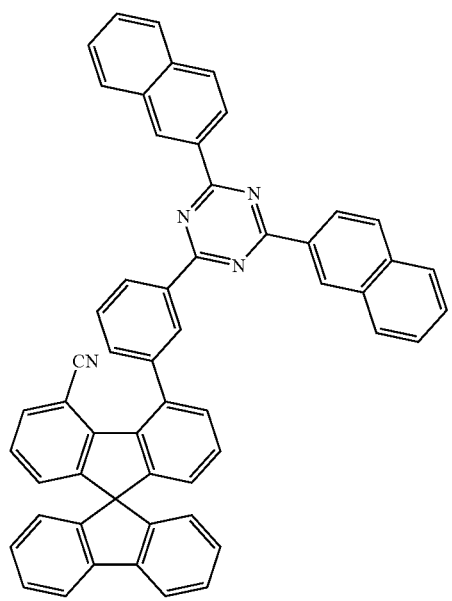
190
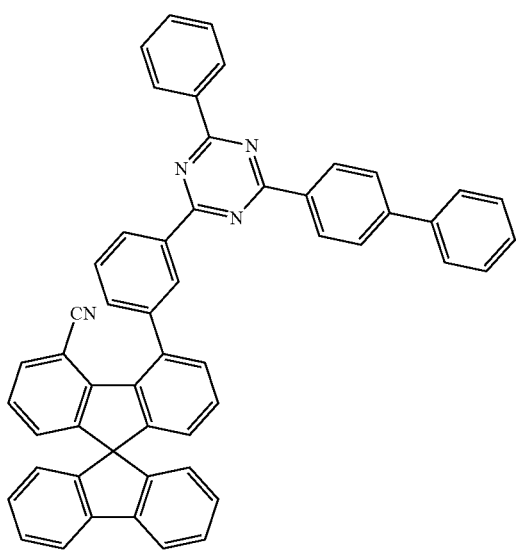
191
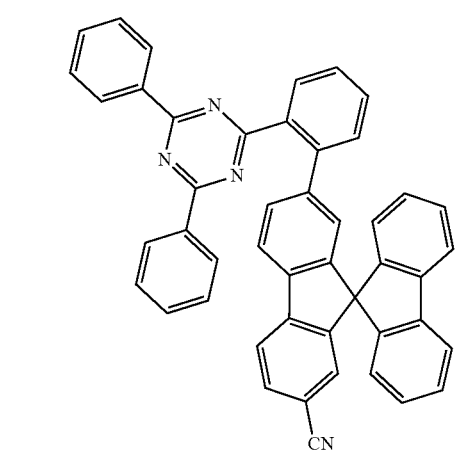
-continued
192
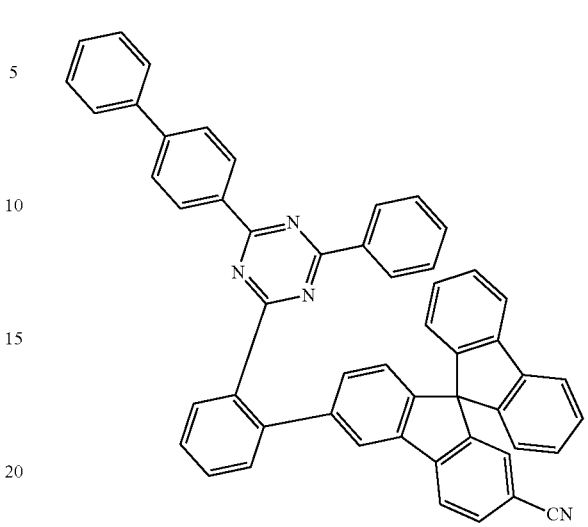
193
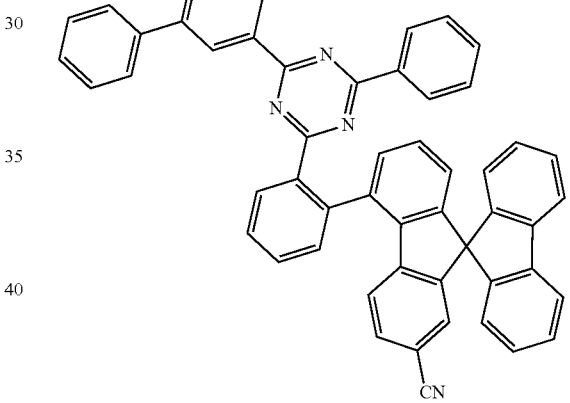
194
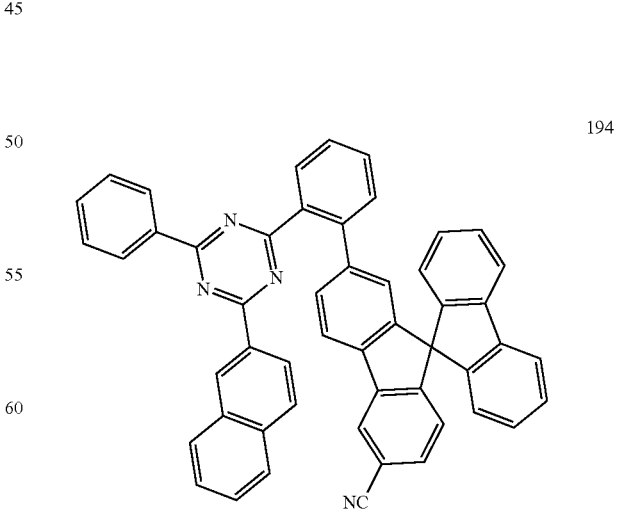

195
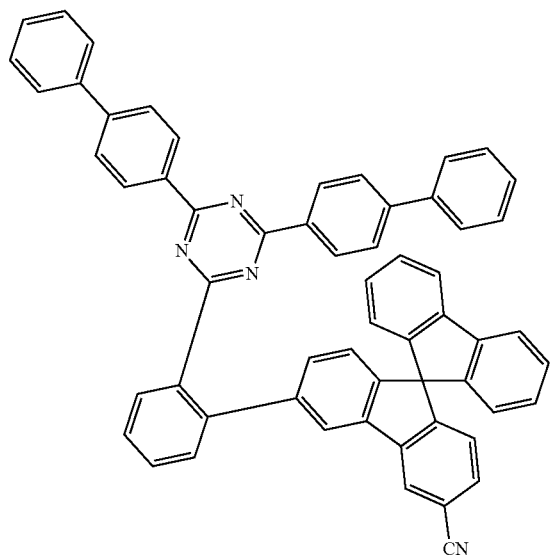
196
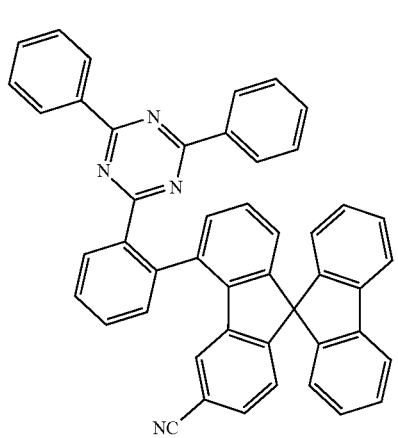
197
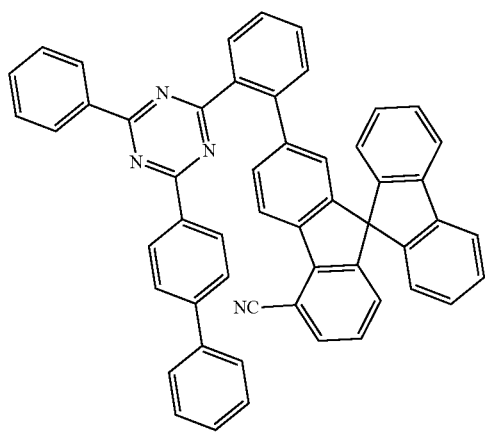
198
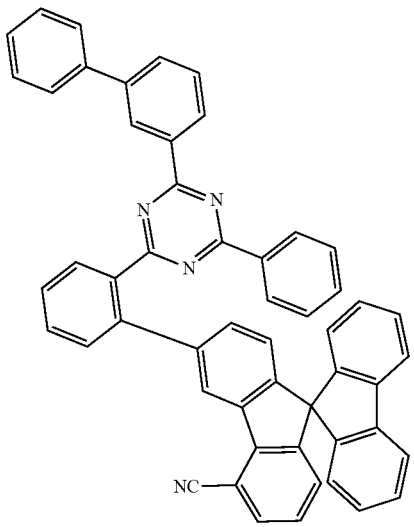
199
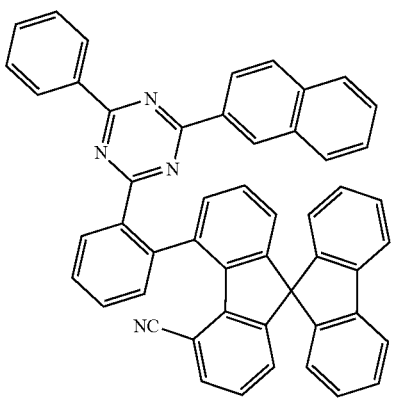
200
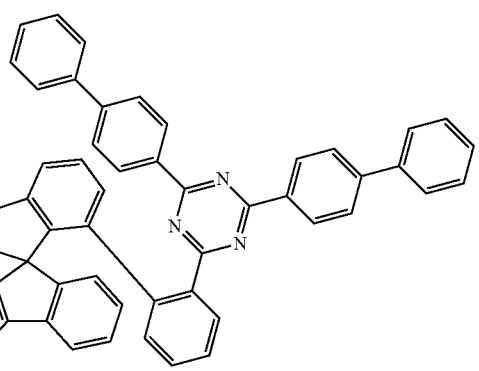

-continued
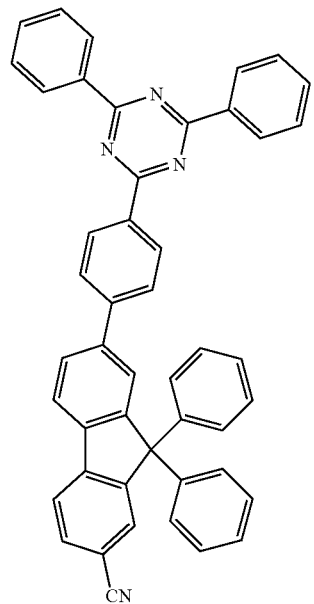
201
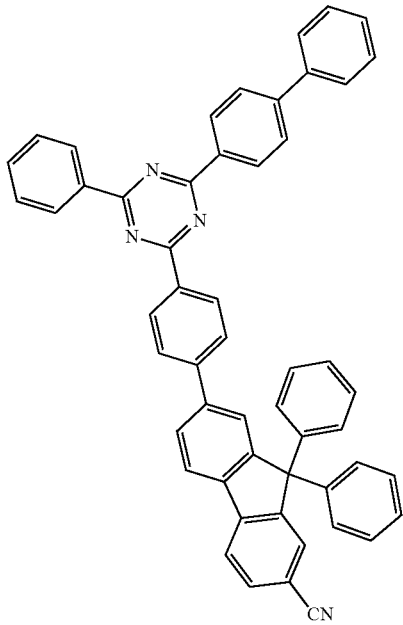
202
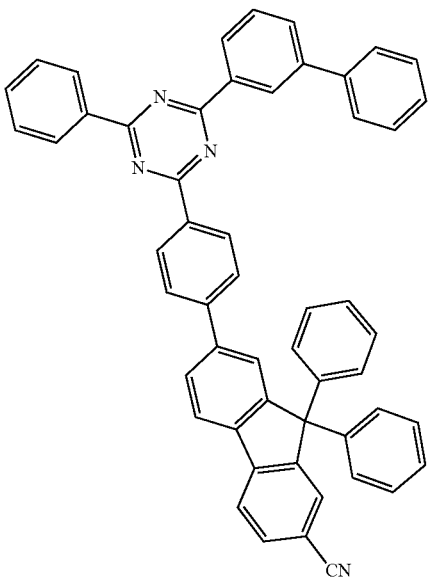
203
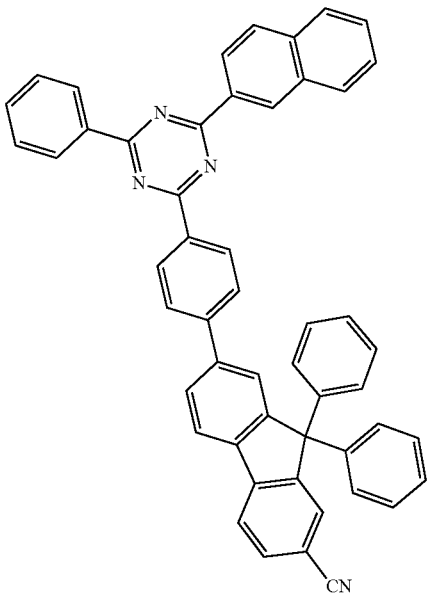
204

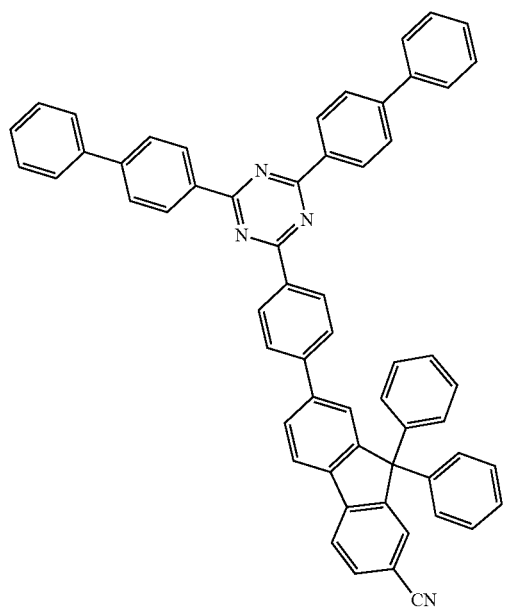
205
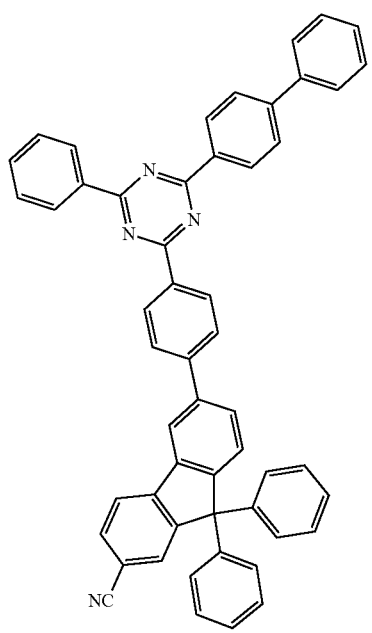
207
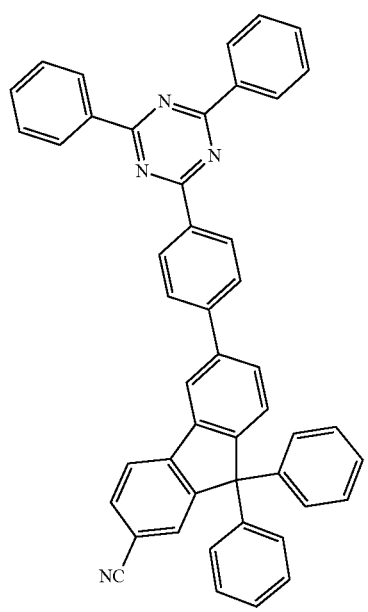
206
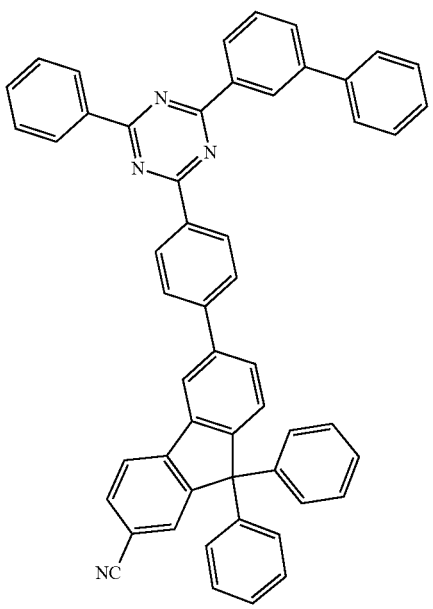
208

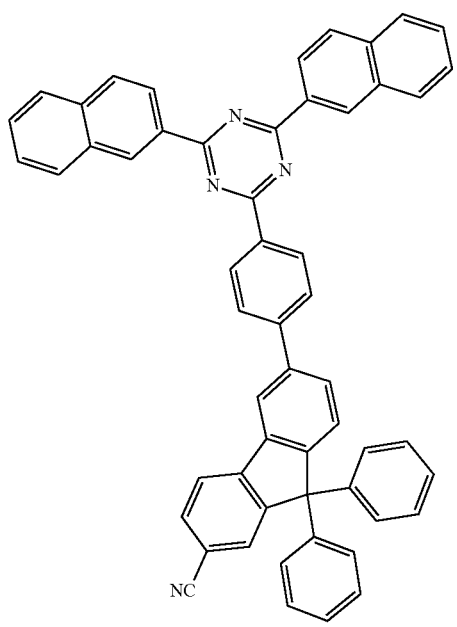
209
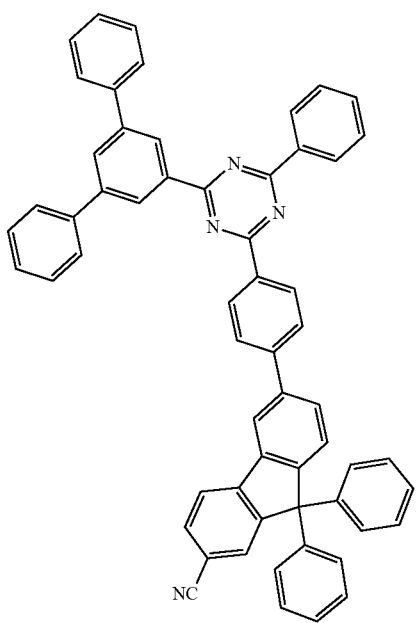
210
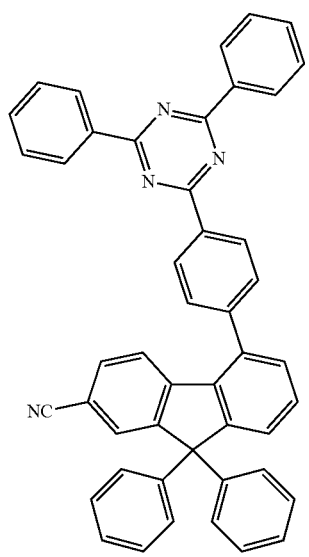
211
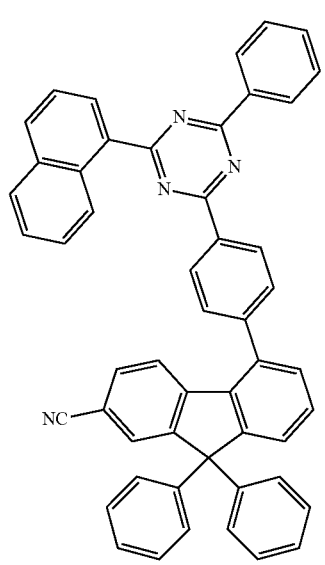
212
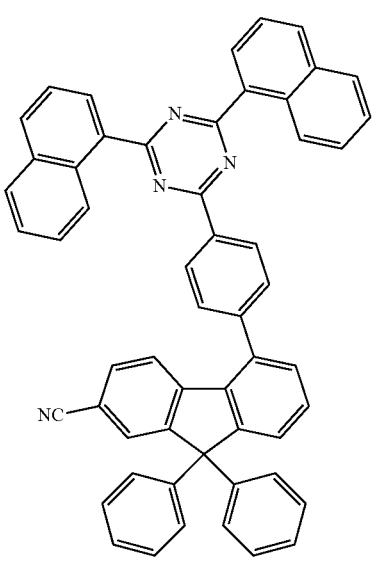
213

-continued
214
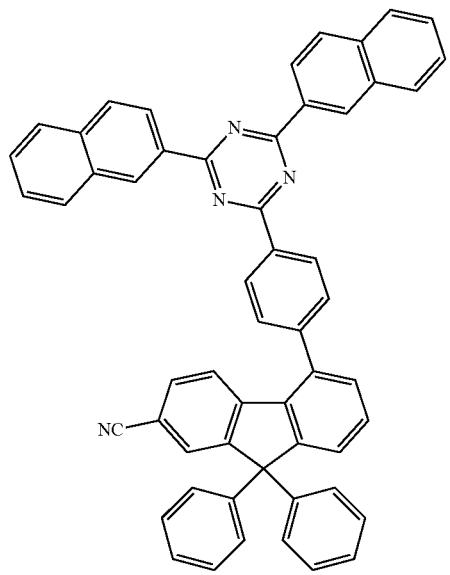
215
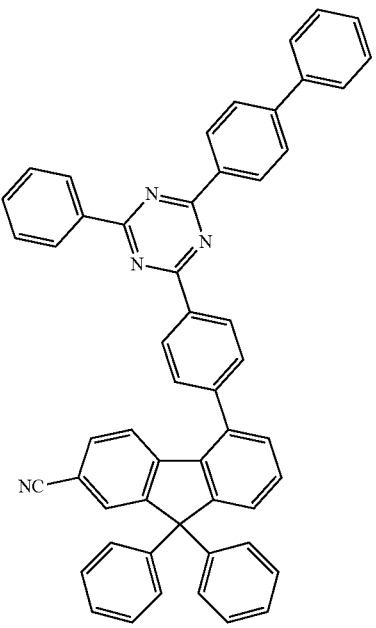
-continued
216
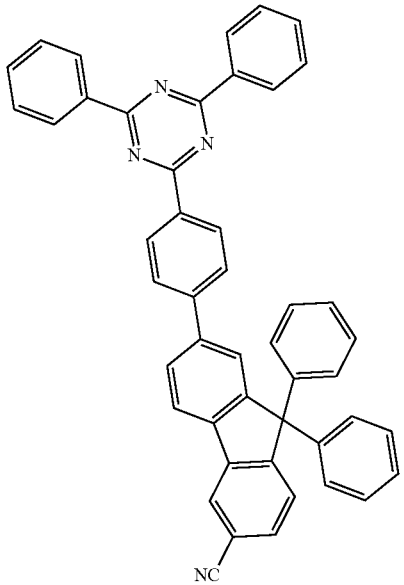
217
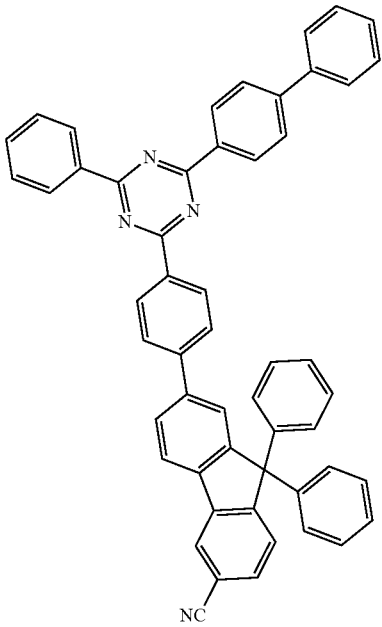

218
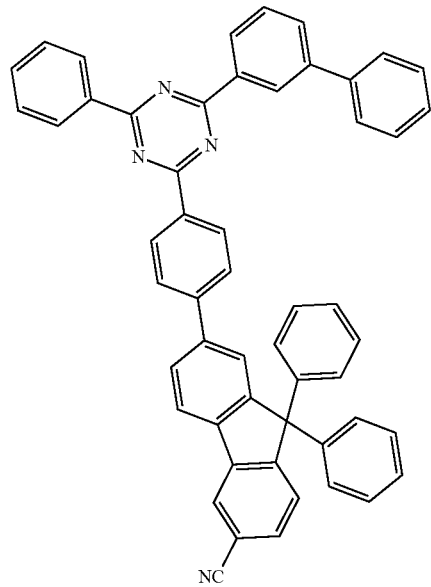
219
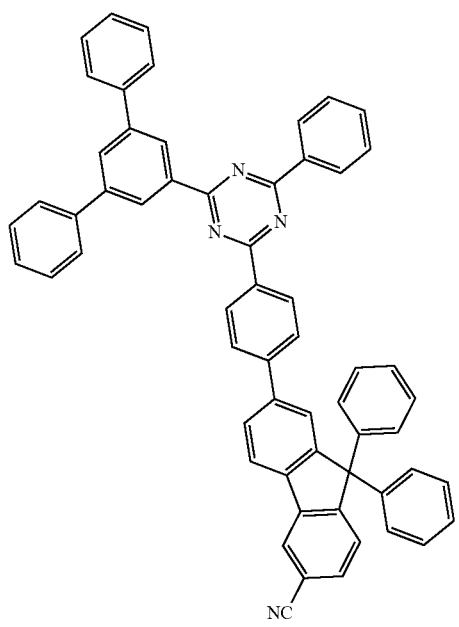
220
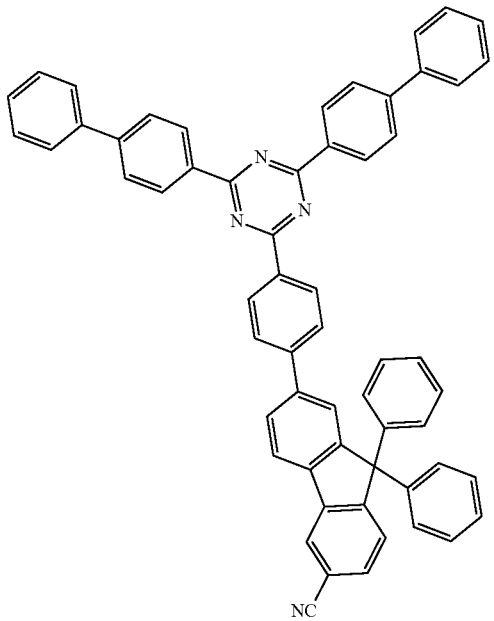
221
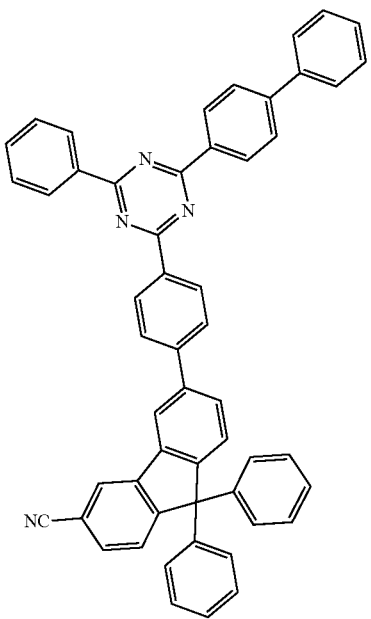

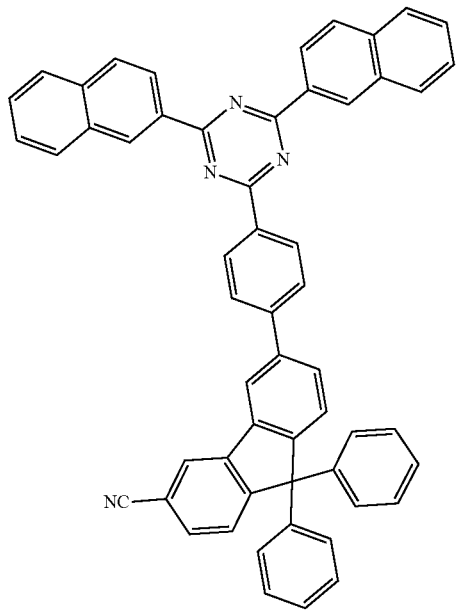
222
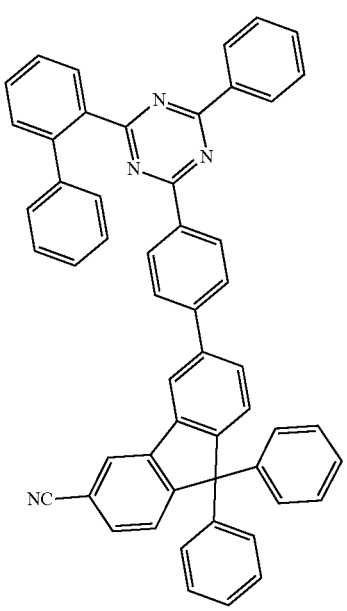
223
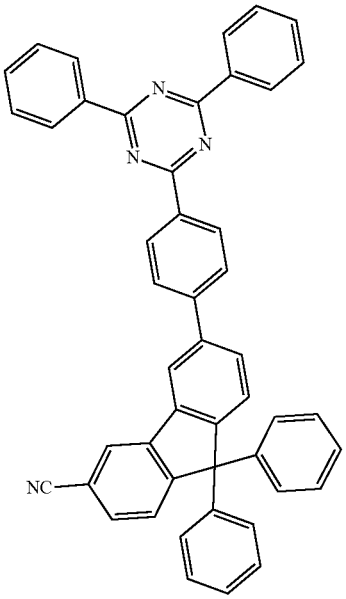
224
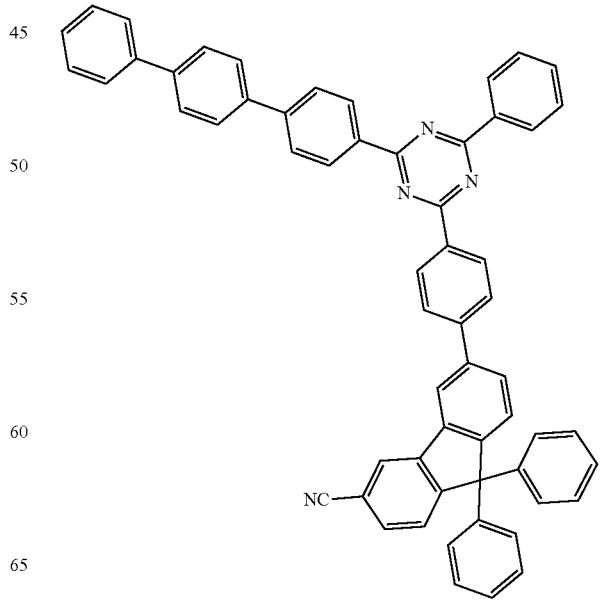
225

226
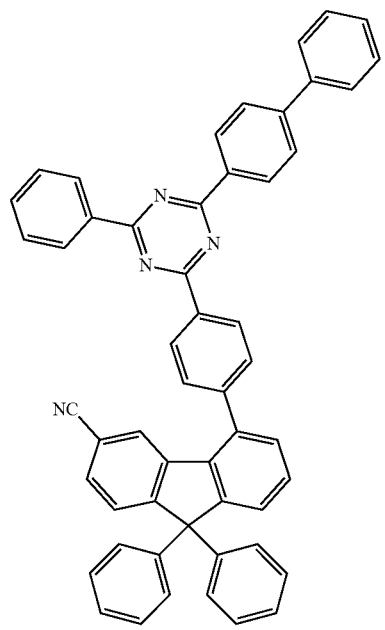
227
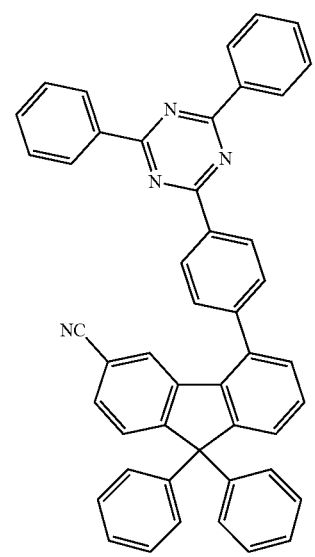
228
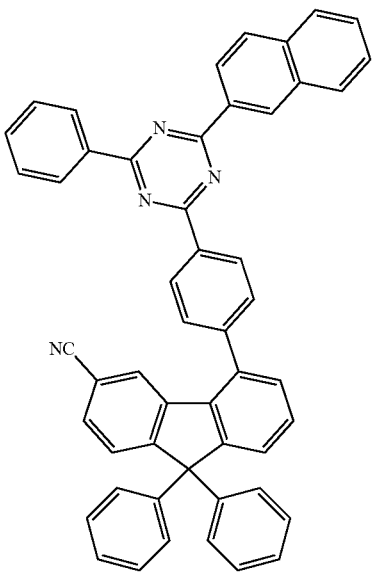
229
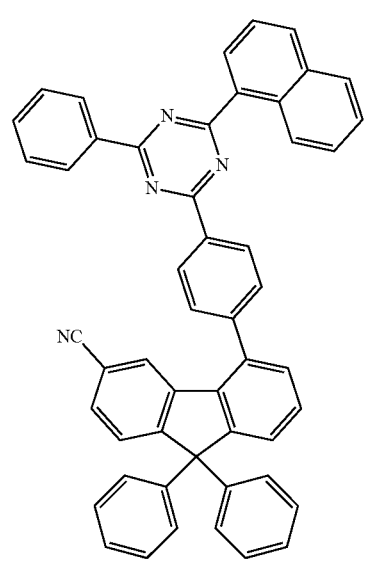
230
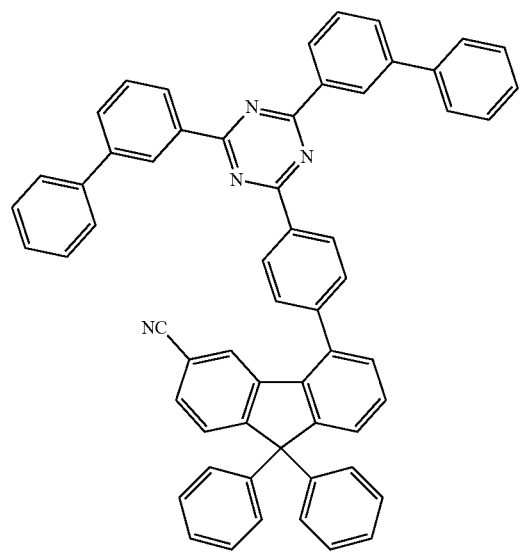

231
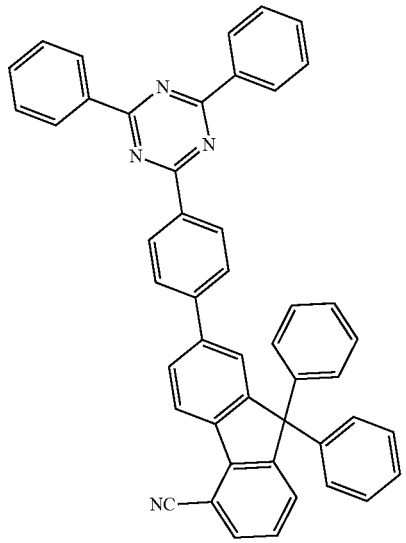
233
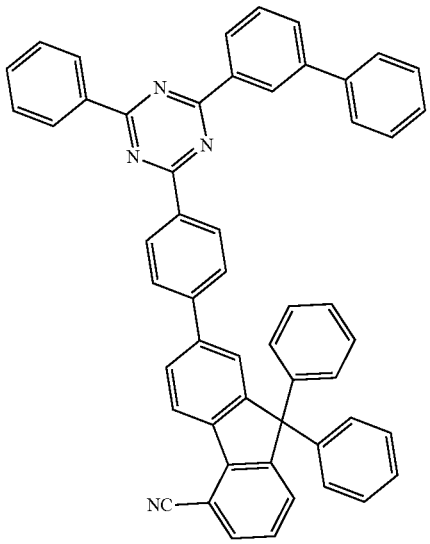
232
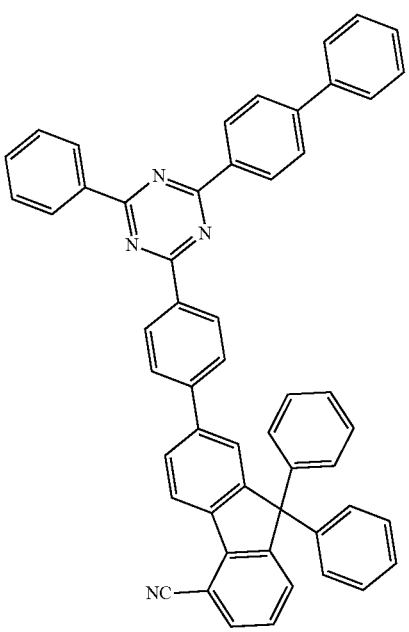
234
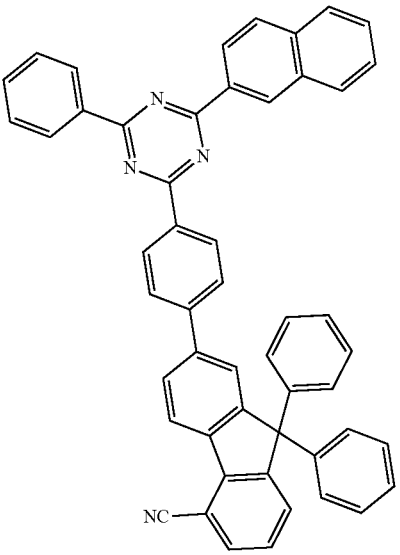

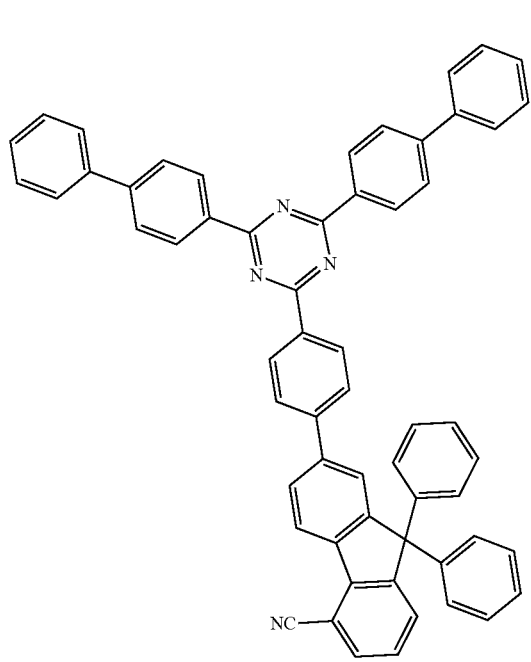
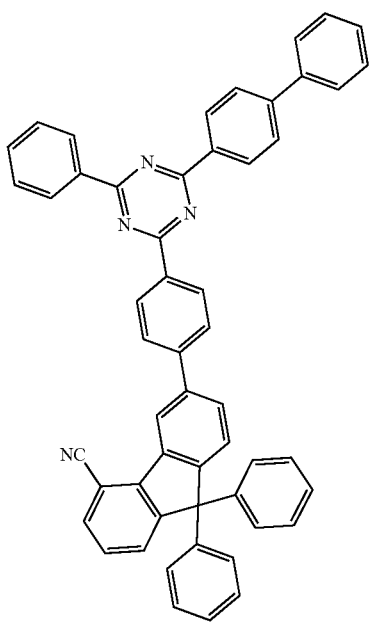

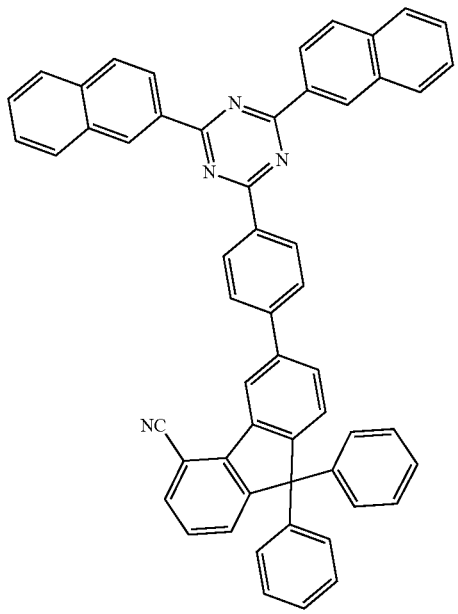
239
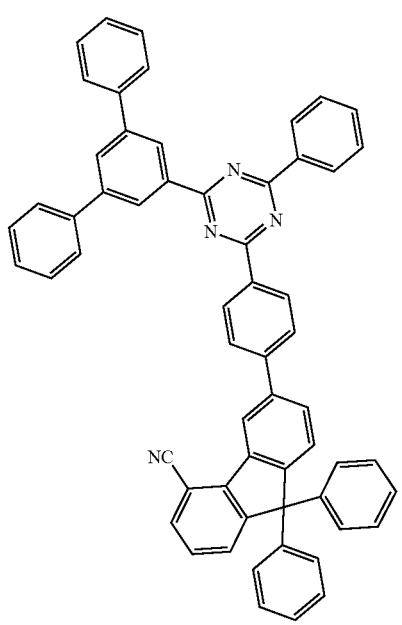
240
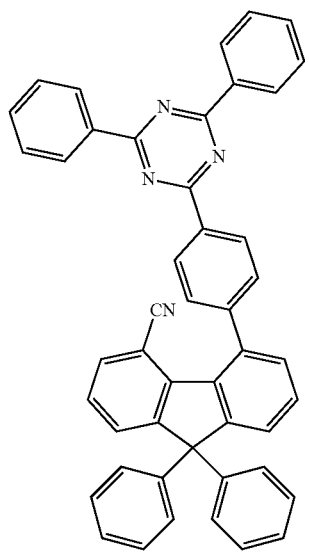
241
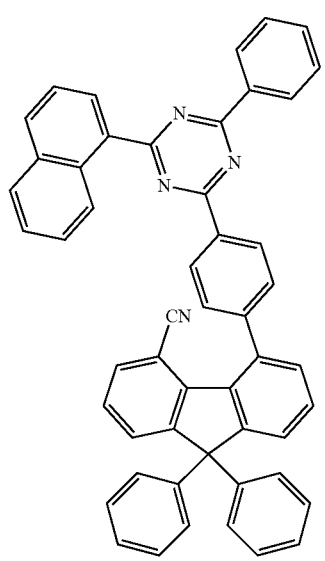
242
243

244
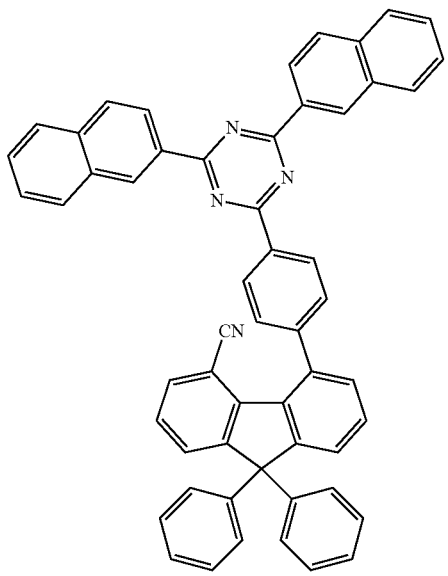
245
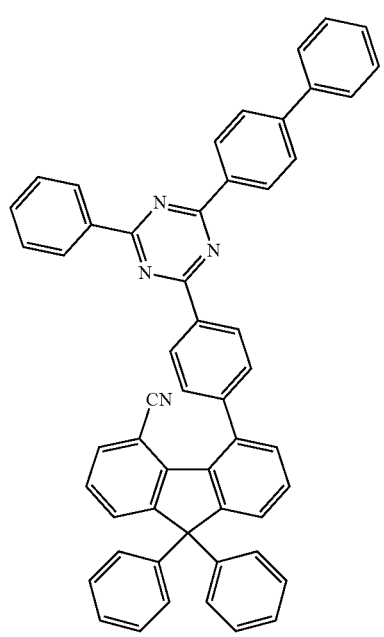
246
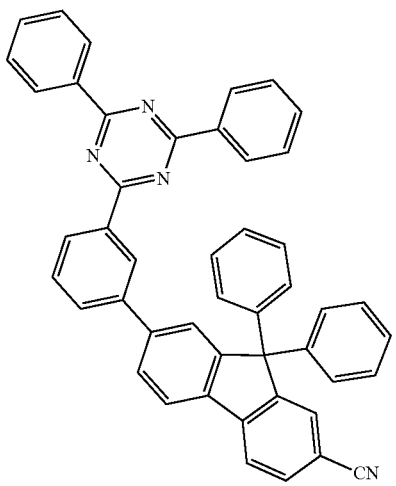
247
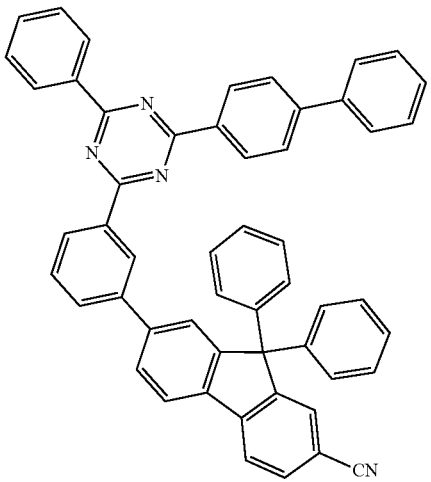
248
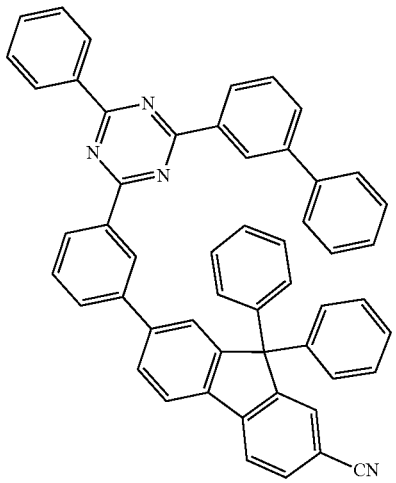

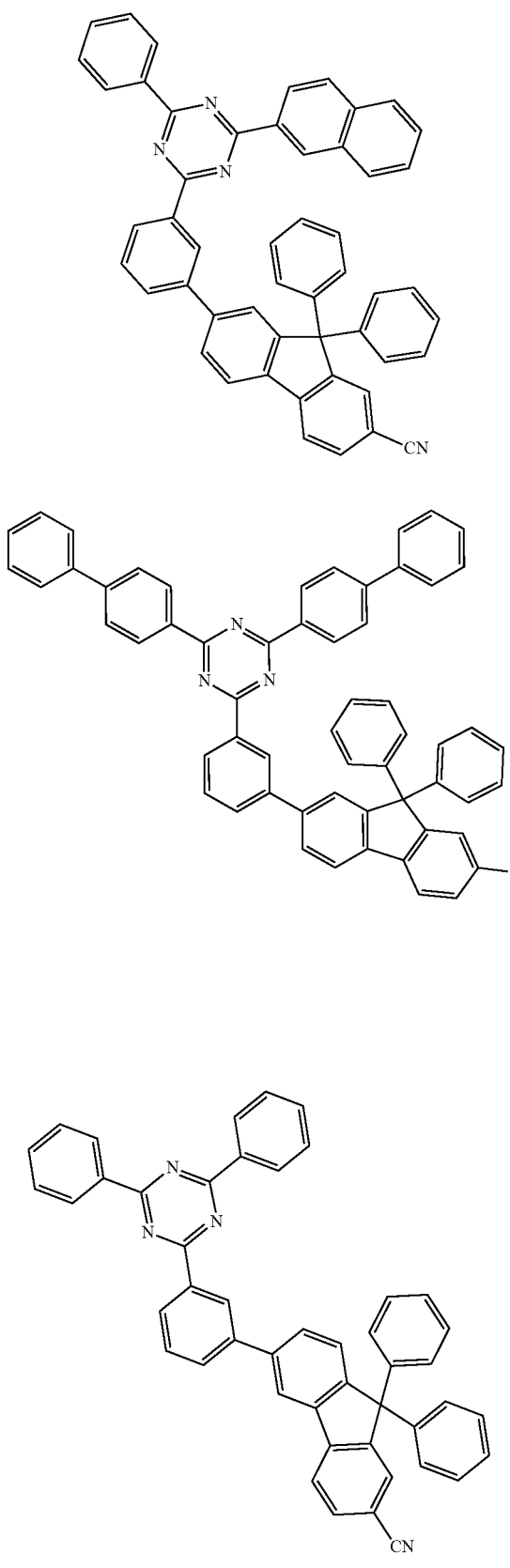
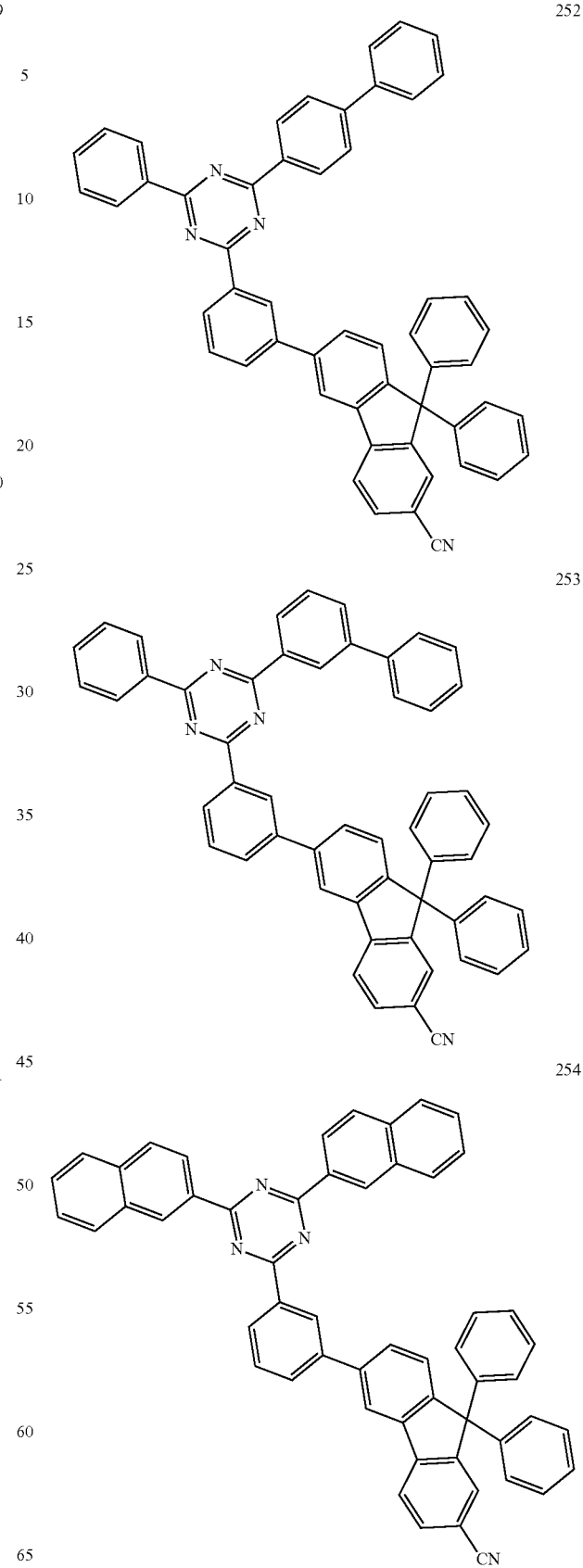

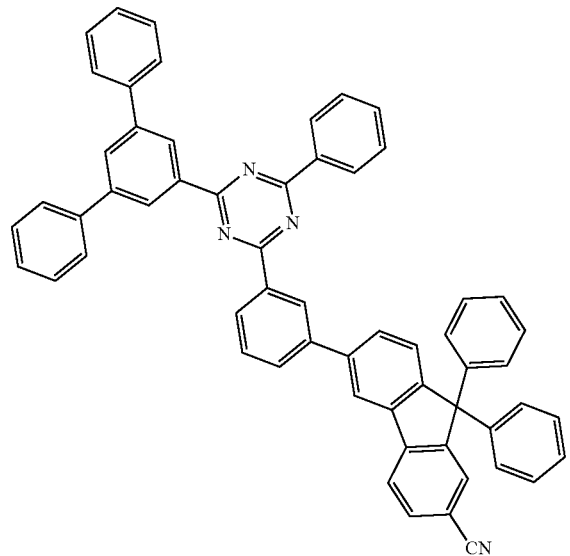
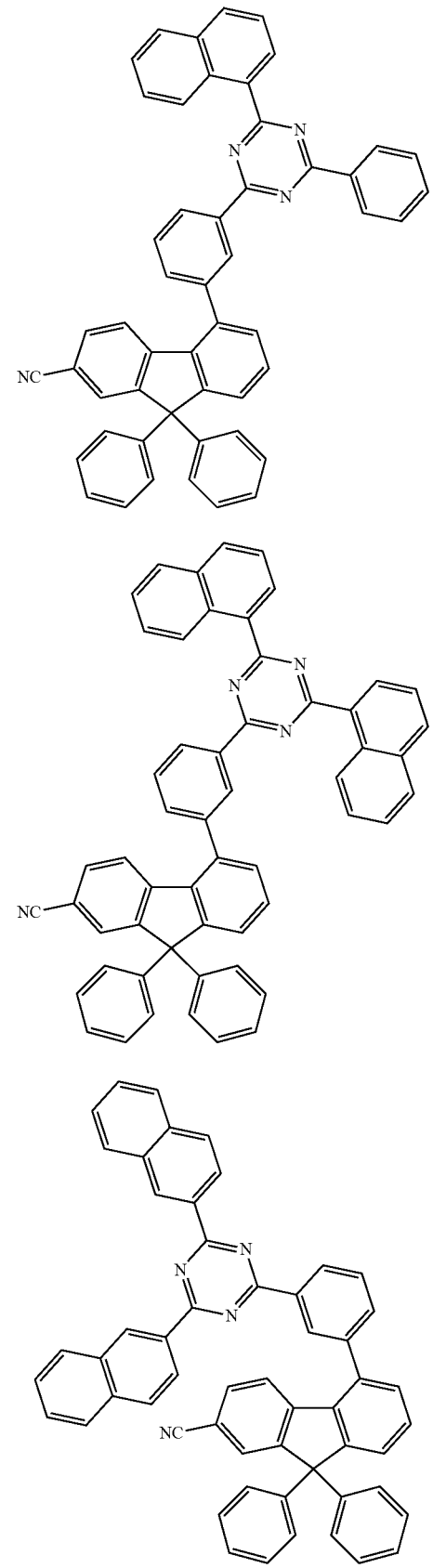

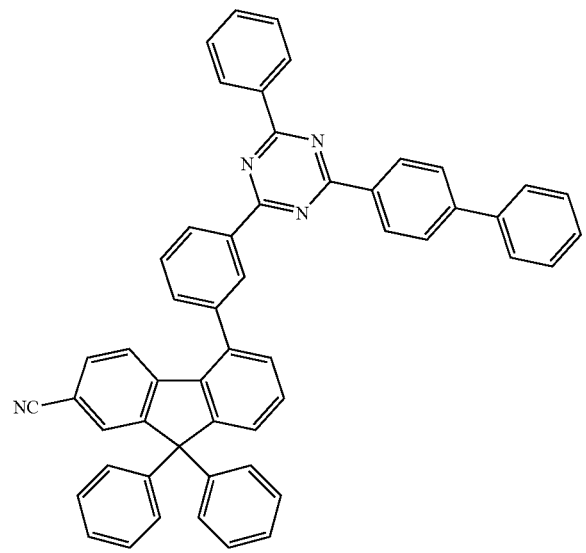
260
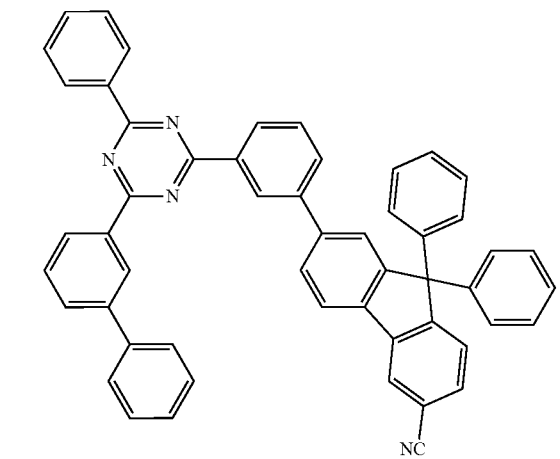
263
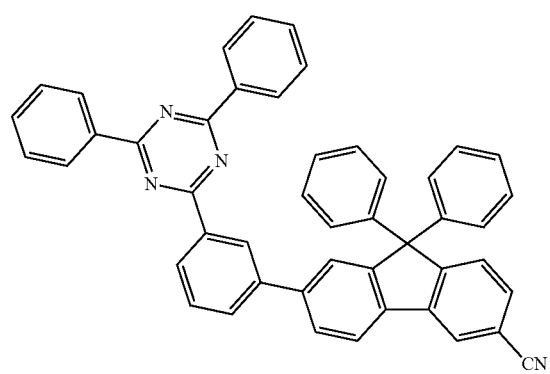
261
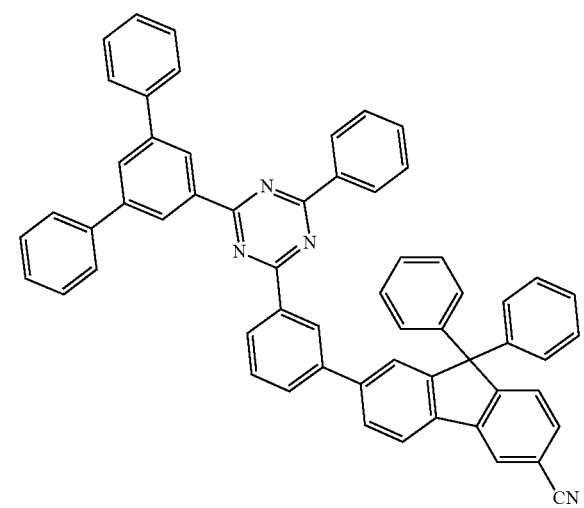
264
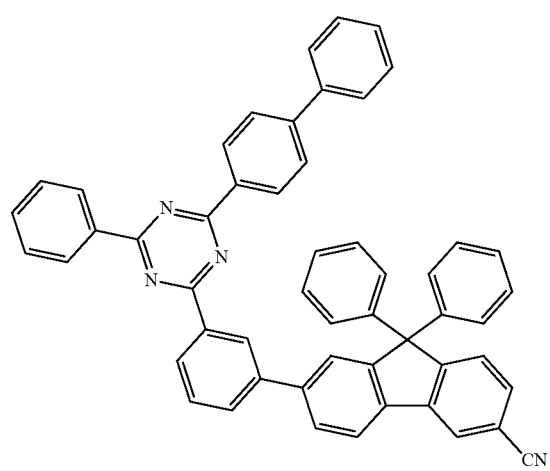
262
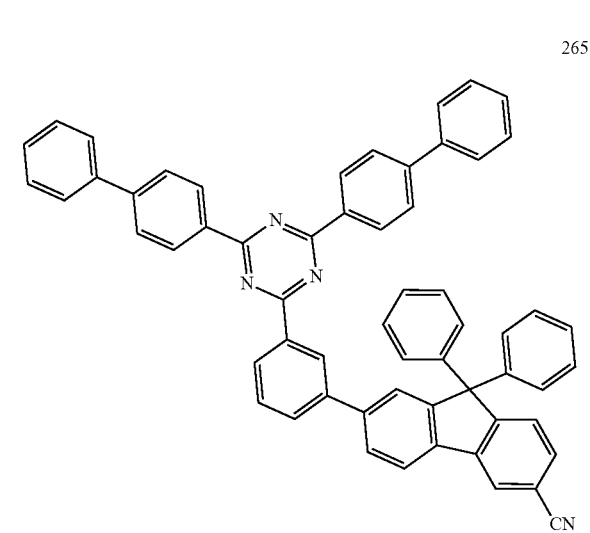
265

266
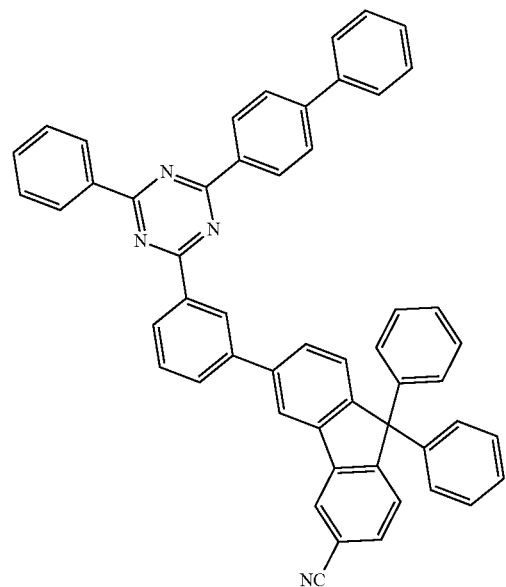
267
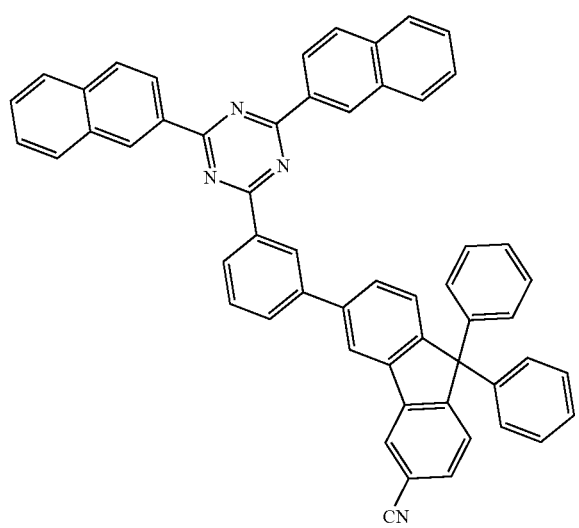
268
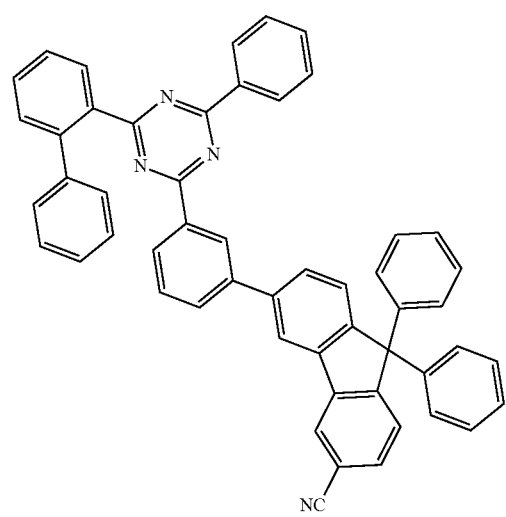
269
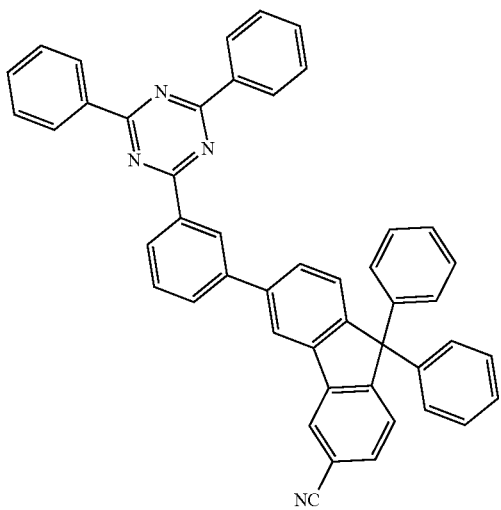
270
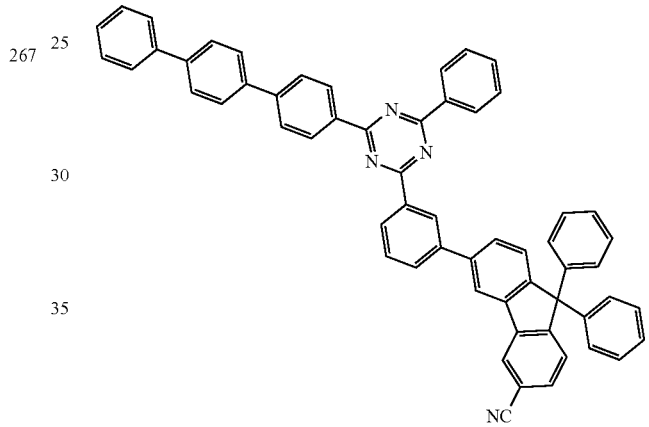
271
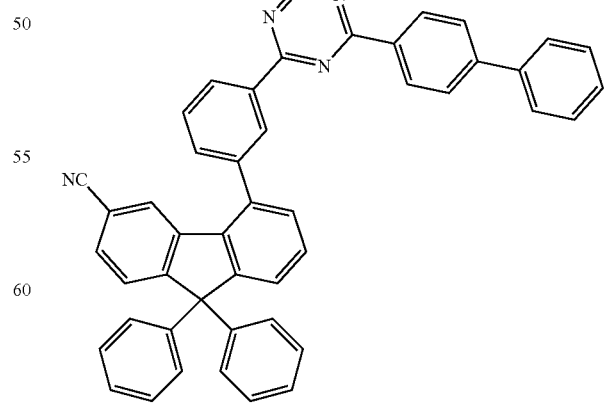

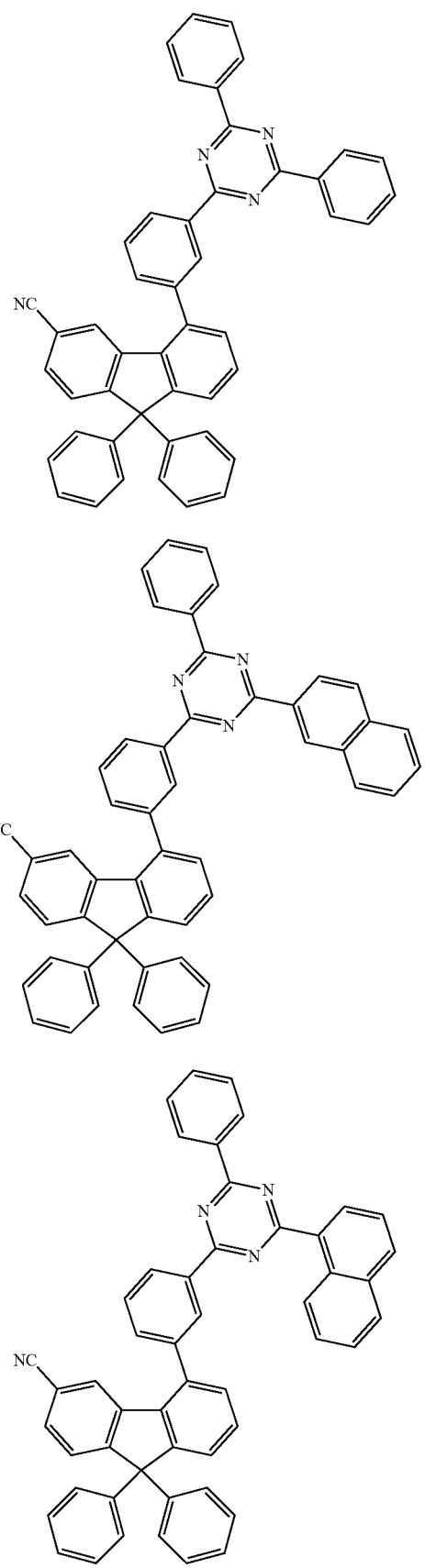
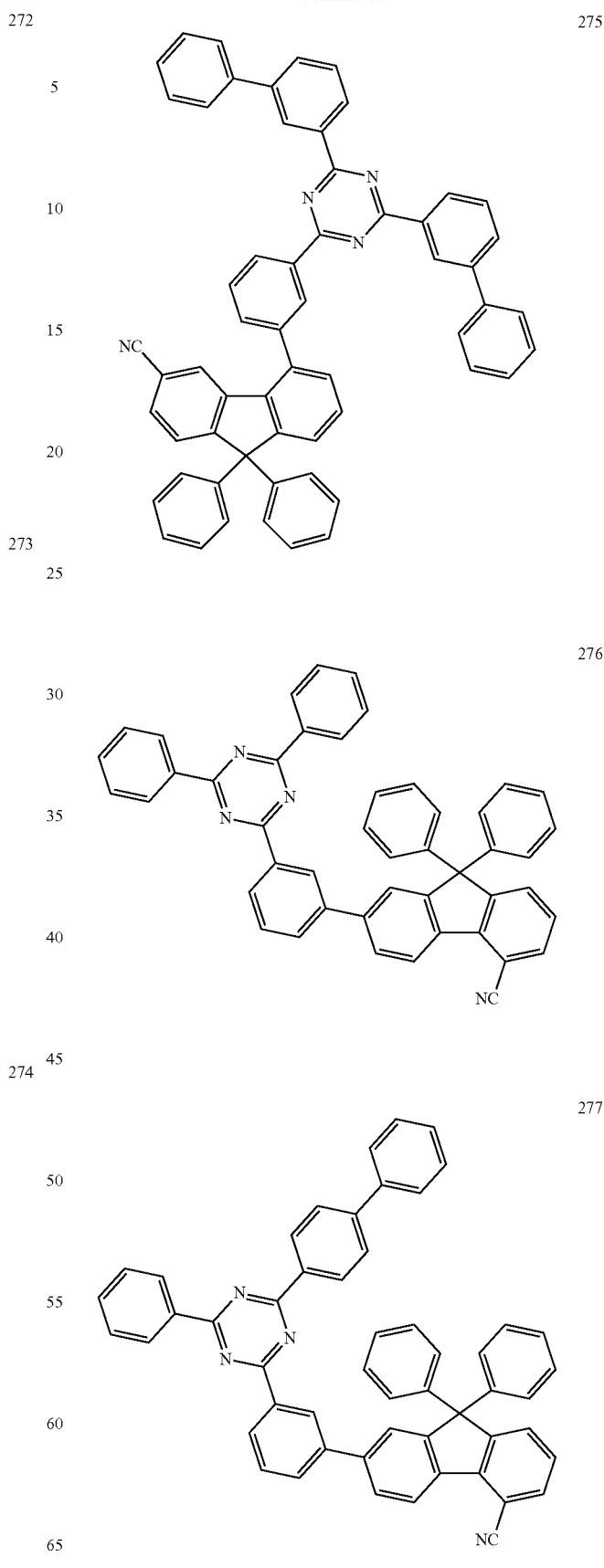

-continued
278
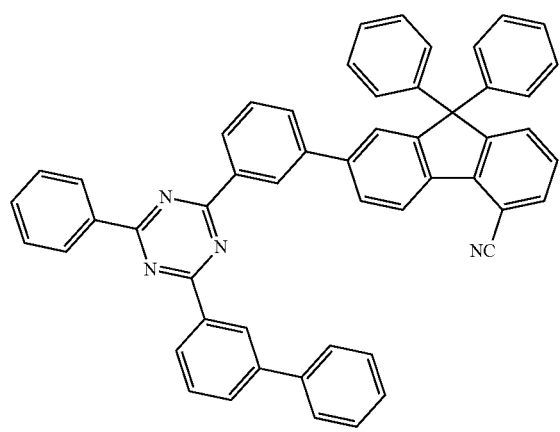
279
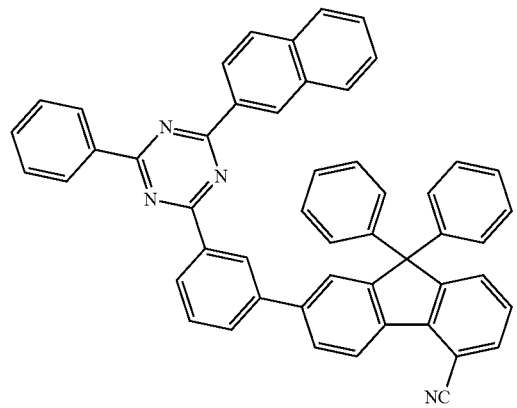
280
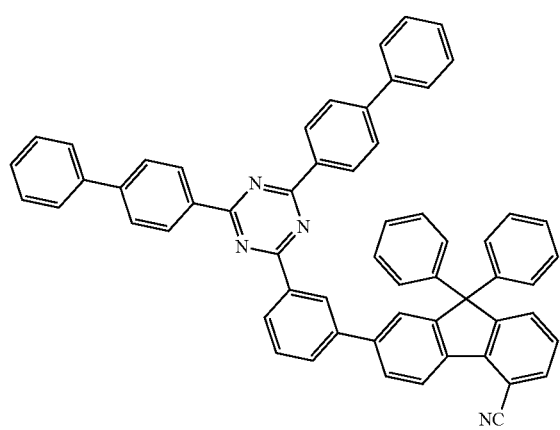
-continued
281
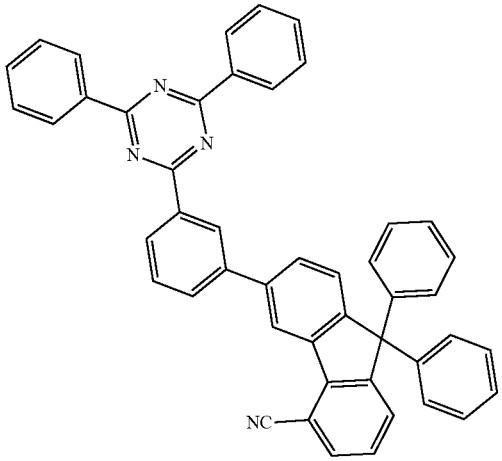
282
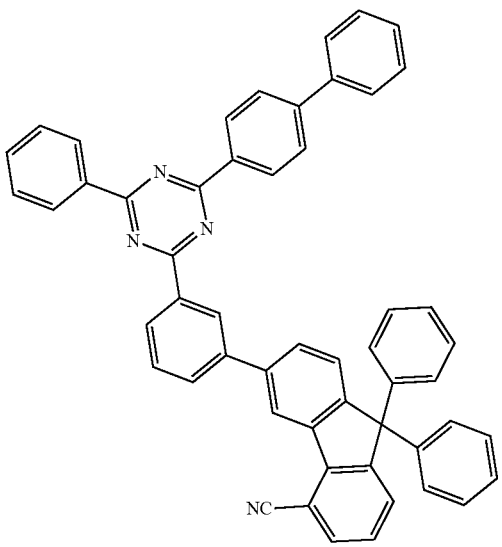
283
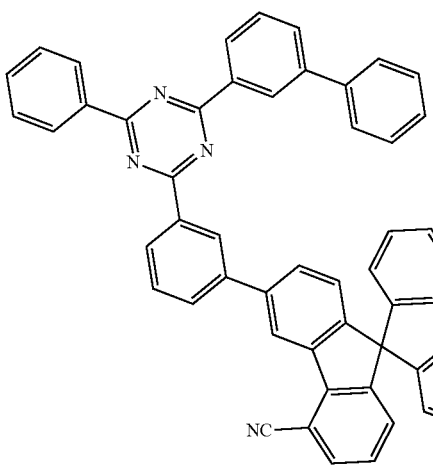

284
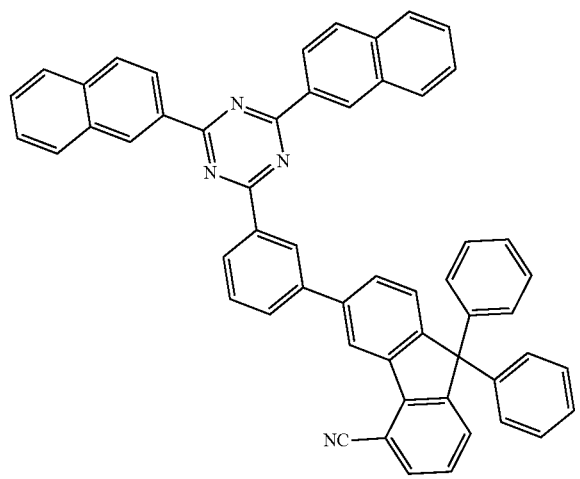
285
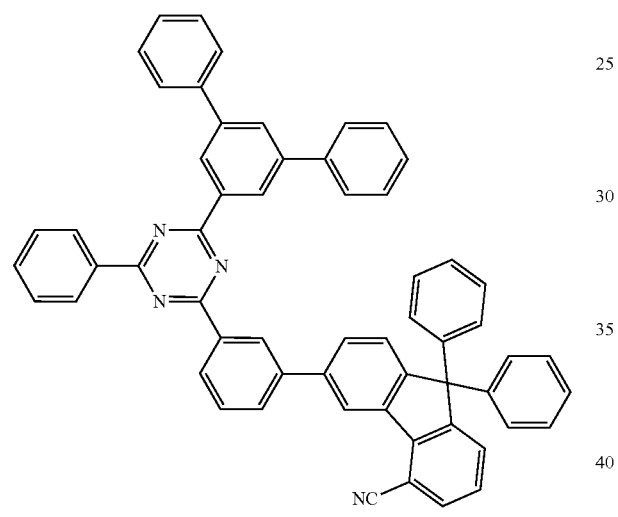
286
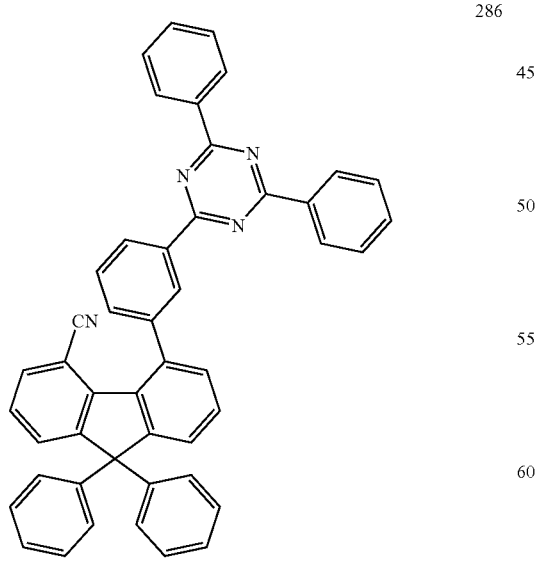
287
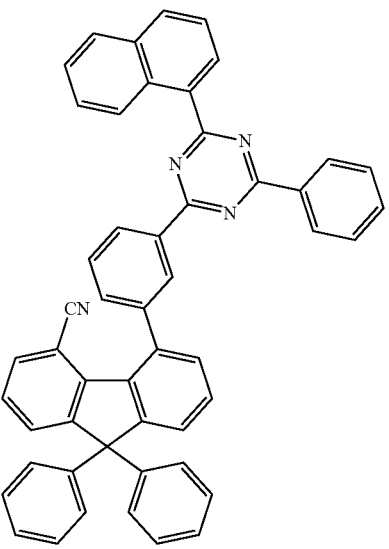
288
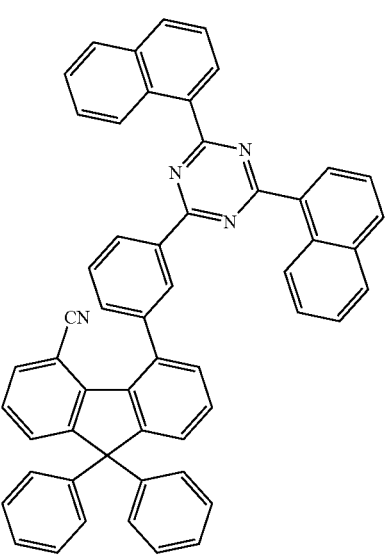

-continued
289
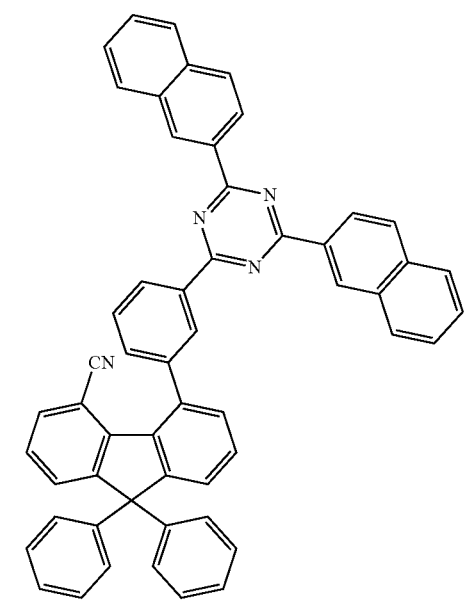
290
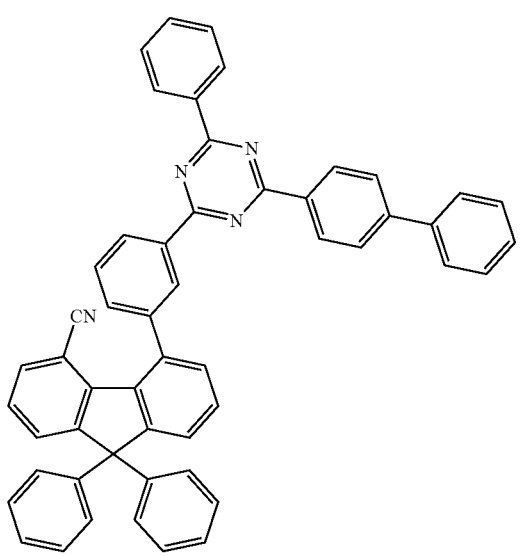
291
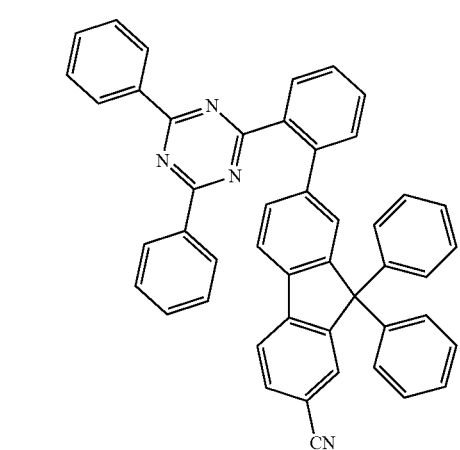
-continued
292
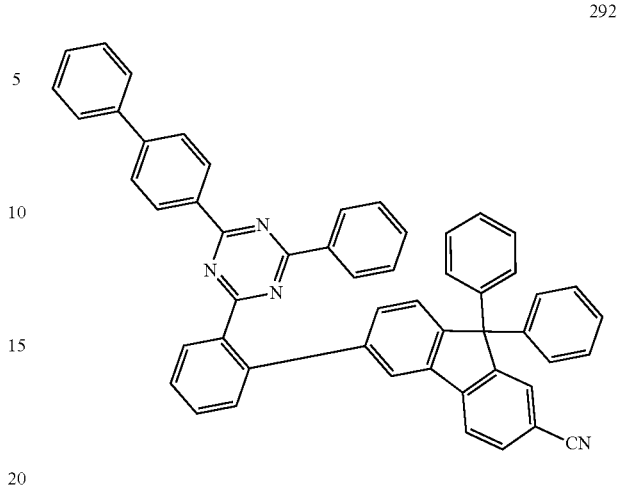
293
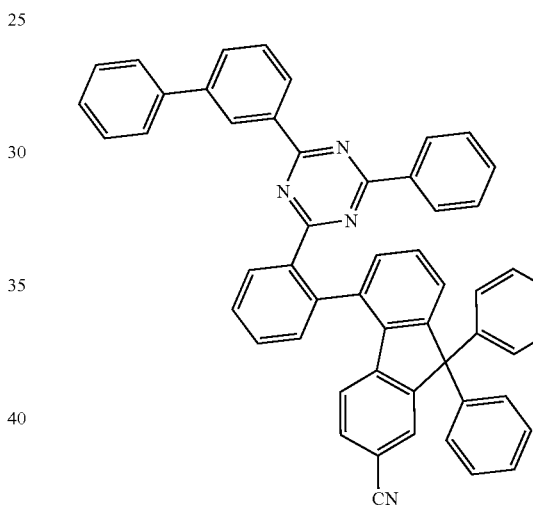
294
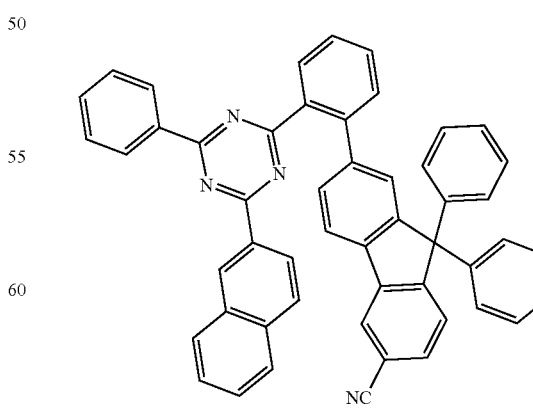

295
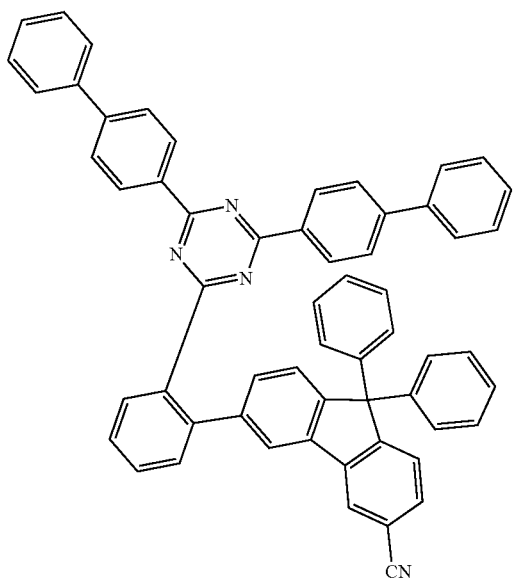
298
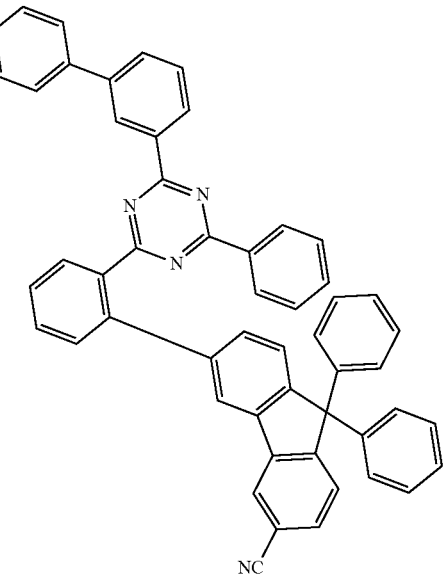
296
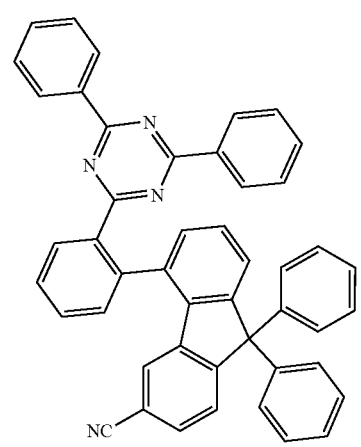
299
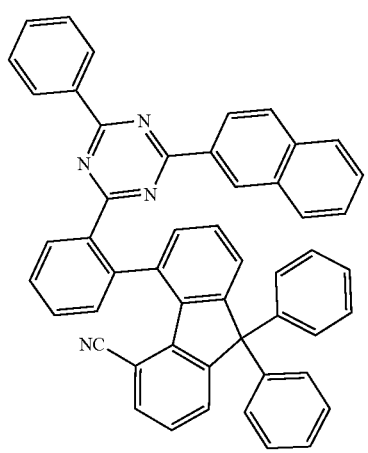
297
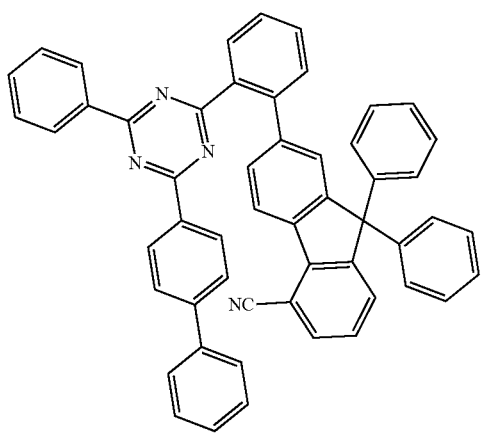
300
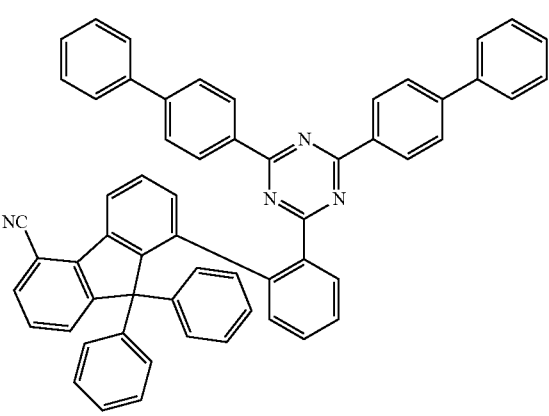

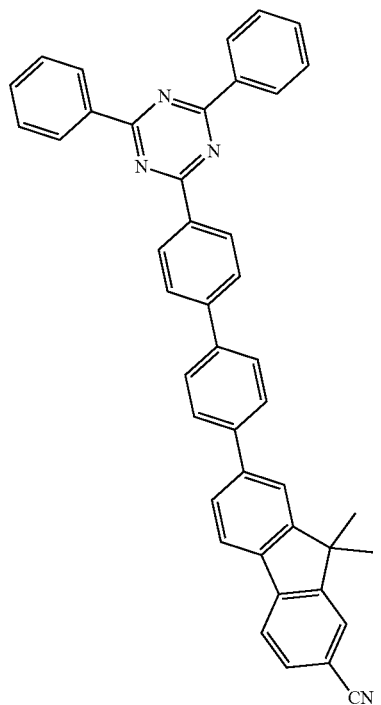
301
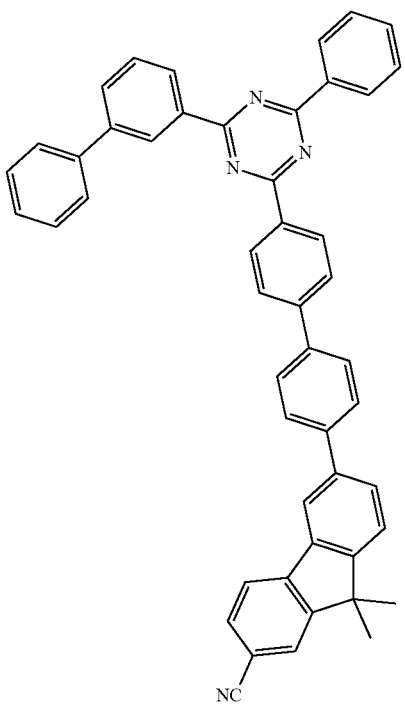
303
-continued
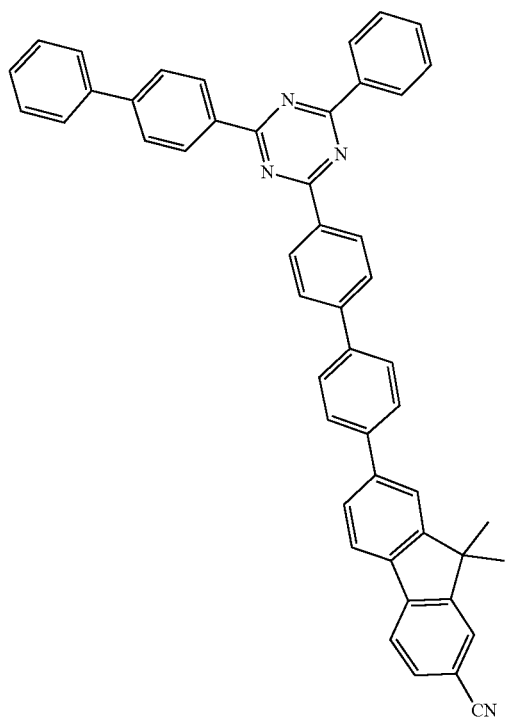
302
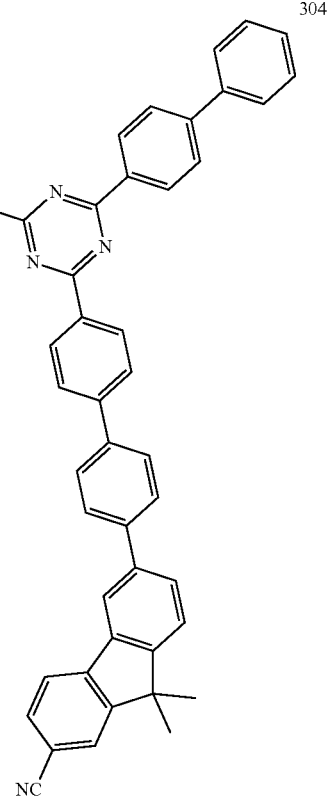
304

-continued
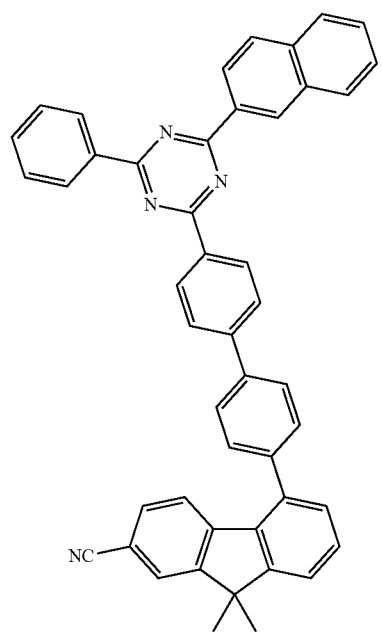
305
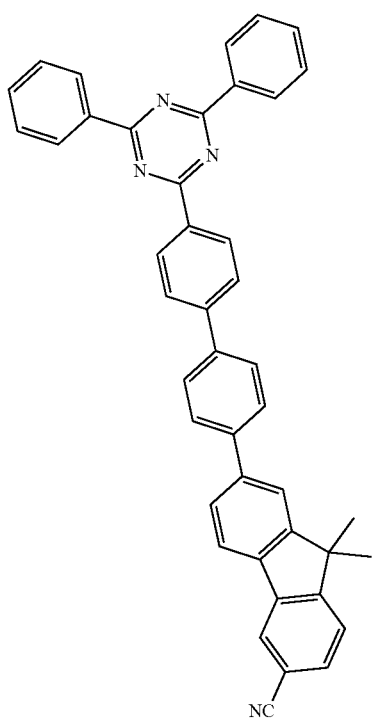
306
-continued
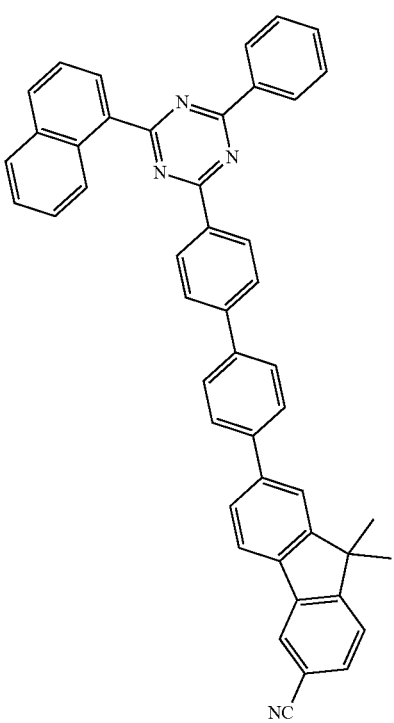
307
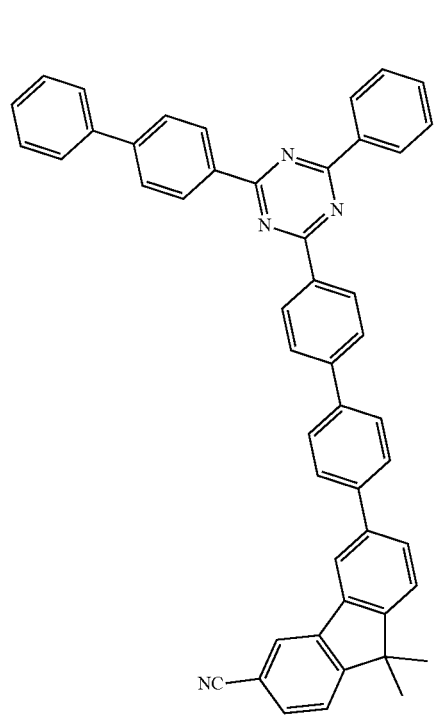
308

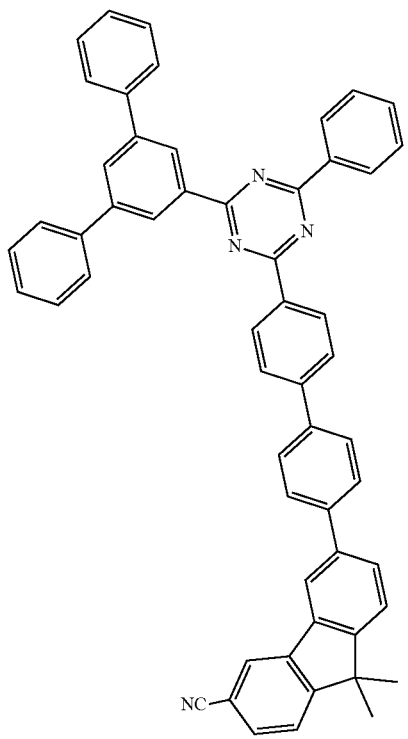
309
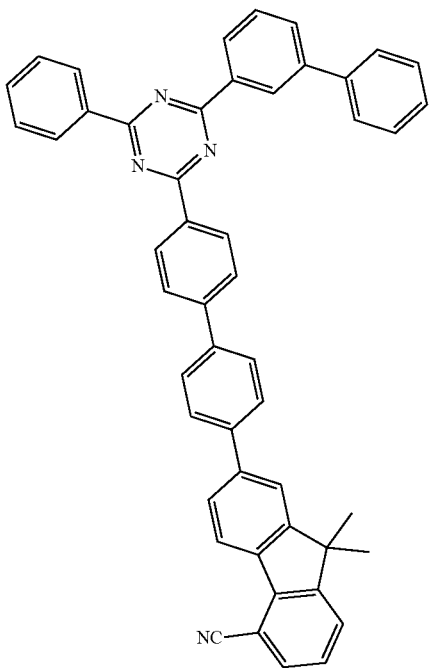
311
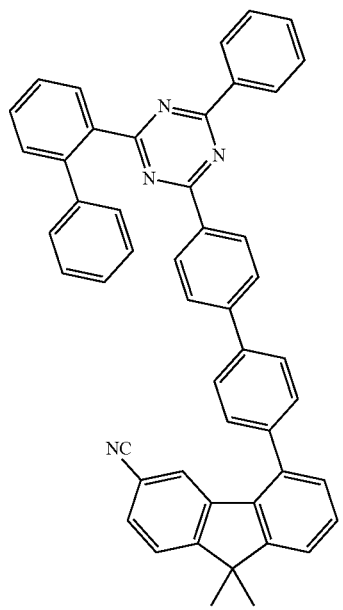
310
312

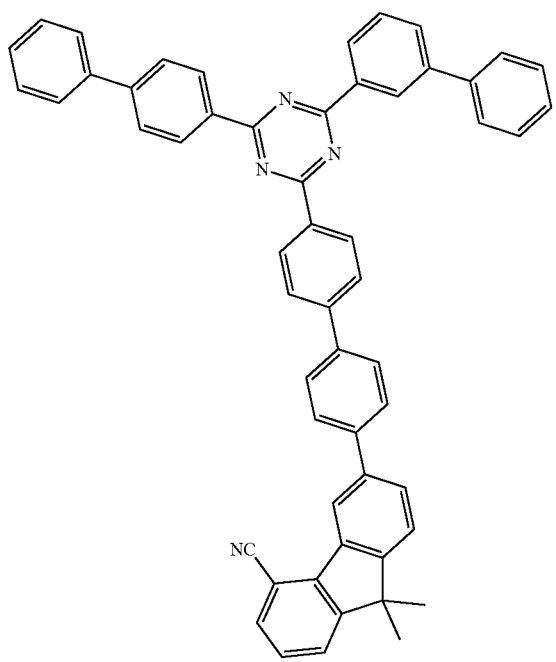
313
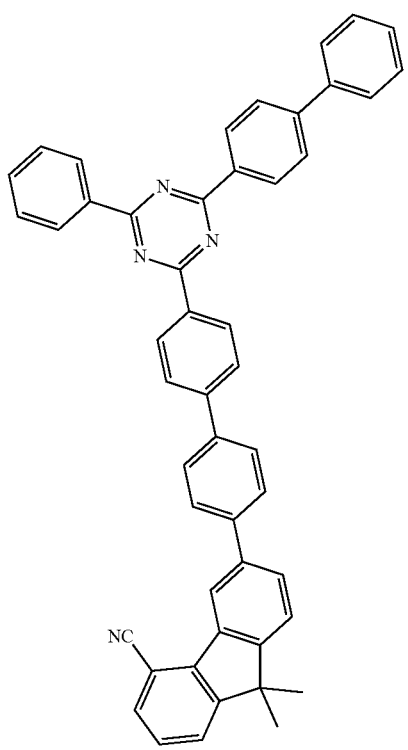
314
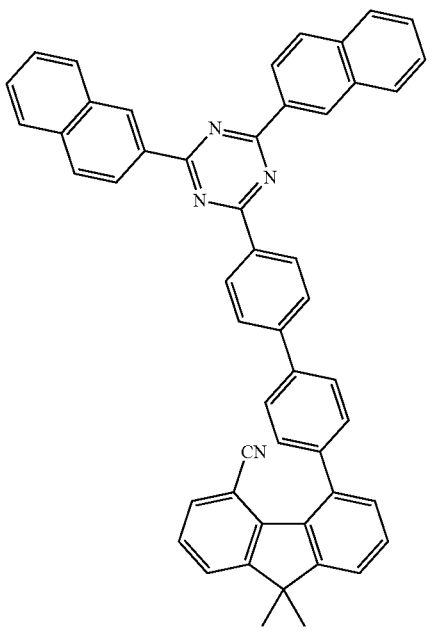
315
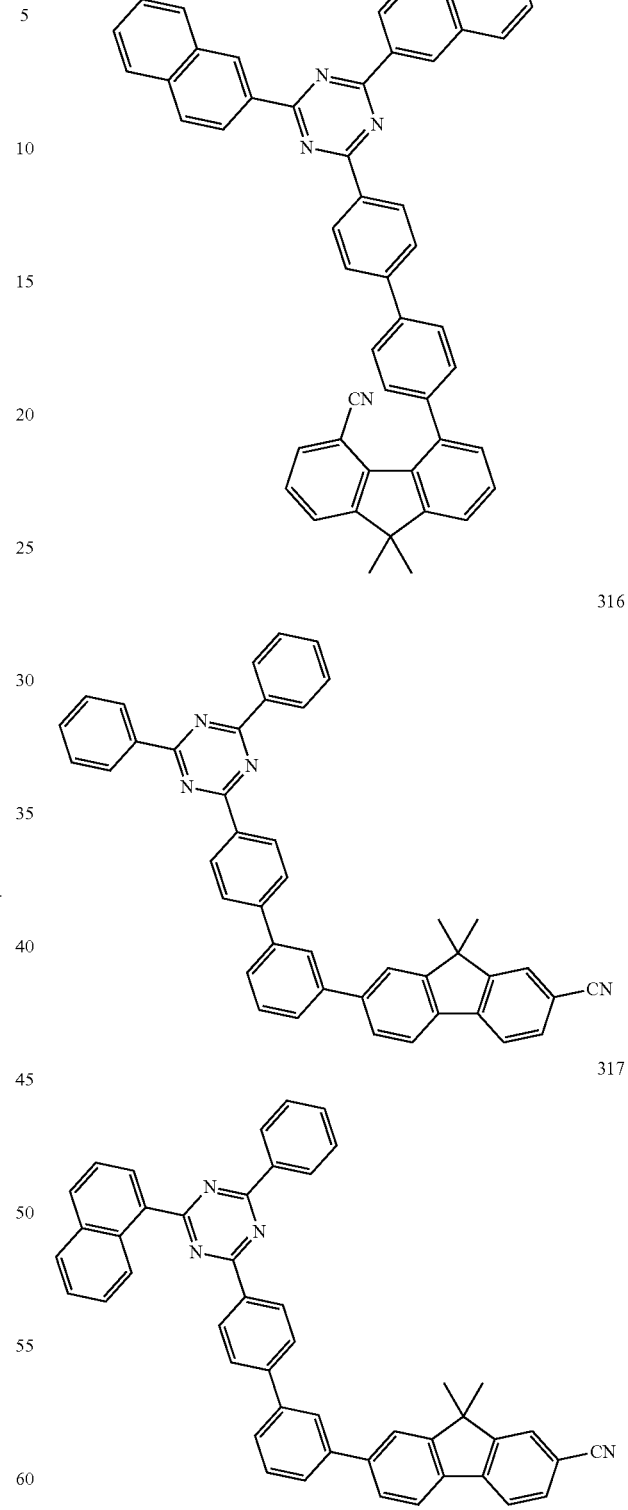
316
317

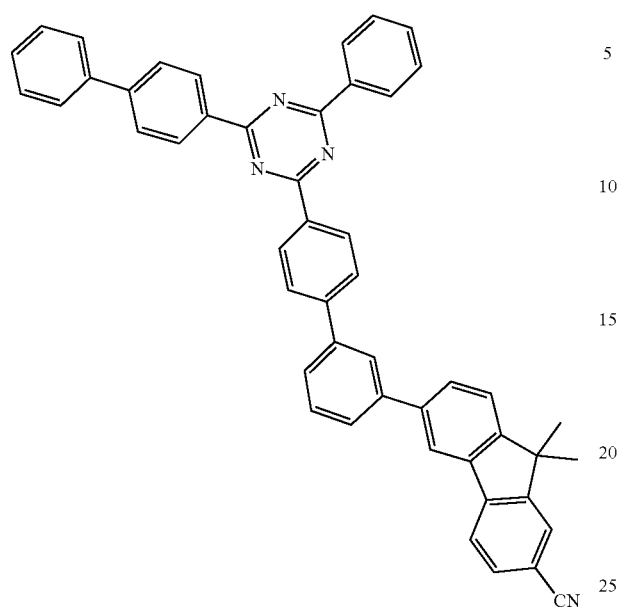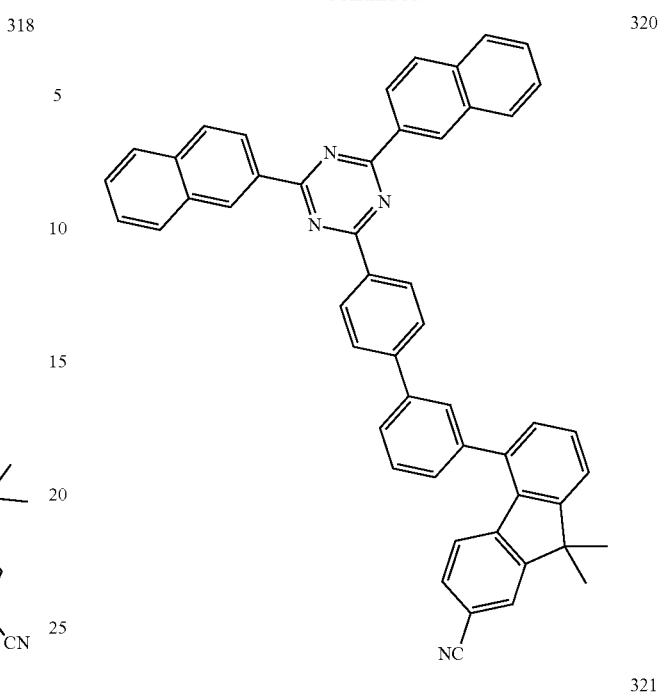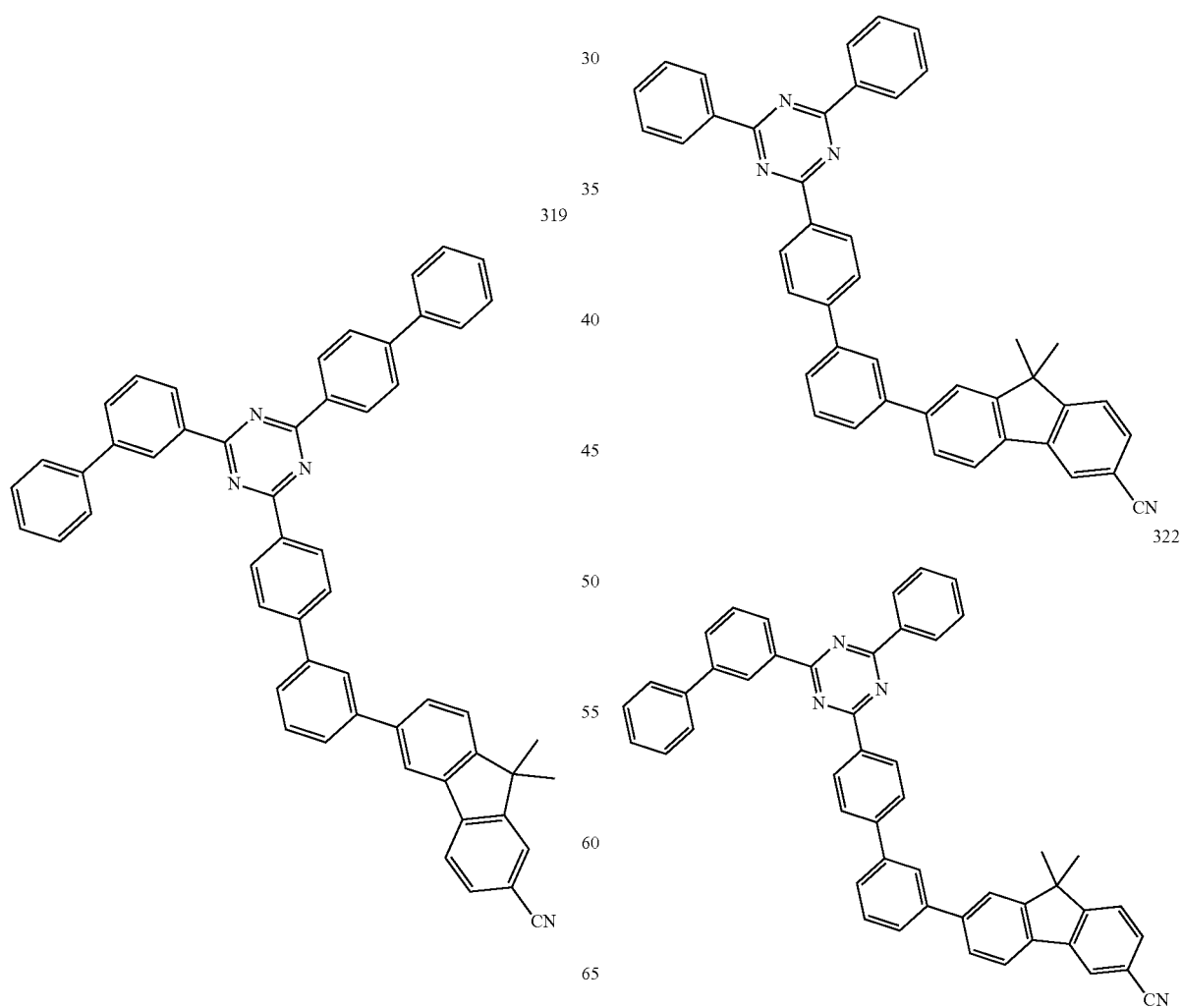

323
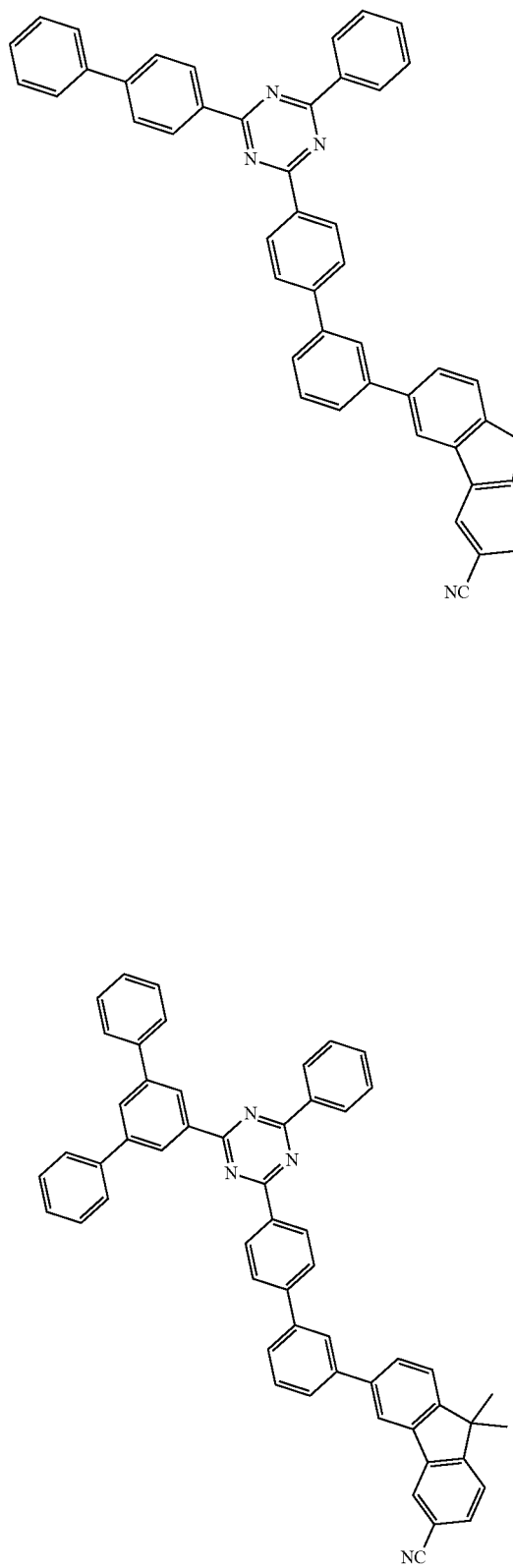
324
325
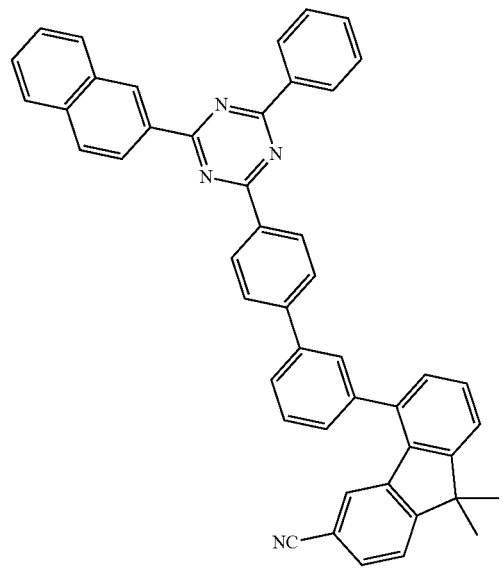
326
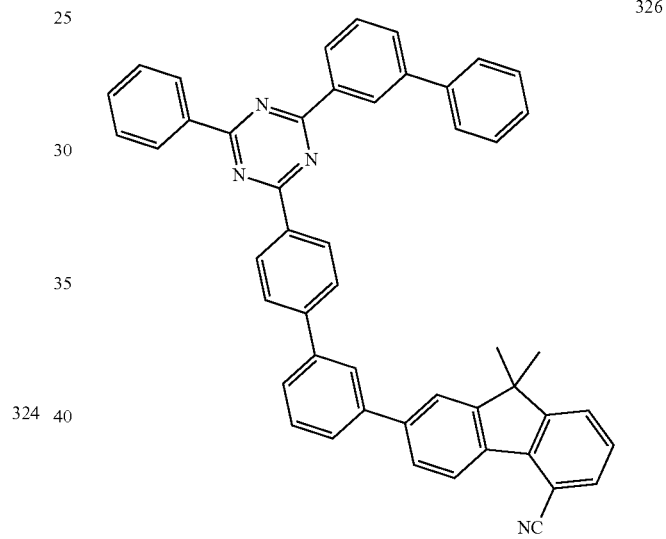
327
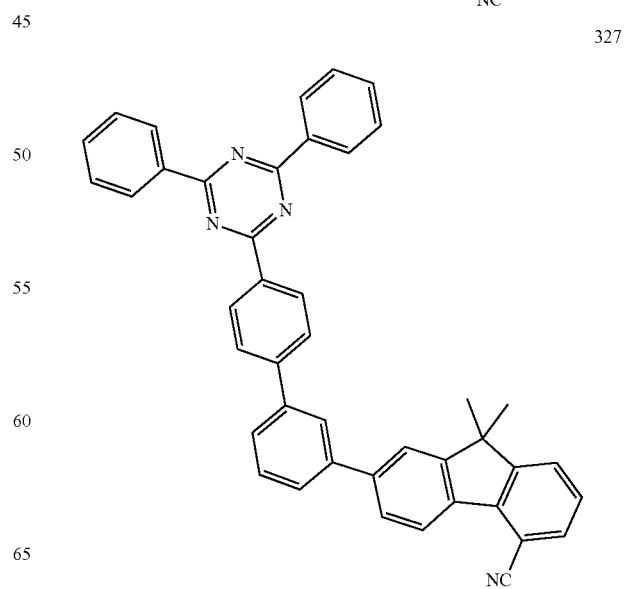

328
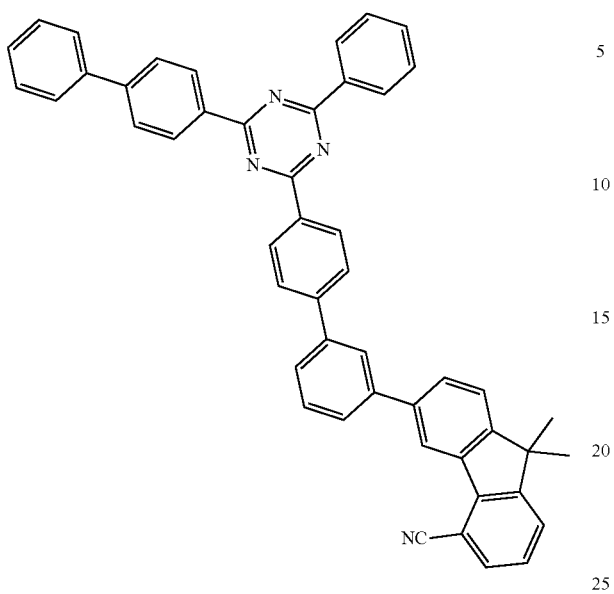
329
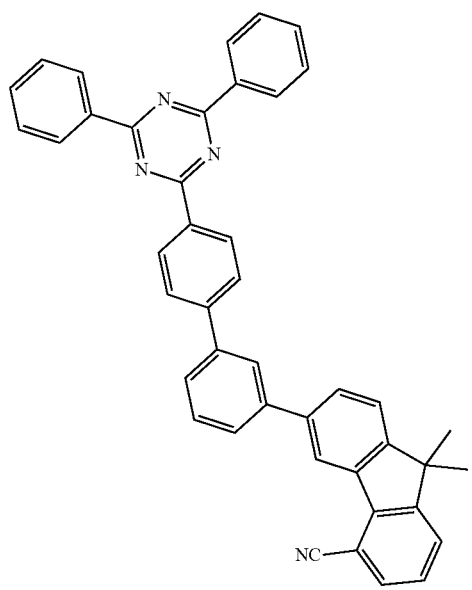
330
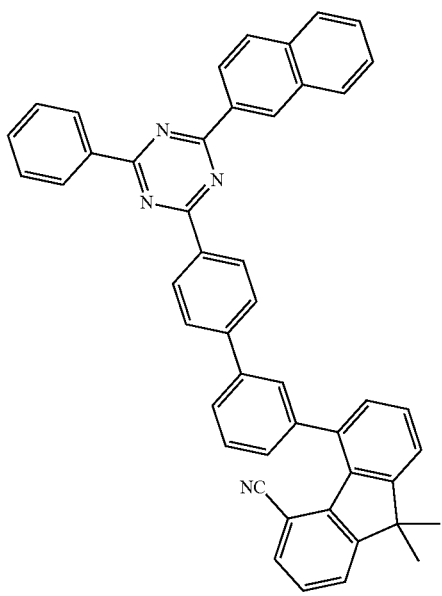
331
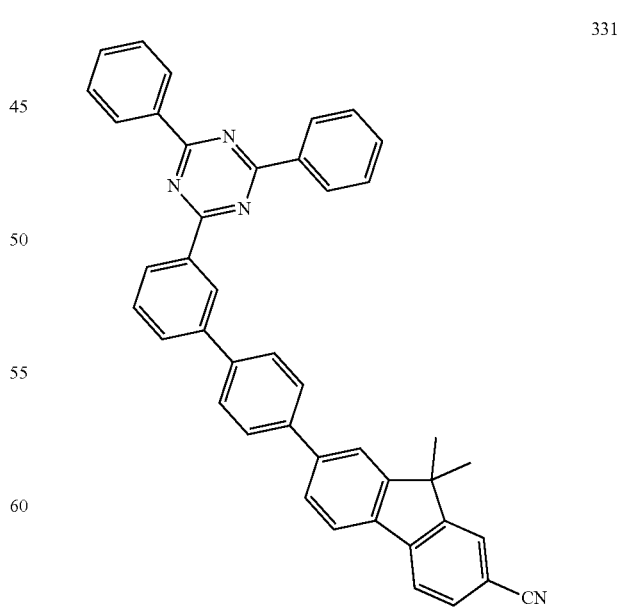

141
-continued
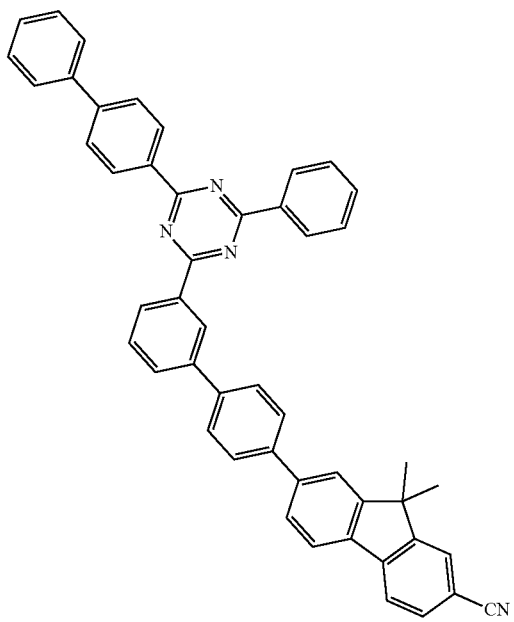
332
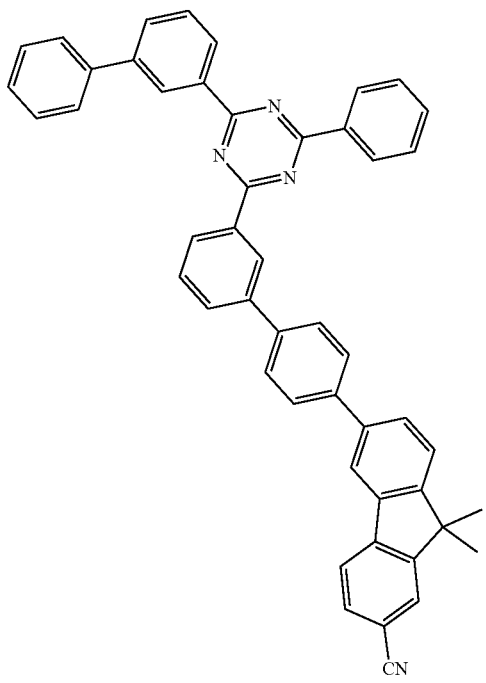
333
142
-continued
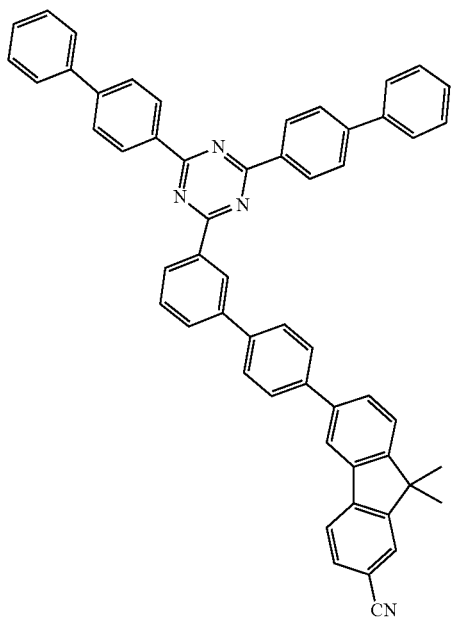
334
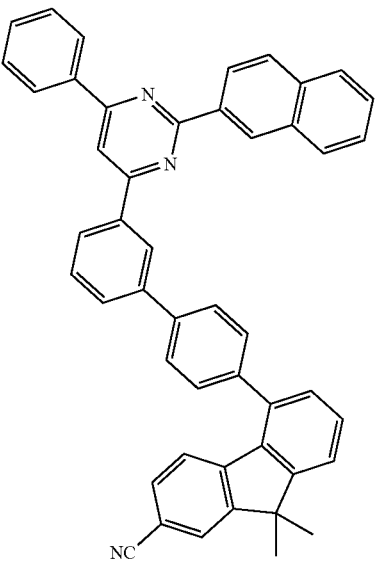
335

336
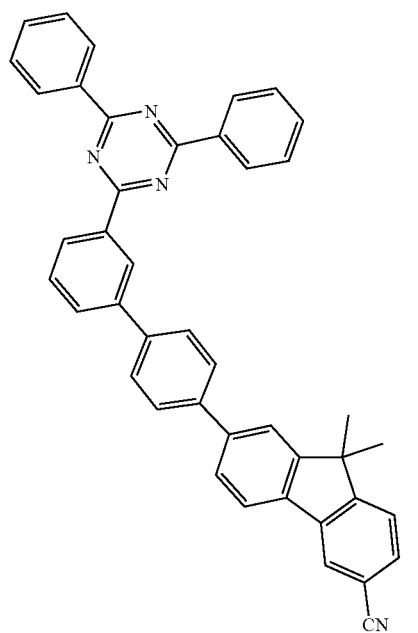
337
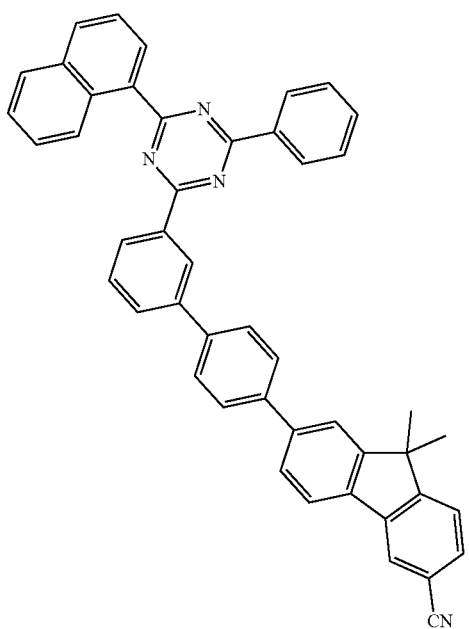
338
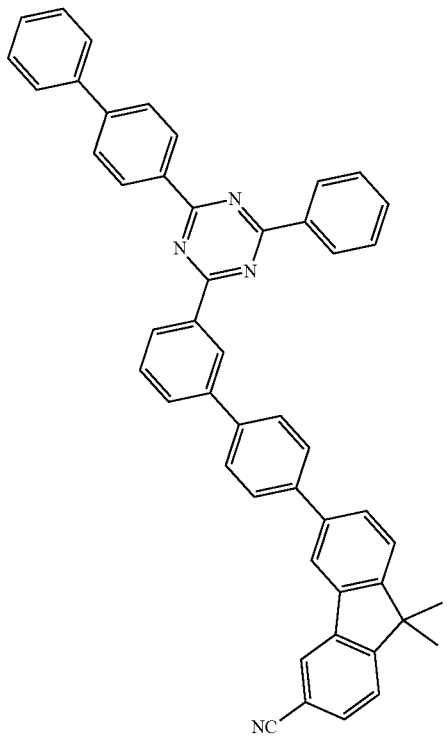
339
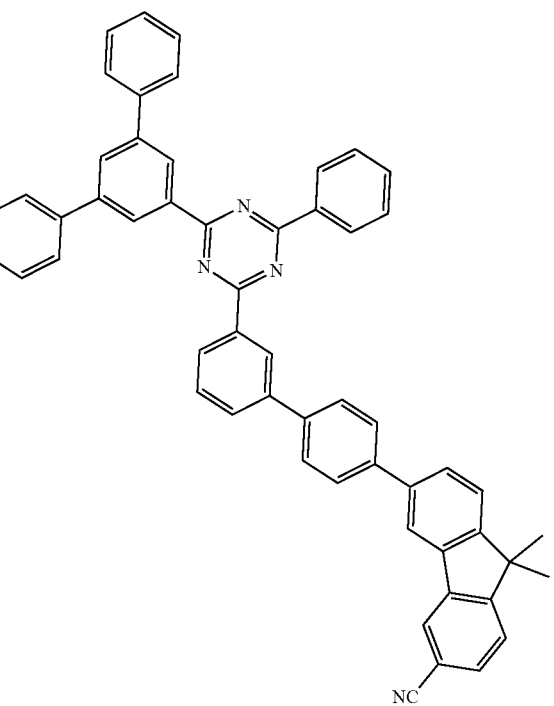

-continued
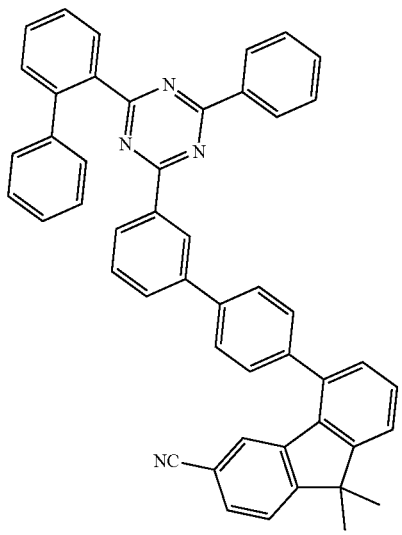
340
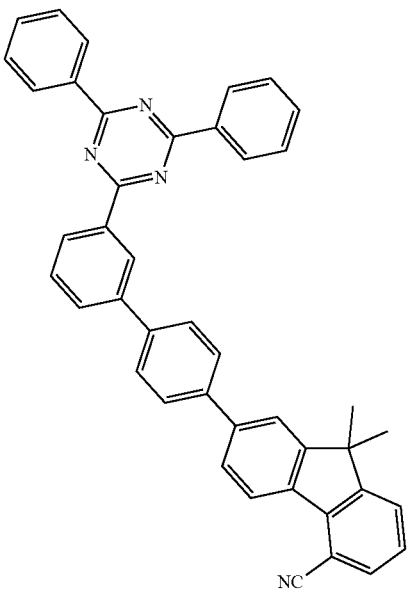
342
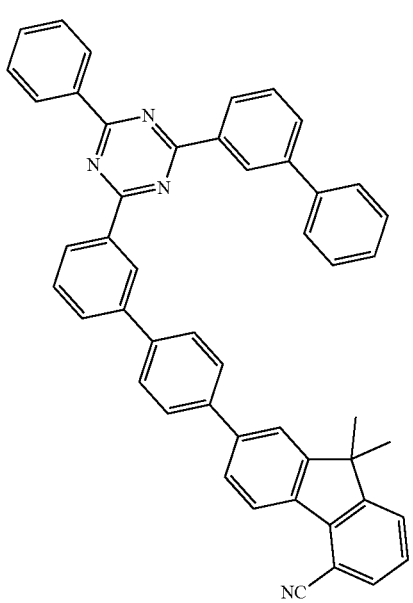
341
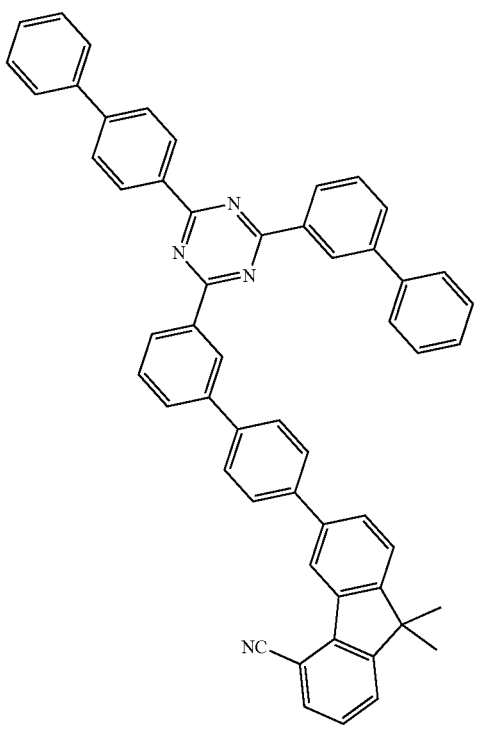
343

147
-continued
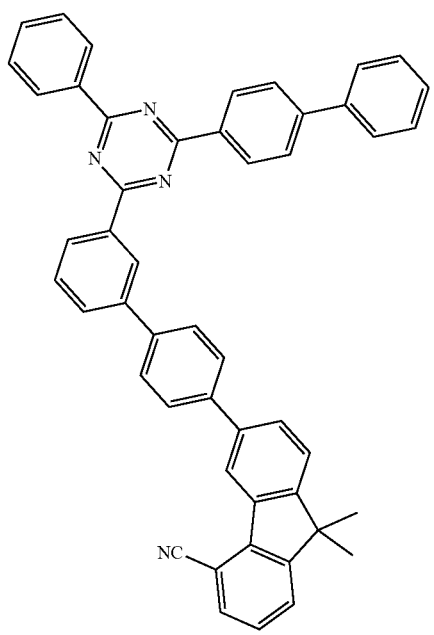
344
148
-continued
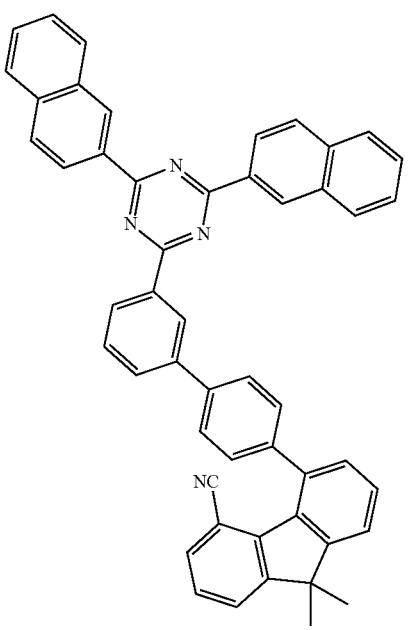
345
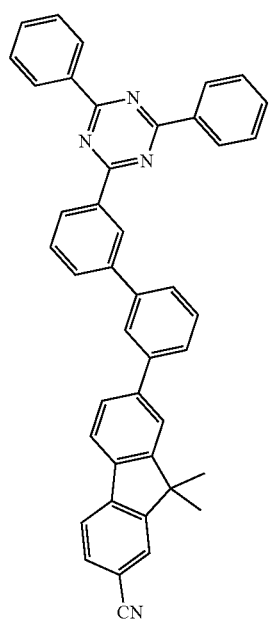
346
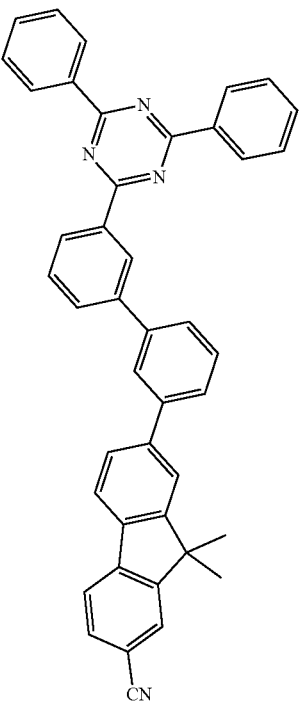
346

149
-continued
347
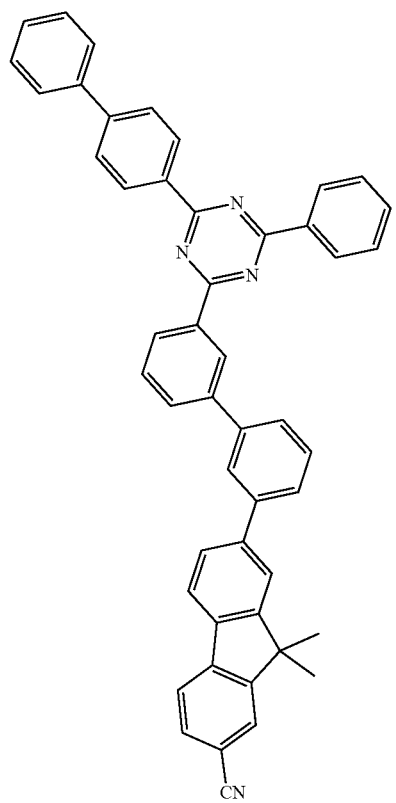
348
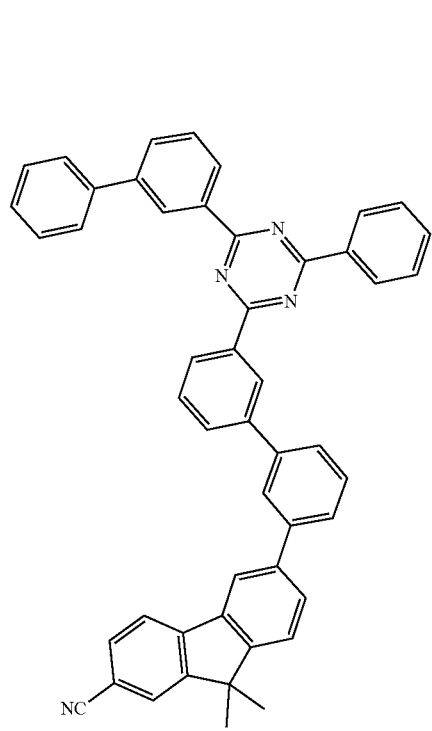
150
-continued
349
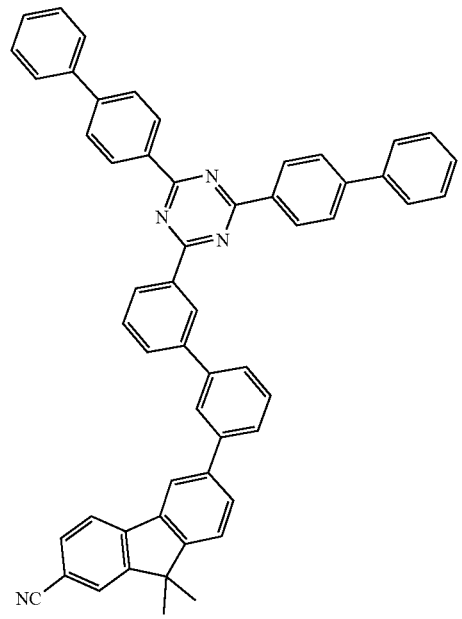
349
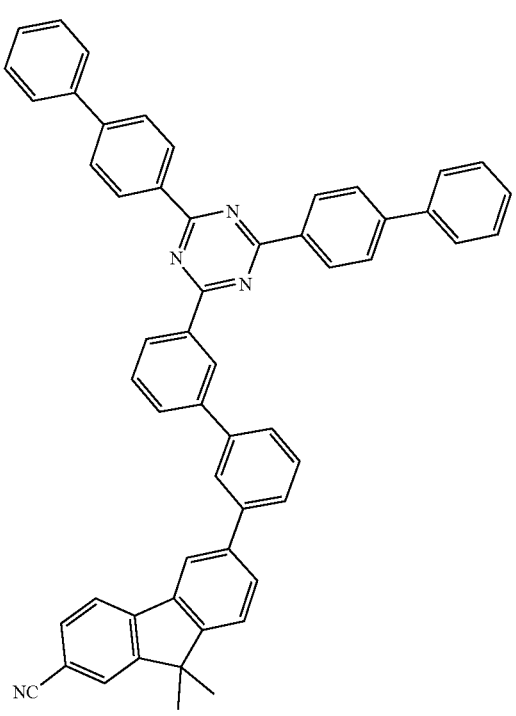

350
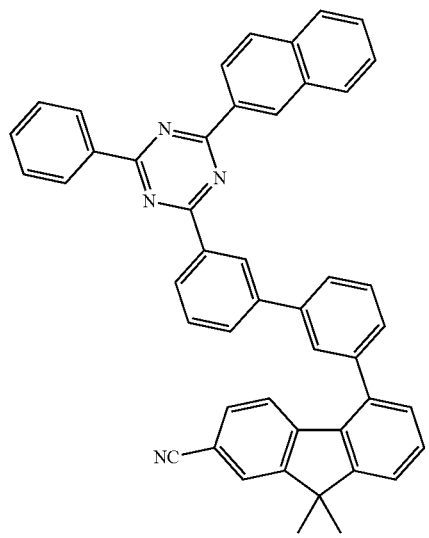
351
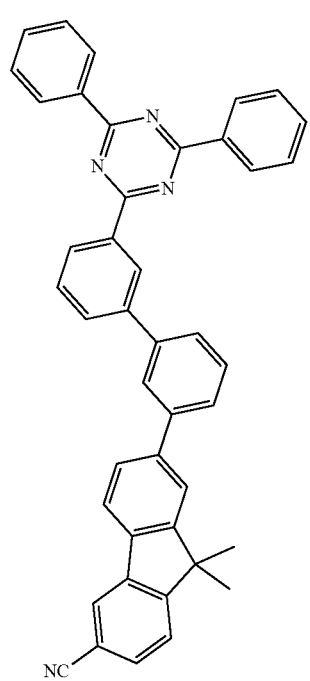
352
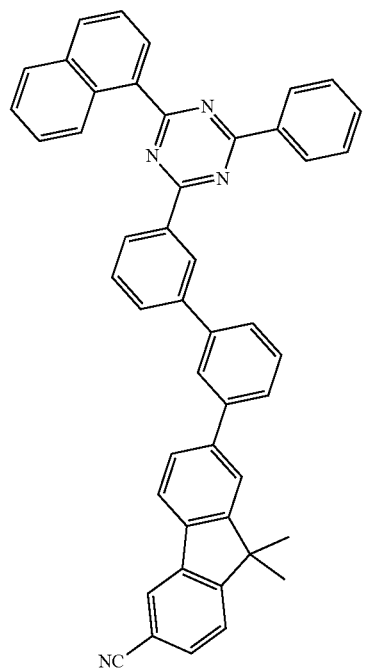
353
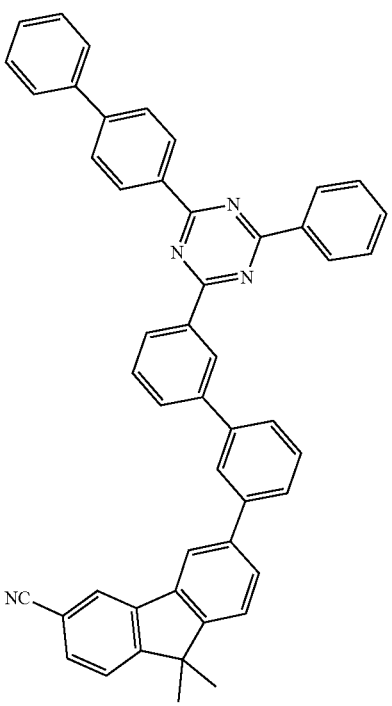

354
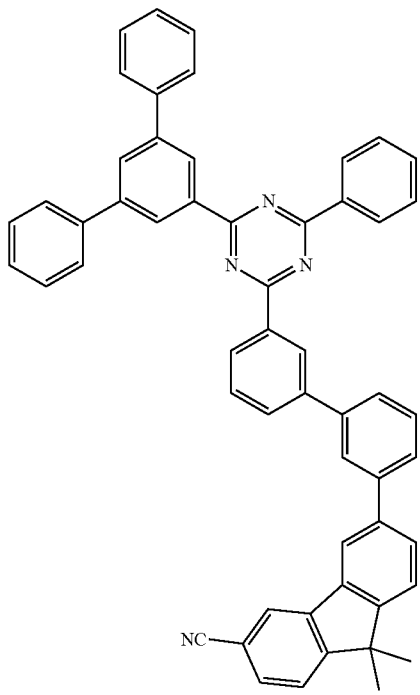
356
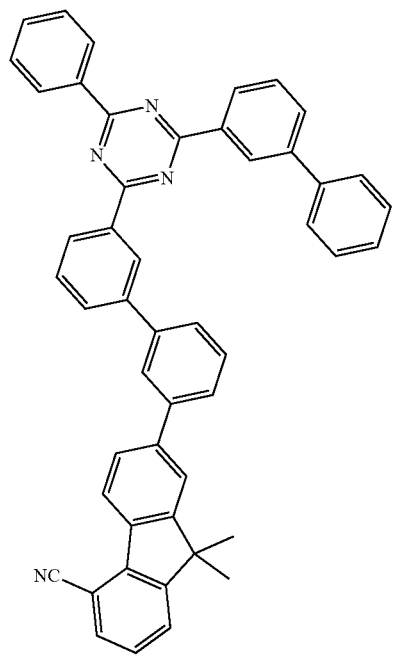
355
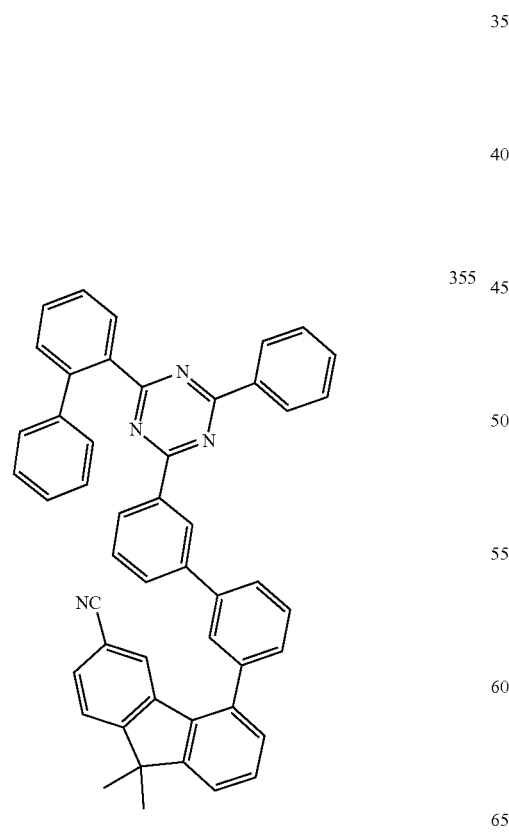
357
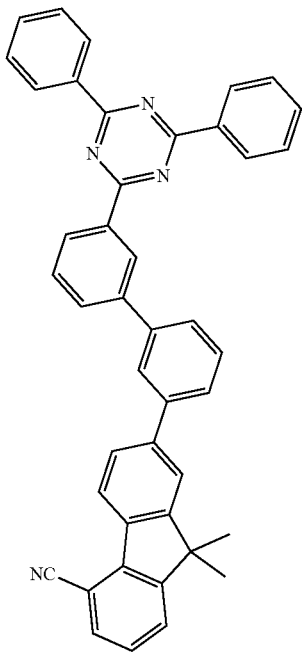

155
-continued
358
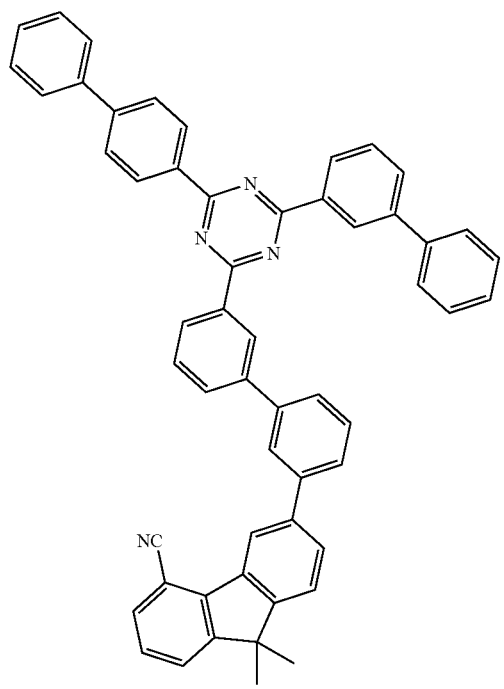
359
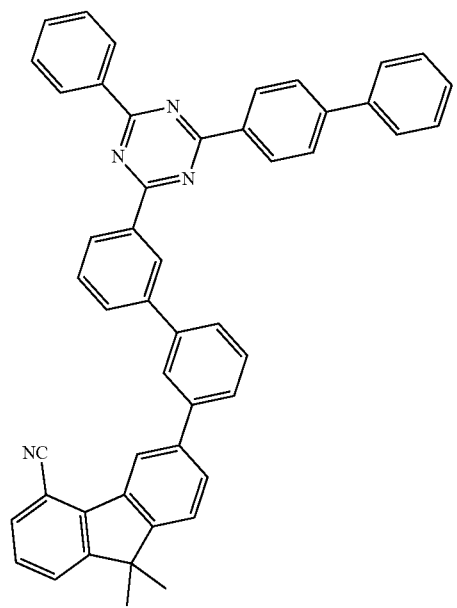
156
-continued
360
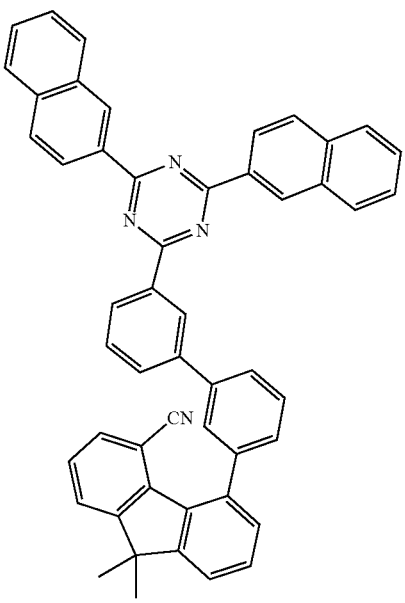
361
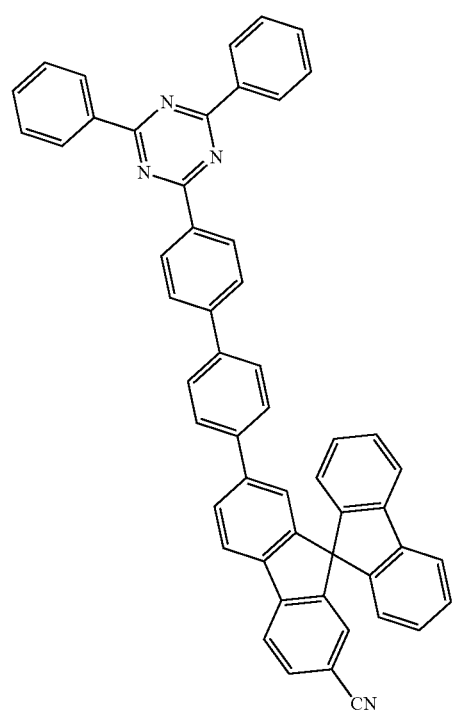

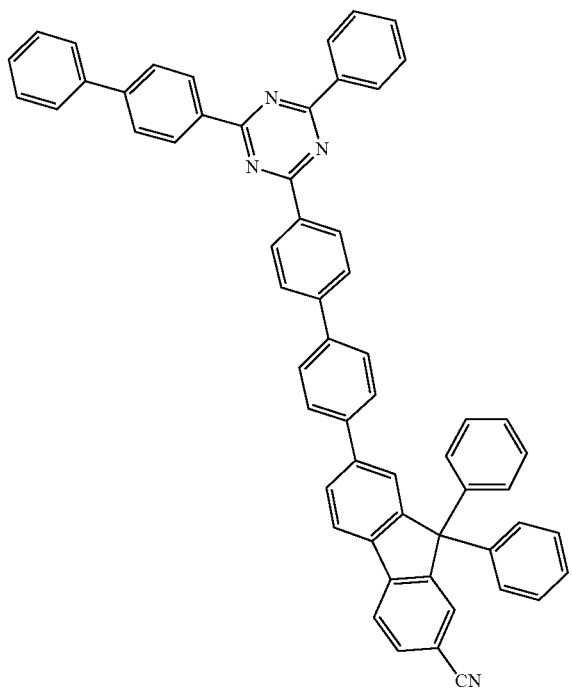
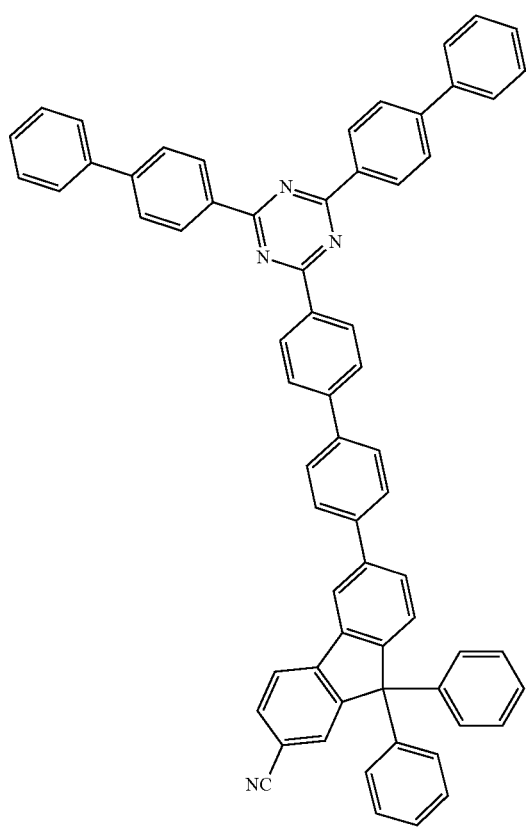

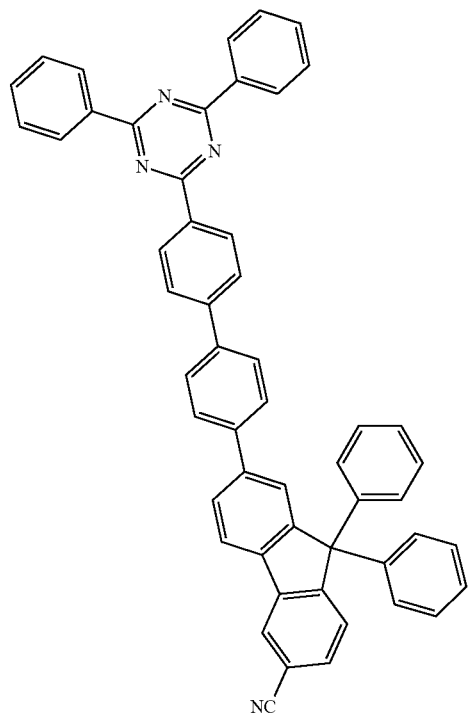
366
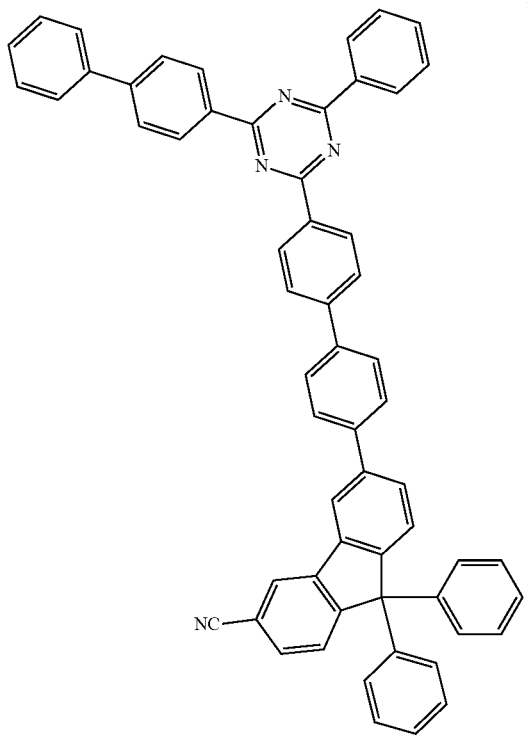
368
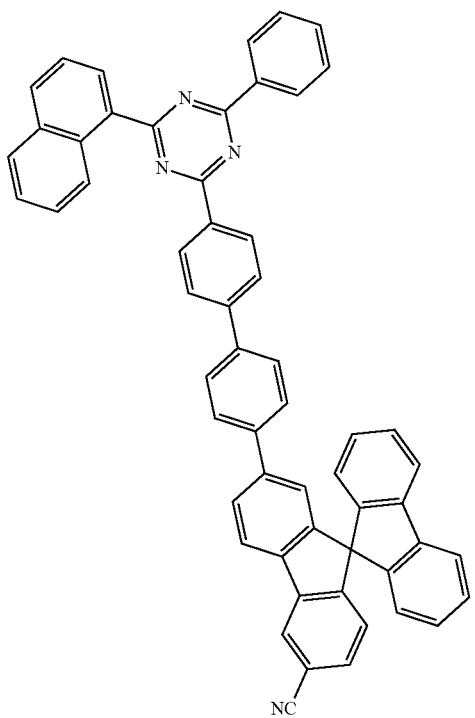
367
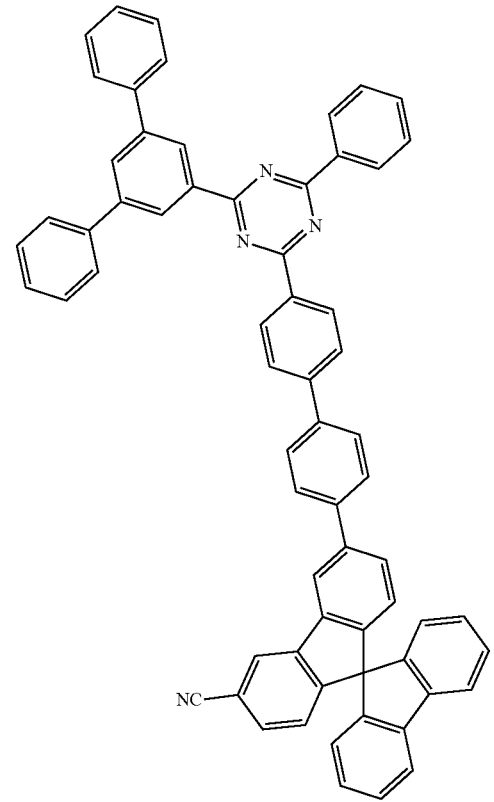
369

370
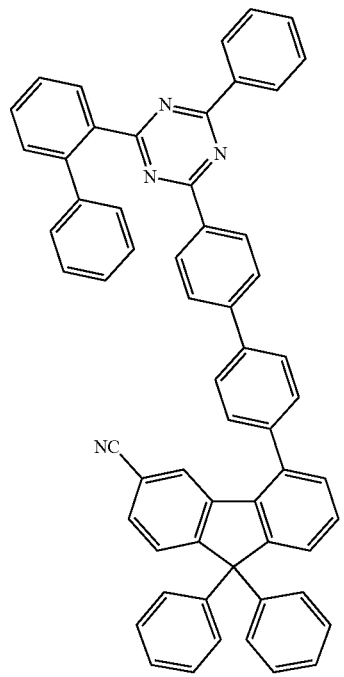
371
372
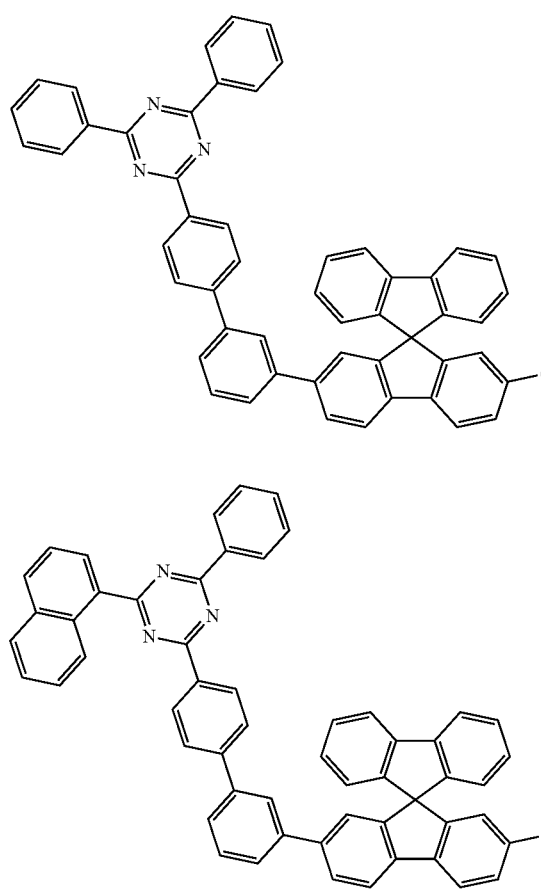
373
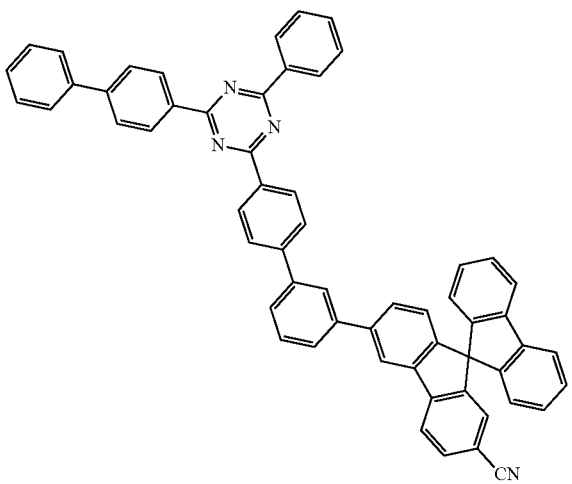
374
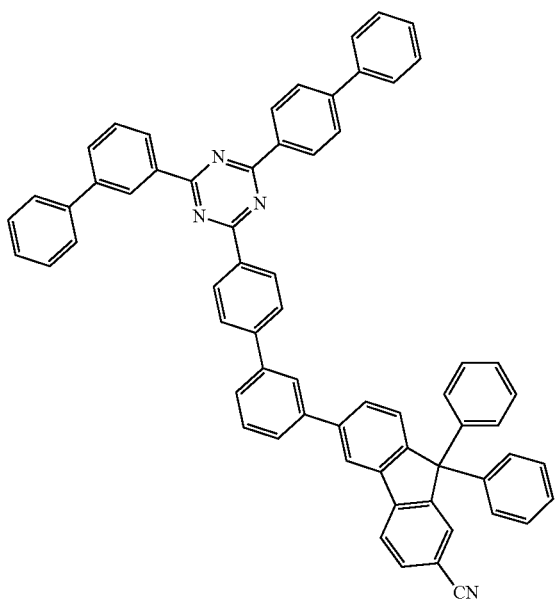

375
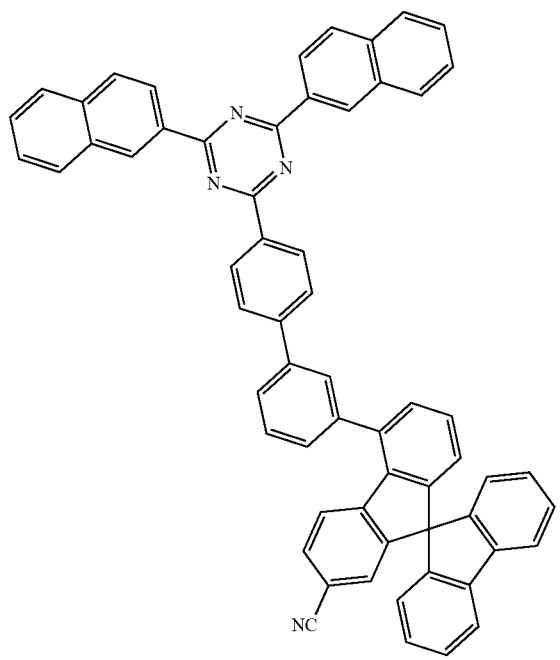
376
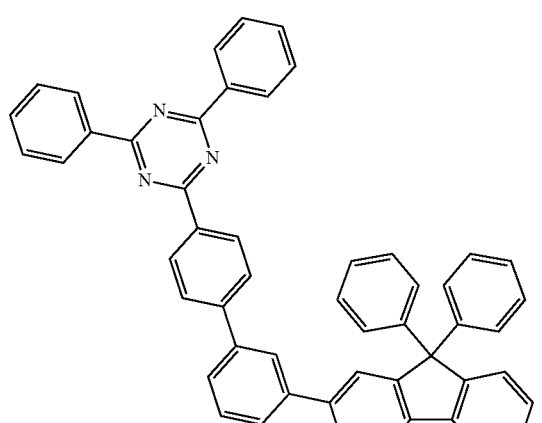
377
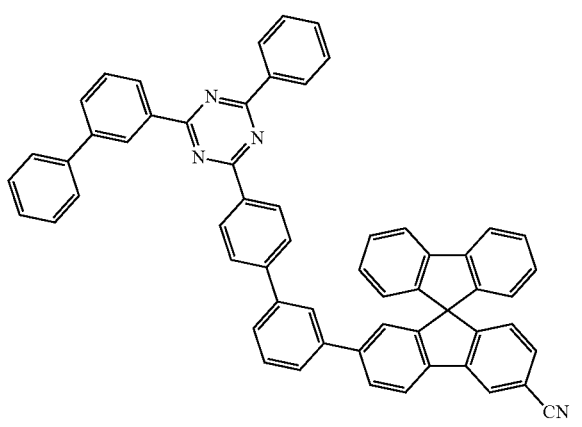
378
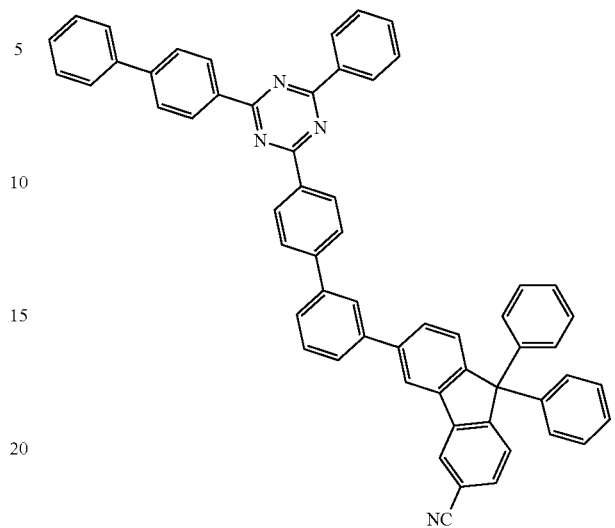
379
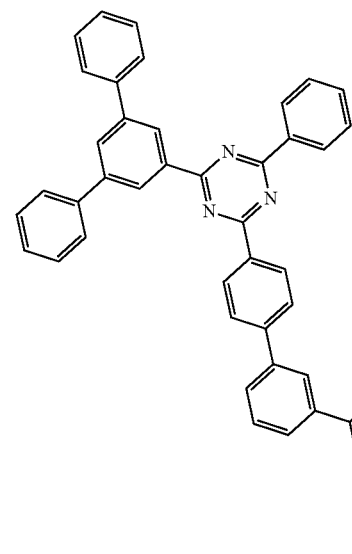

165  
166
380
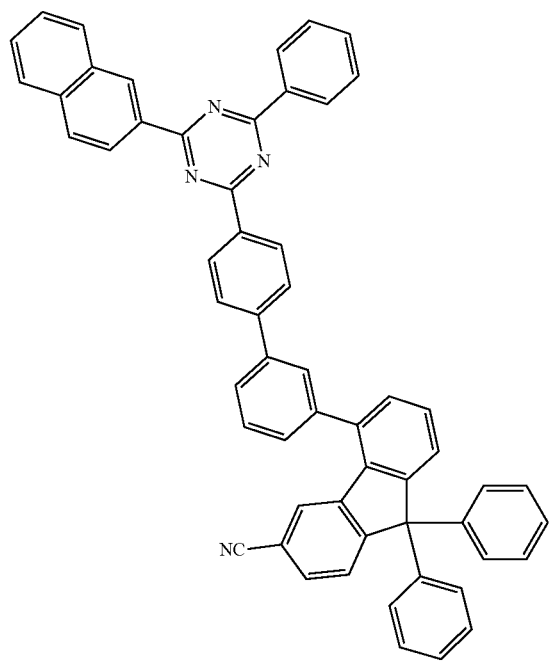
382
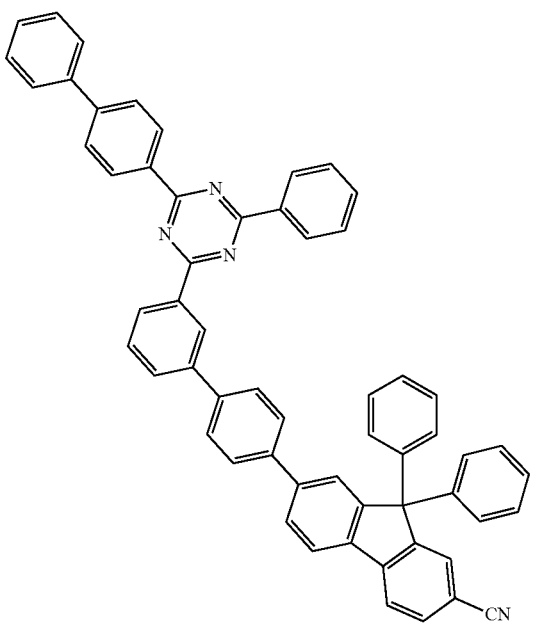
381
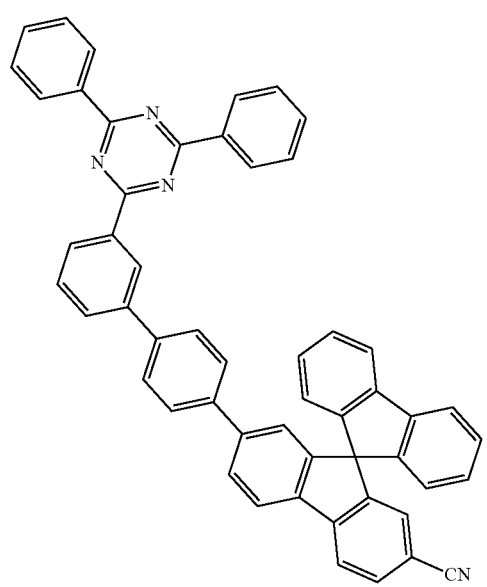
383
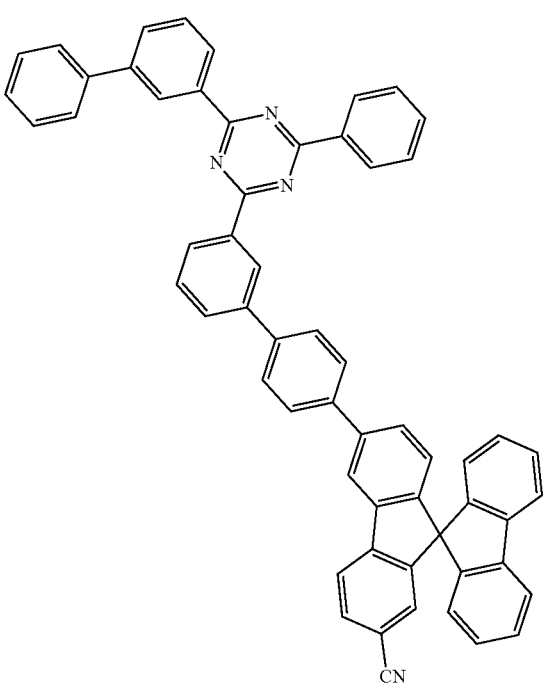

-continued
384
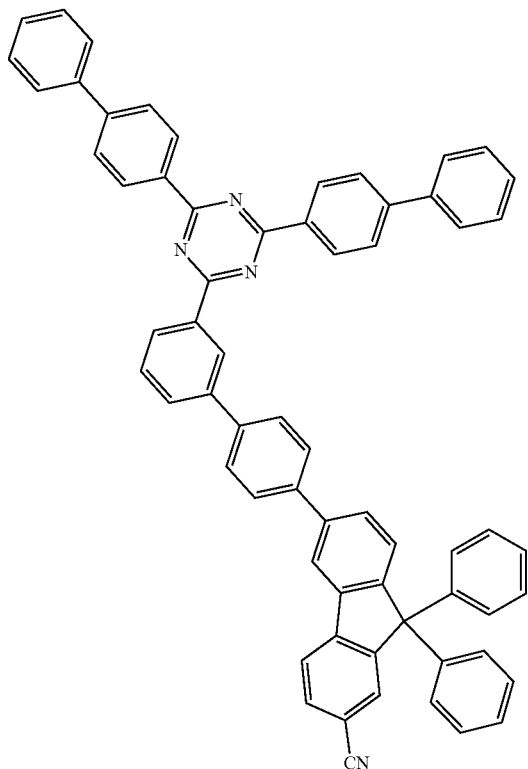
385
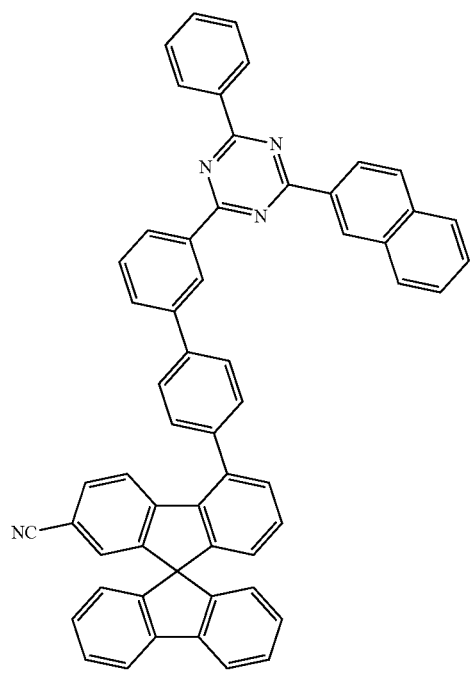
-continued
386
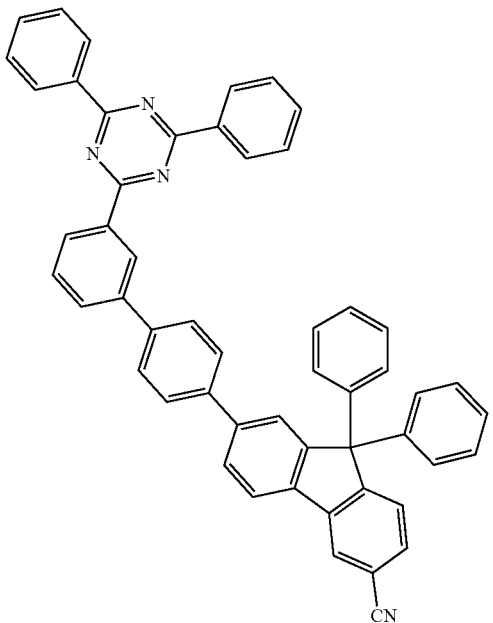
387
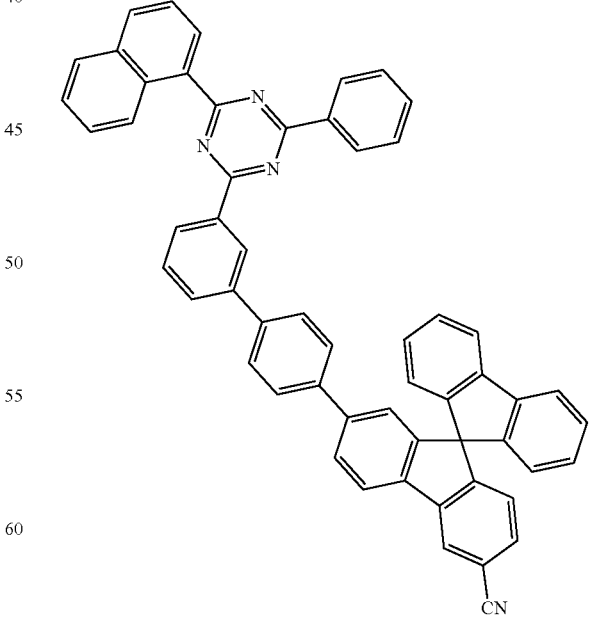

388
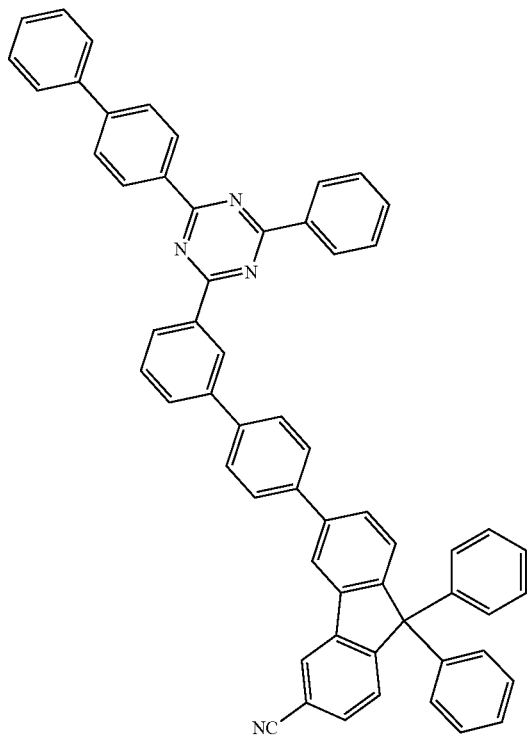
389
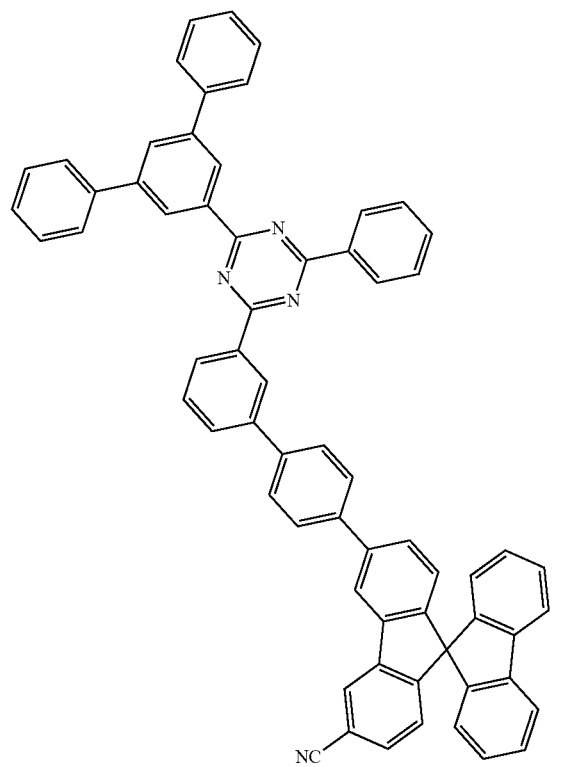
390
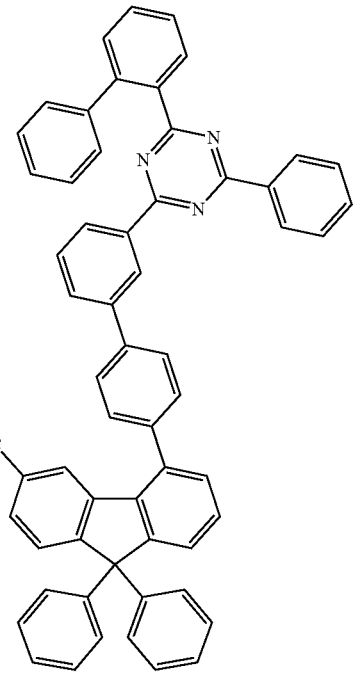
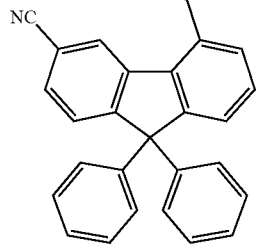
391
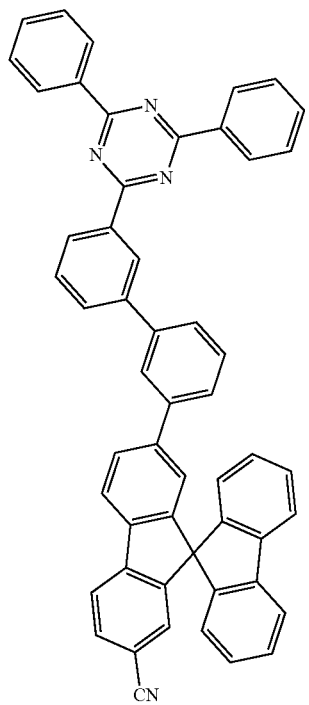

392
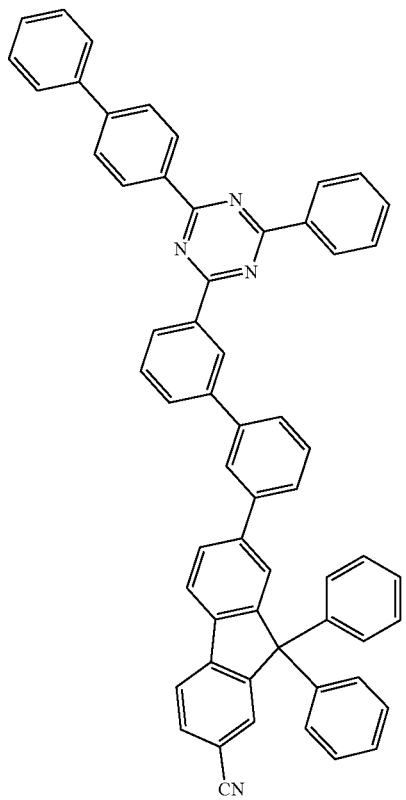
393
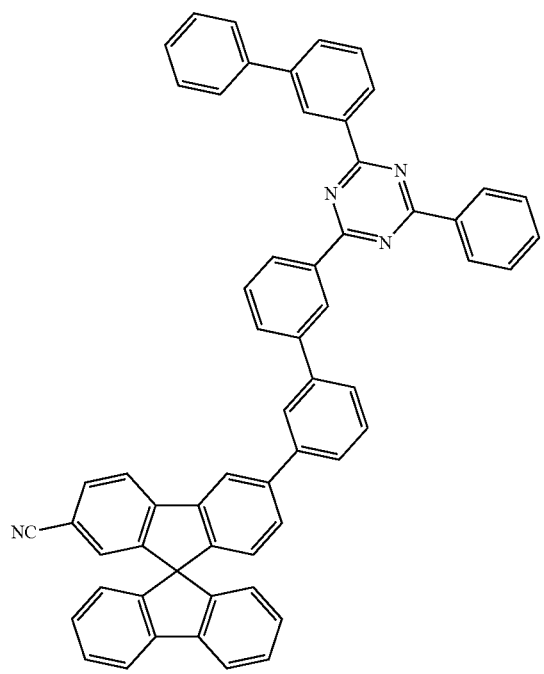
394
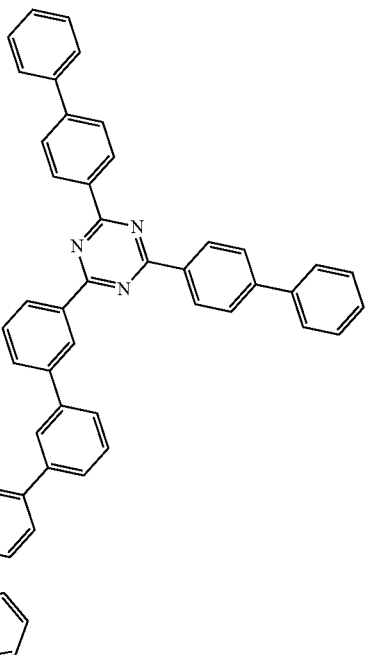
395
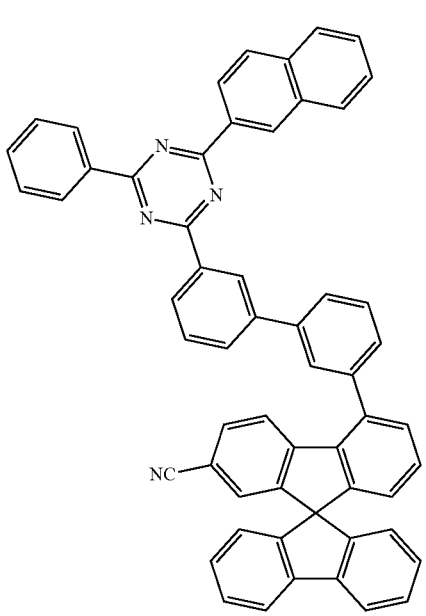

173
-continued
396
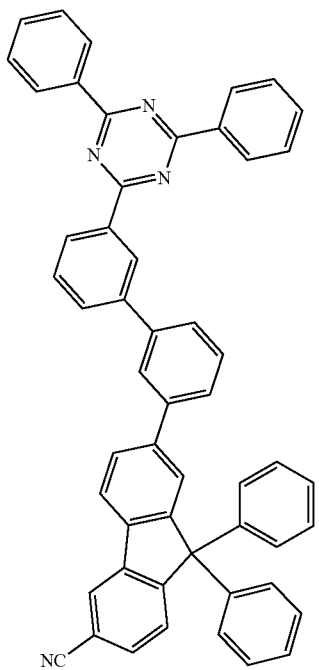
397
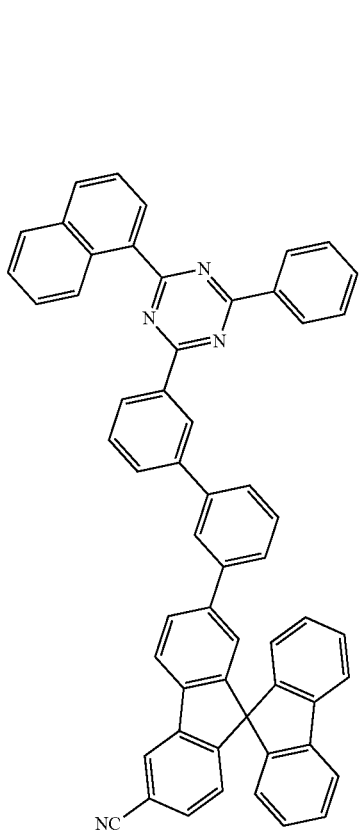
174
-continued
398
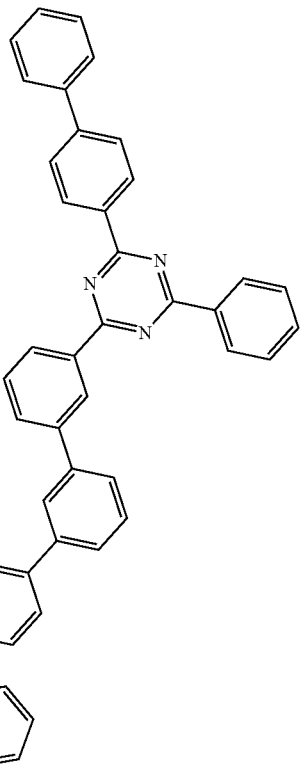
399
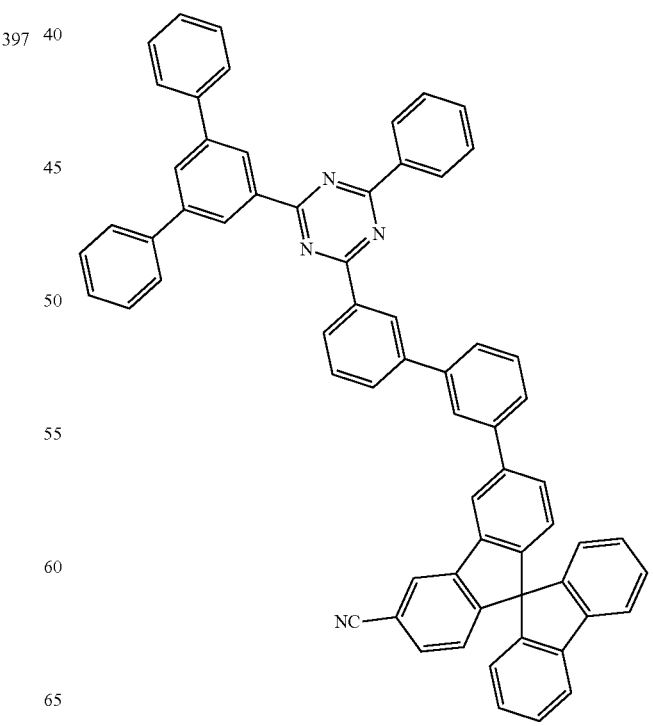

175
-continued
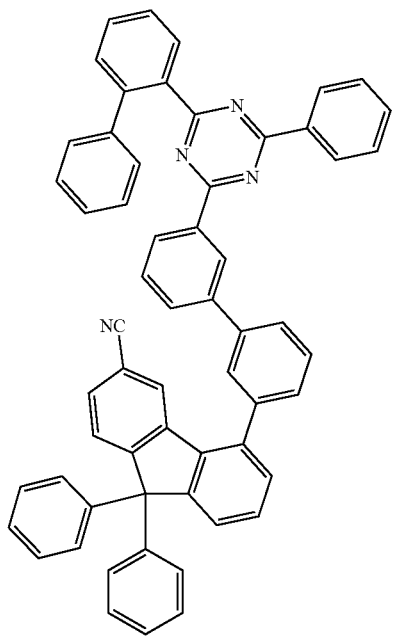
400
176
-continued
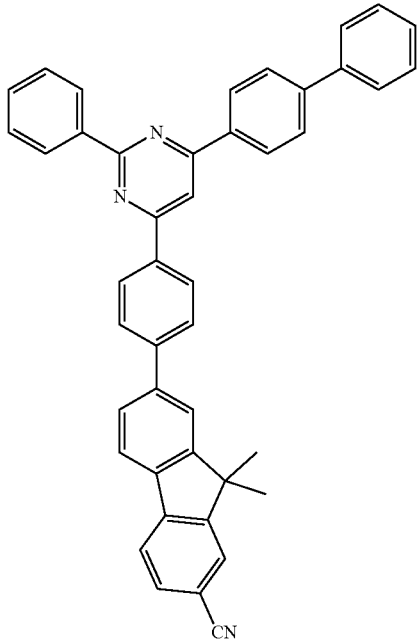
402
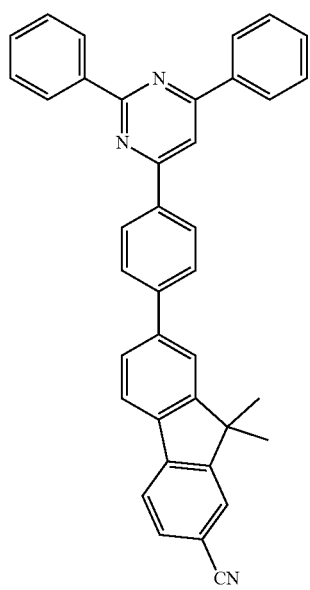
401
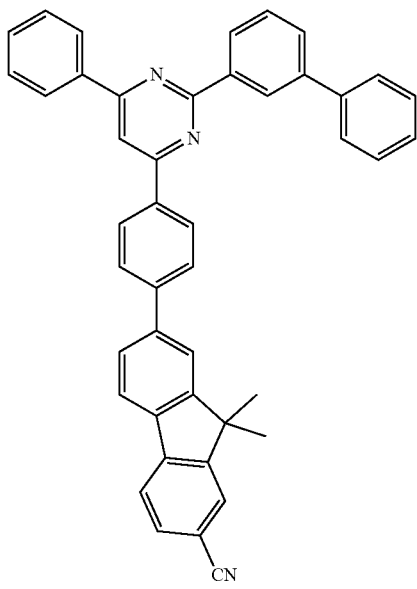
403

-continued
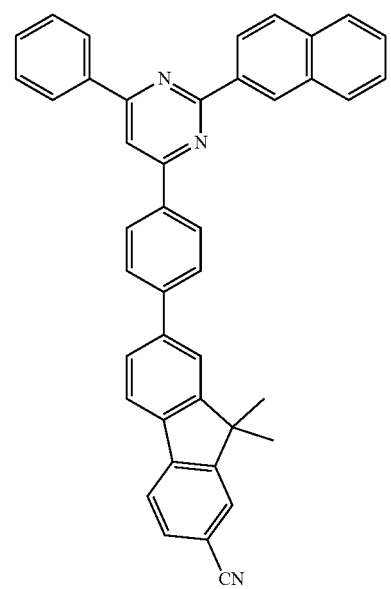
404
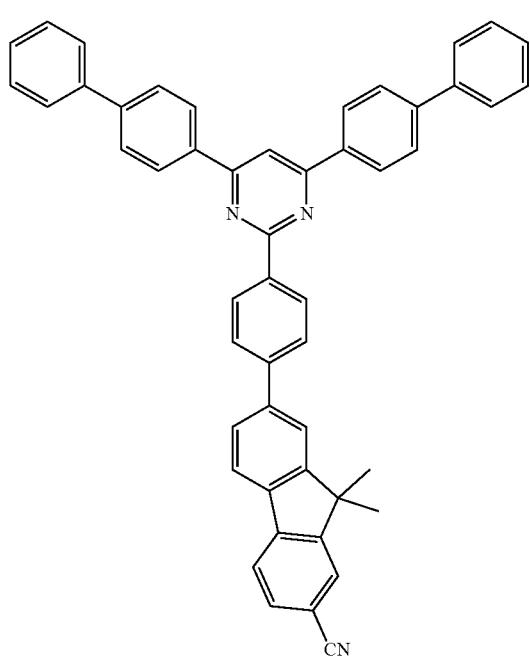
405
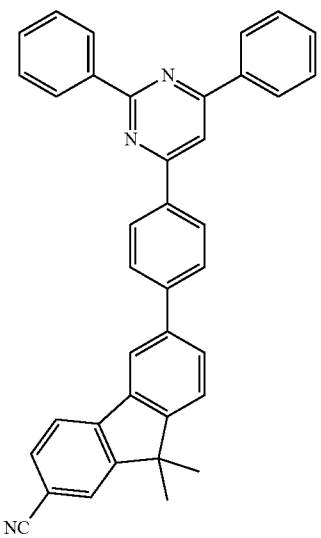
406
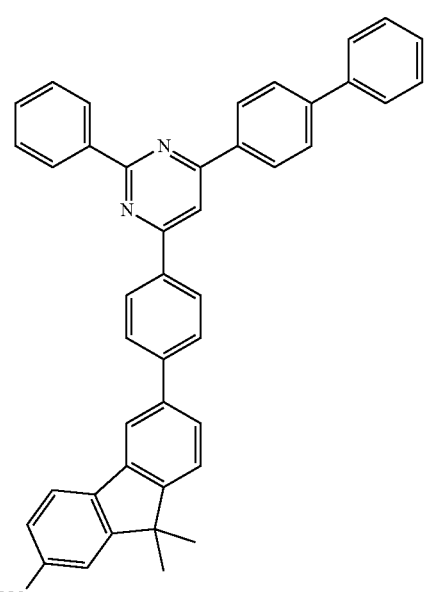
407
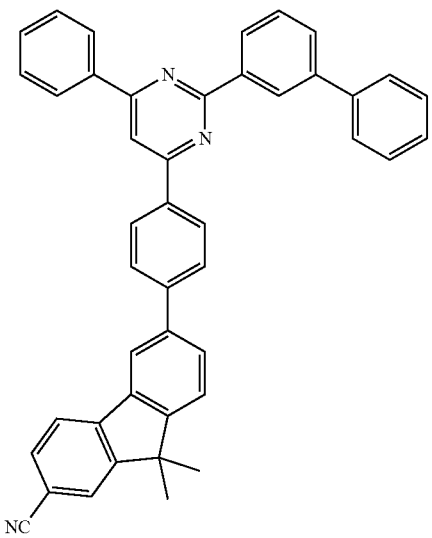
408

409
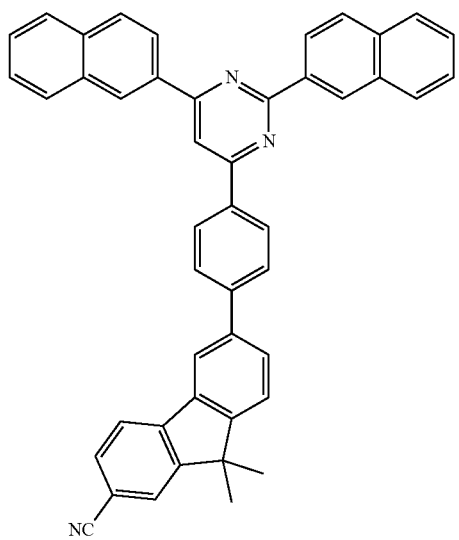
410
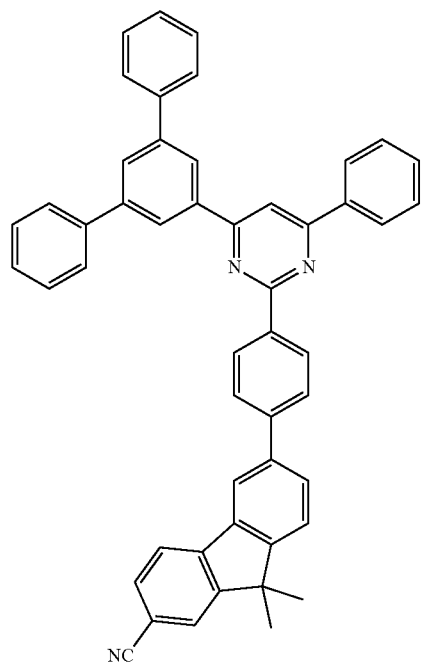
411
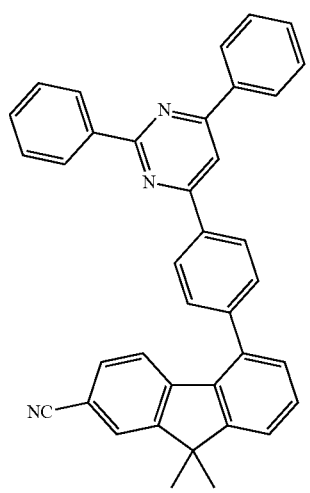
412
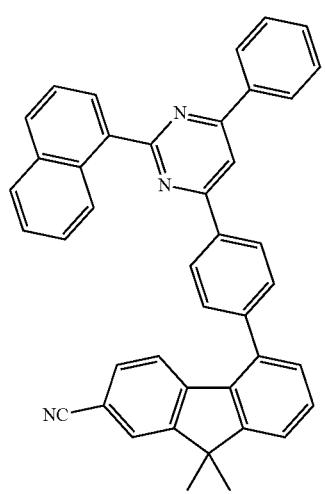
413
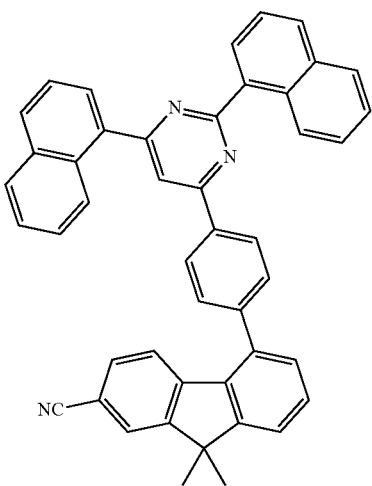

181
-continued
414
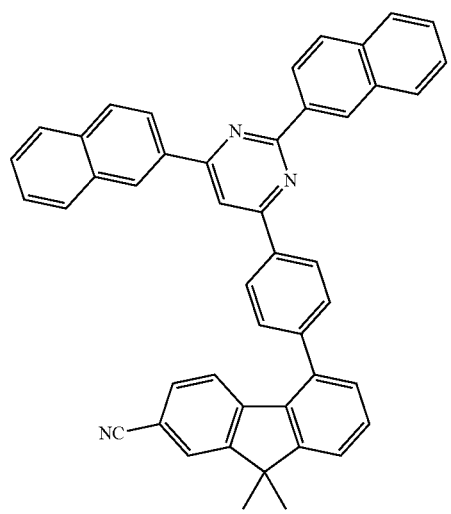
415
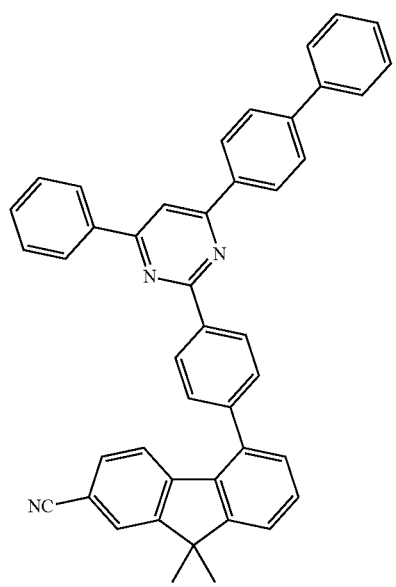
416
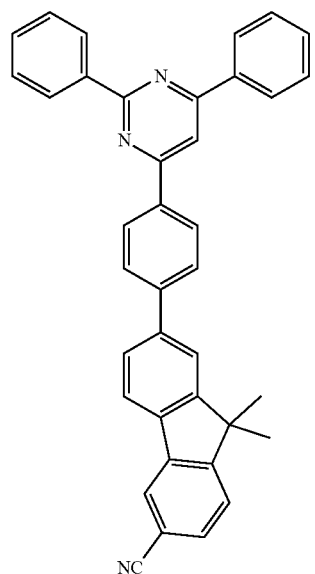
182
-continued
417
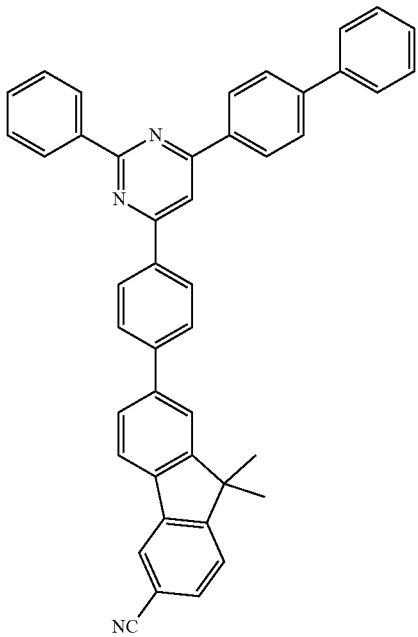
418
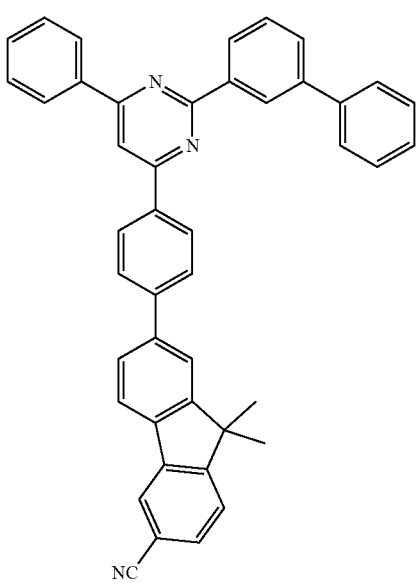

419
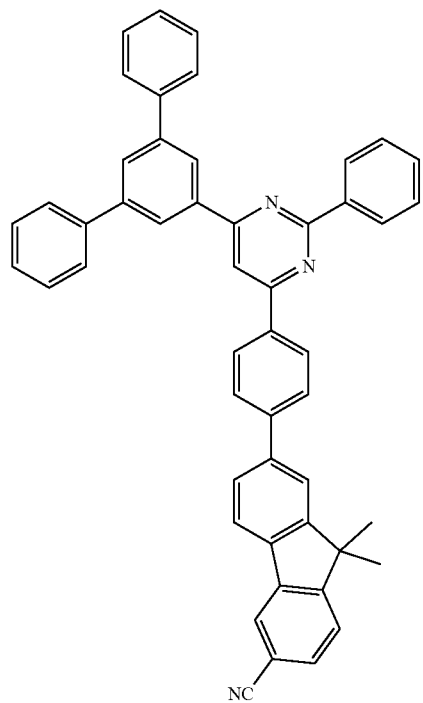
420
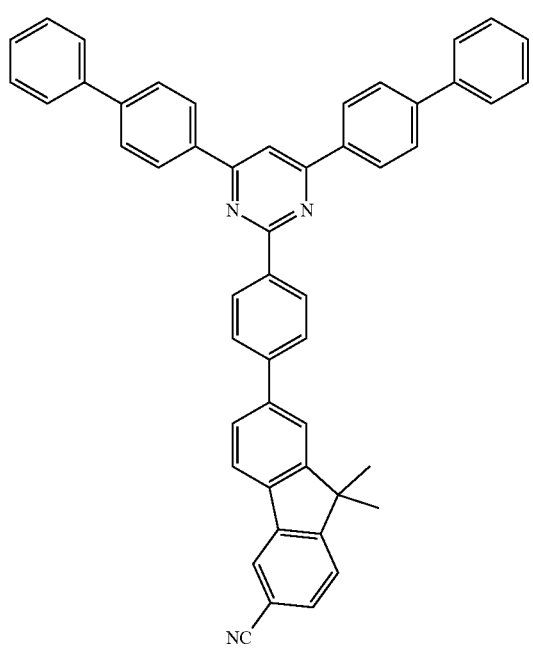
421
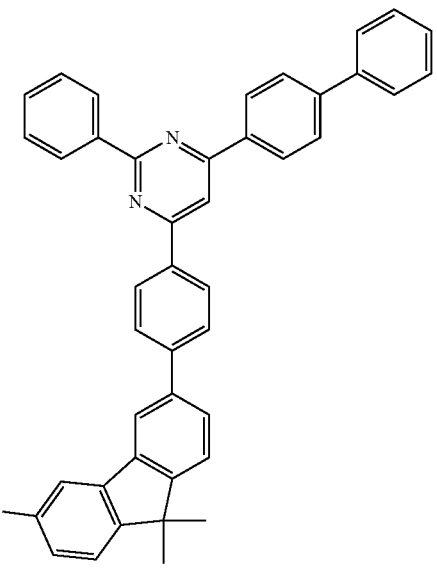
421
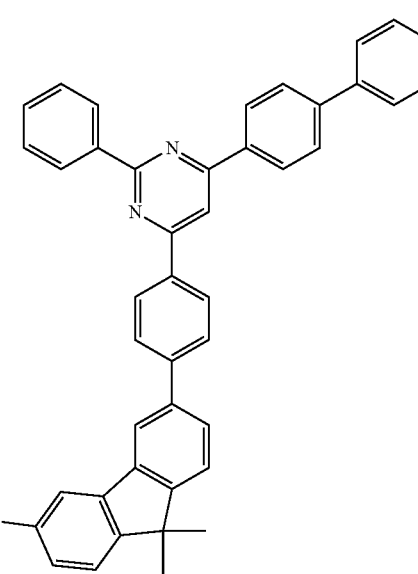
422
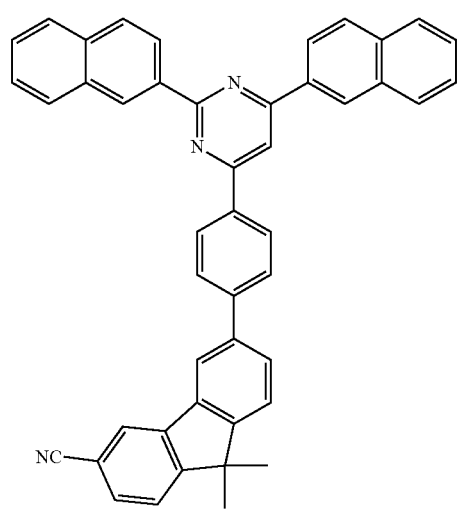

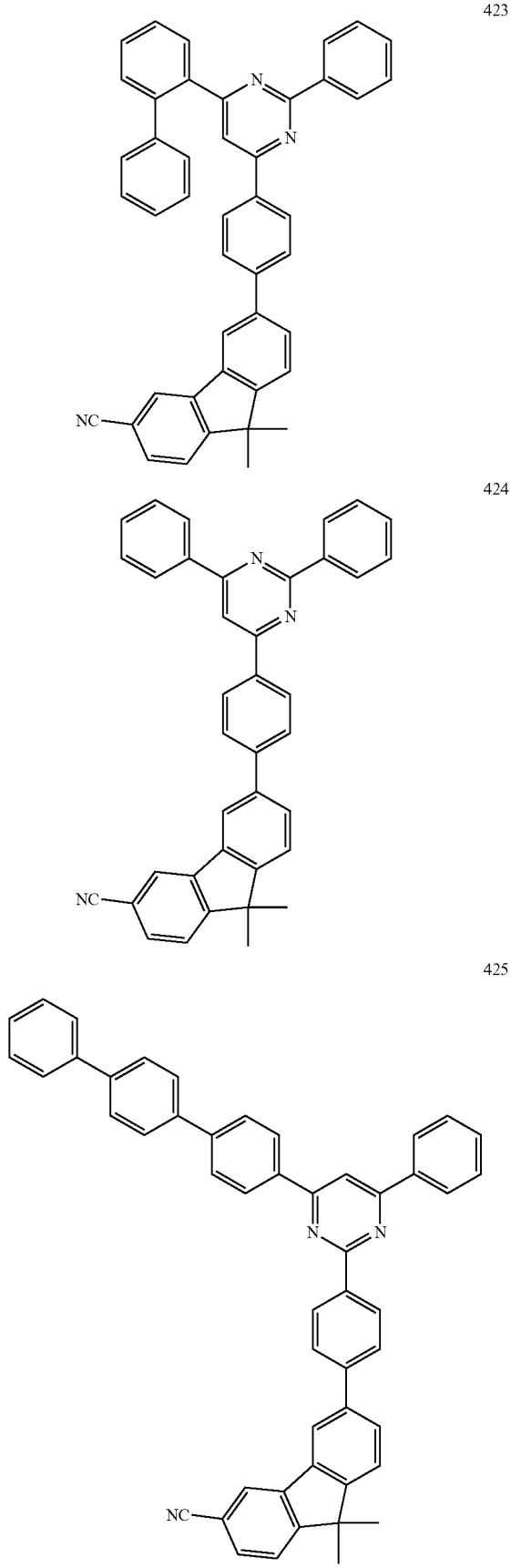
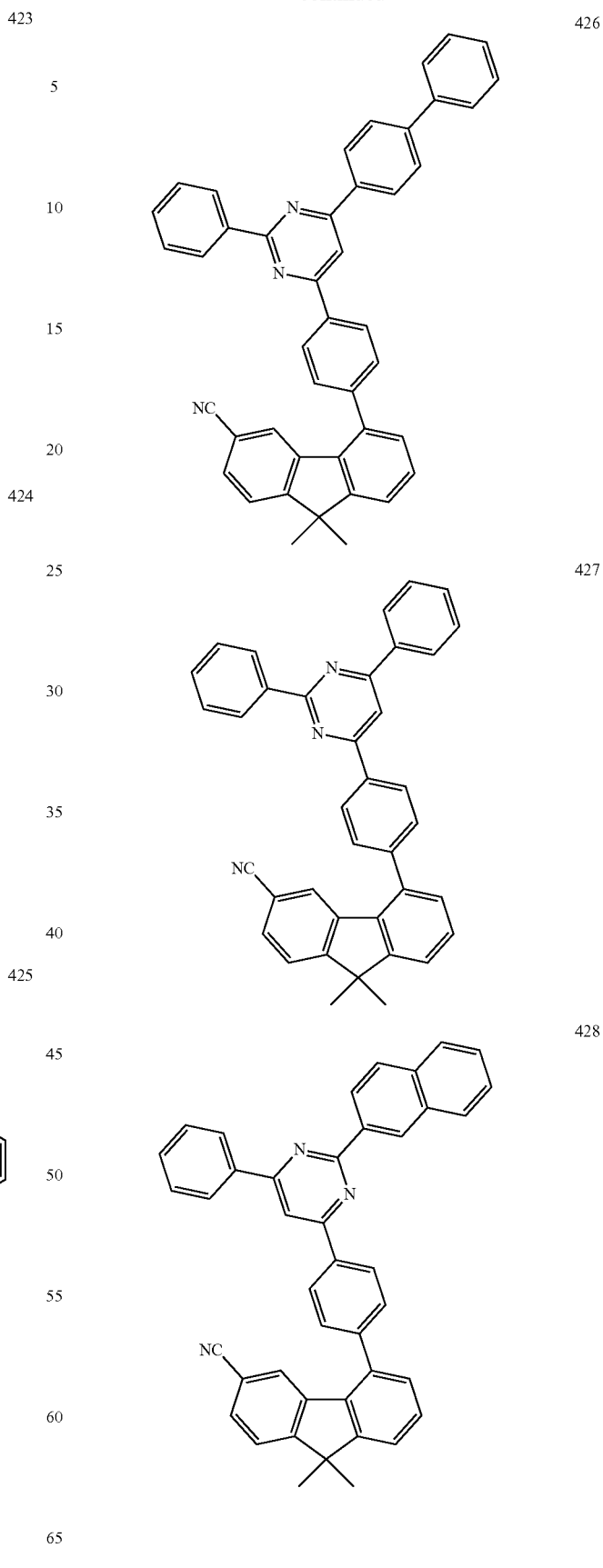

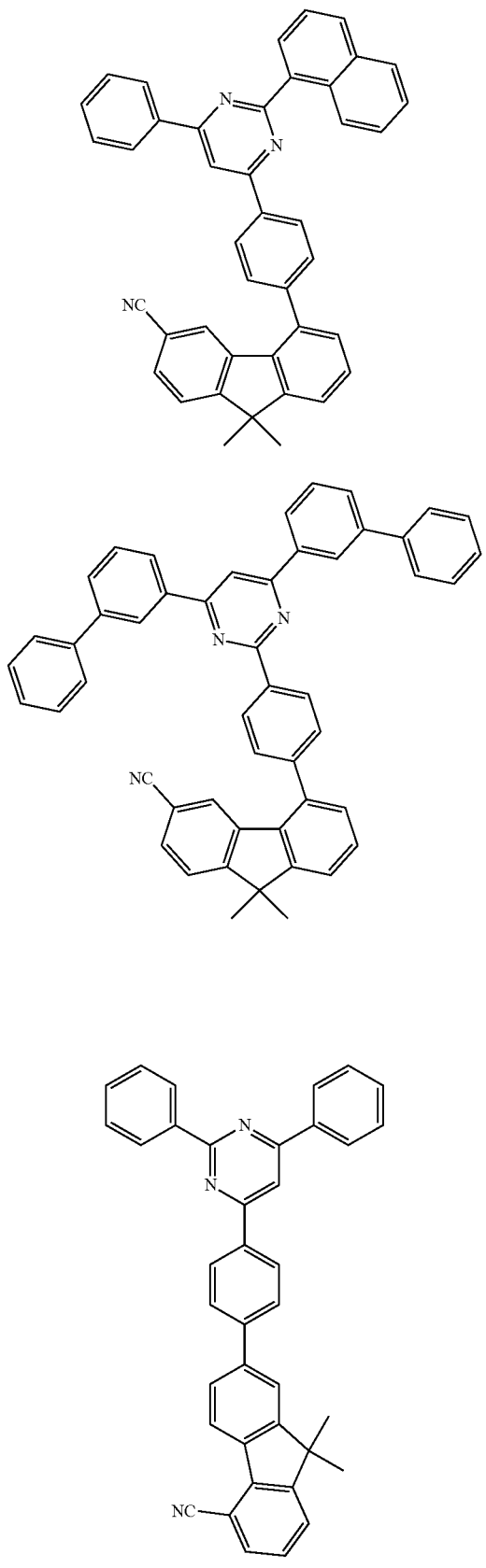
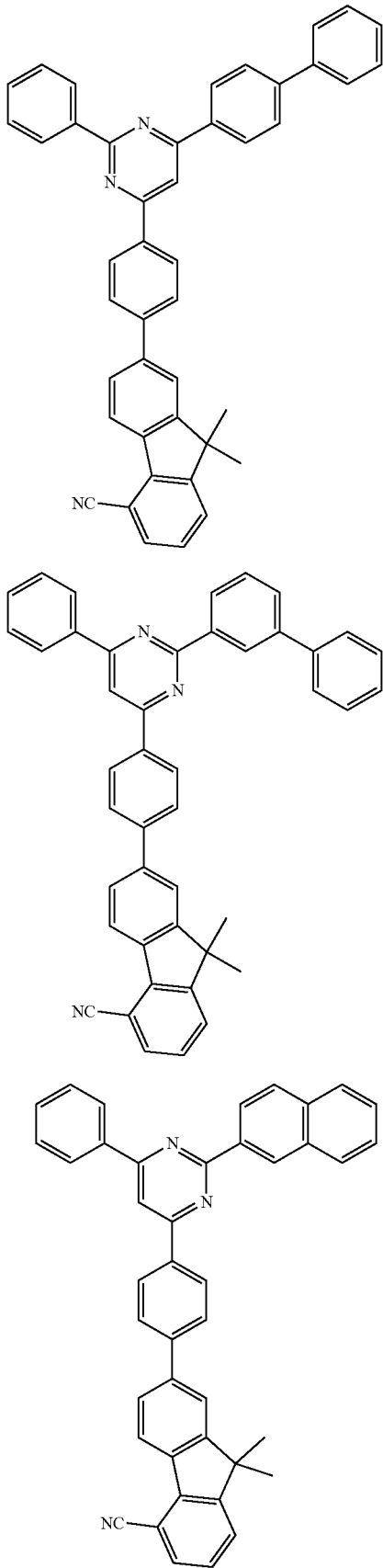

189
-continued
435
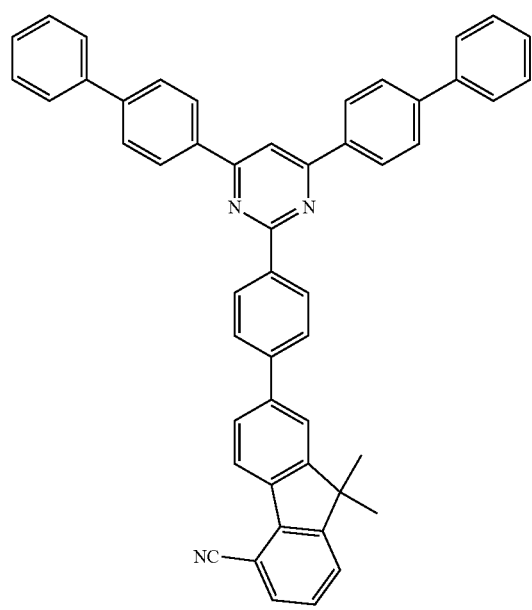
436
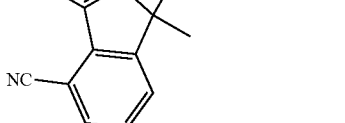
190
-continued
437
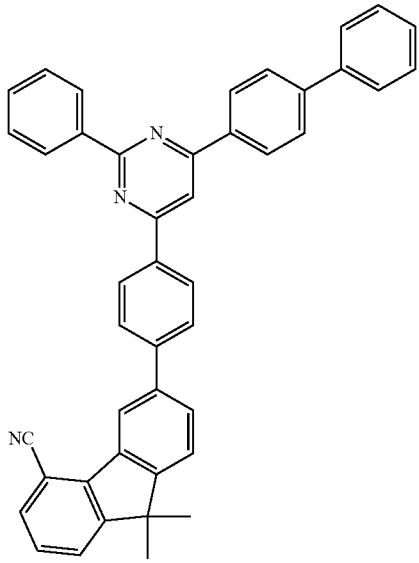
438
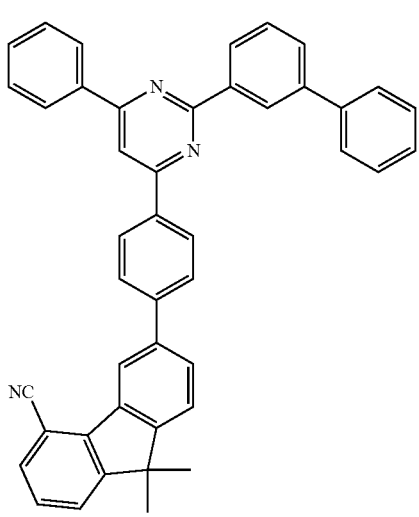
439
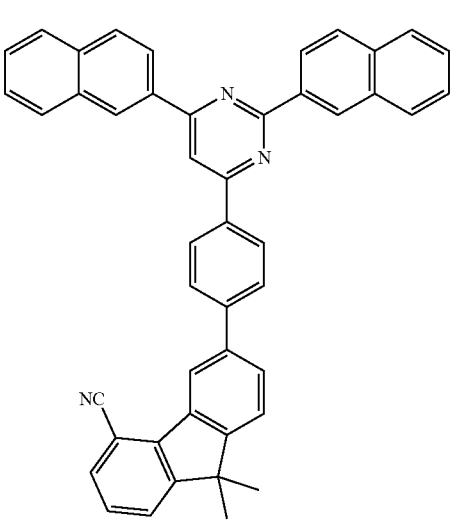

440
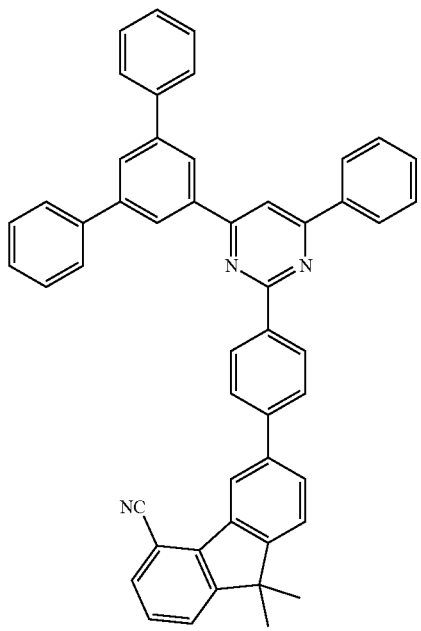
441
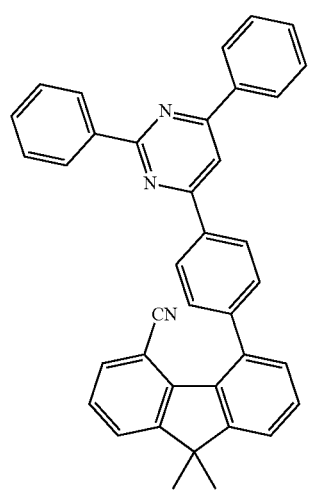
442
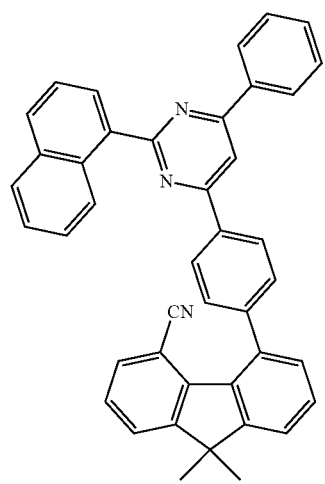
443
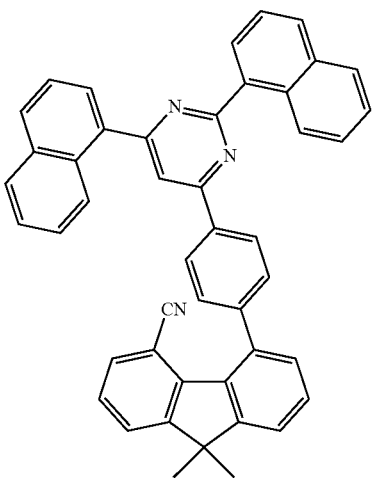
444
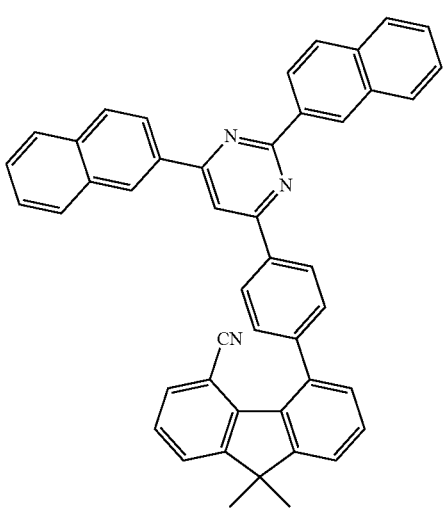
445
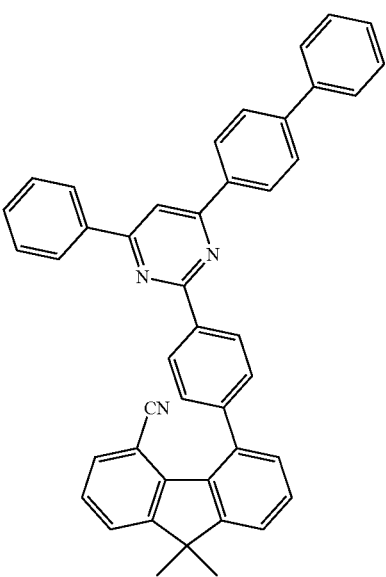

446 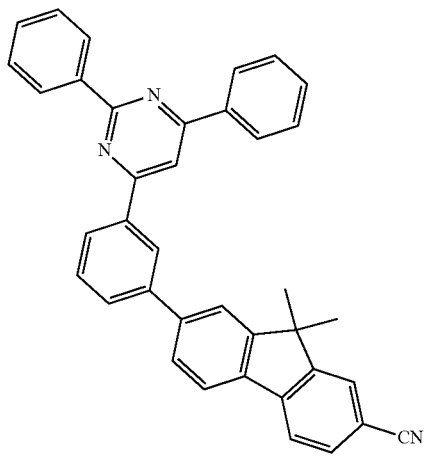
447 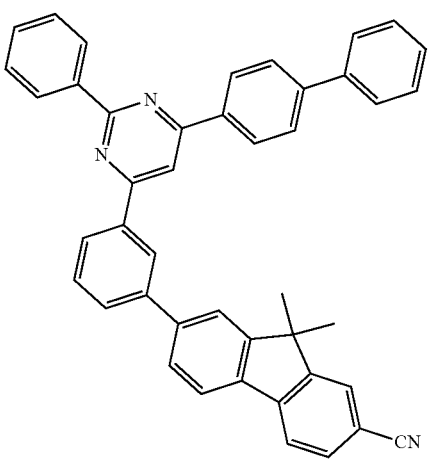
448 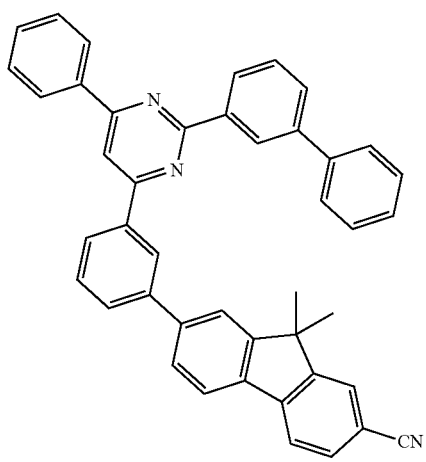
449 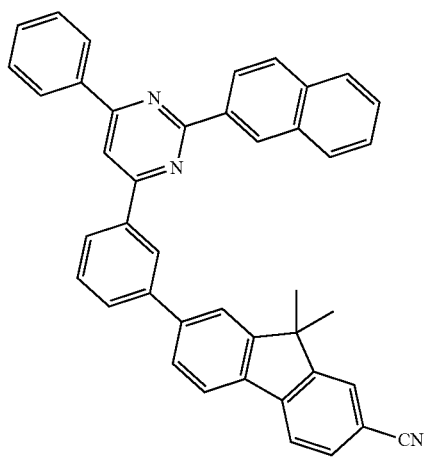
450
451 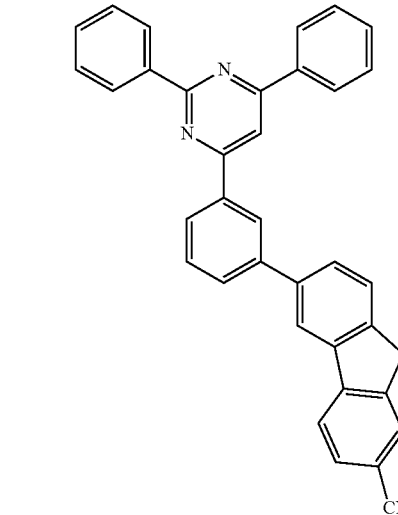

452
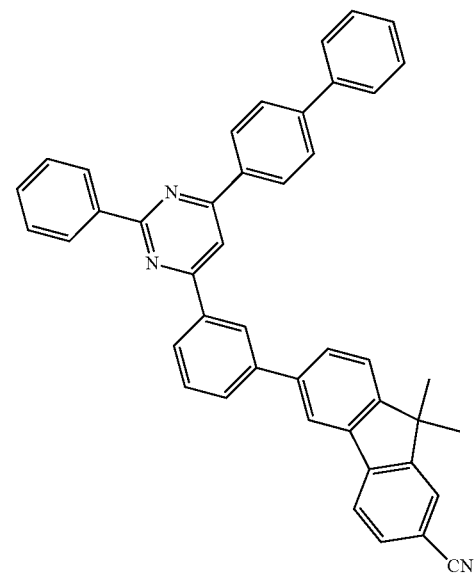
453
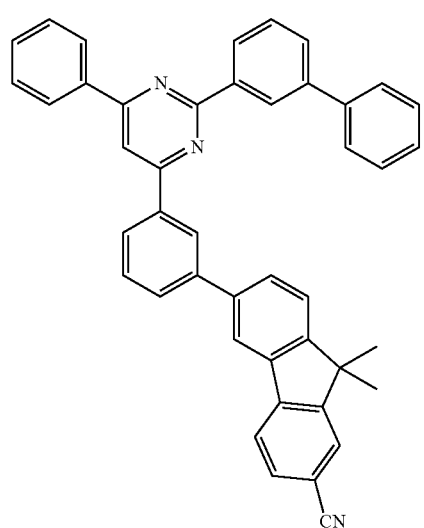
454
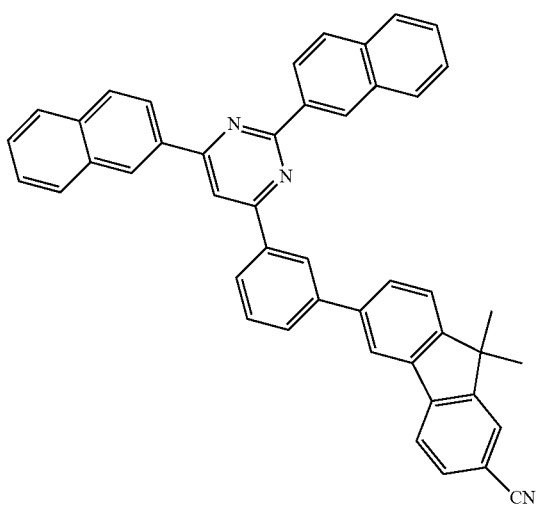
455
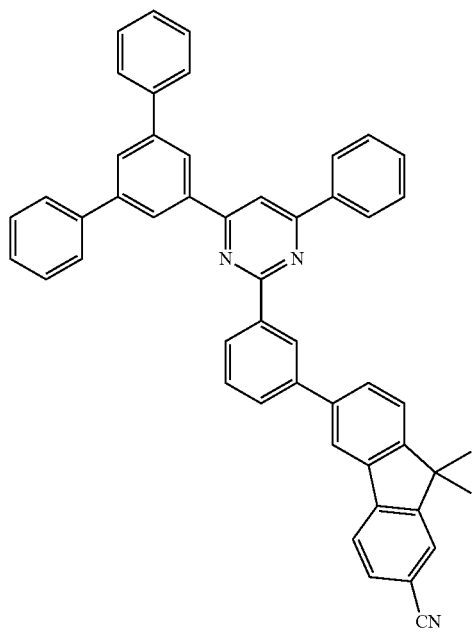
456
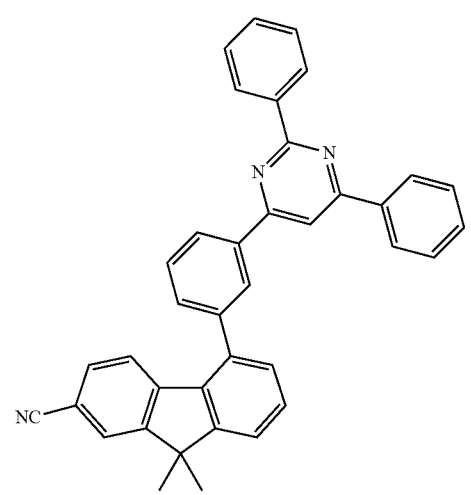
457
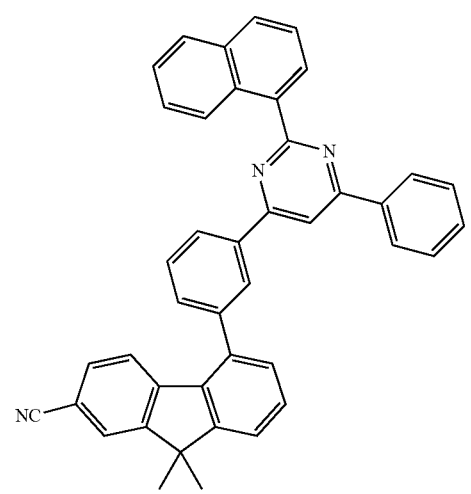

458
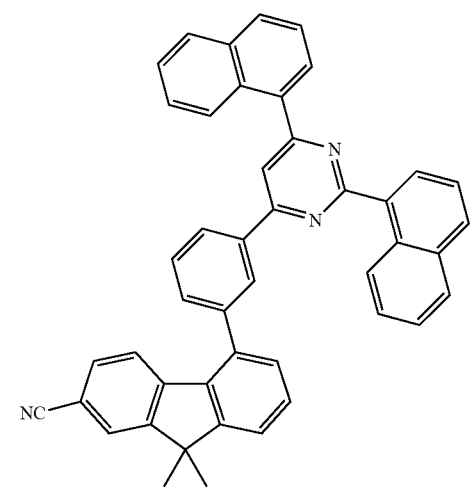
459
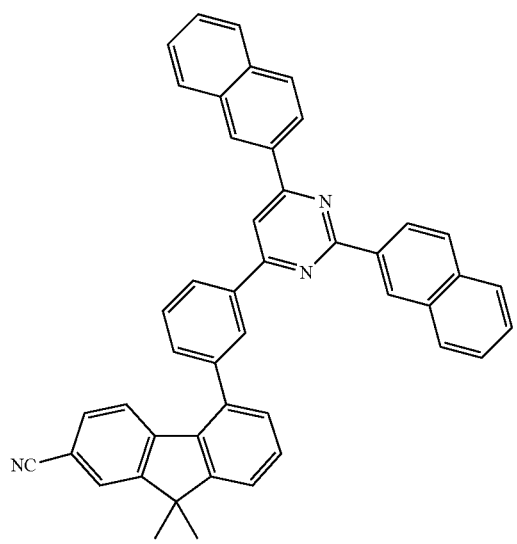
460
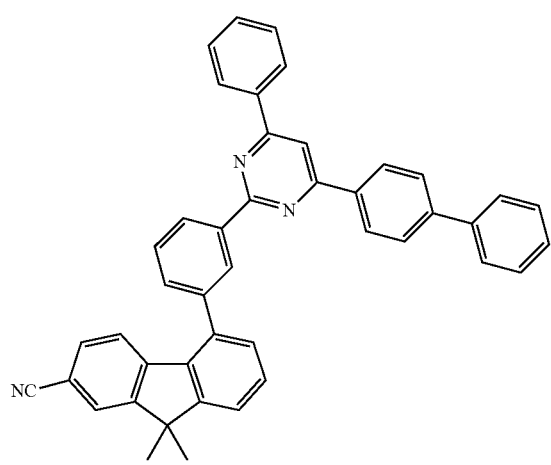
461
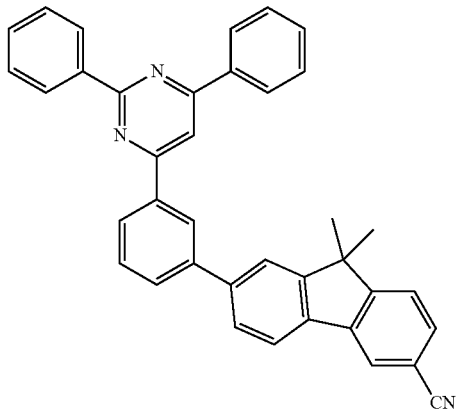
462
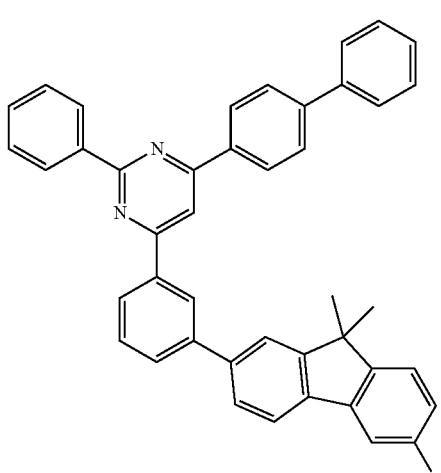
463
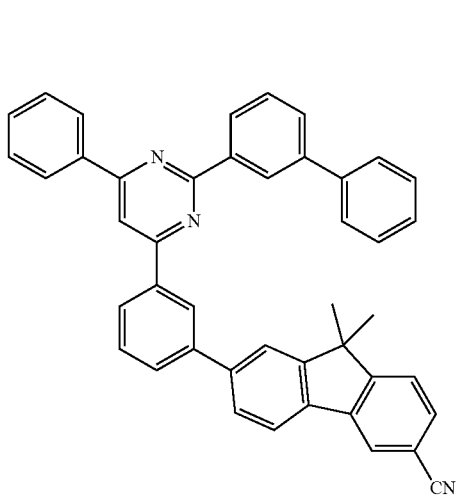

464
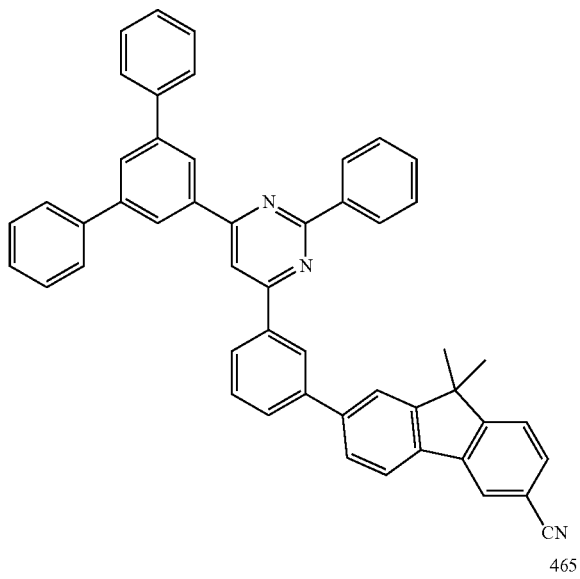
465
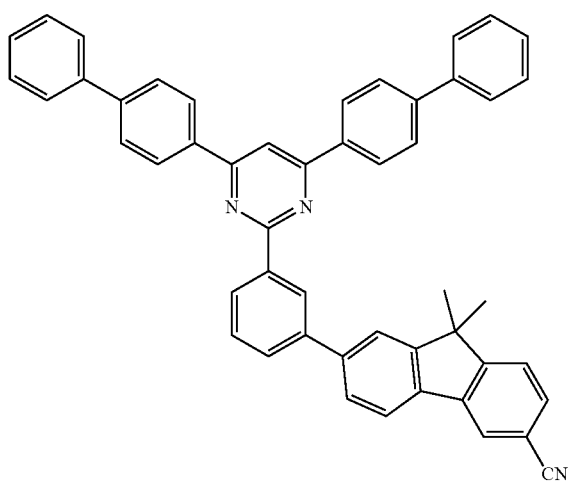
466
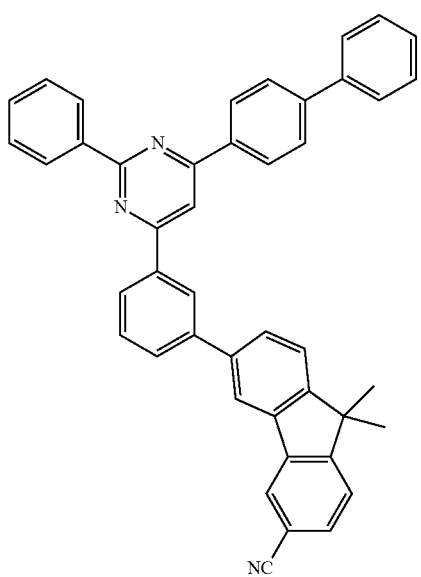
467
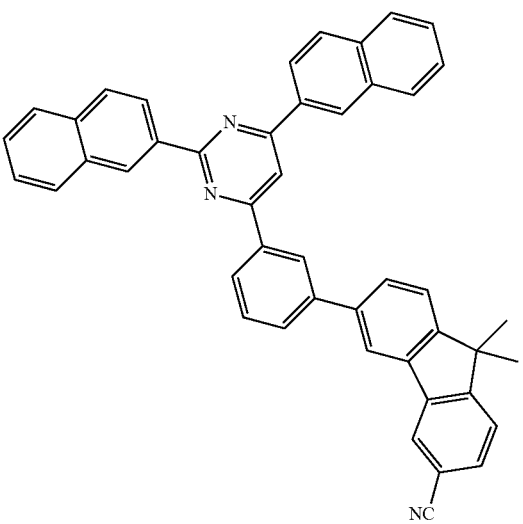
468
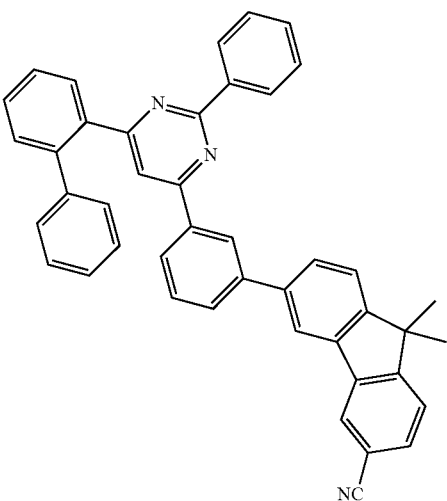
469
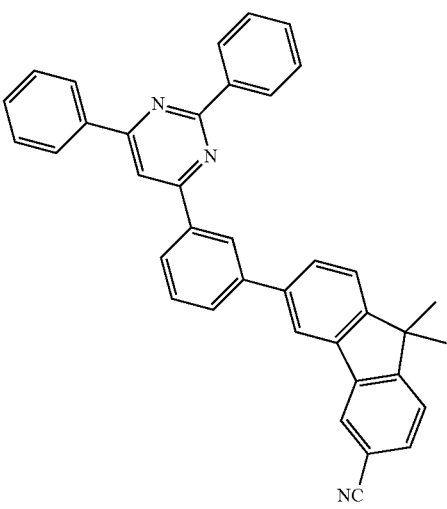

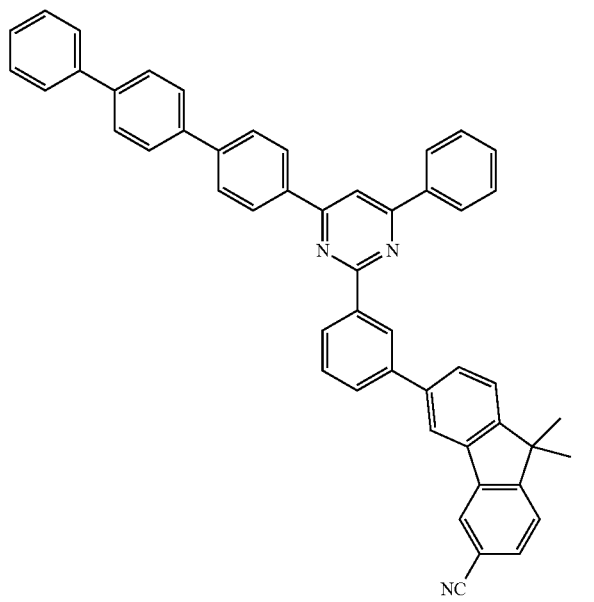
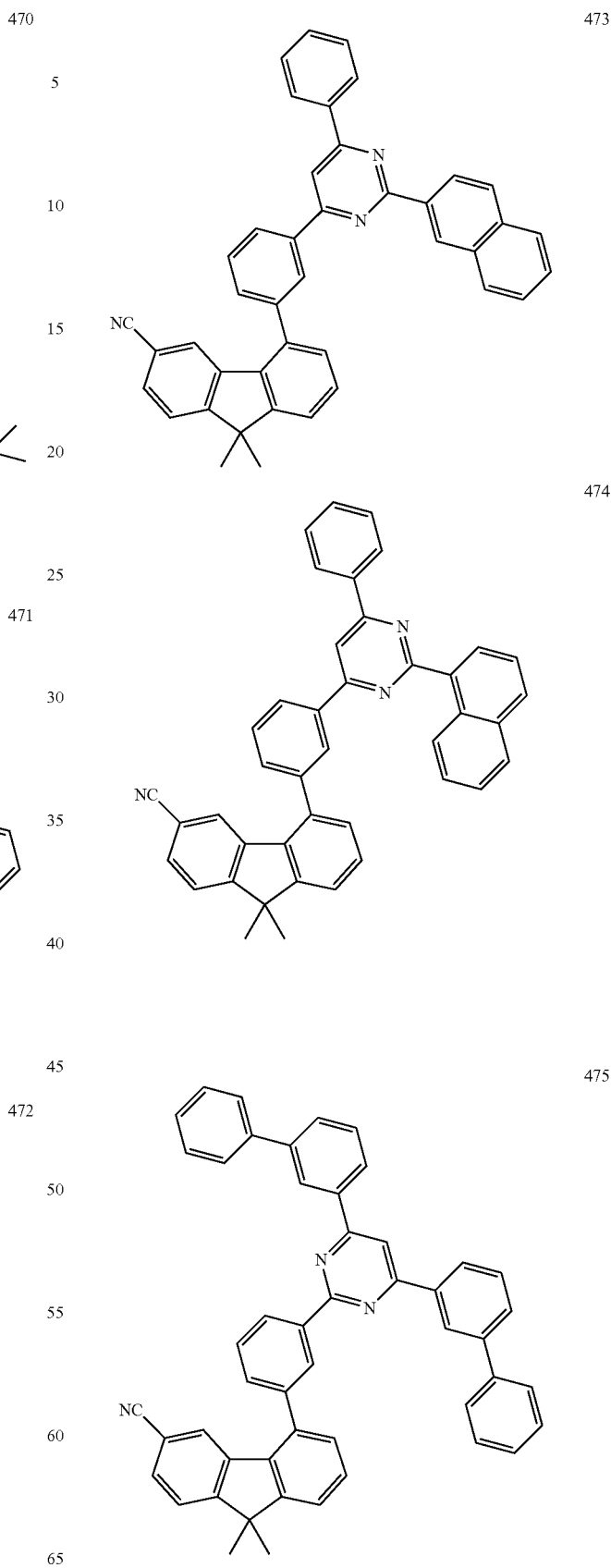

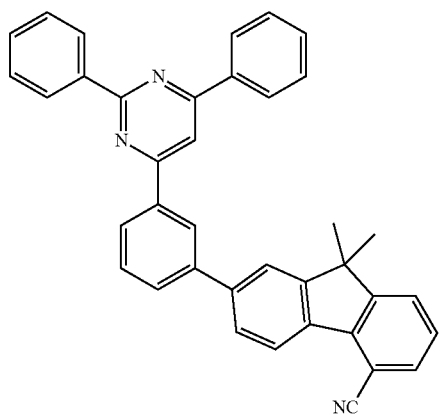
476
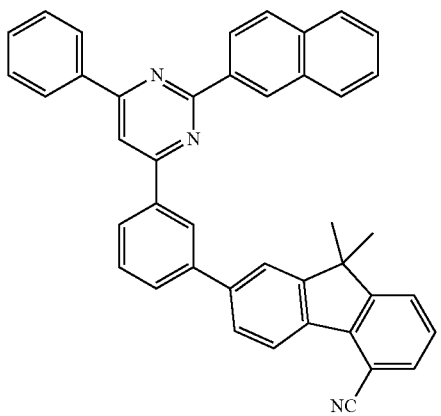
479
477
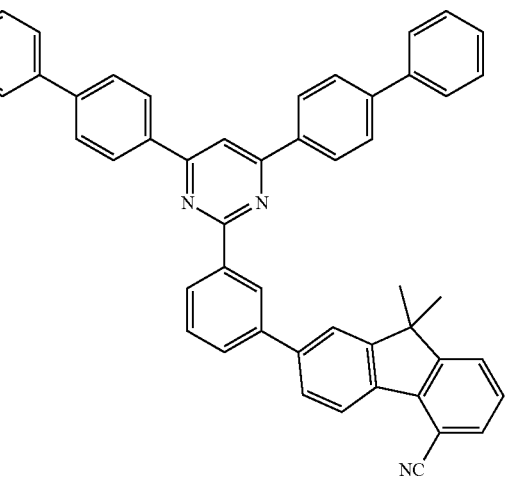
480
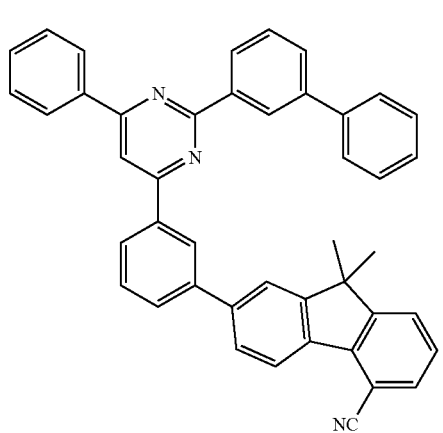
478
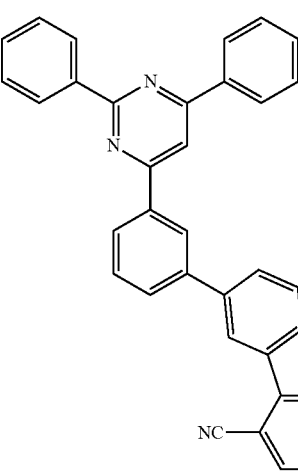
481

-continued
482
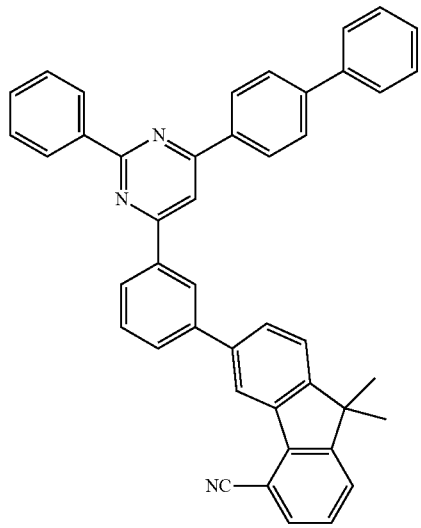
483
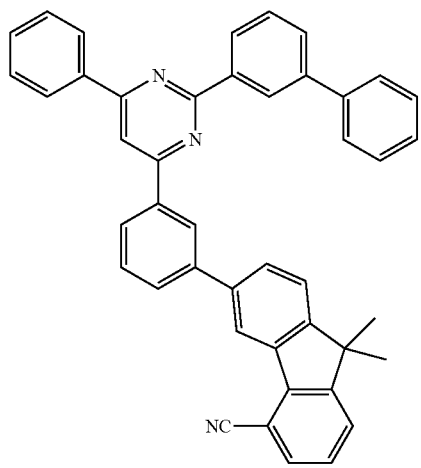
484
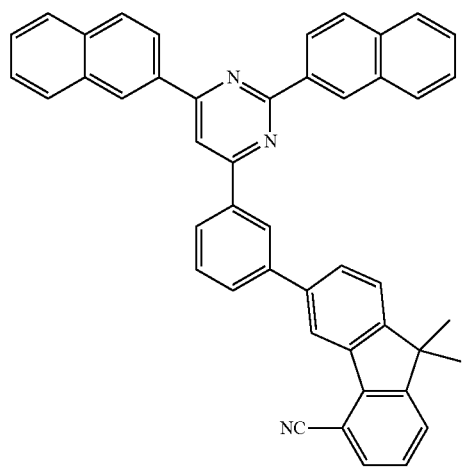
-continued
485
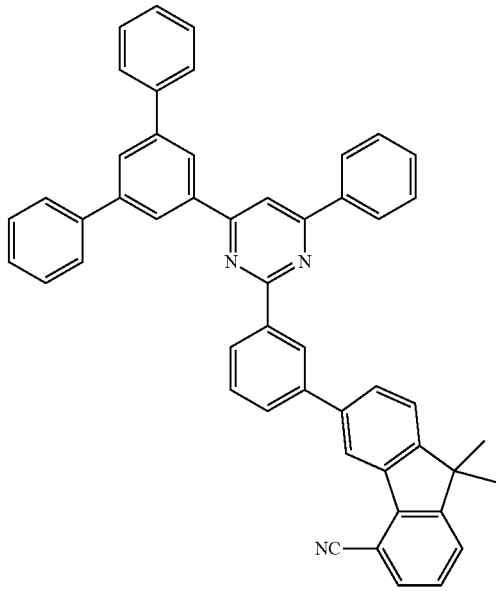
486
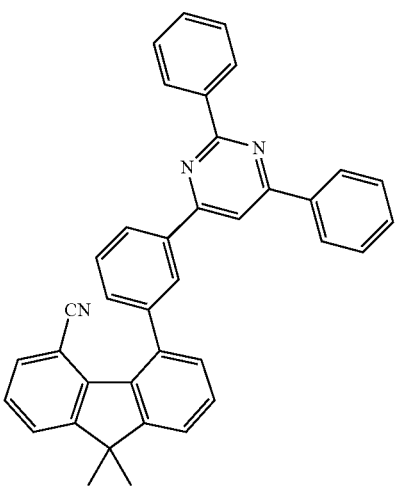
487
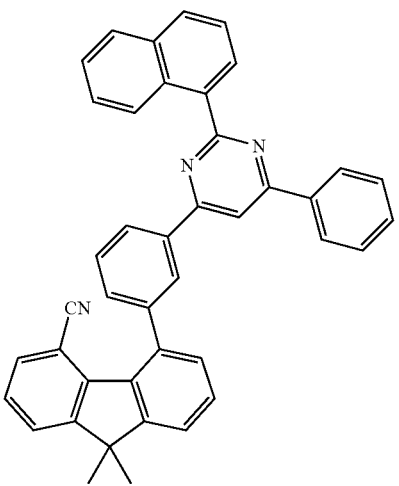

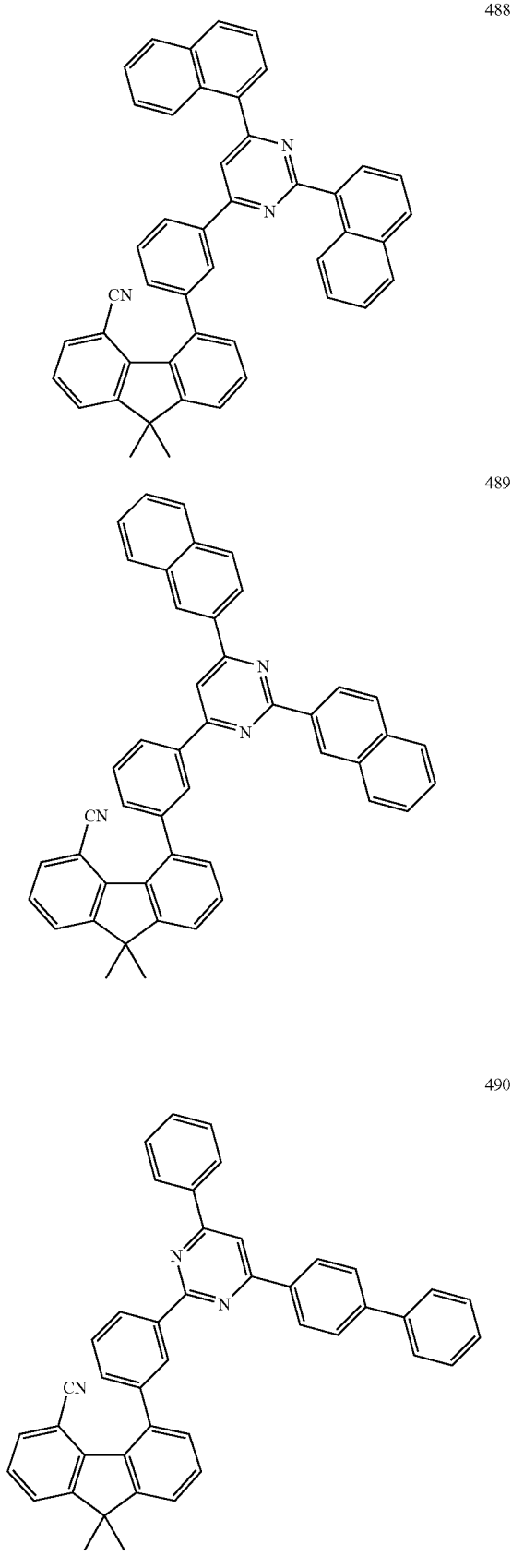
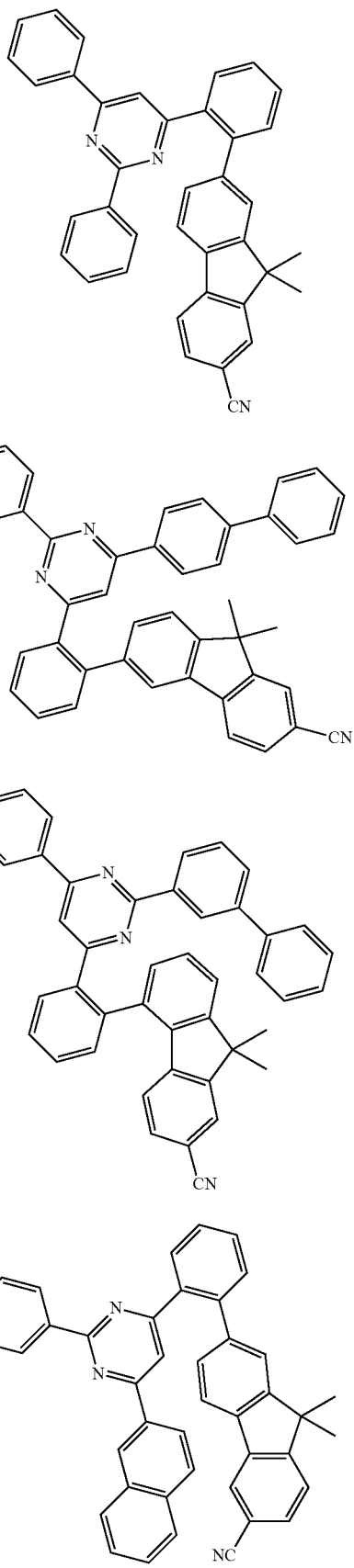

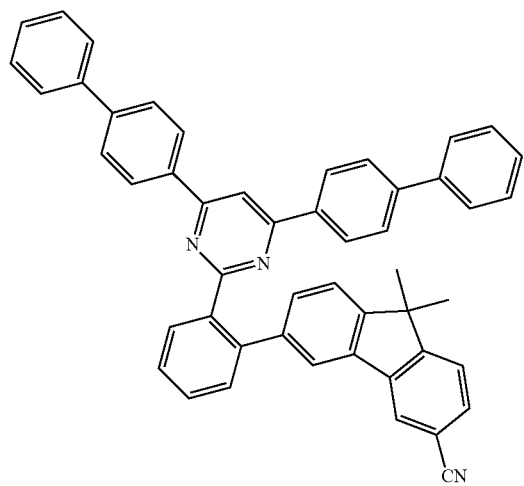
495
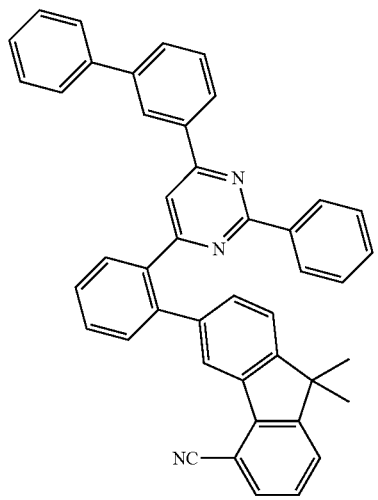
498
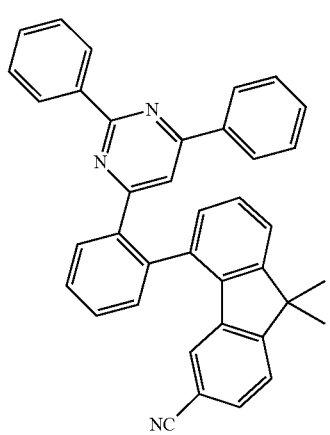
496
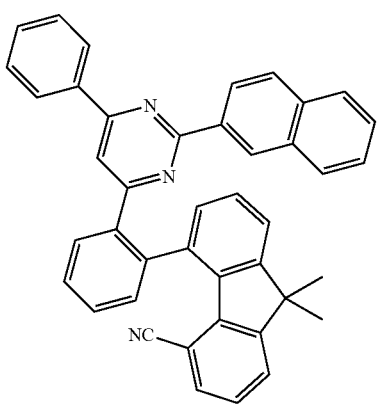
499
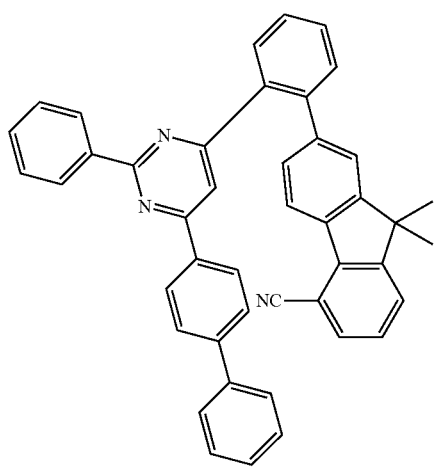
497
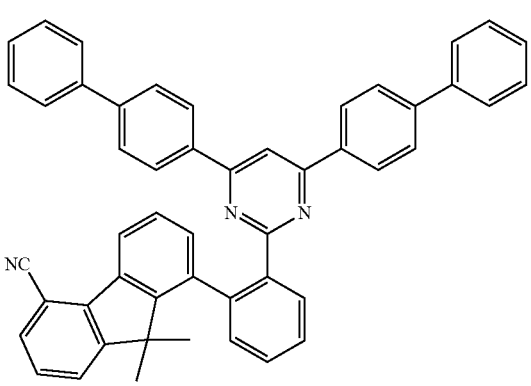
500

211
-continued
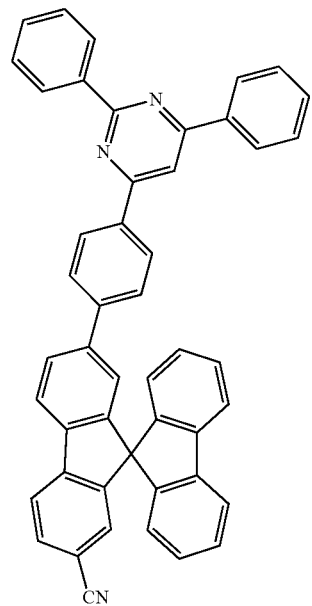
501
212
-continued
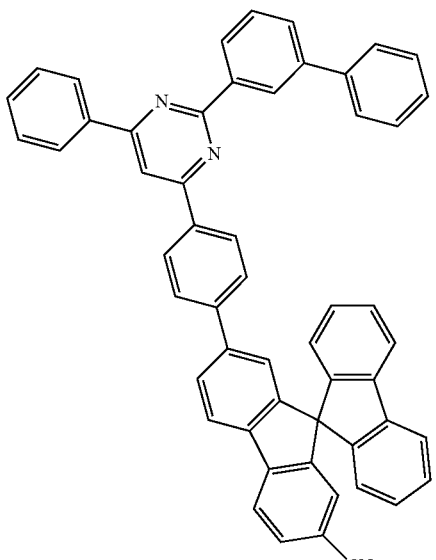
503
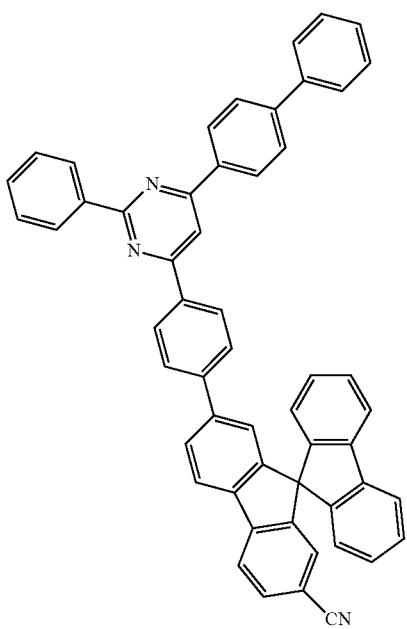
502
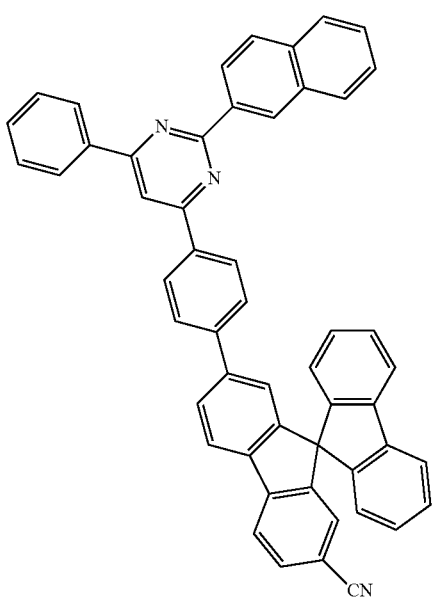
504

213 214
-continued -continued
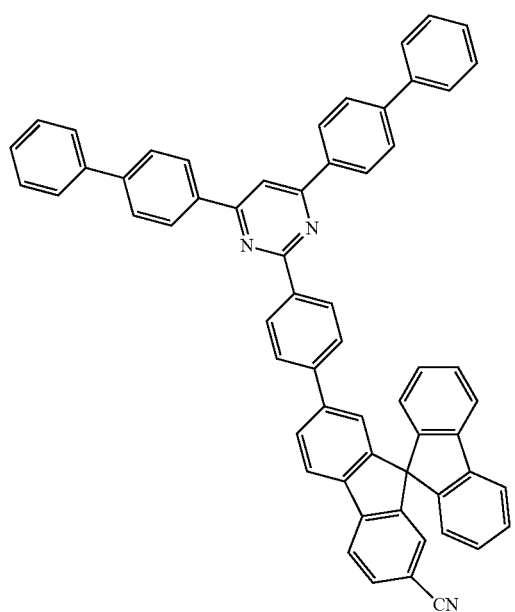
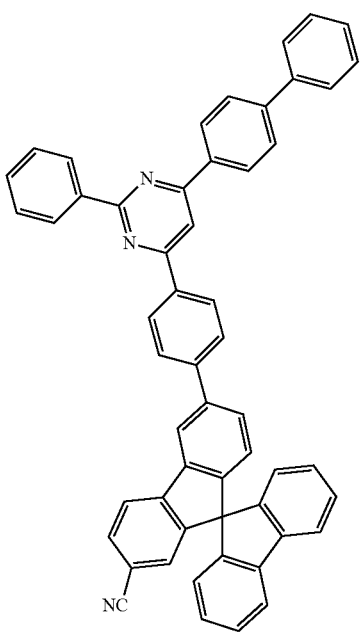

509
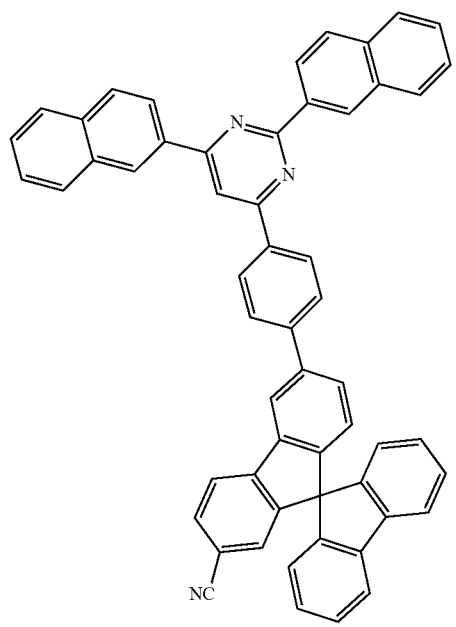
510
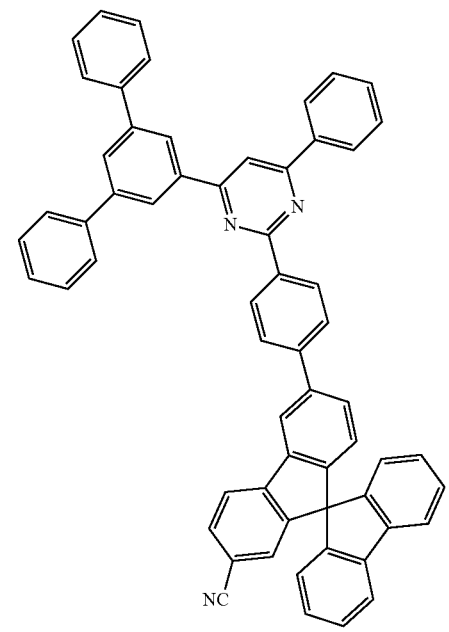
511
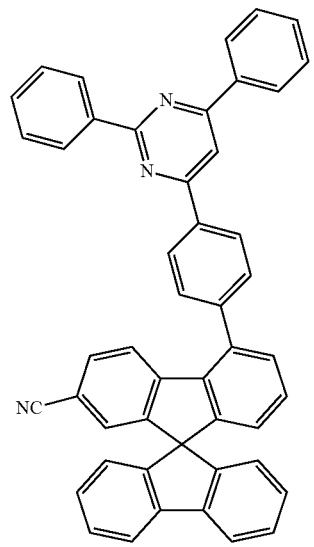
512
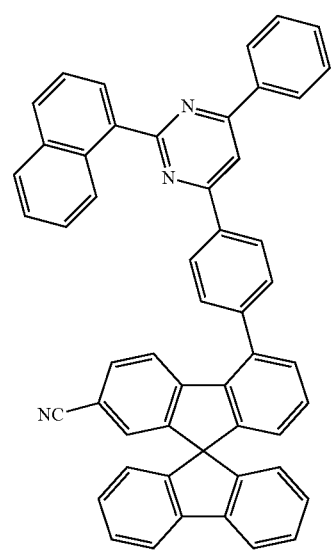
513
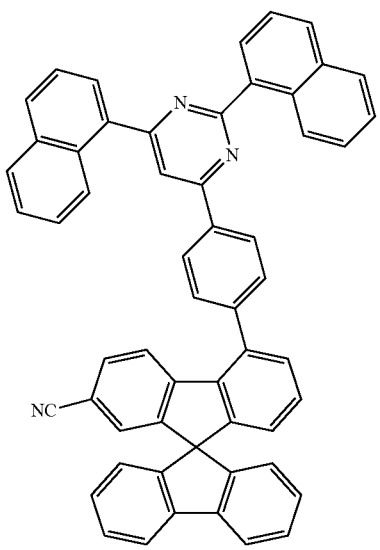

-continued
514
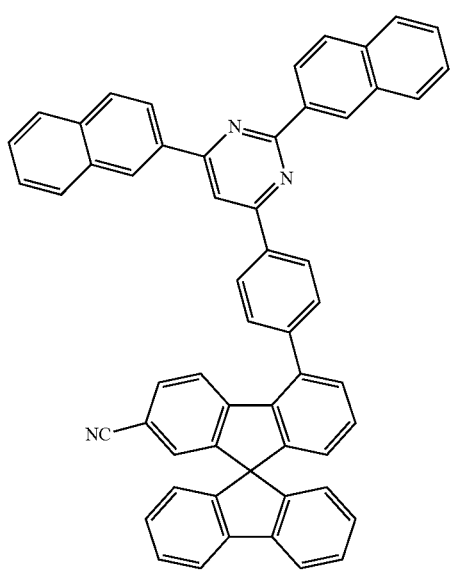
515
516
-continued
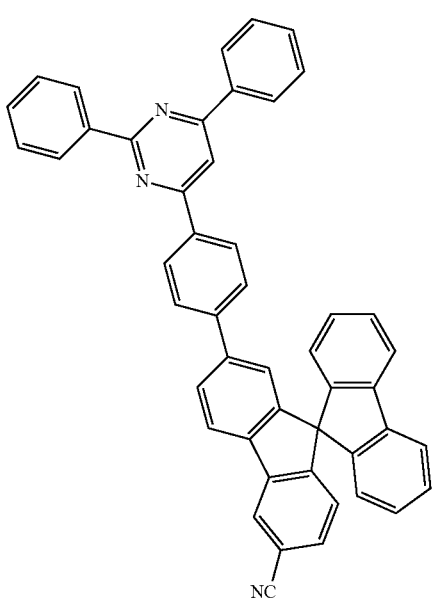
517

219
-continued
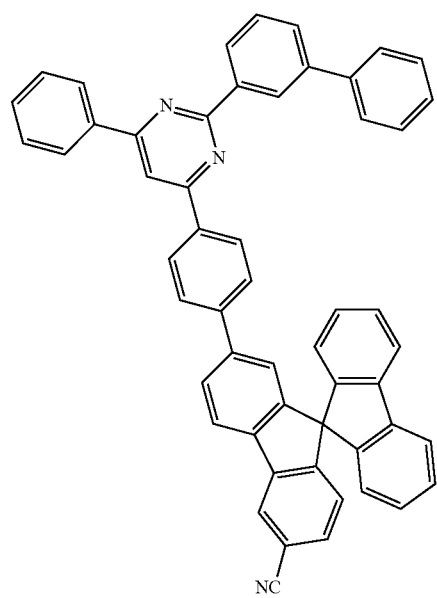
518
220
-continued
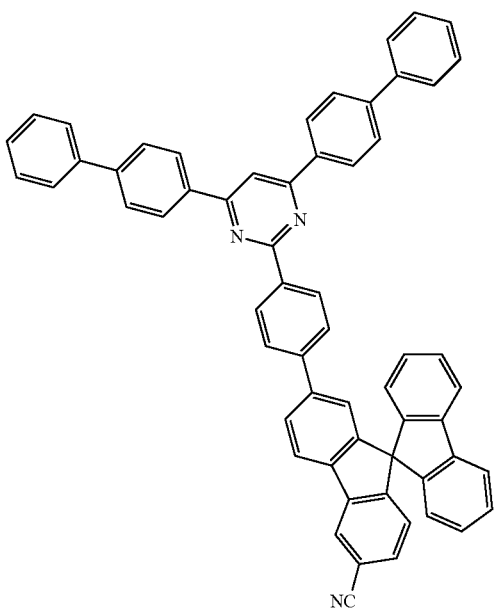
520
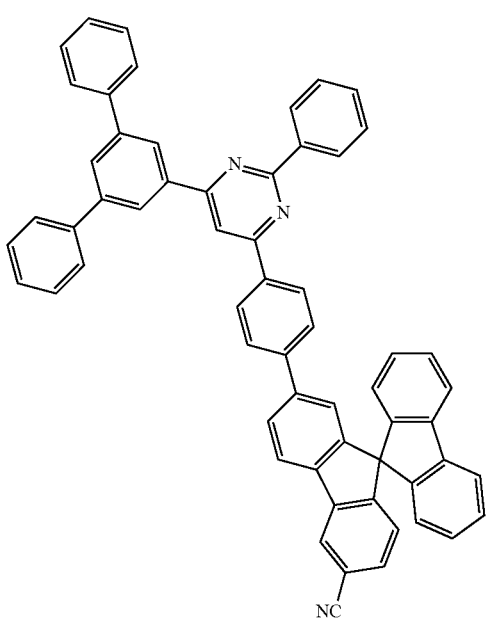
519
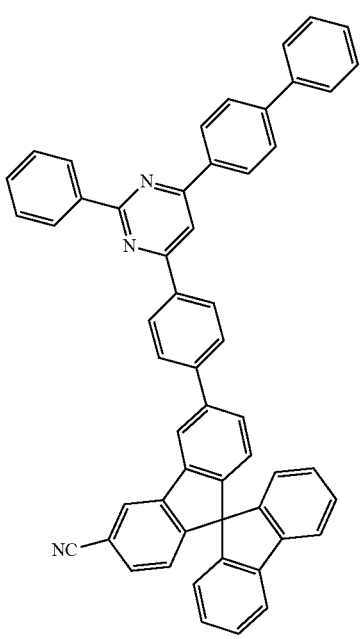
521

221
-continued
522
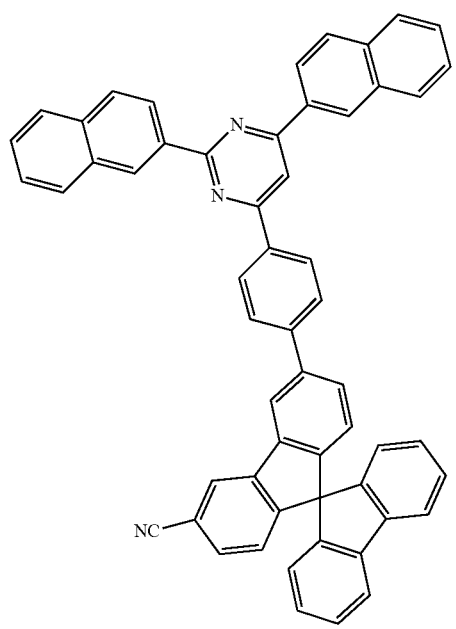
523
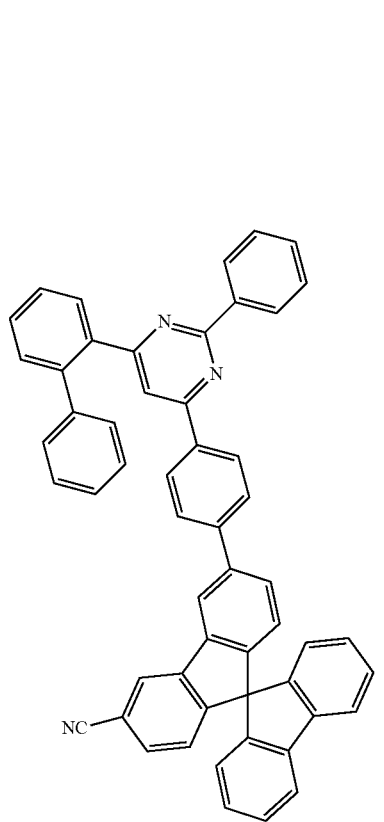
222
-continued
524
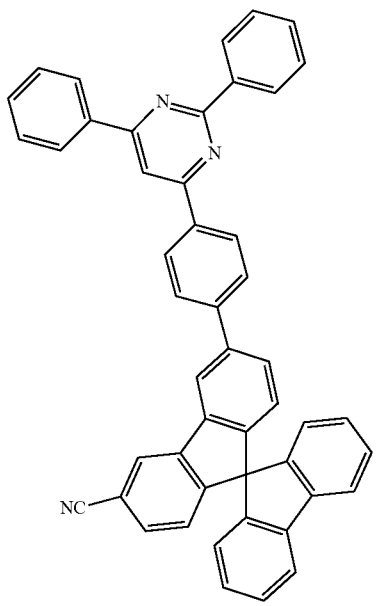
525
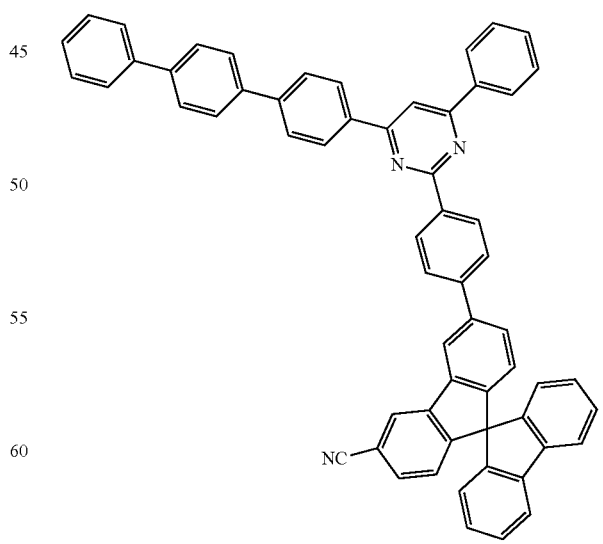

526
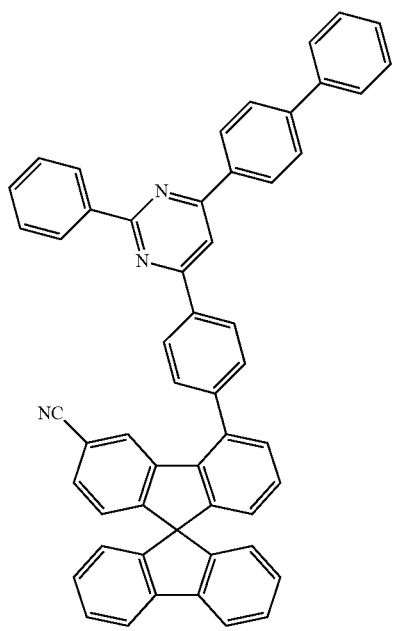
527
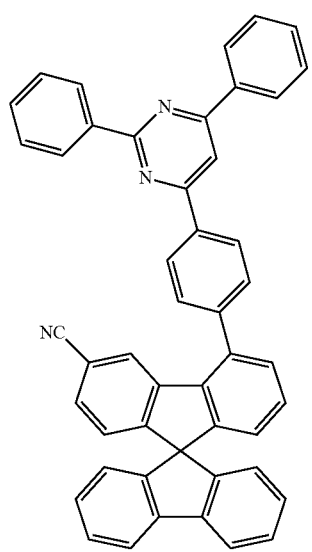
528
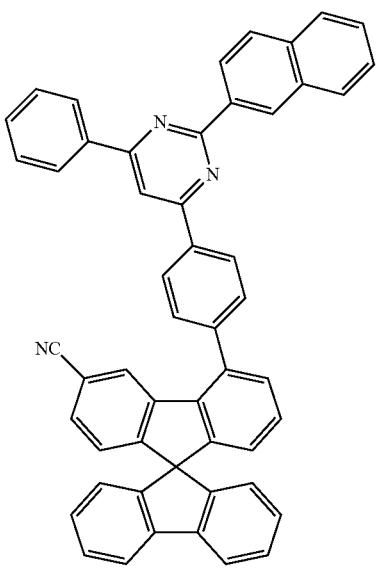
529
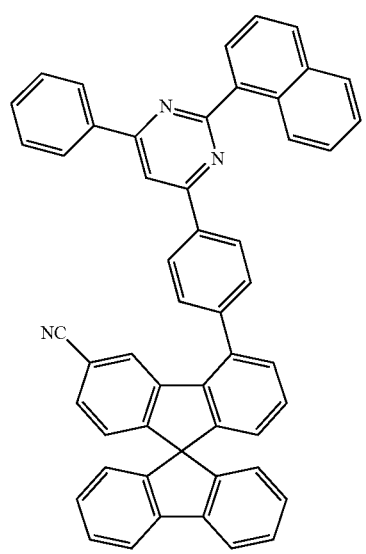
530
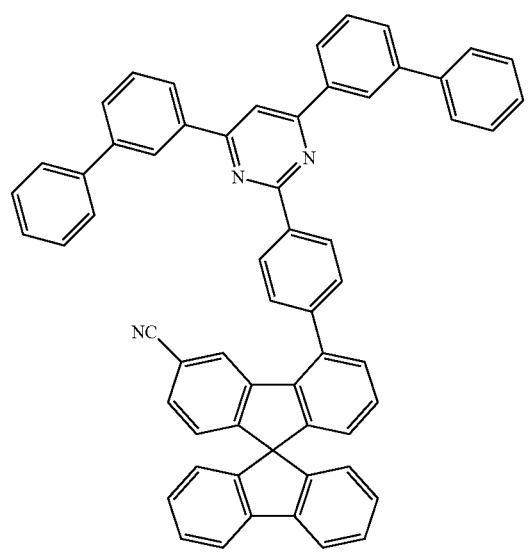

531
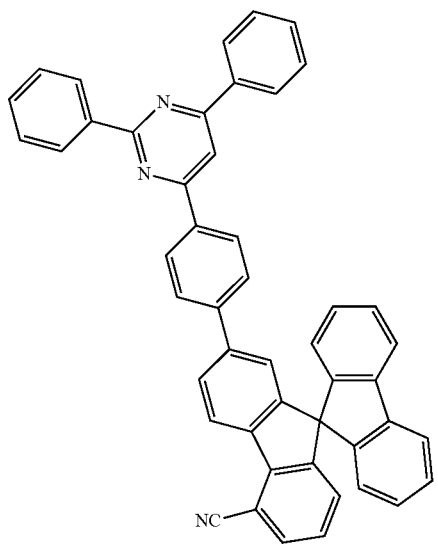
532
533
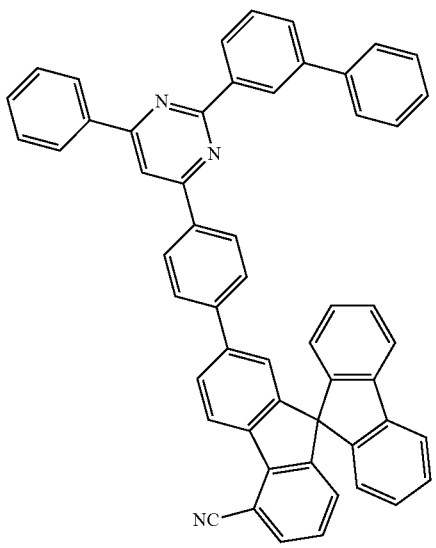
534
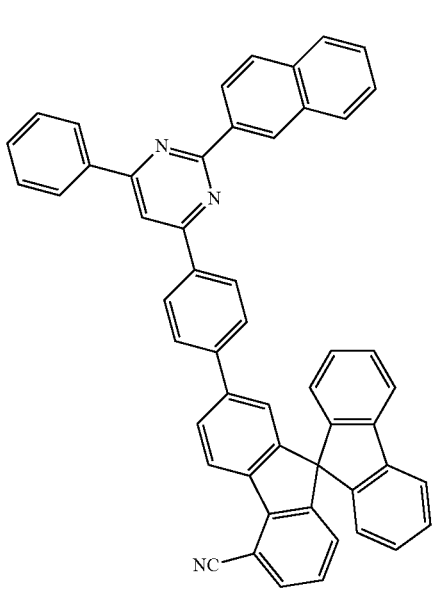

535
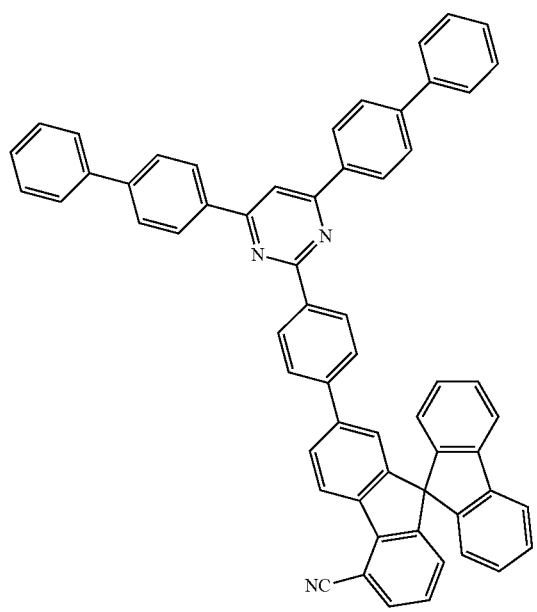
536
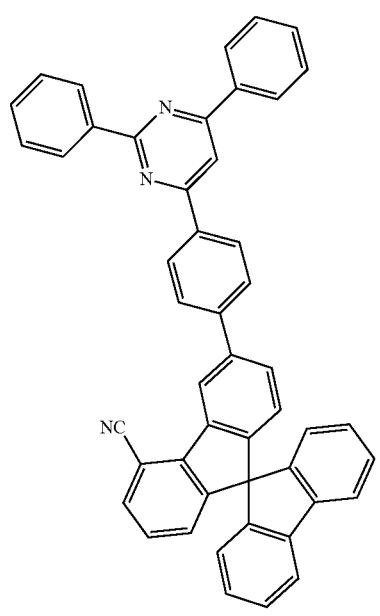
537
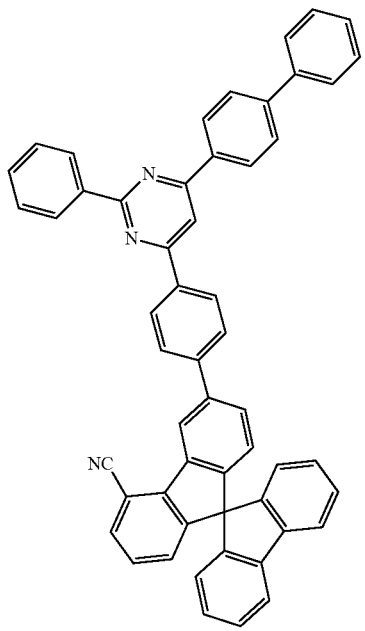
538
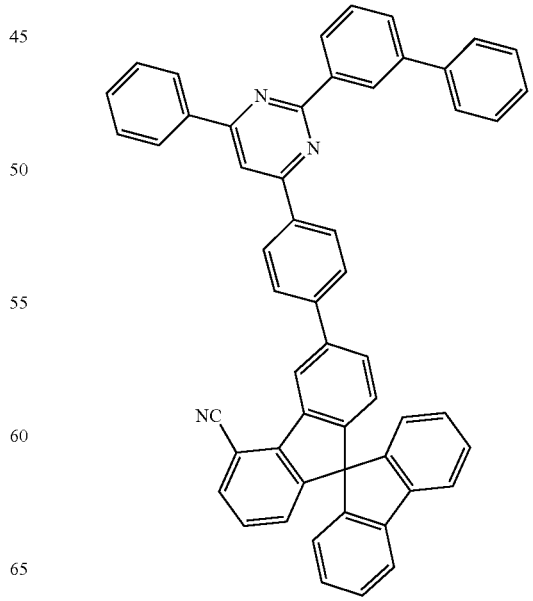

539
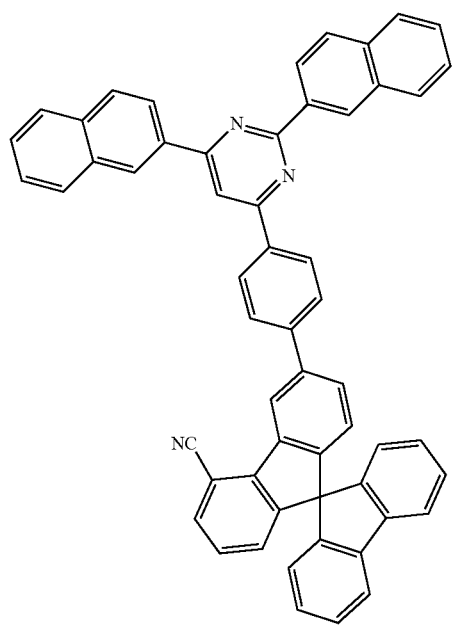
540
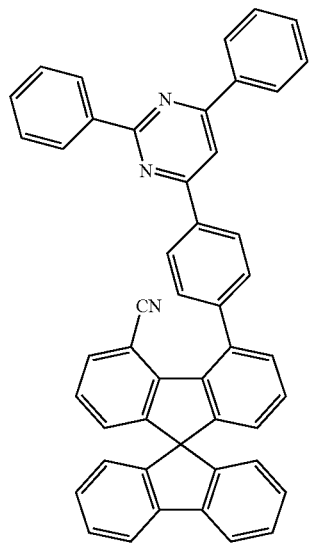
541
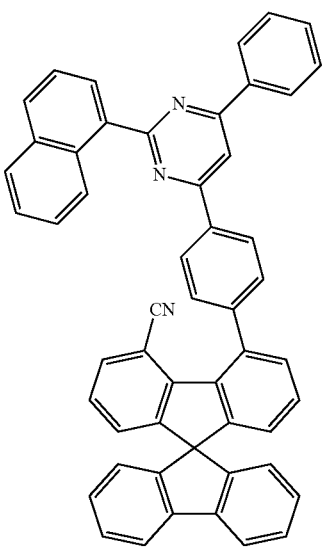
542
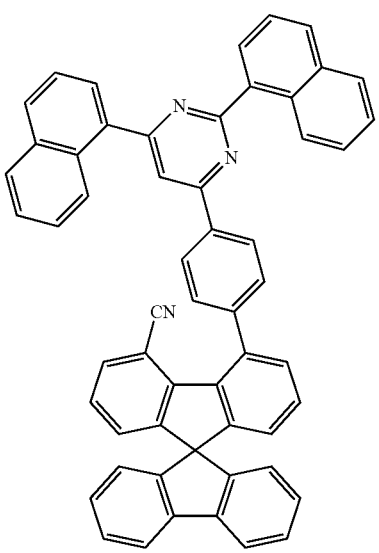
543

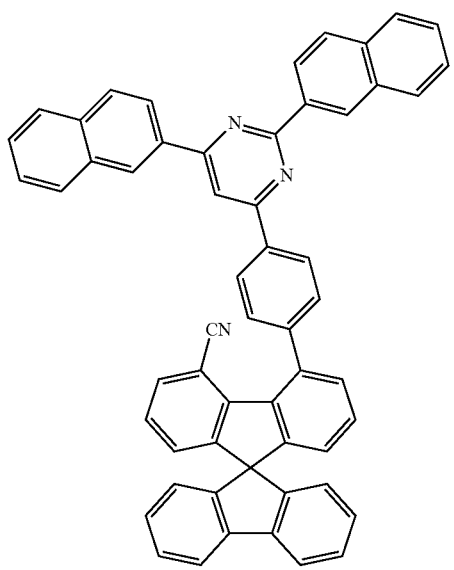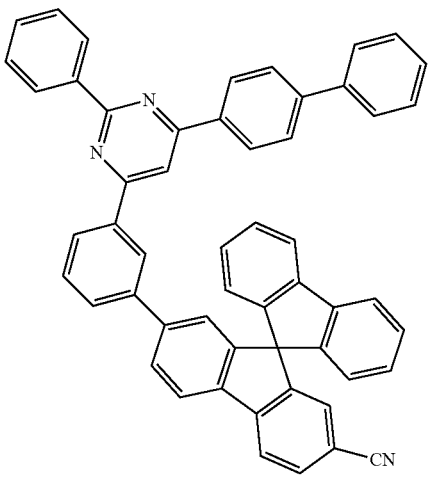

550
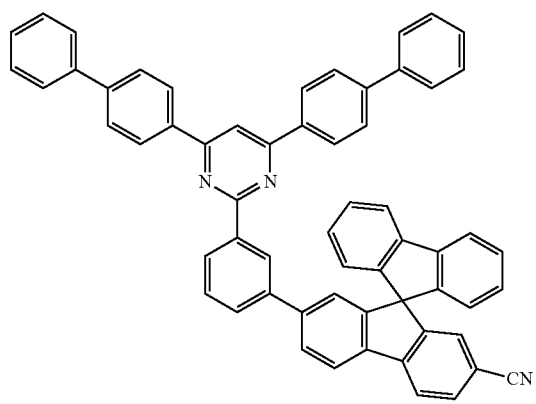
551
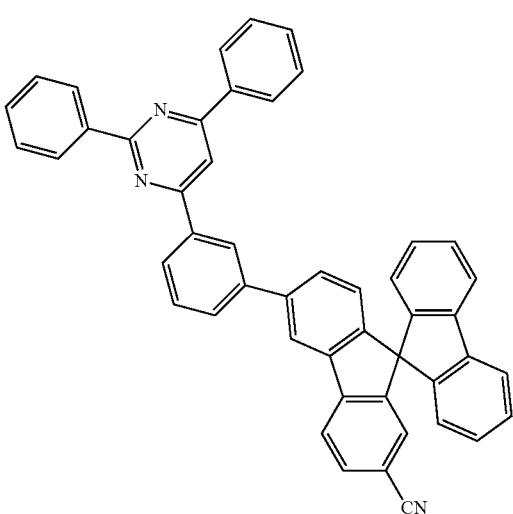
552
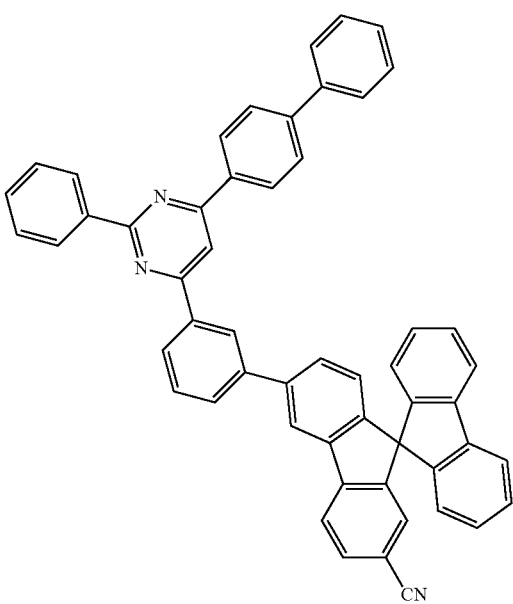
553
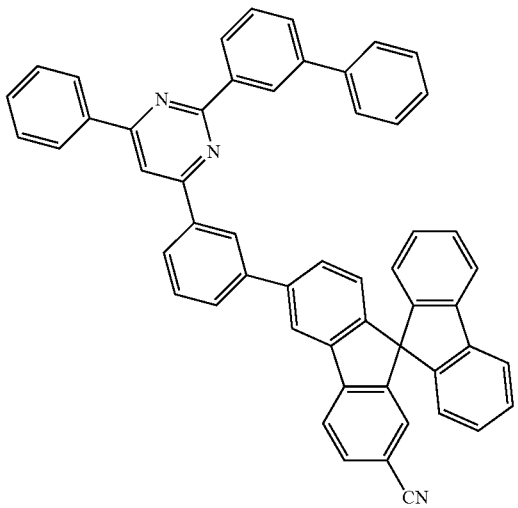
554
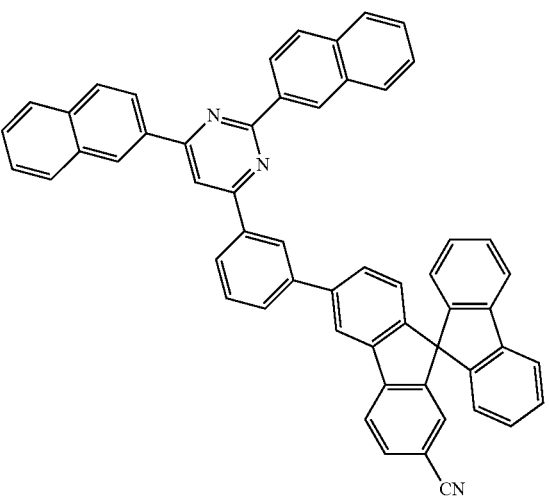
555
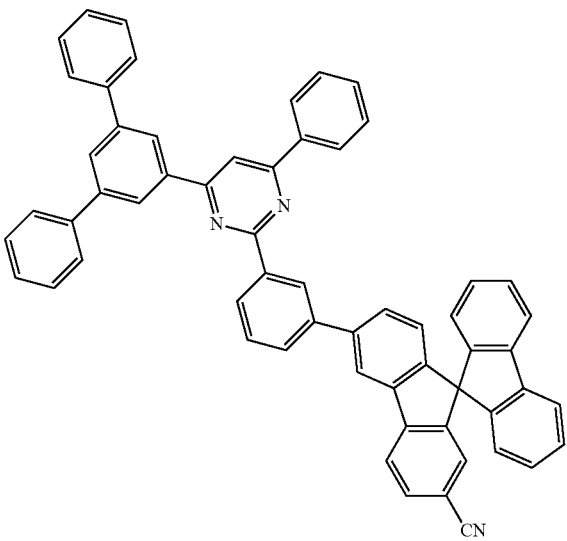

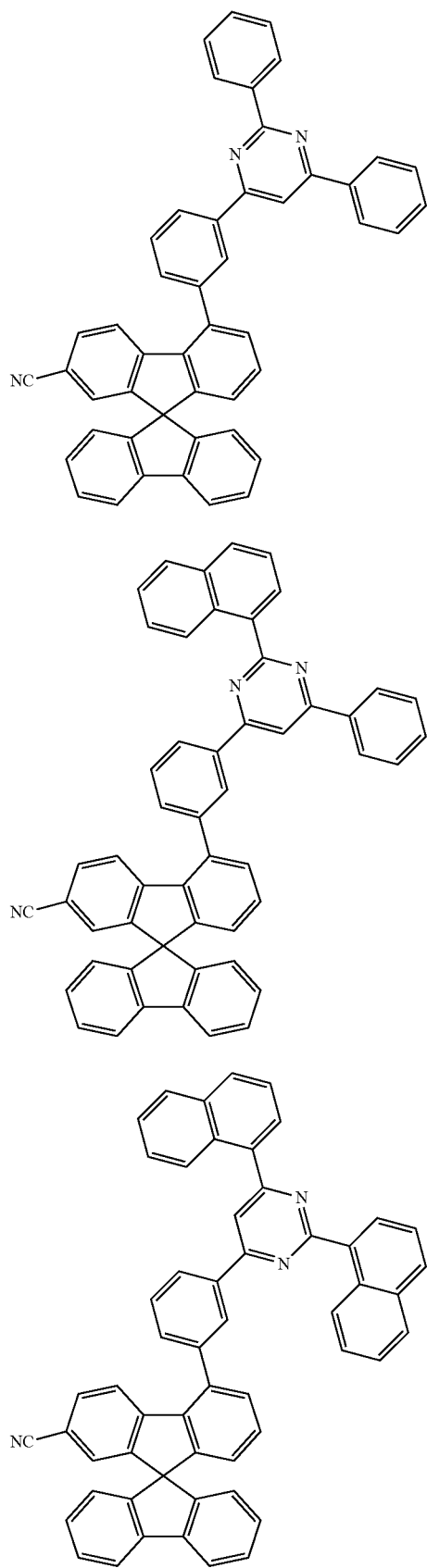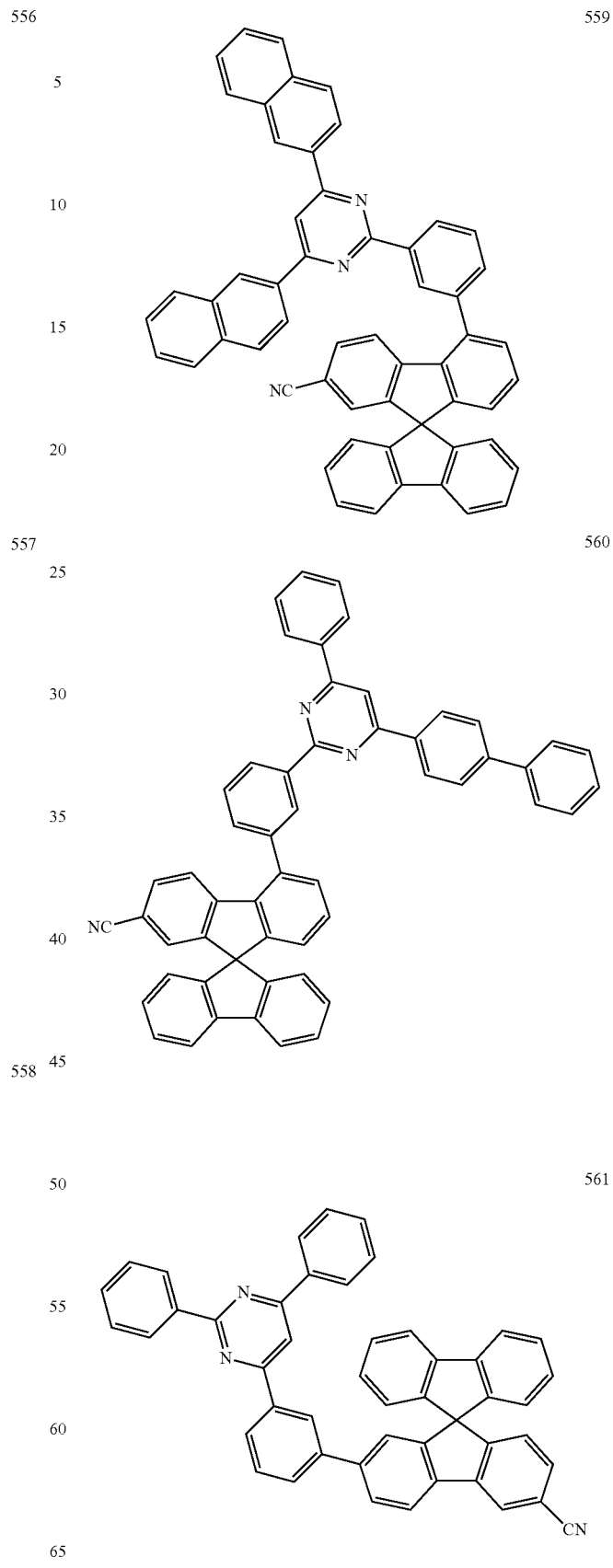

562
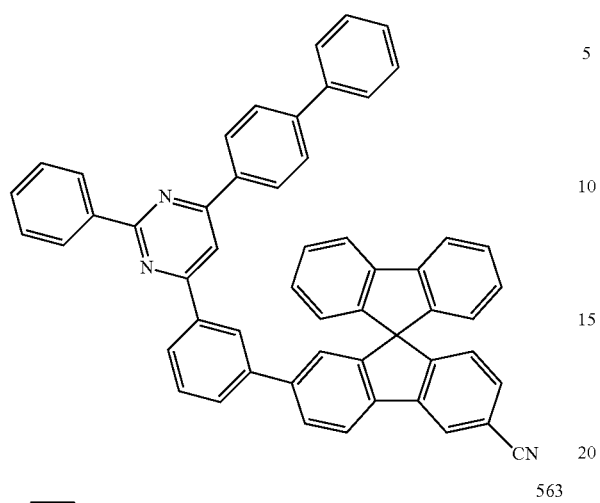
563
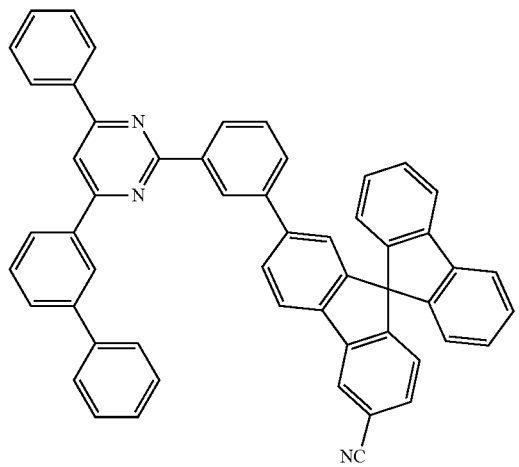
564
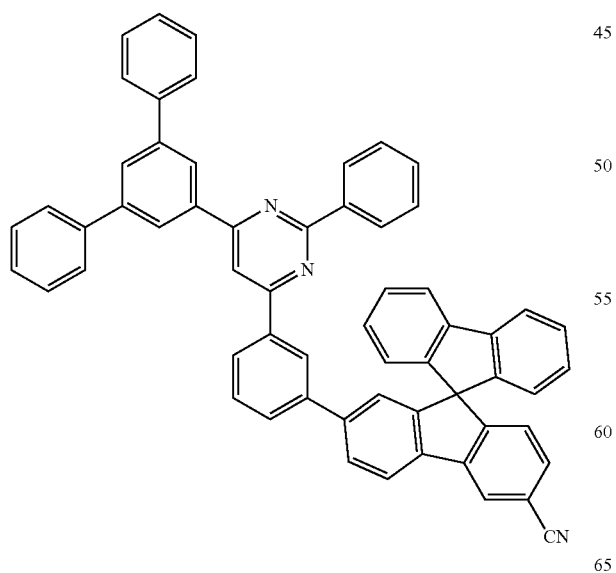
565
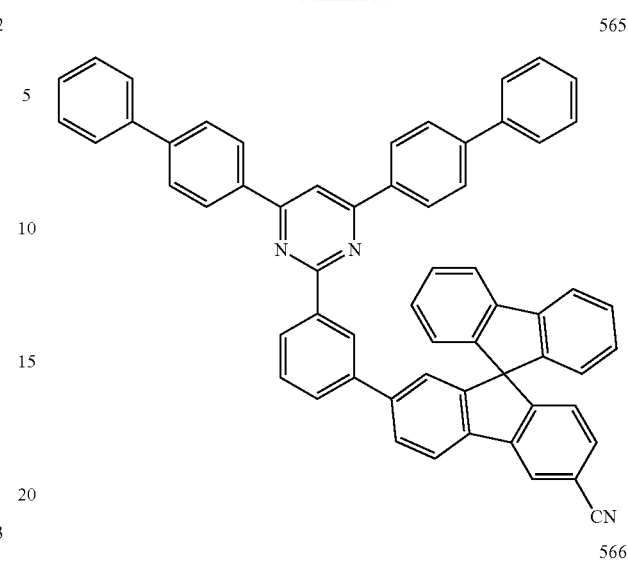
566
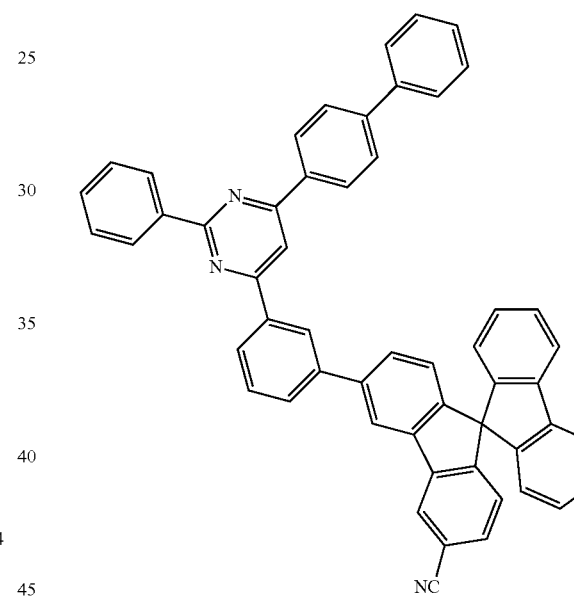
567
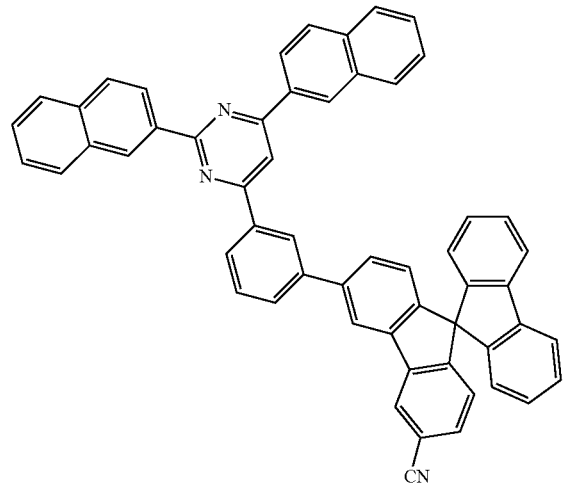

-continued
568
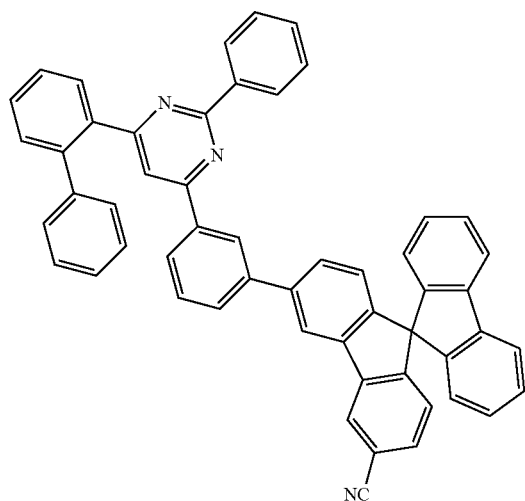
569
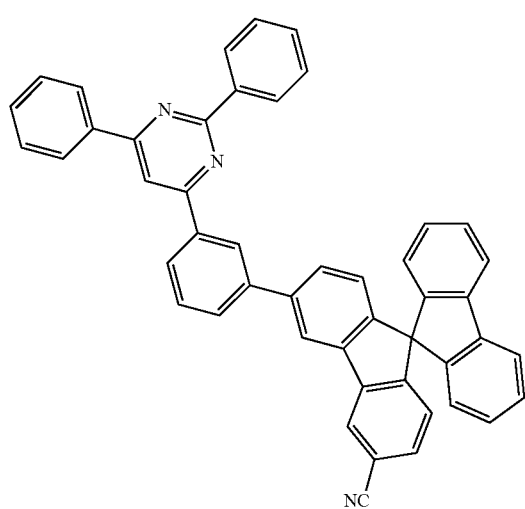
570
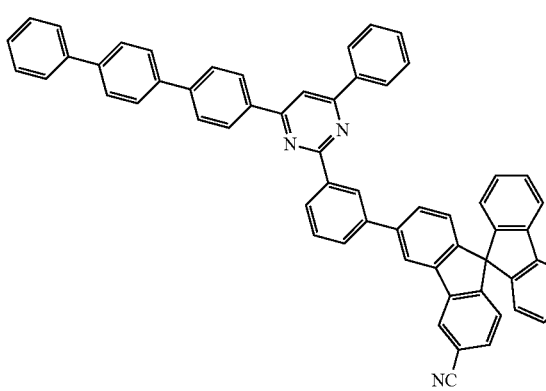
-continued
571
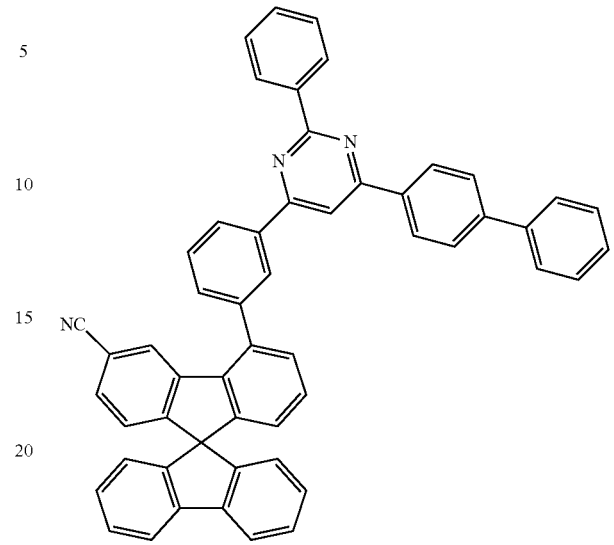
572
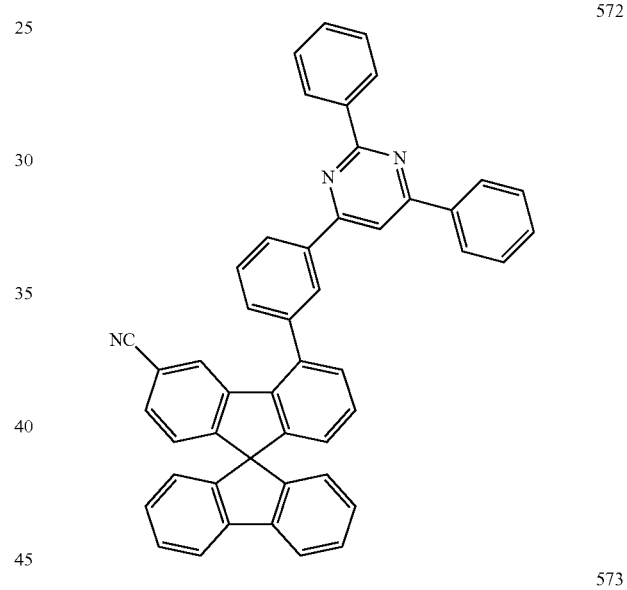
573
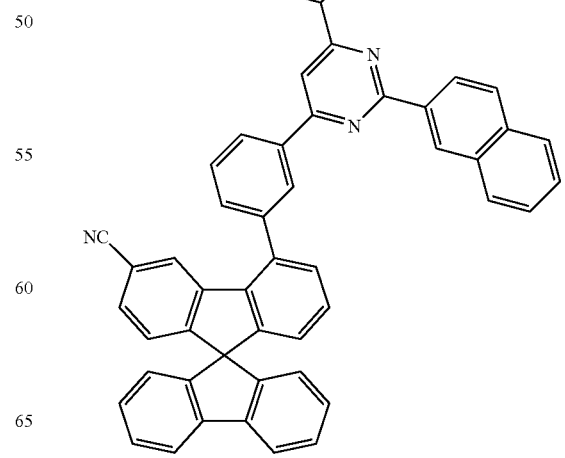

574
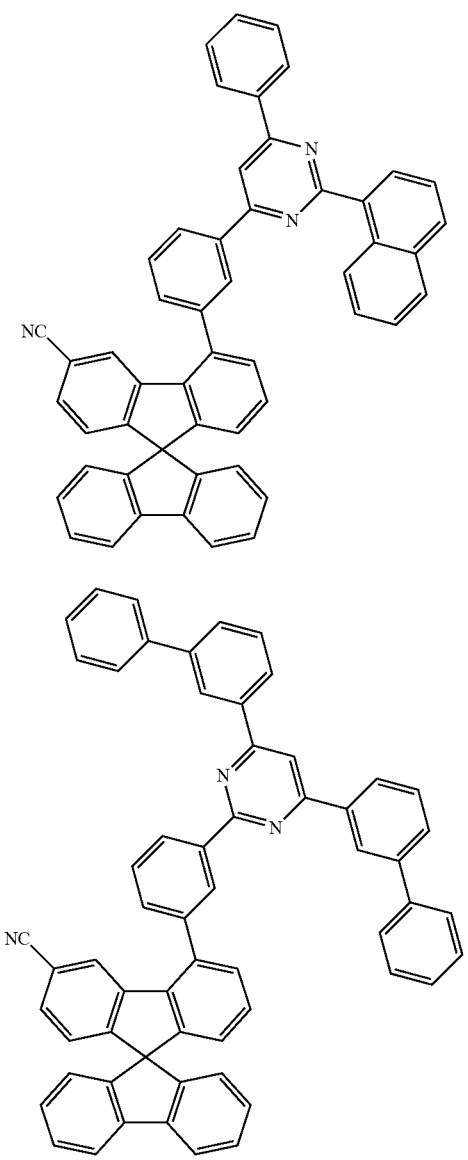
575
576
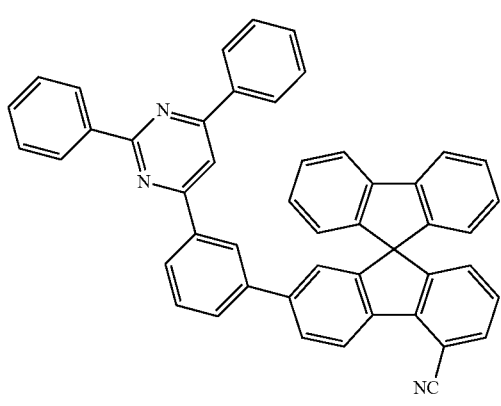
577
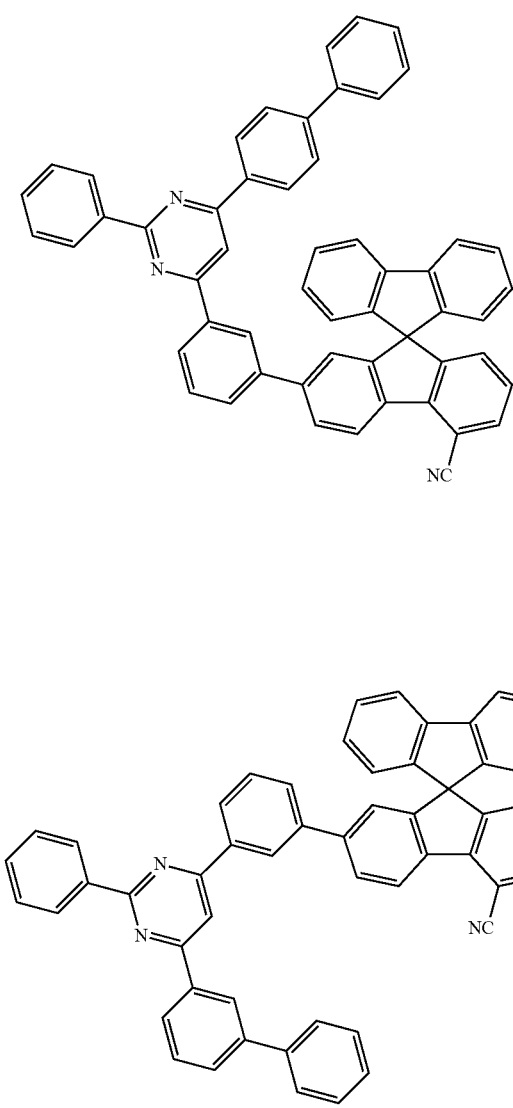
578
579
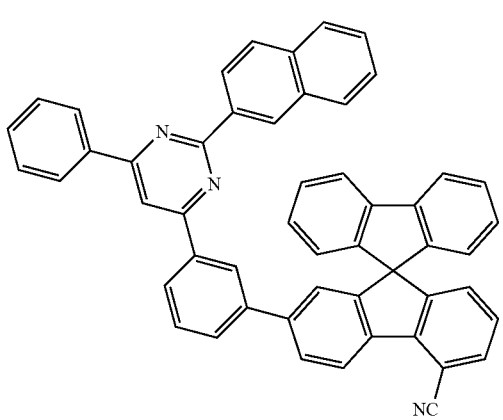

-continued
580
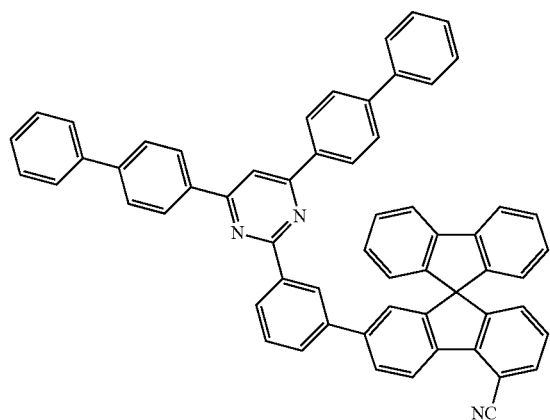
581
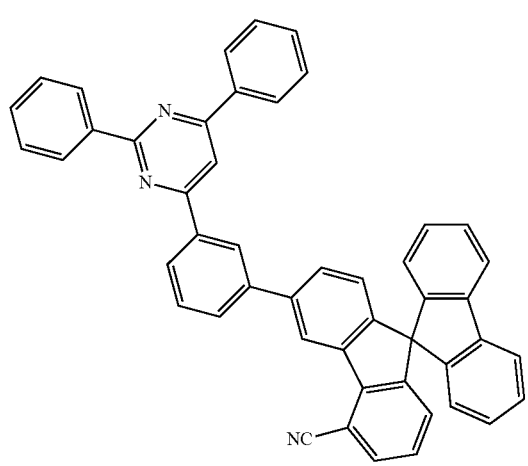
582
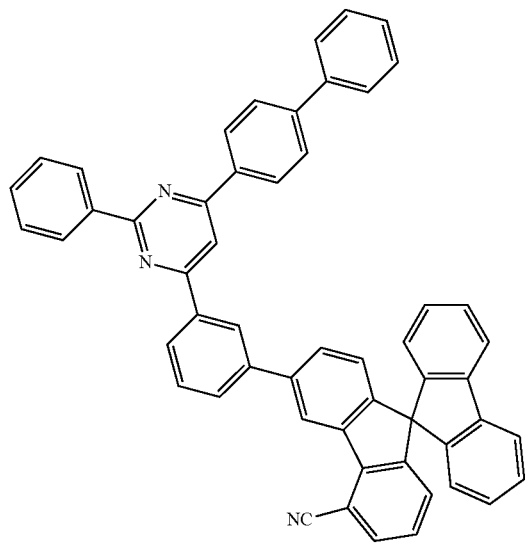
-continued
583
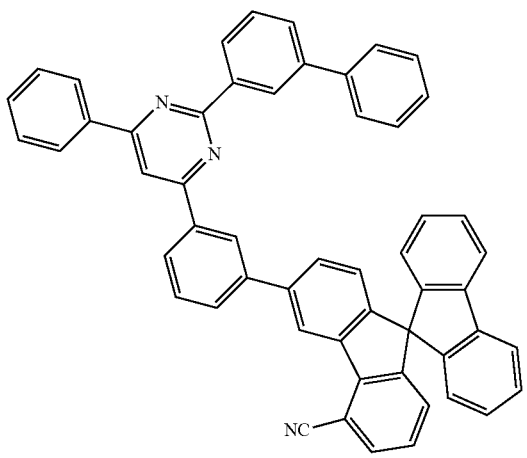
584
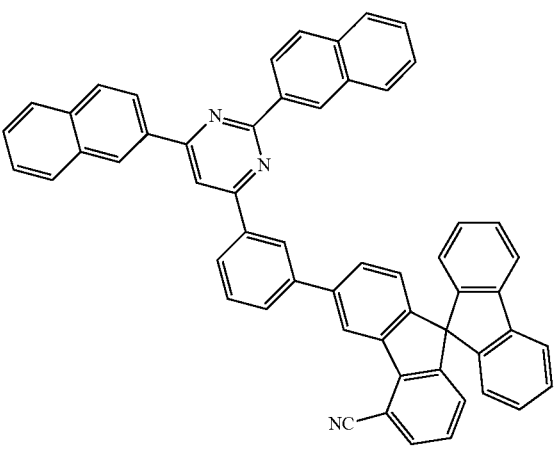
585
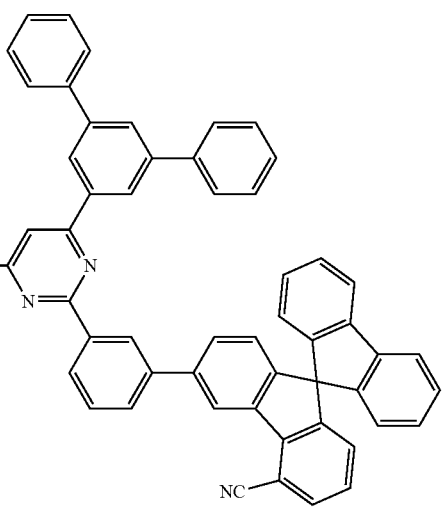

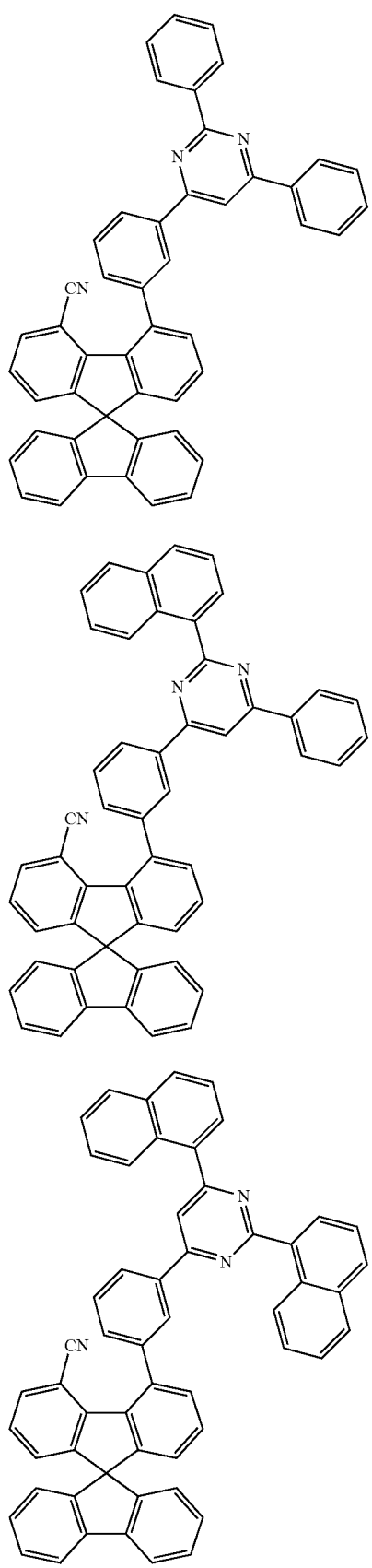
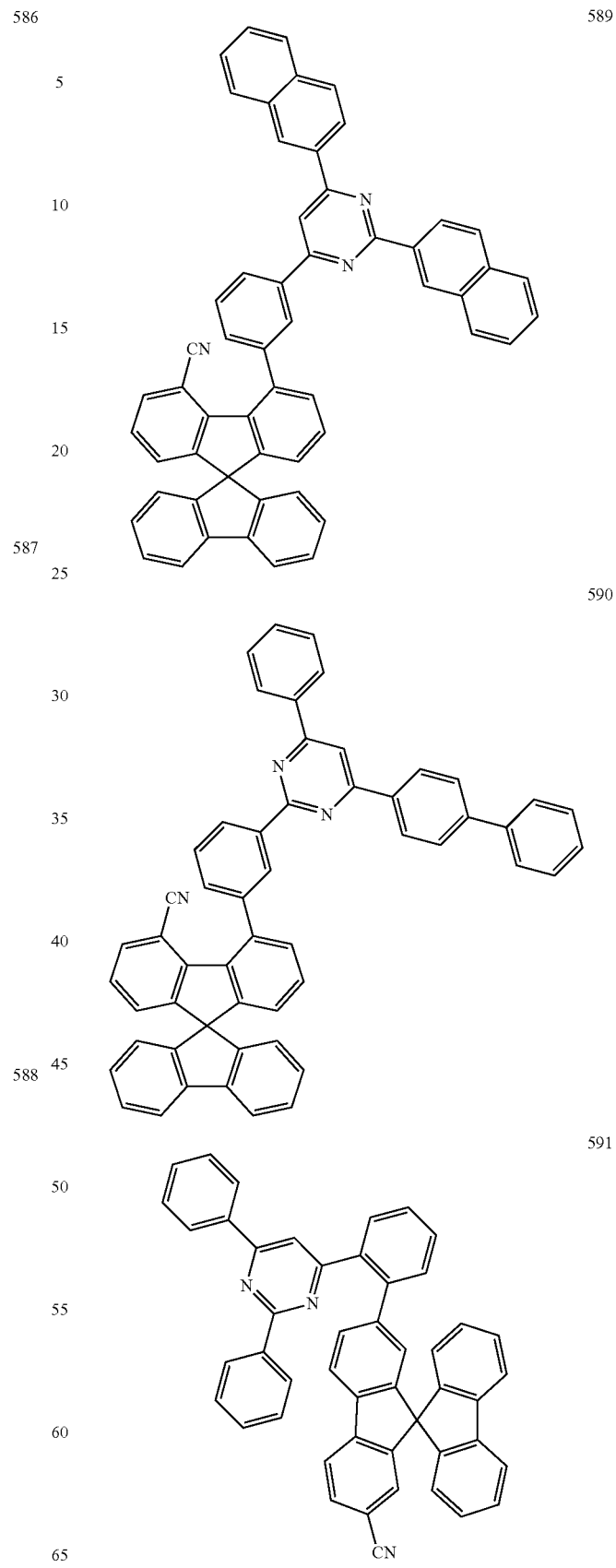

592
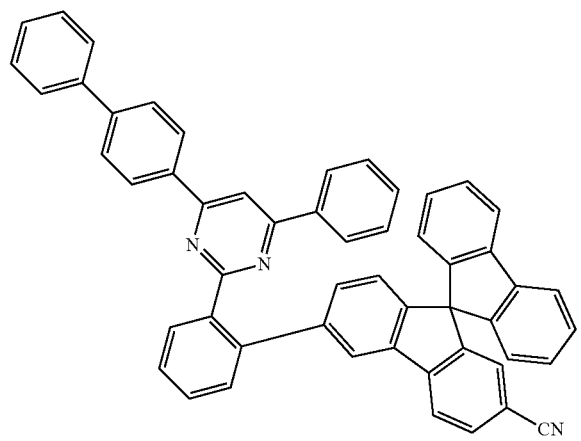
593
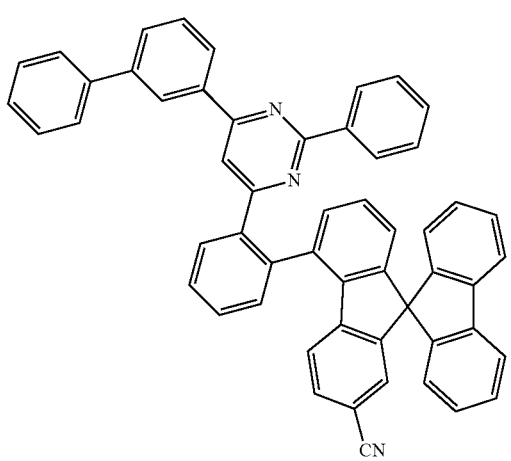
594
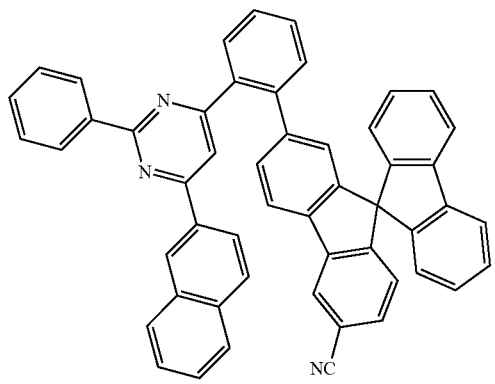
595
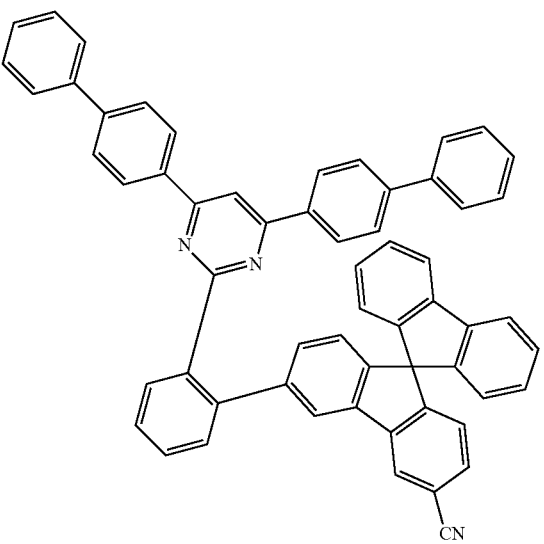
596
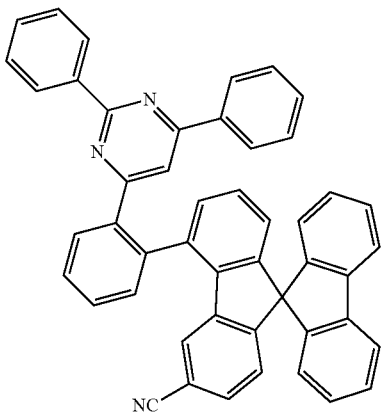
597
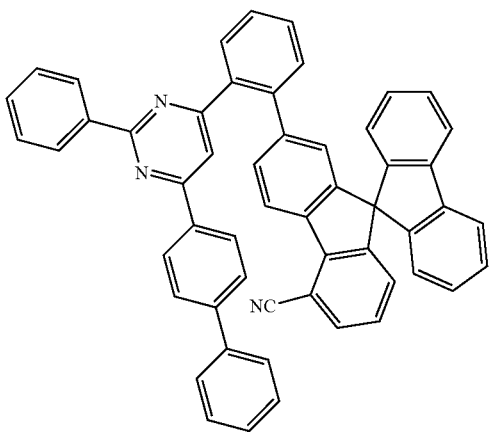

249
-continued
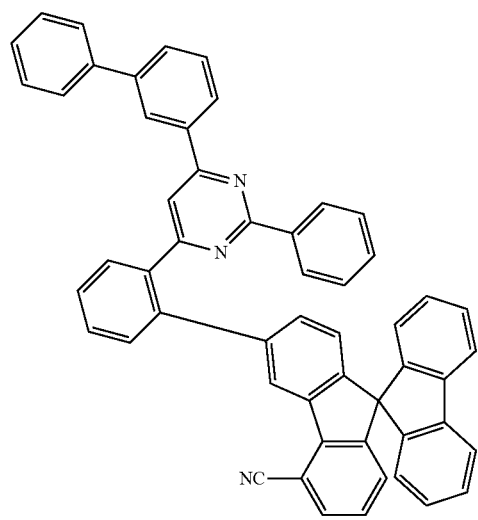
598
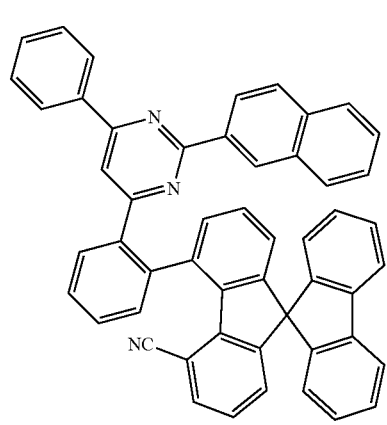
599
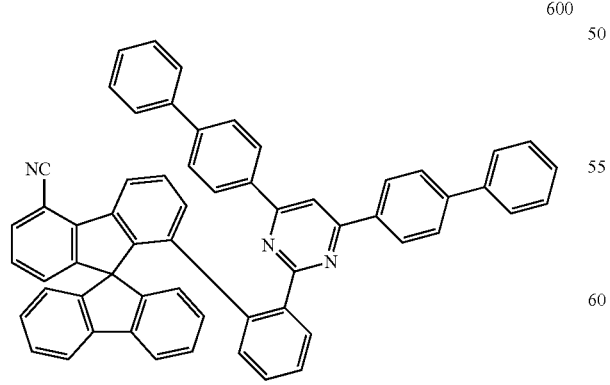
600
250
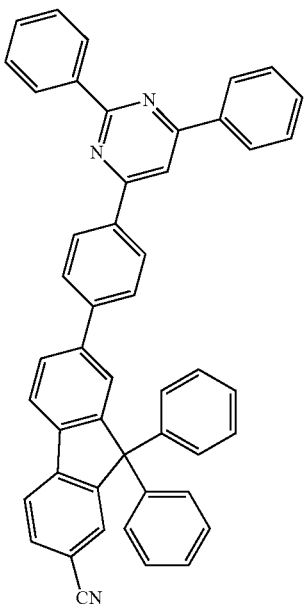
601
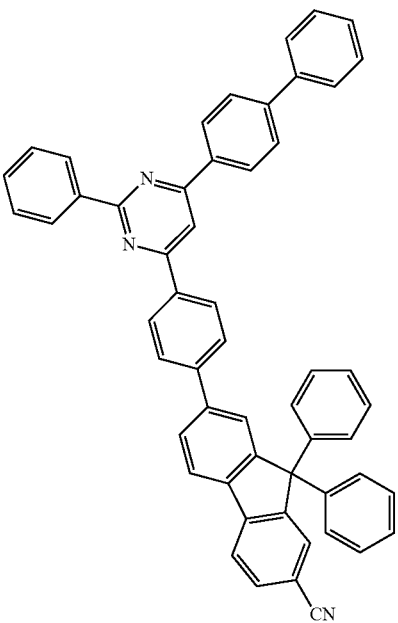
602

251
-continued
603
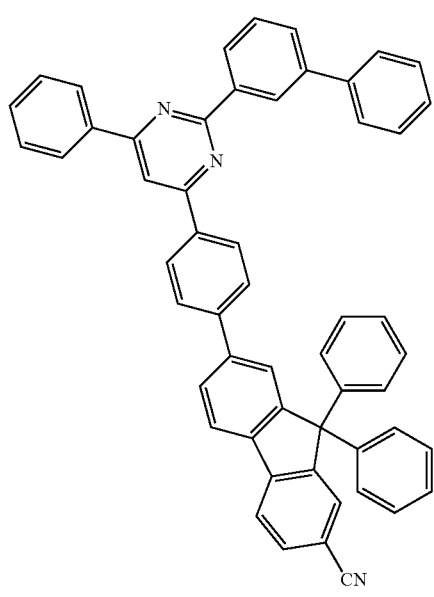
604
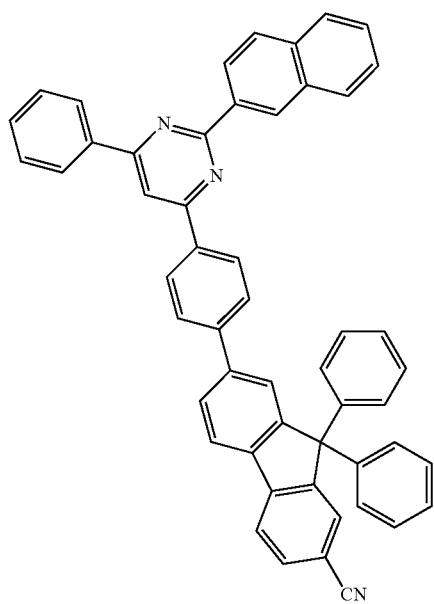
252
-continued
605
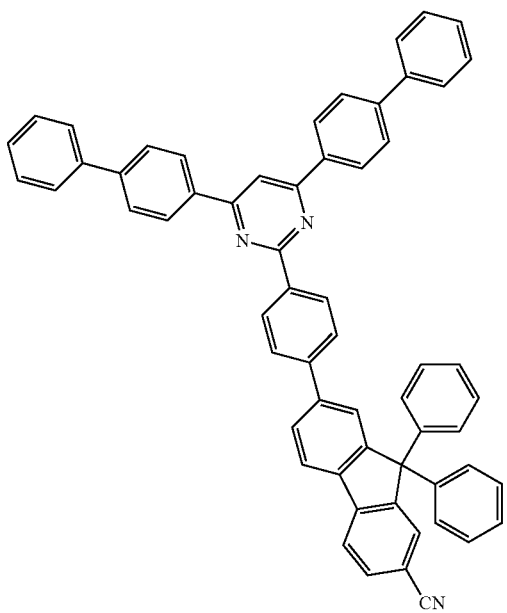
606
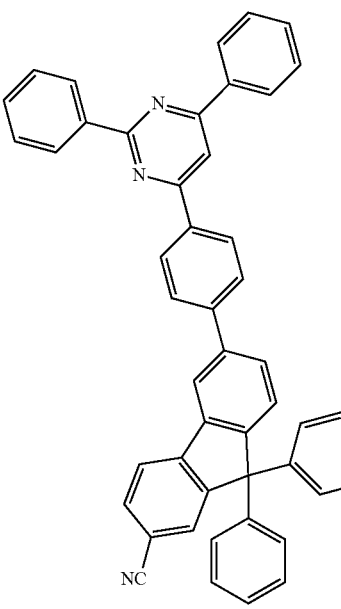

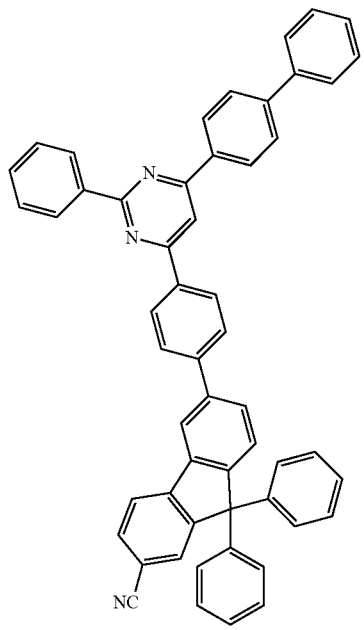
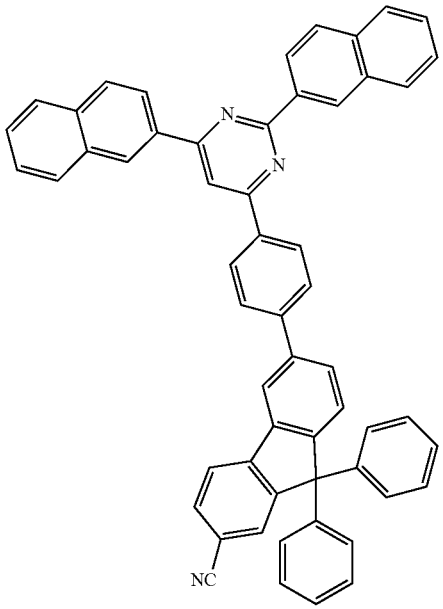

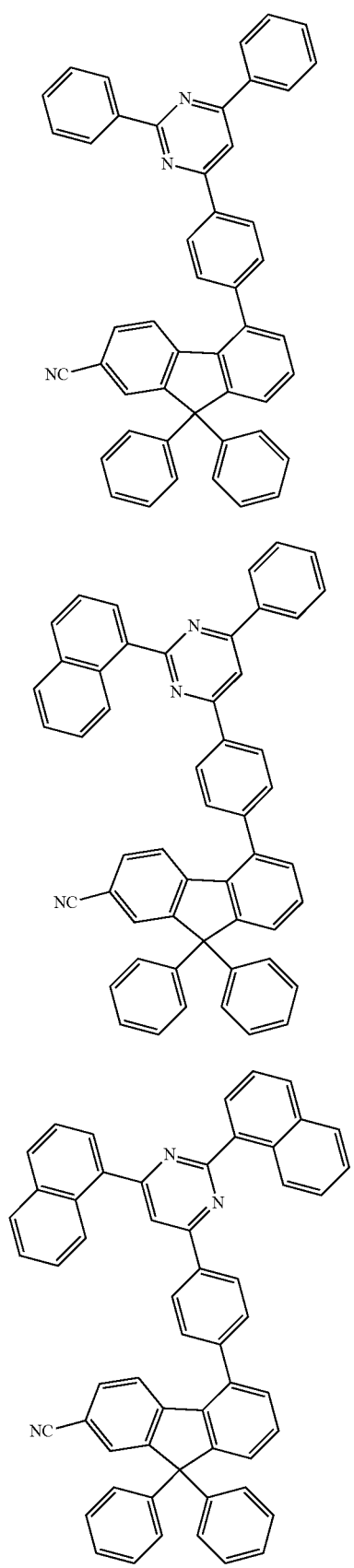

-continued
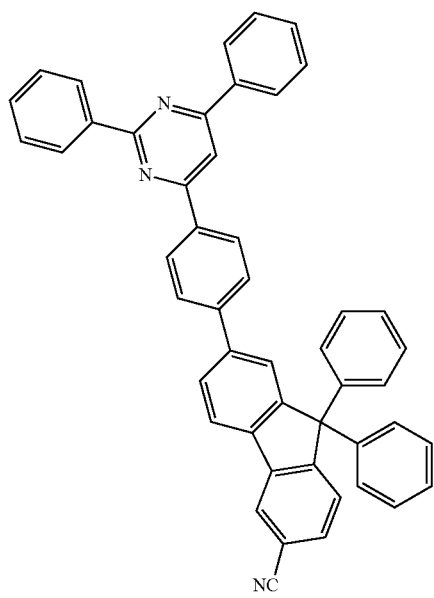
616
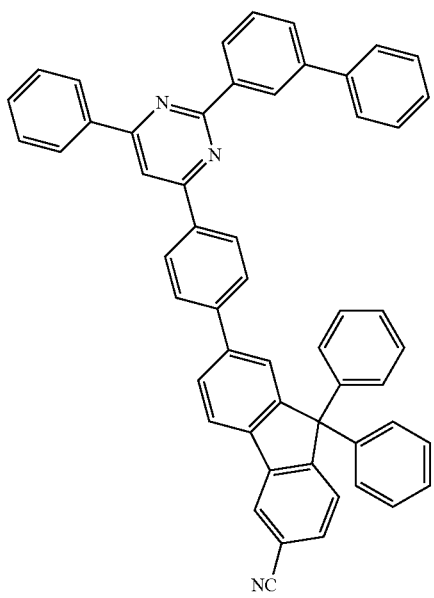
618
617
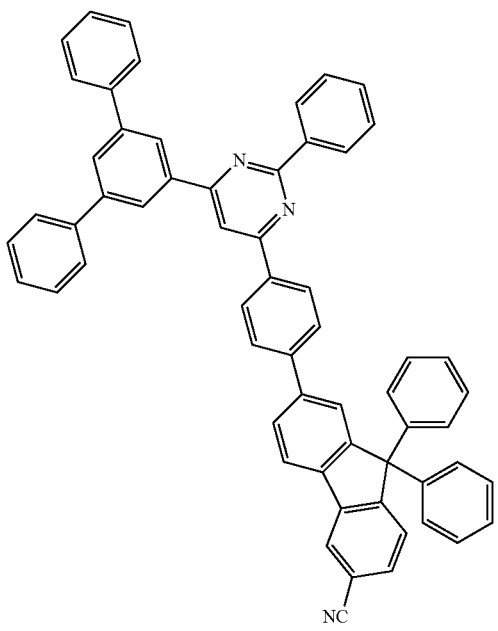
619

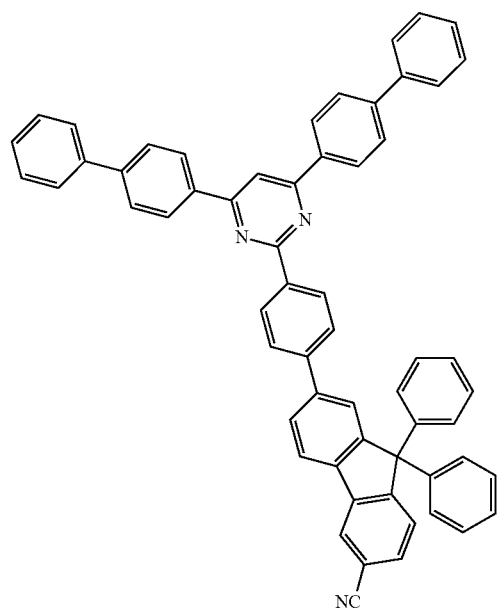
620
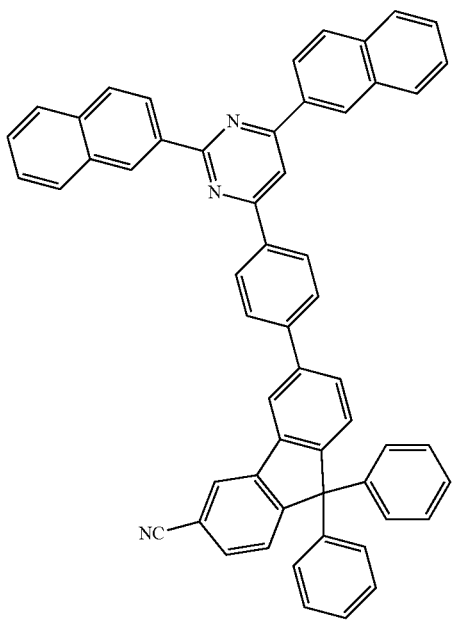
622
621
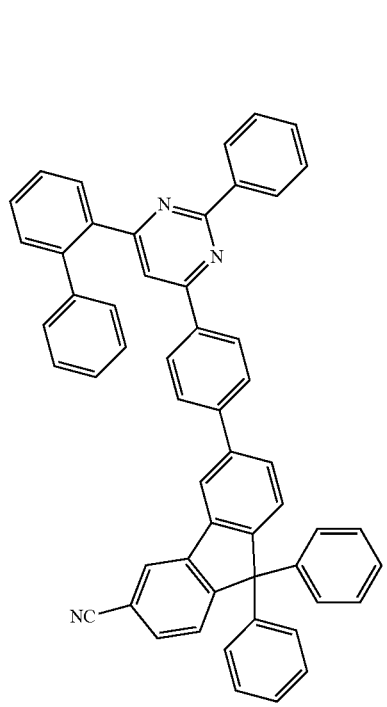
623

261
-continued
624
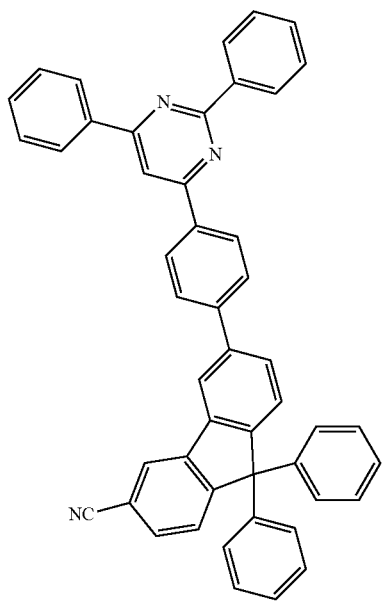
625
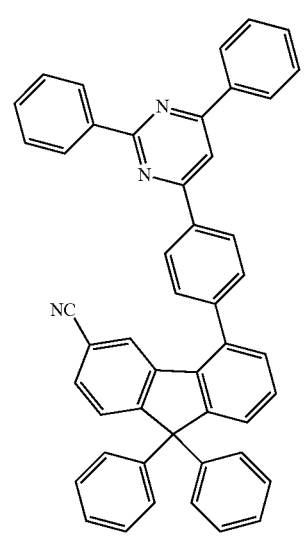
262
-continued
626
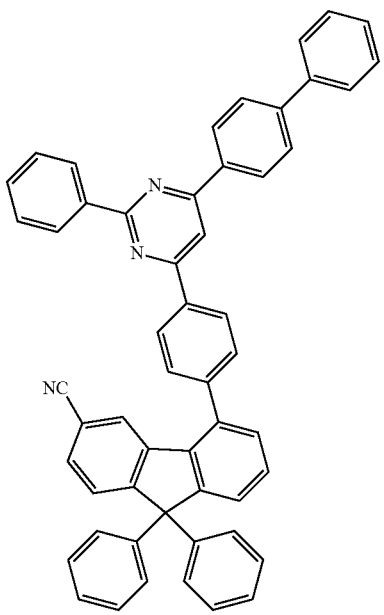
627
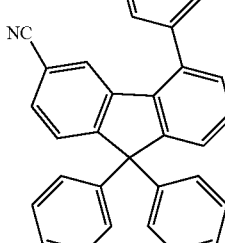

263
-continued
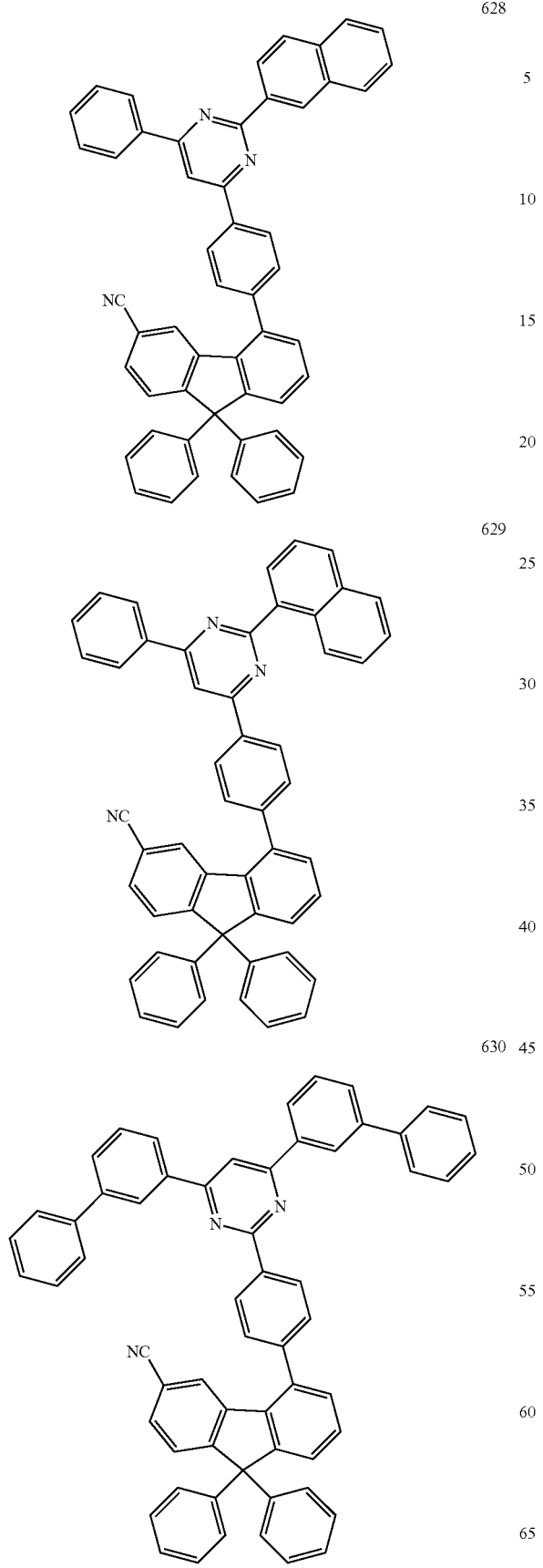
264
-continued
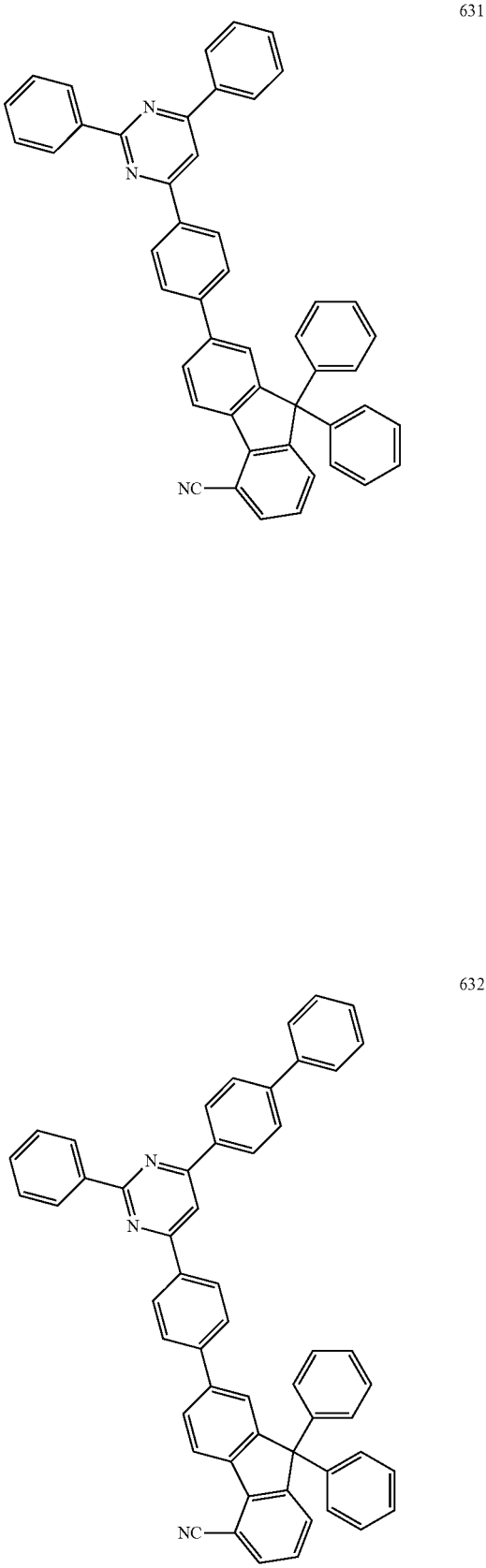

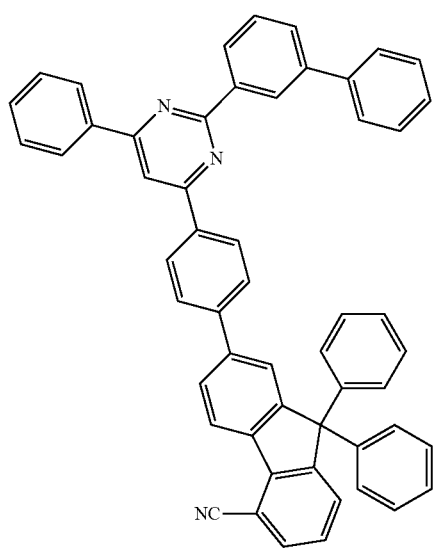
633
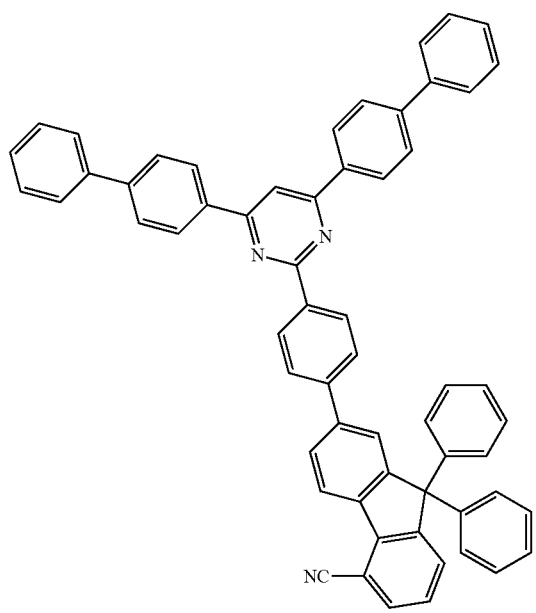
635
634
636
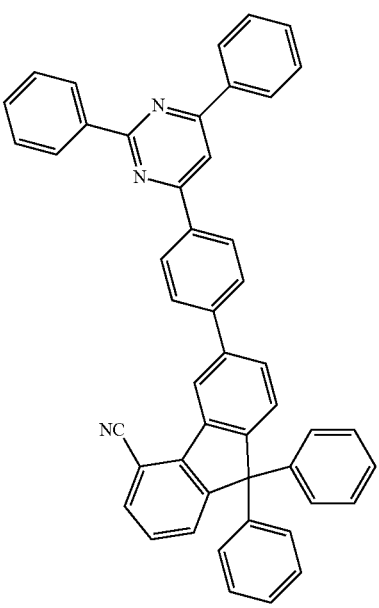

637
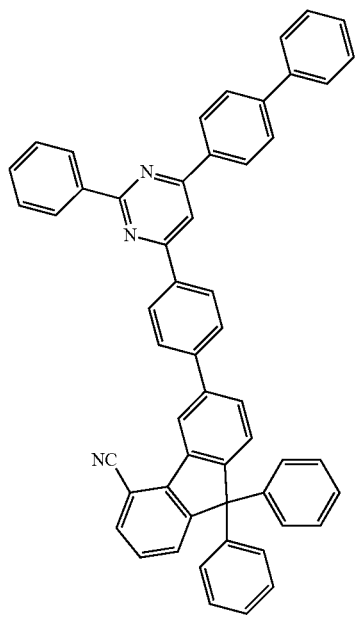
638
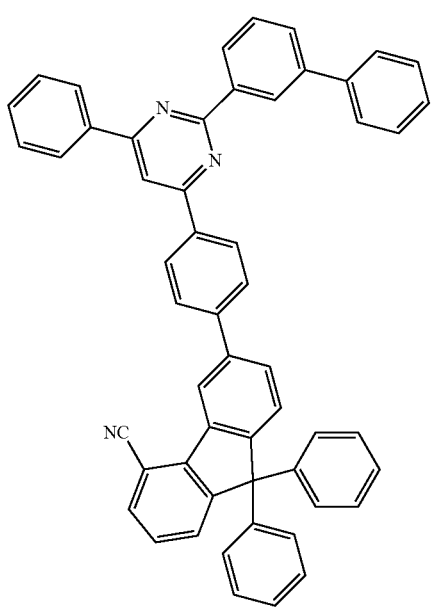
639
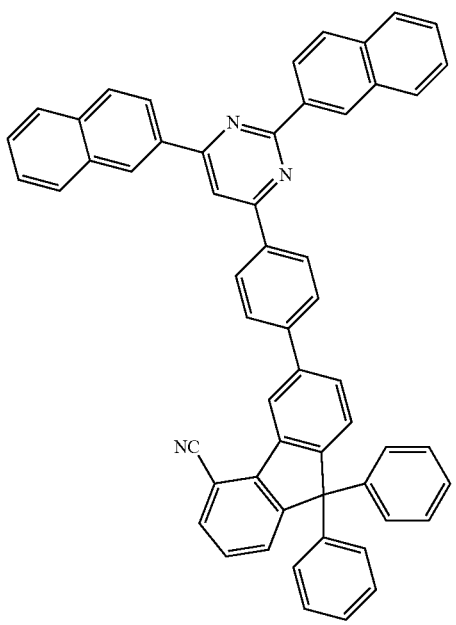
640
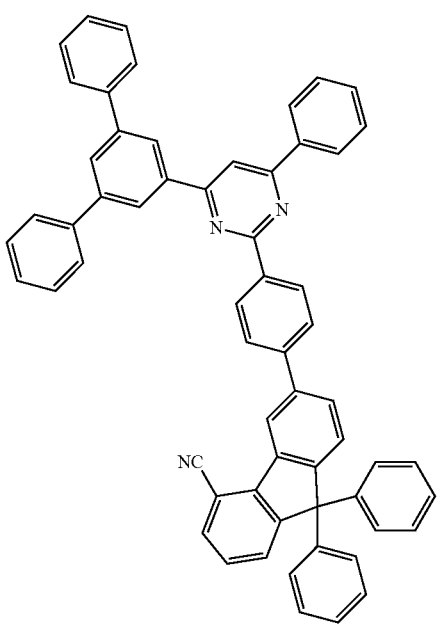

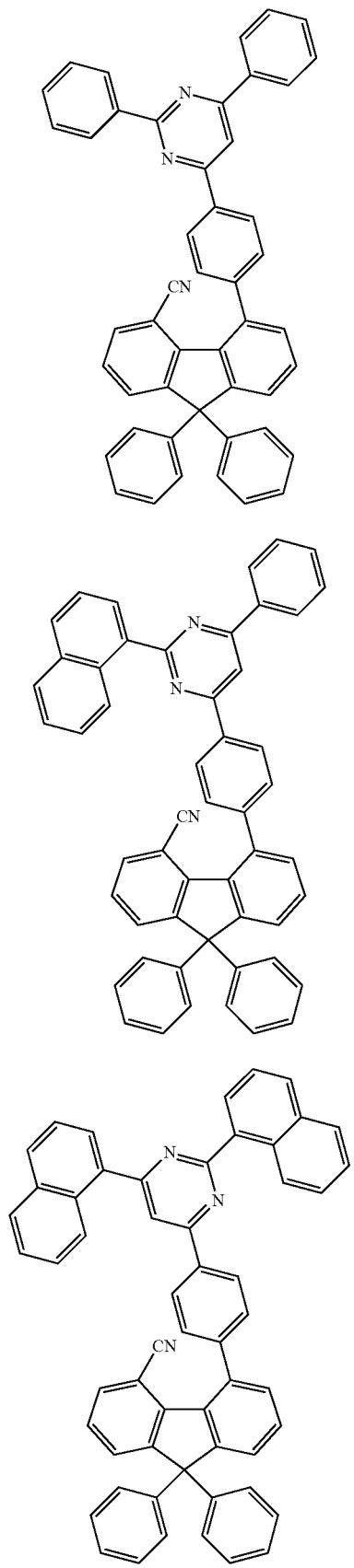
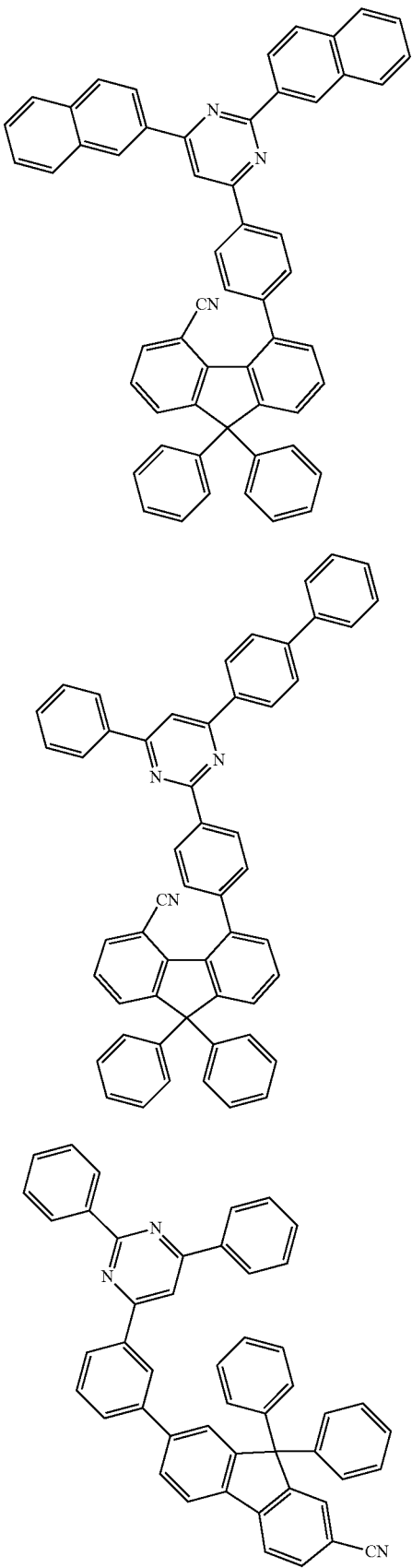

647
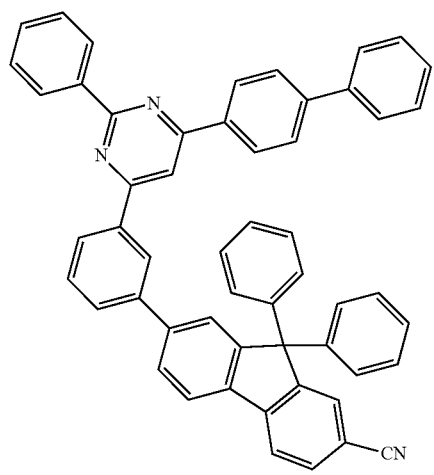
648
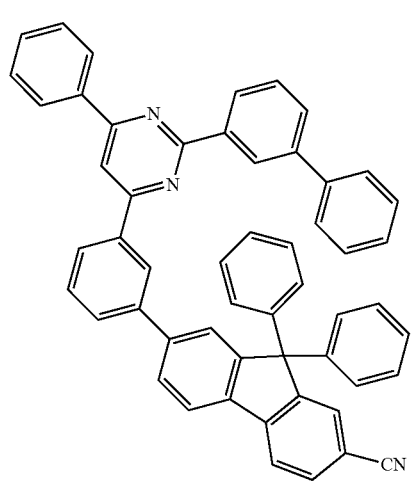
649
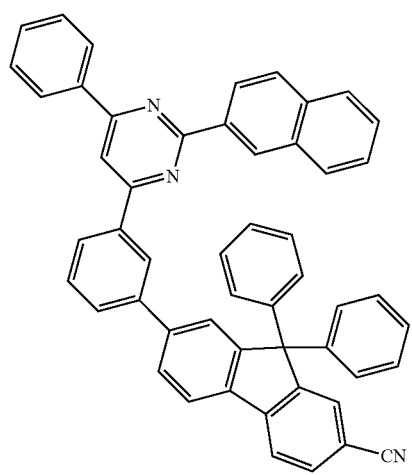
650
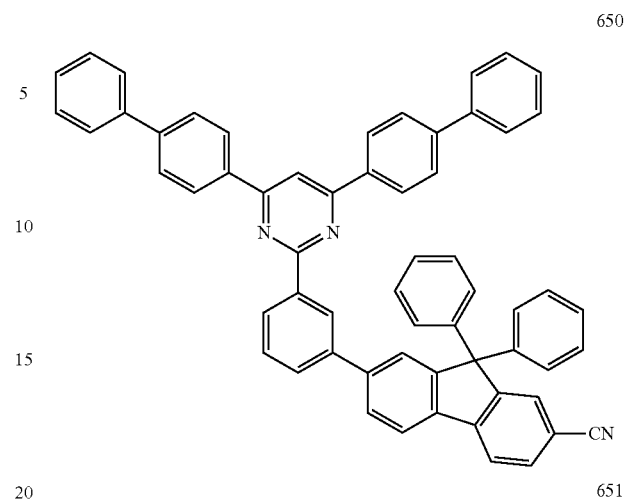
651
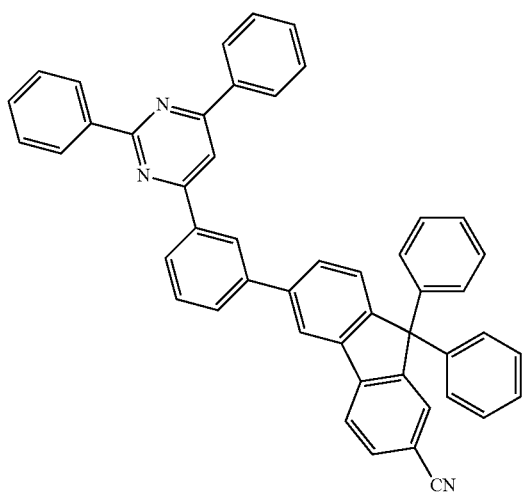
652
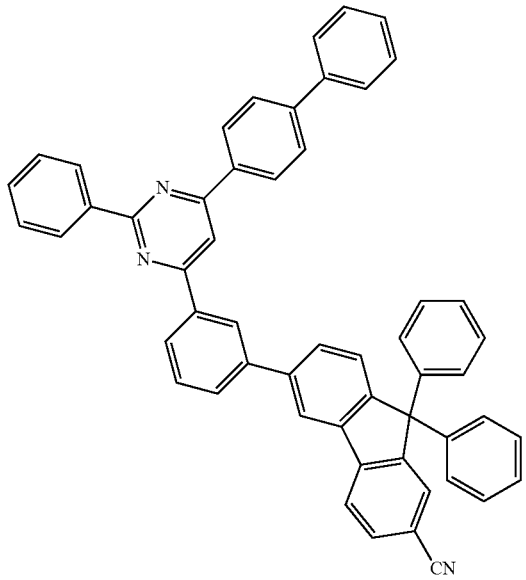

273
-continued
653
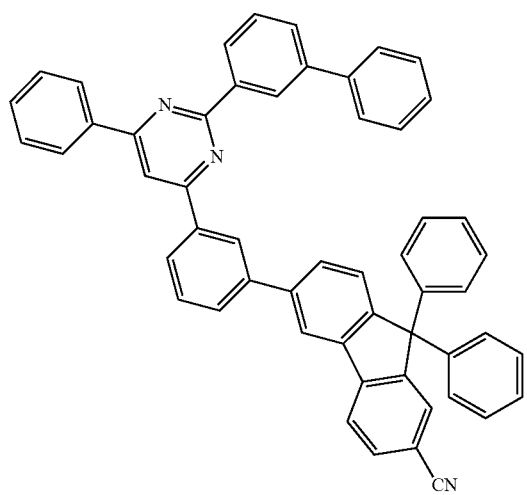
654
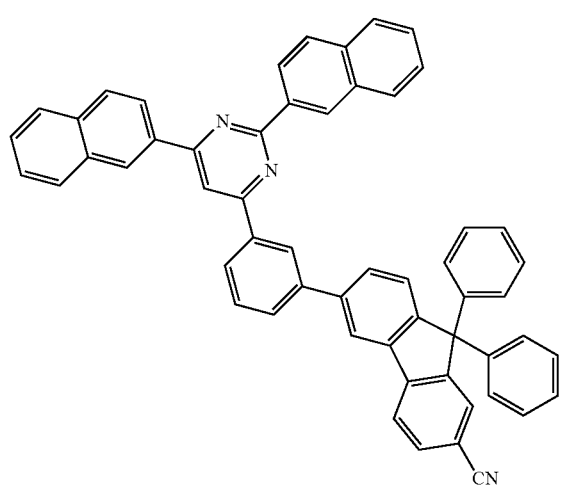
655
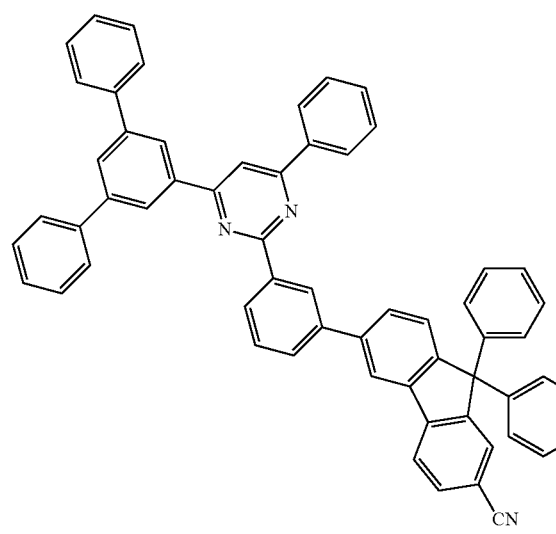
274
-continued
656
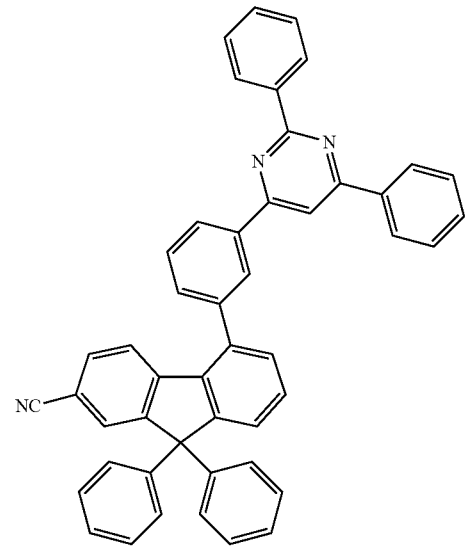
657
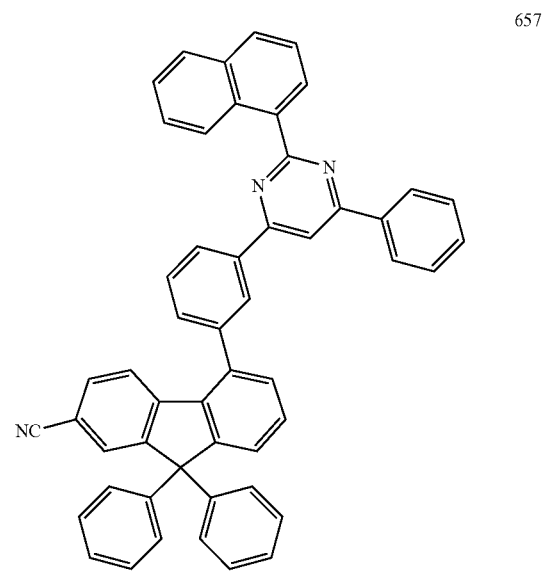
658
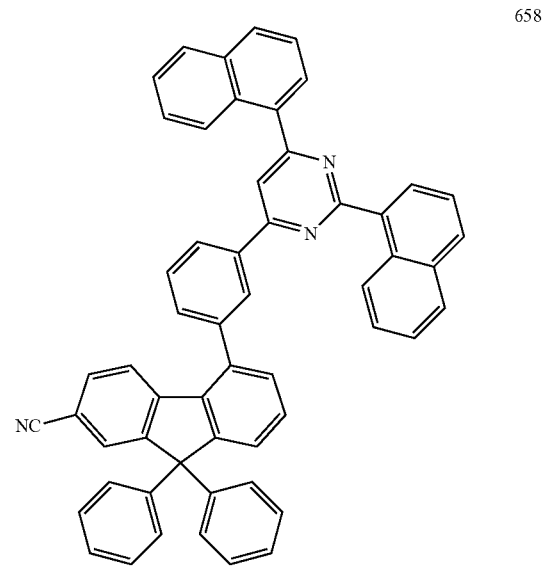

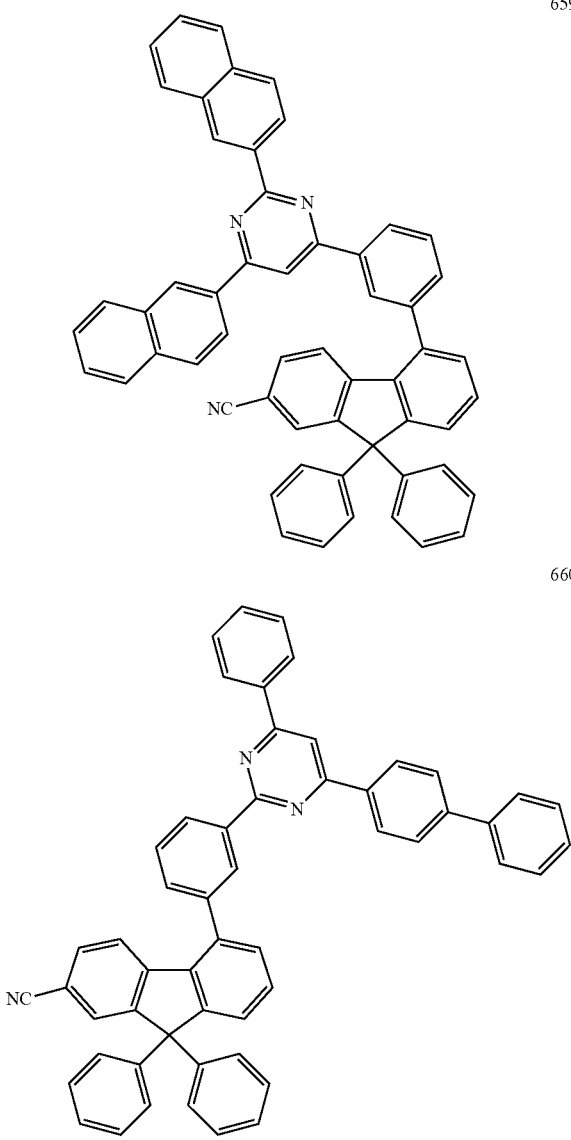
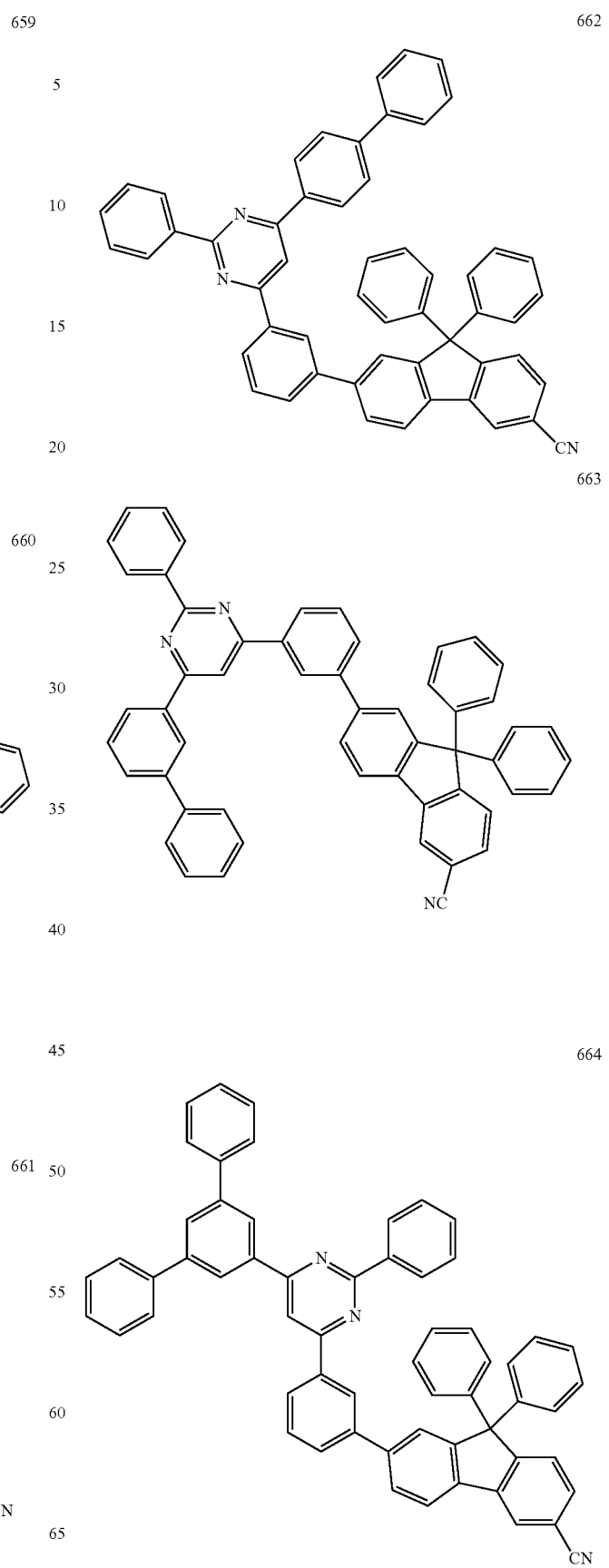

665
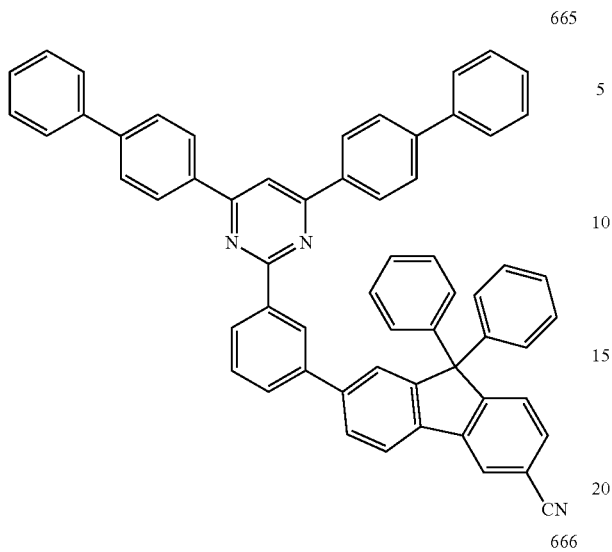
666
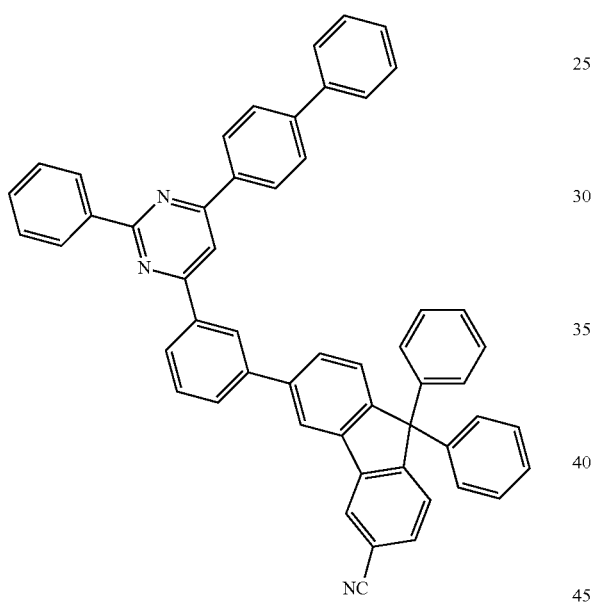
668
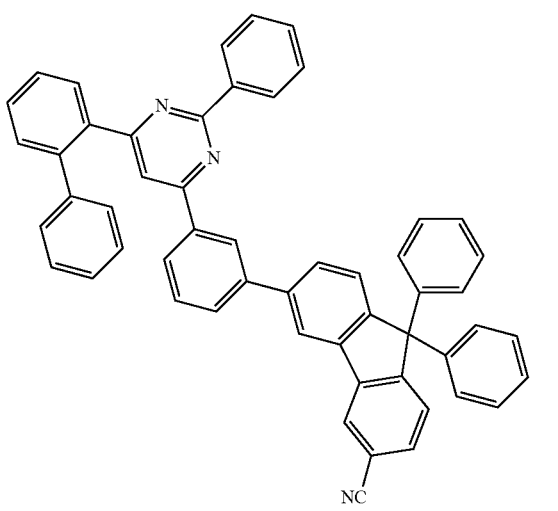
669
670
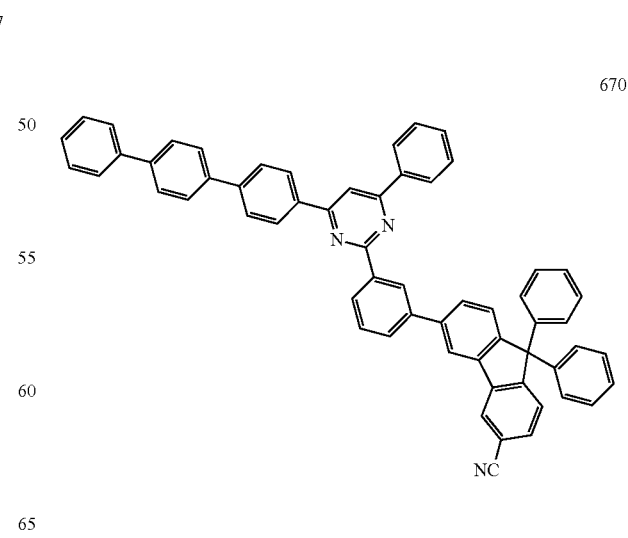

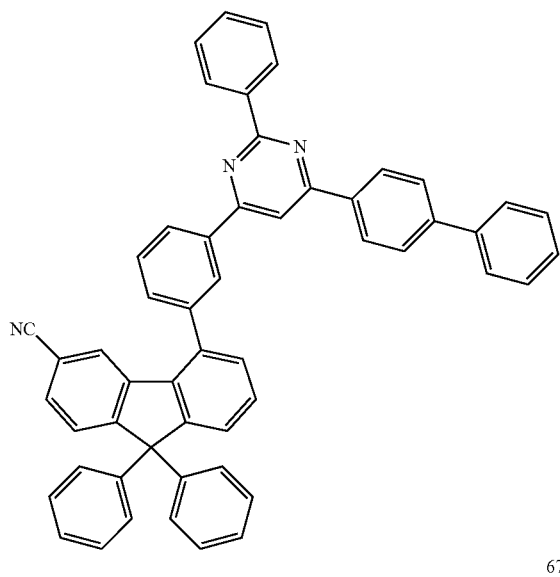
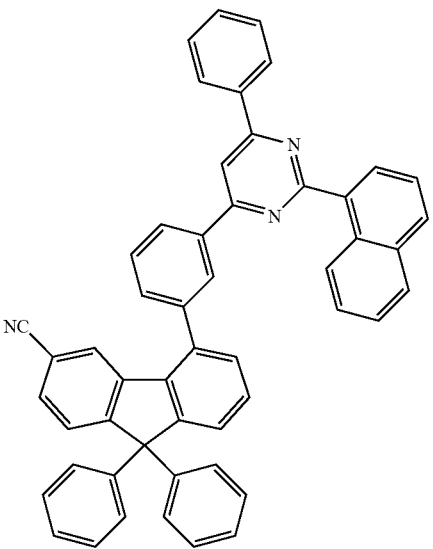
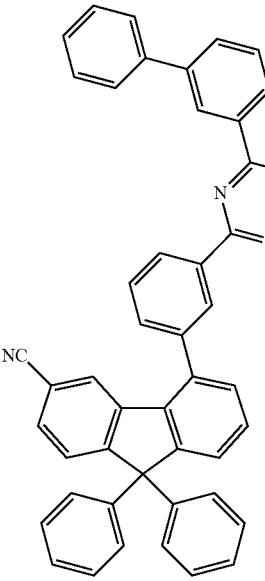
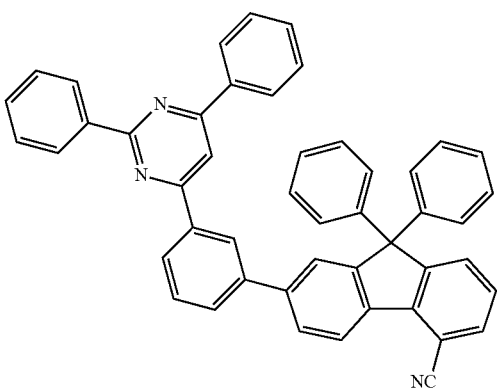

677
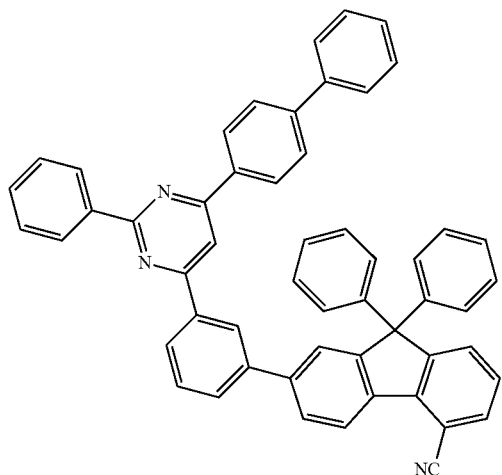
678
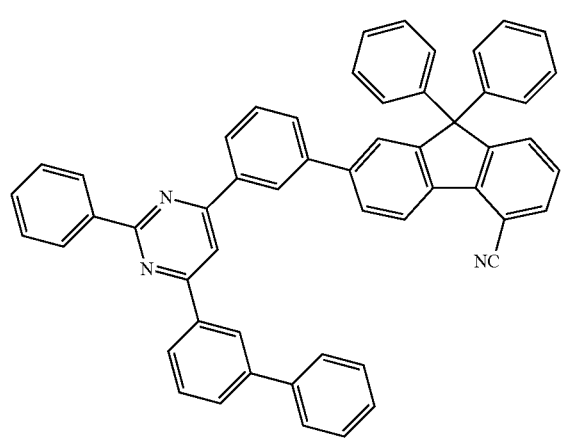
679
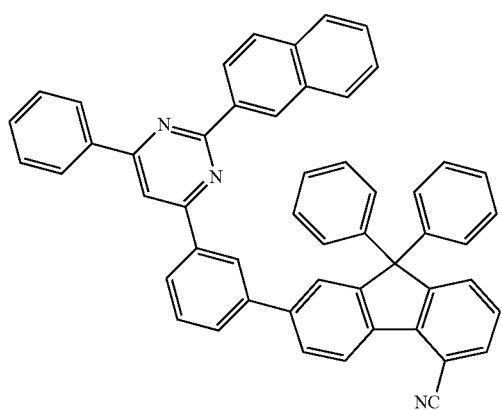
680
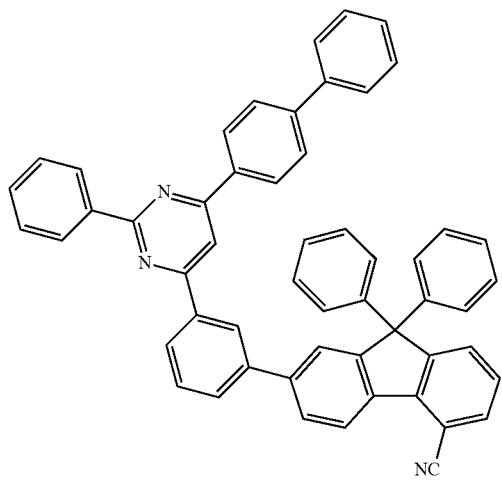
681
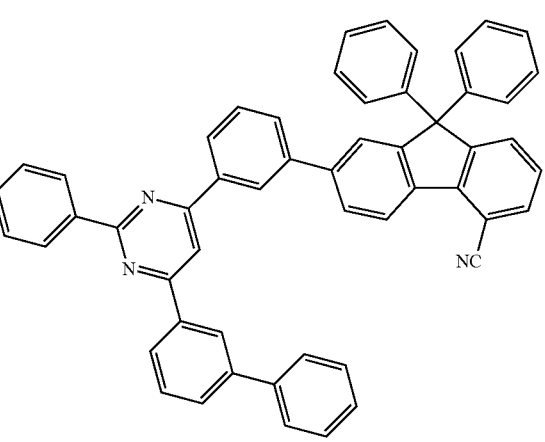
682
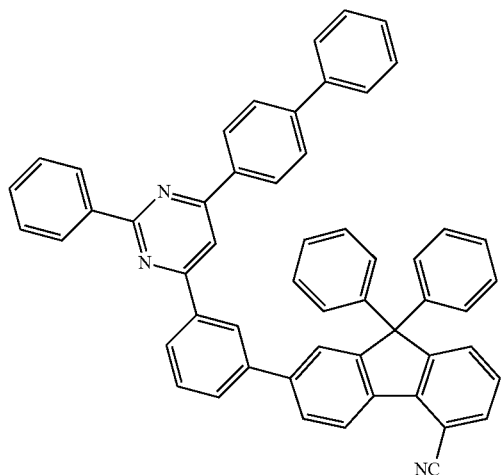

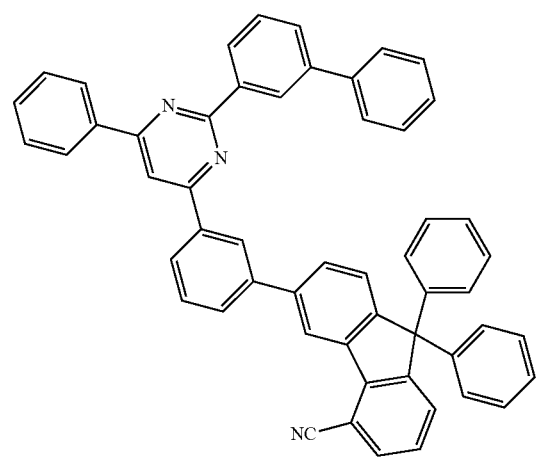
683
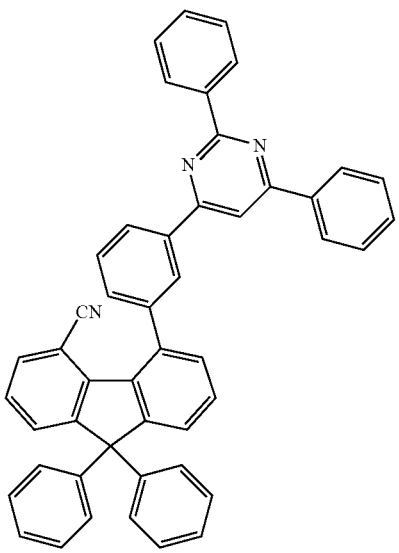
686
684
687
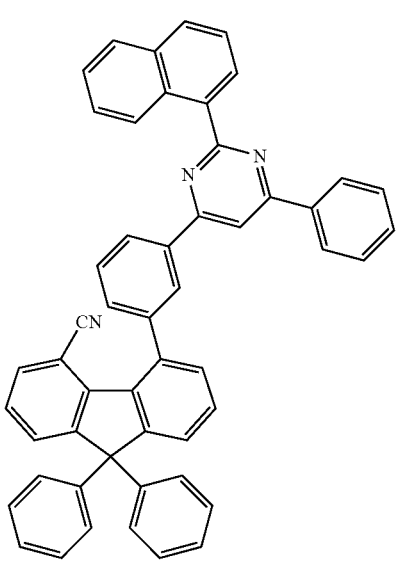
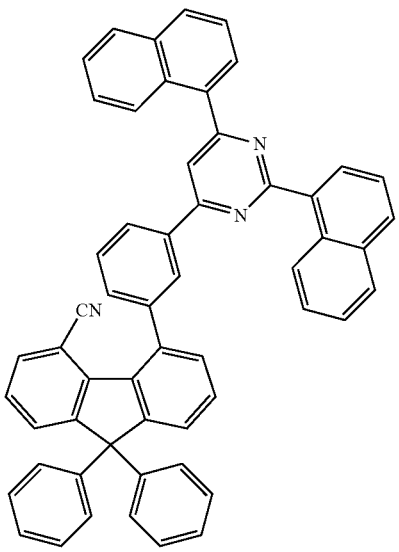
685
688

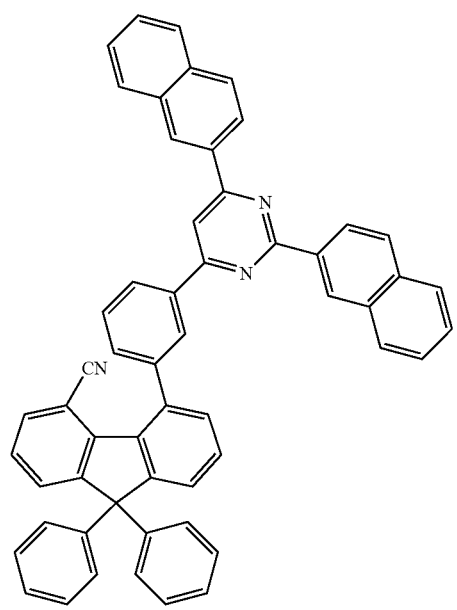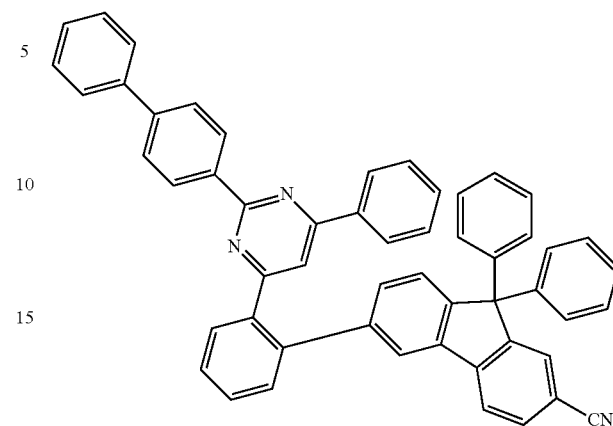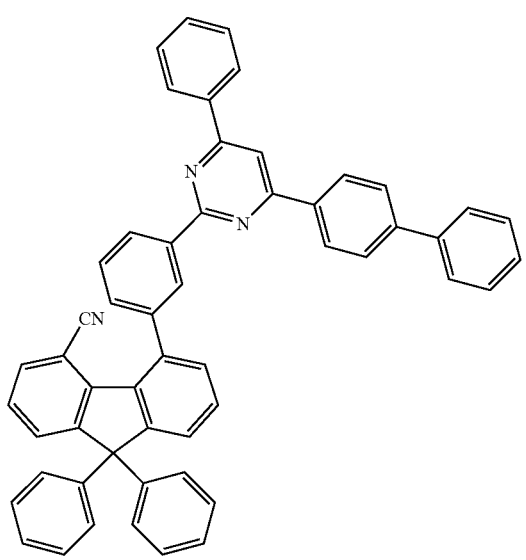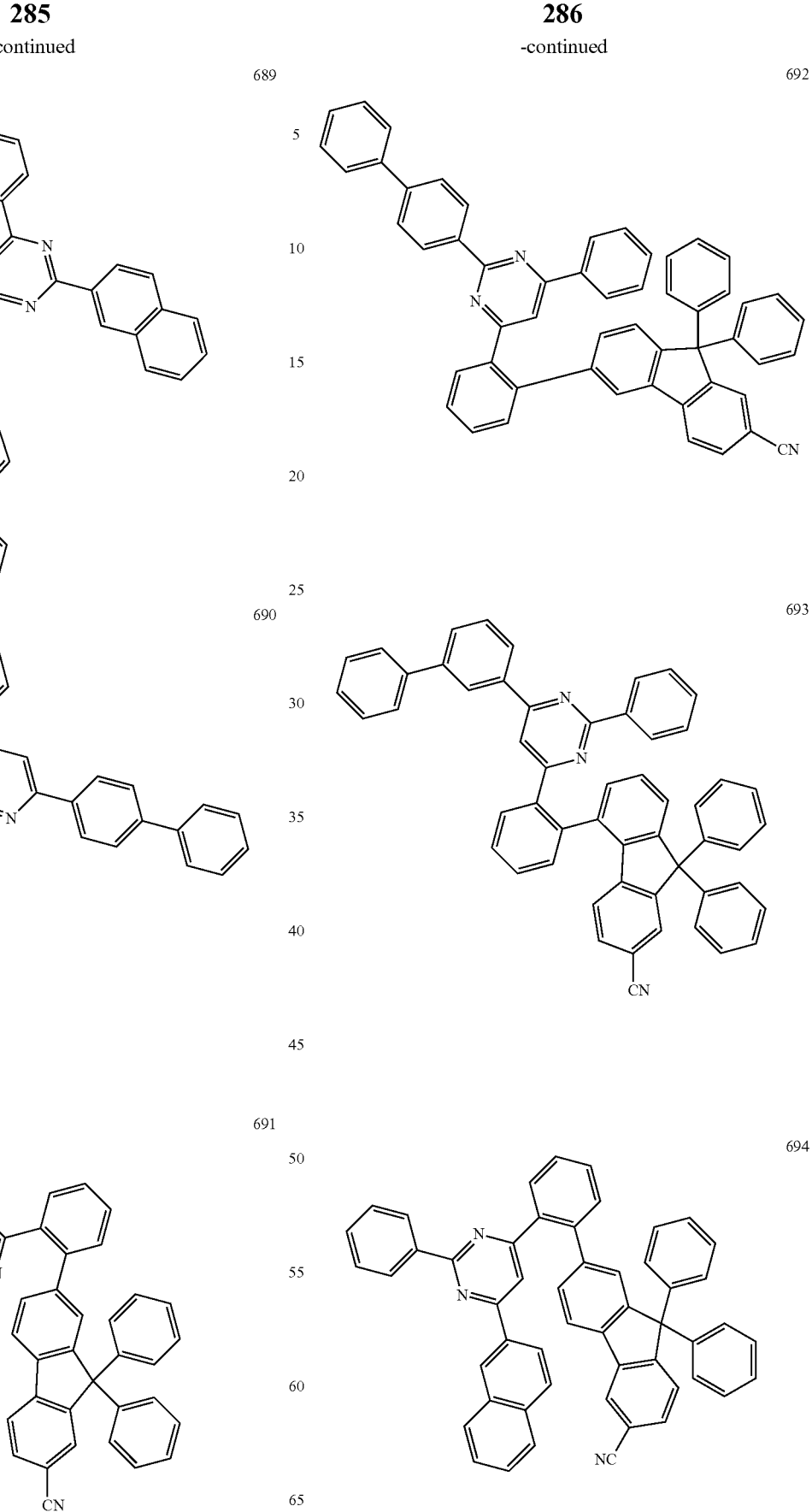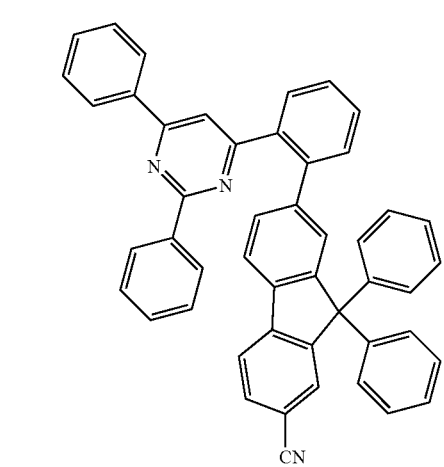

287
-continued
695
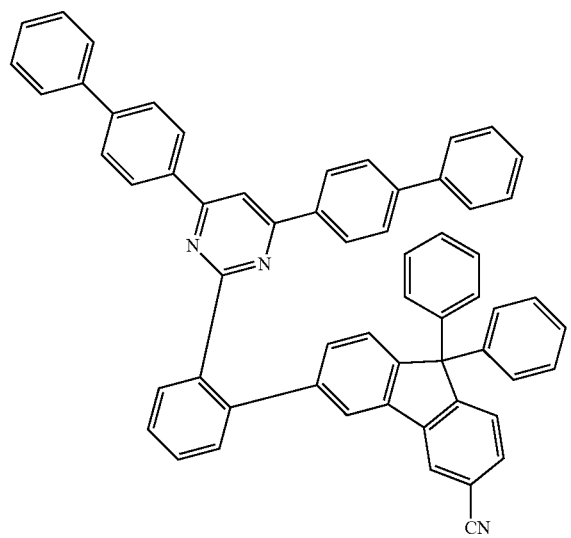
696
697
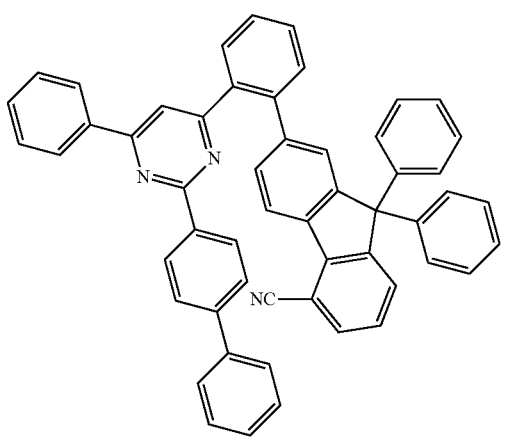
288
-continued
698
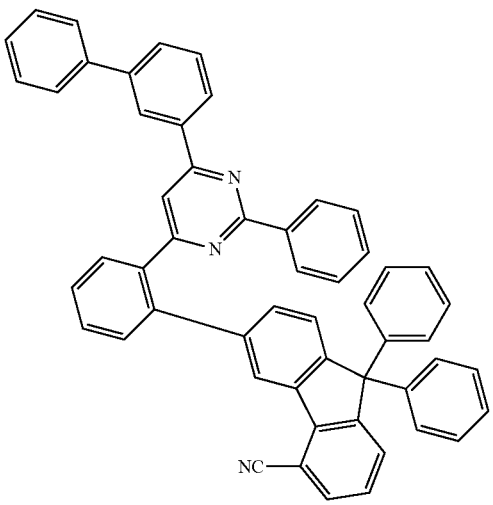
699
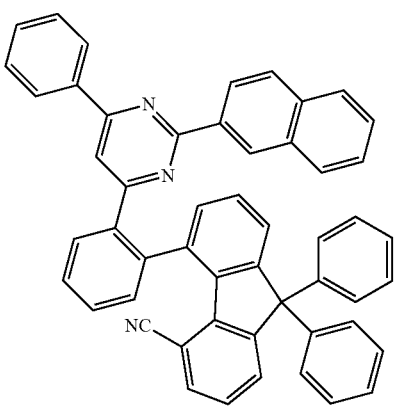
700
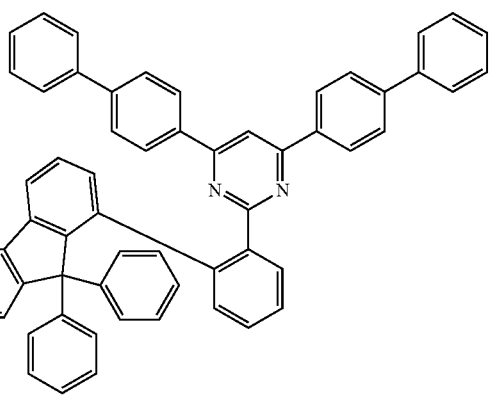

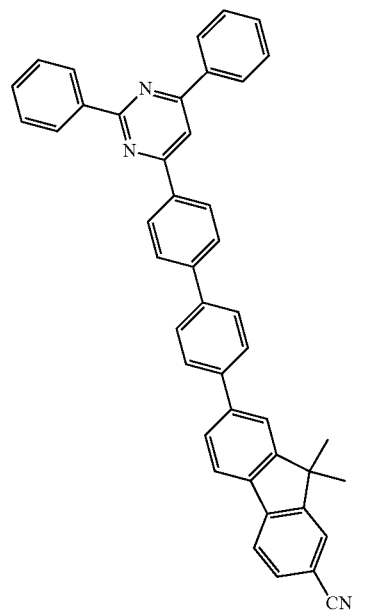
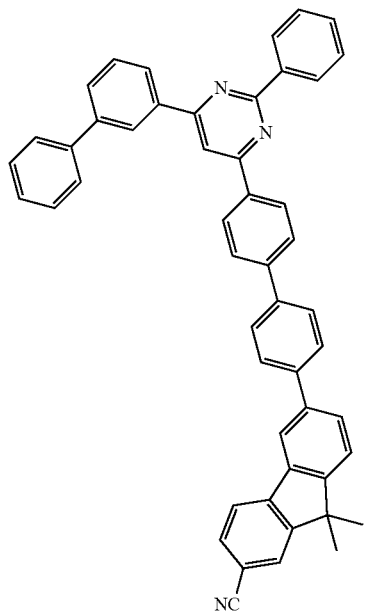

291
-continued
705
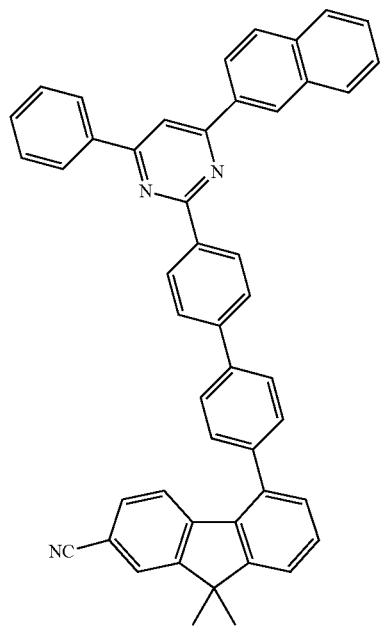
706
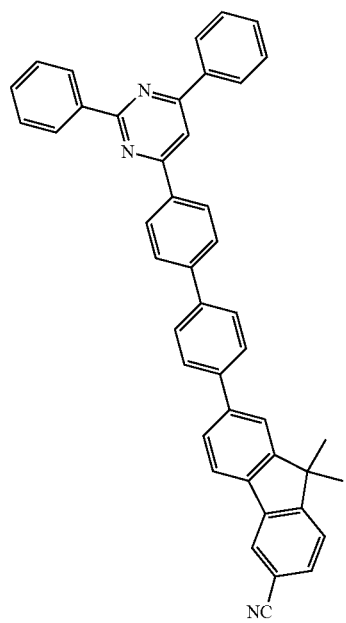
292
-continued
707
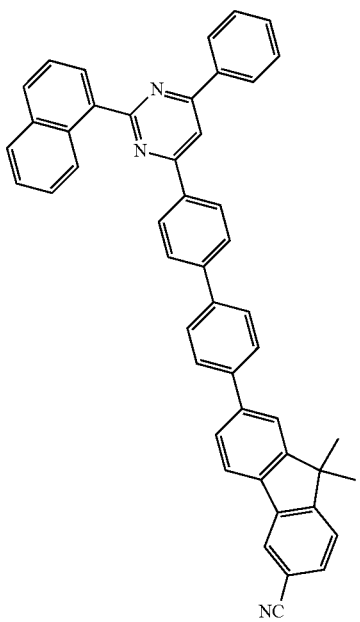
708

293
709
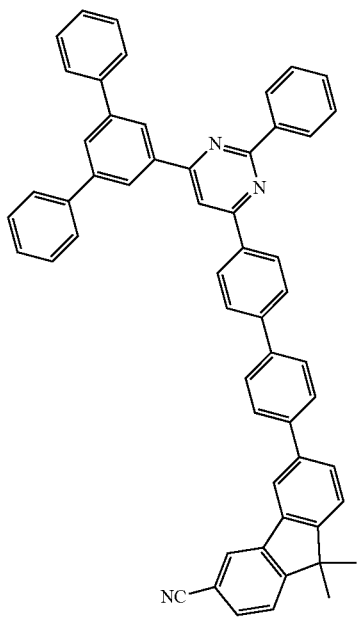
294
711
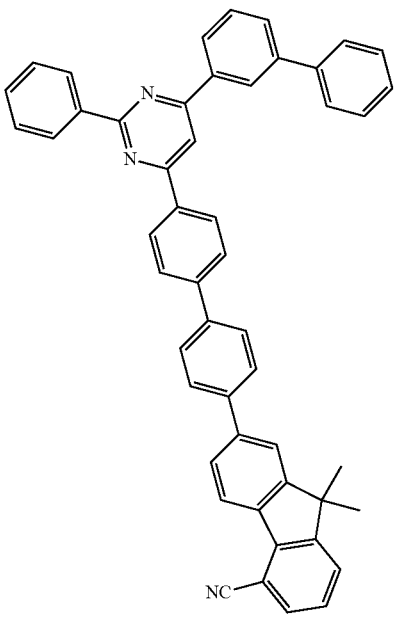
710
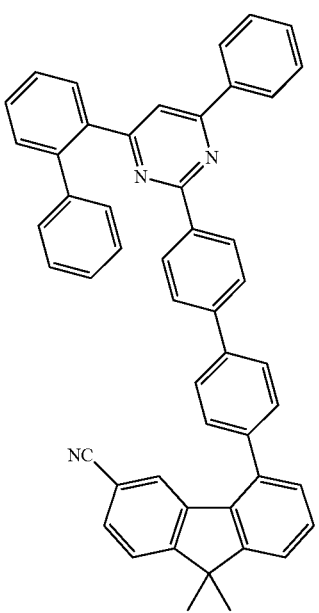
712
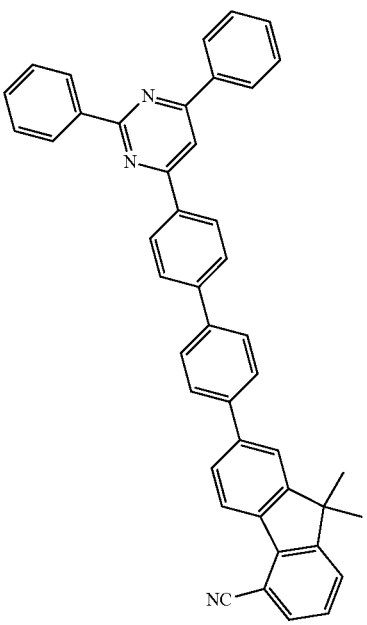

-continued
713
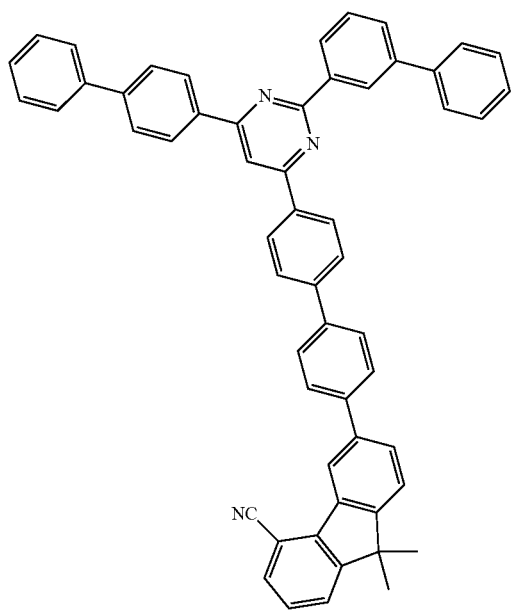
714
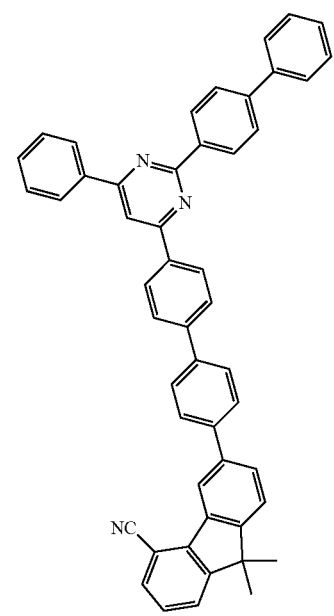
-continued
715
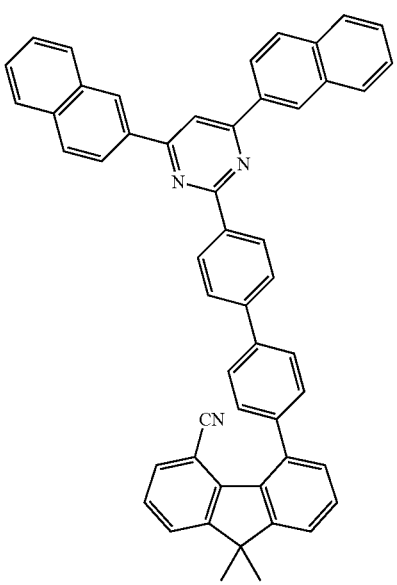
716
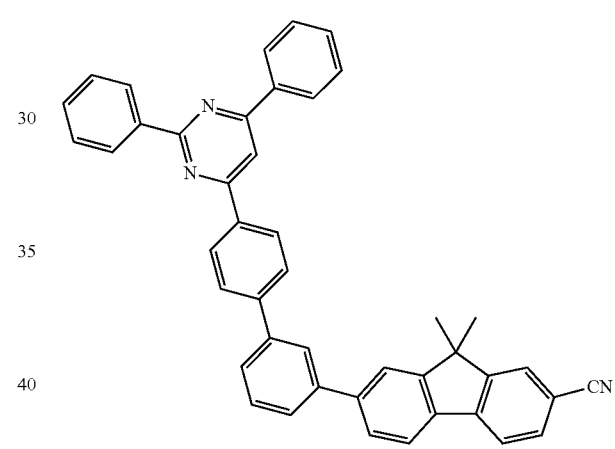
717
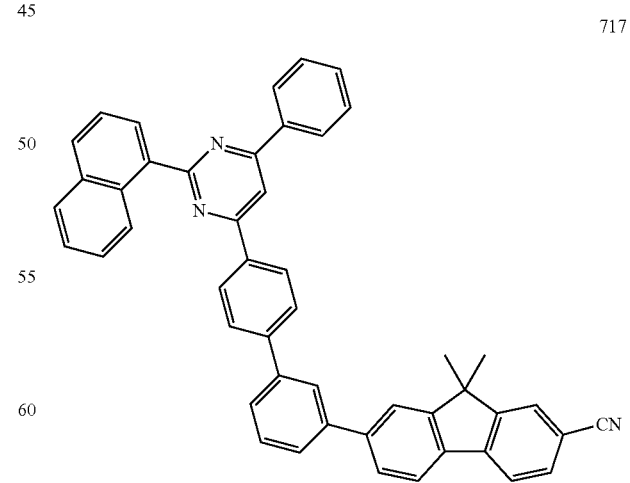

-continued
718
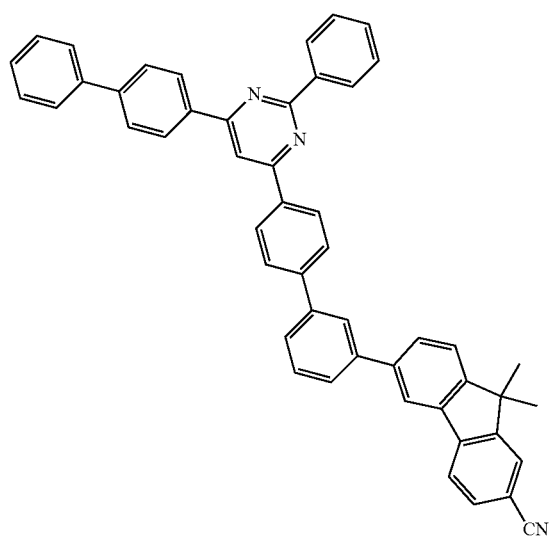
719
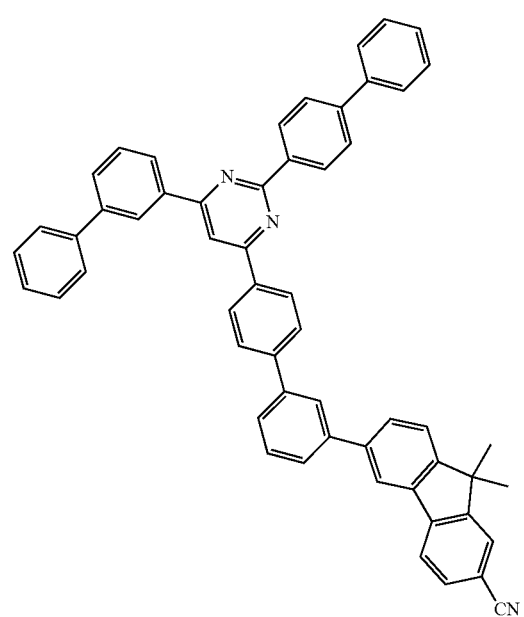
720
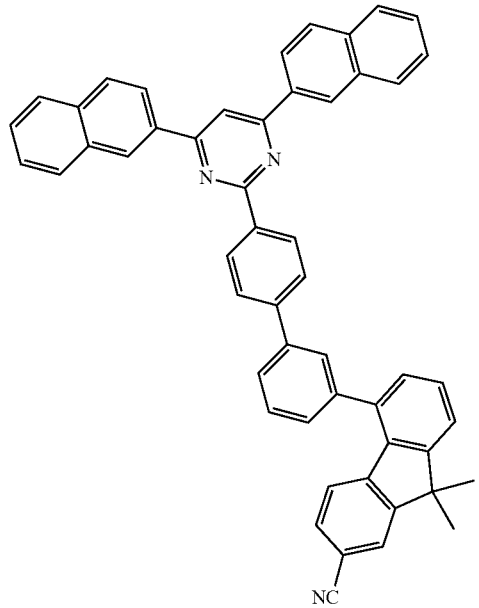
721
722
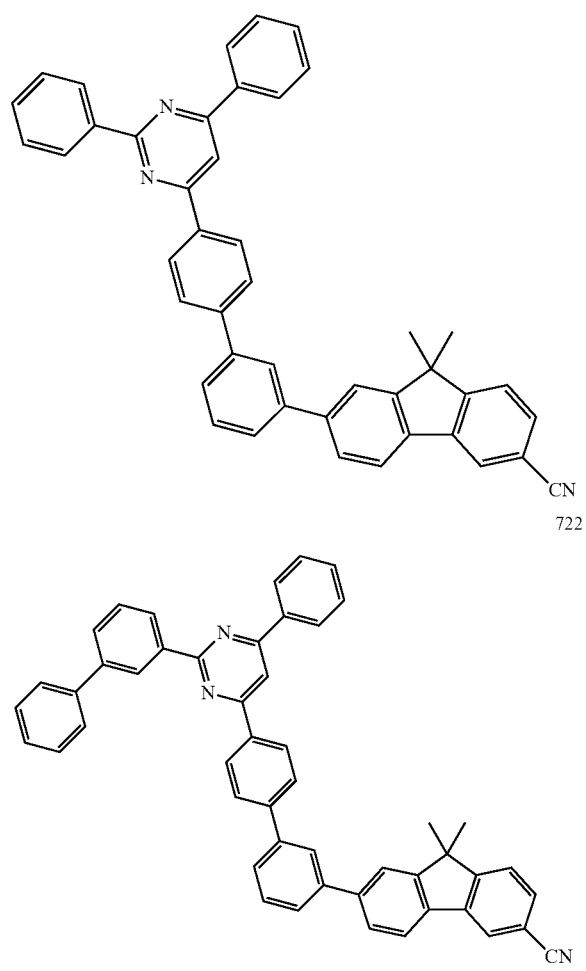

723
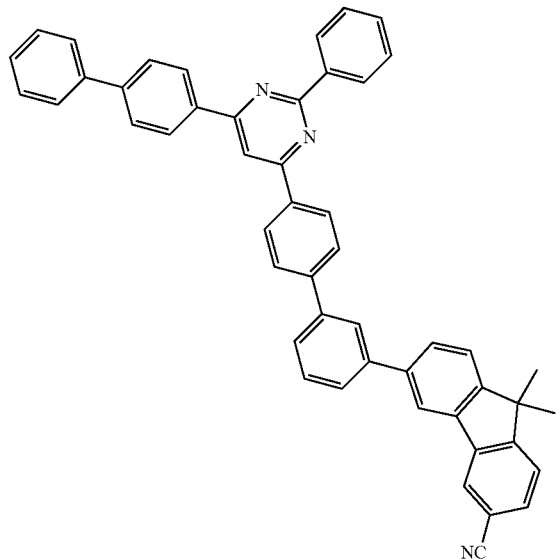
724
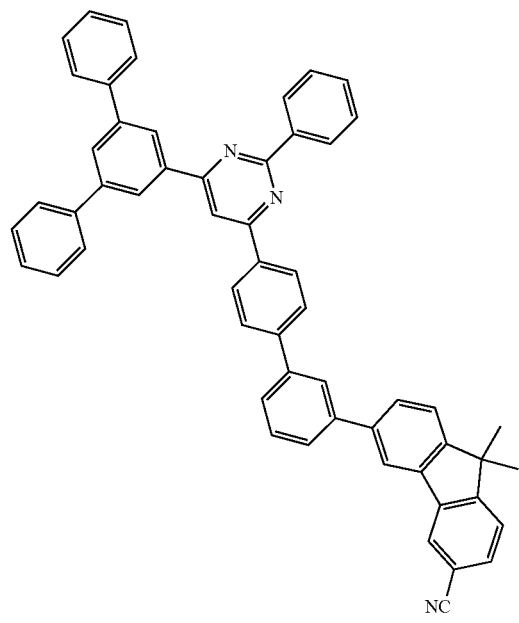
725
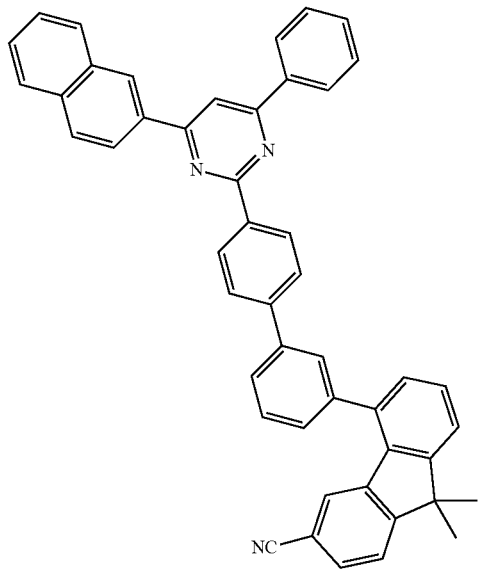
726
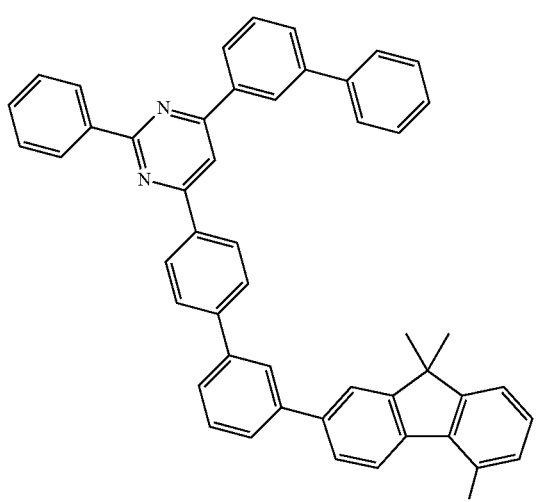
727

728
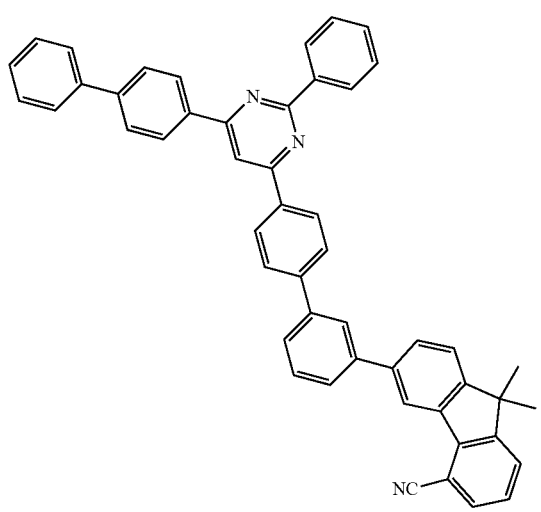
730
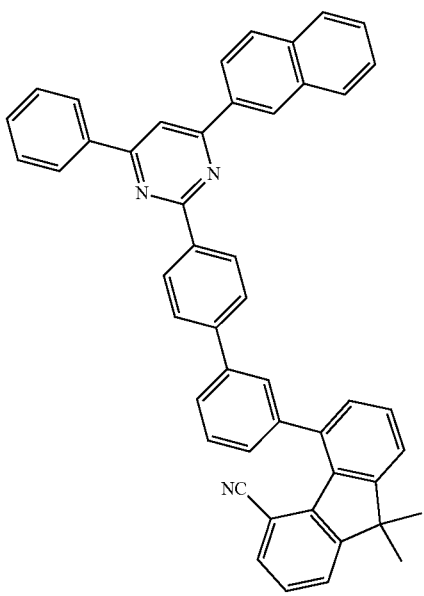
729
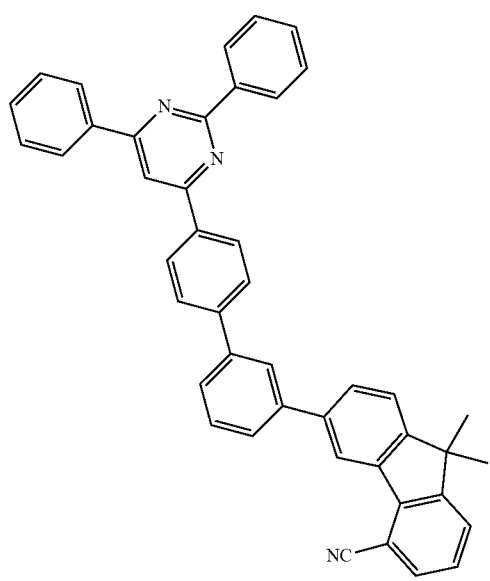
731
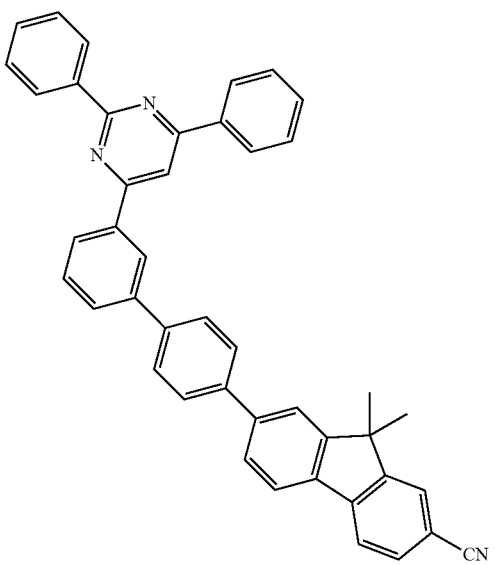

303
-continued
732
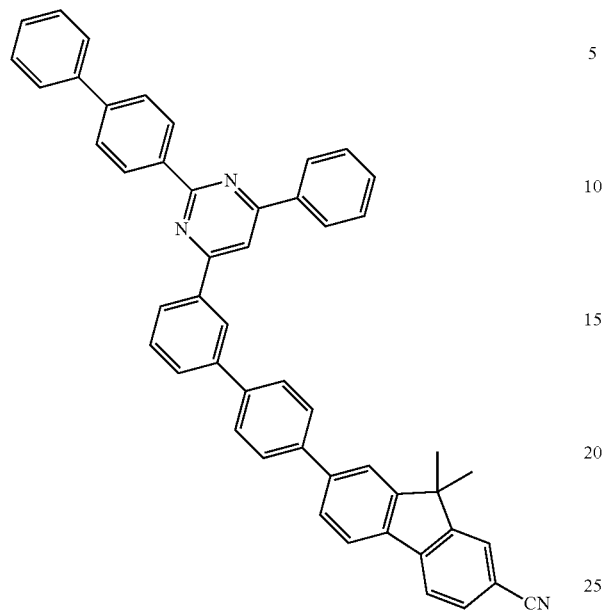
733
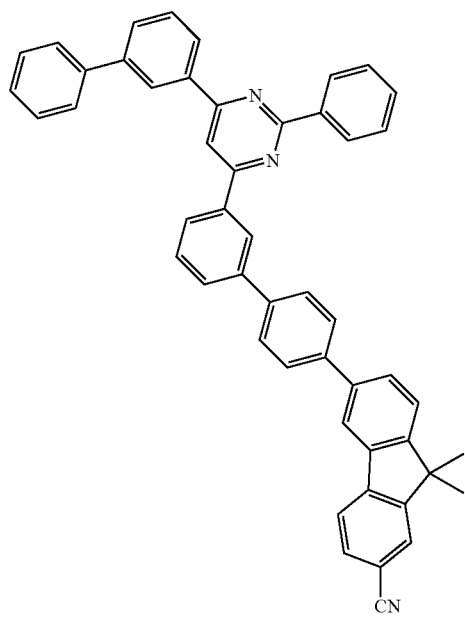
304
-continued
734
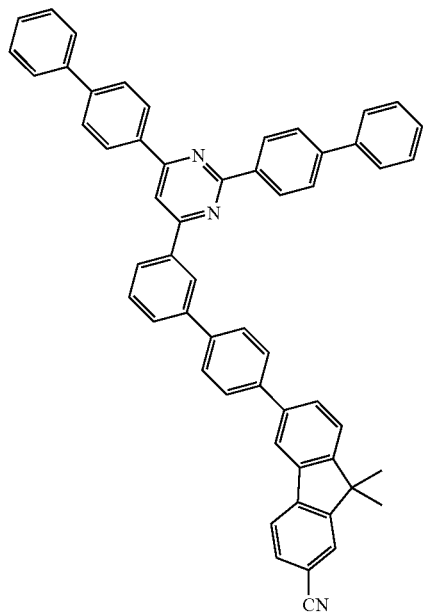
735
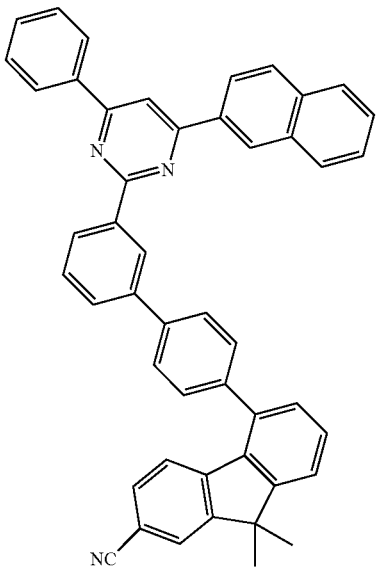

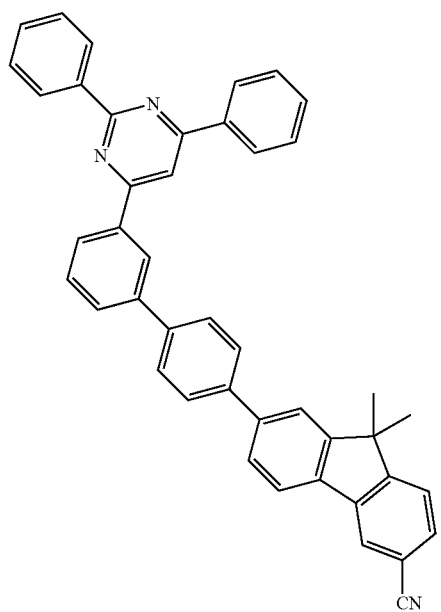
736
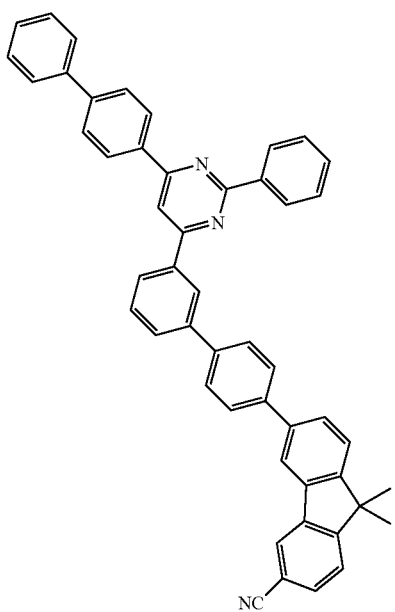
738
737
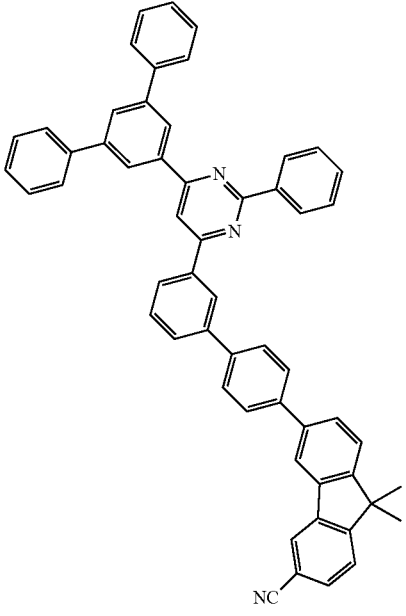
739

307
-continued
308
-continued
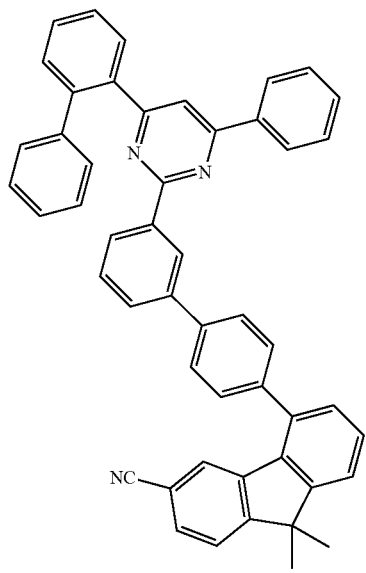
740
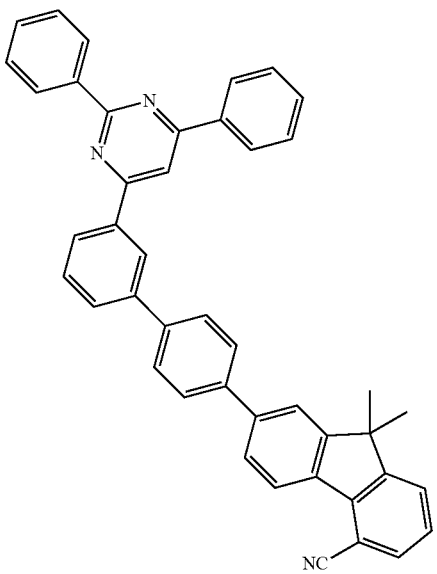
742
741
743

309
-continued
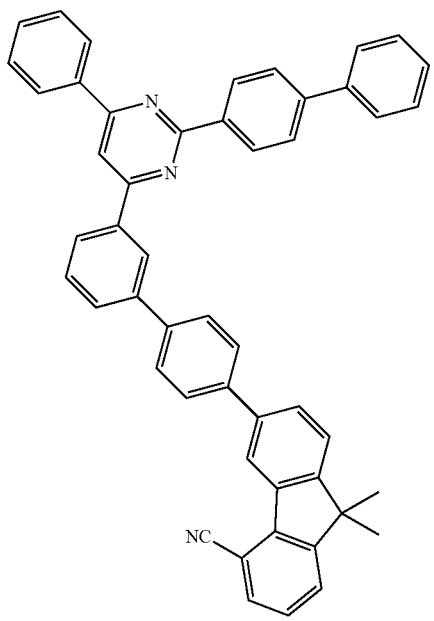
744
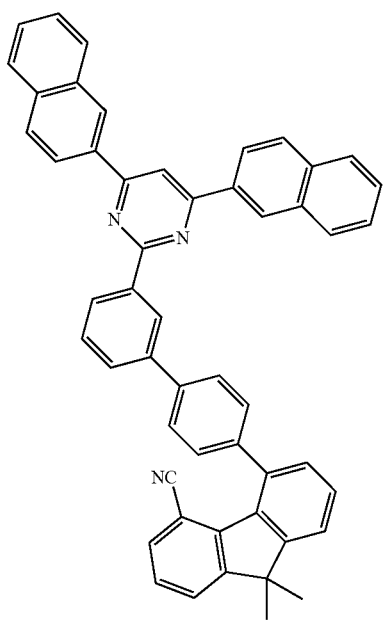
745
310
-continued
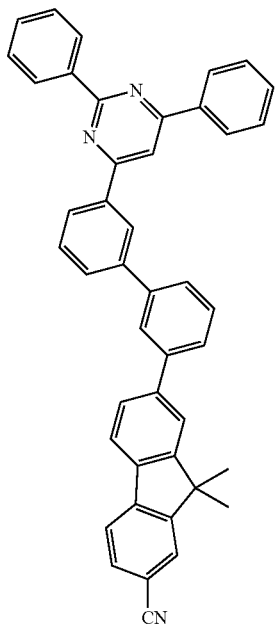
746
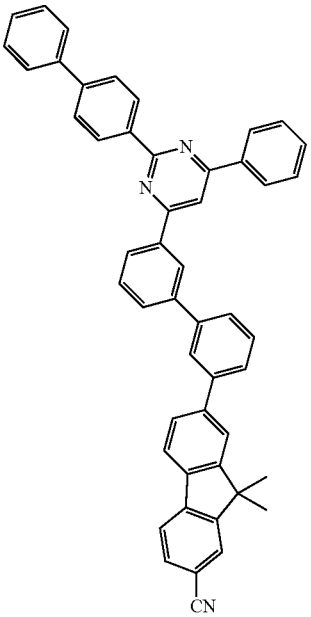
747

311
-continued
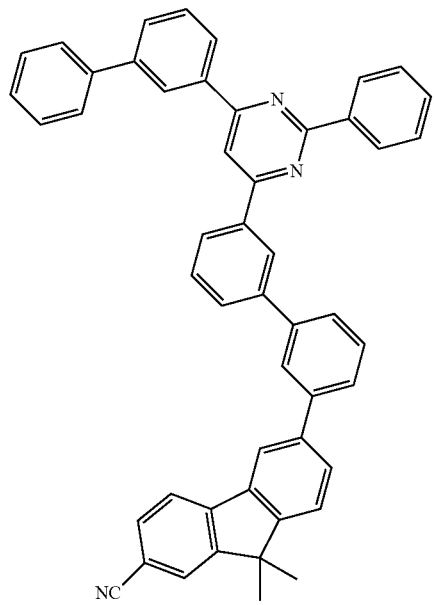
748
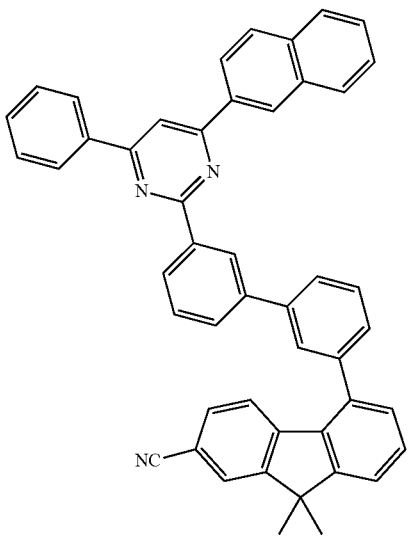
750
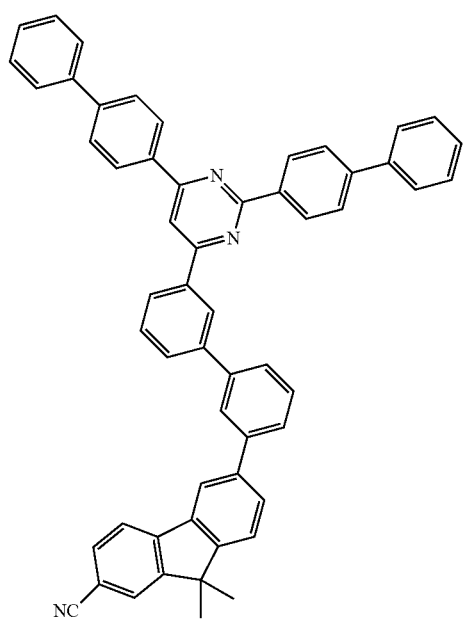
749
312
-continued
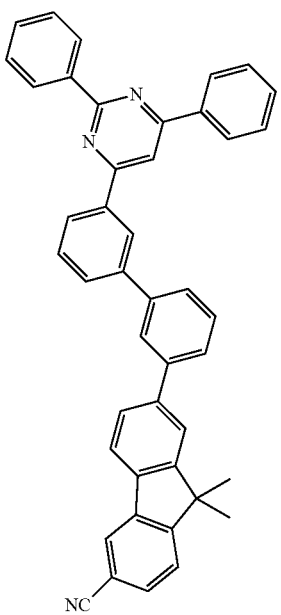
751

-continued
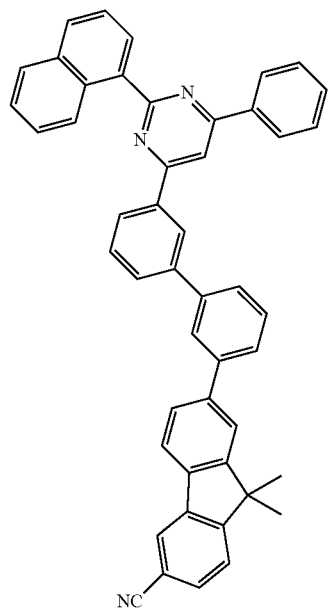
752
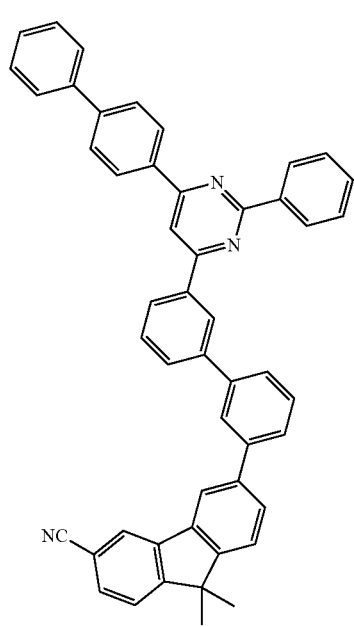
753
-continued
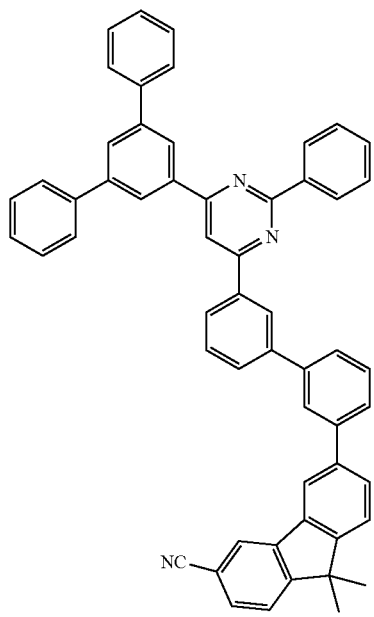
754
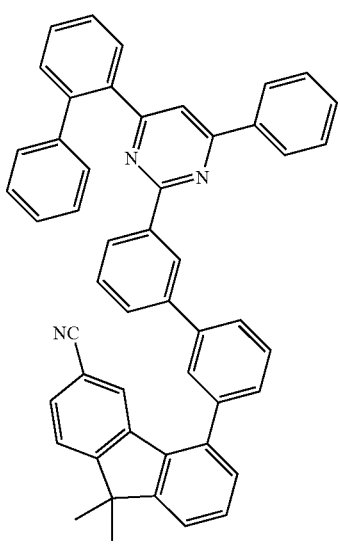
755

315
-continued
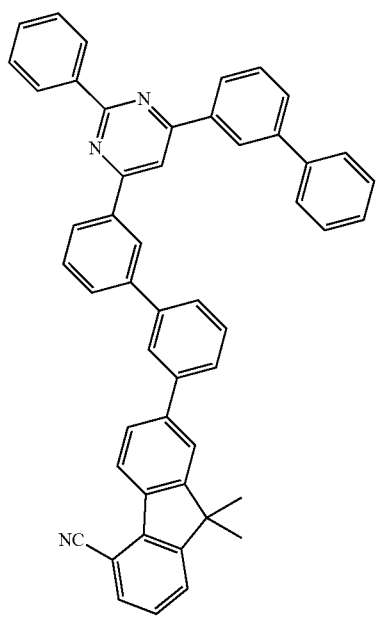
756
316
-continued
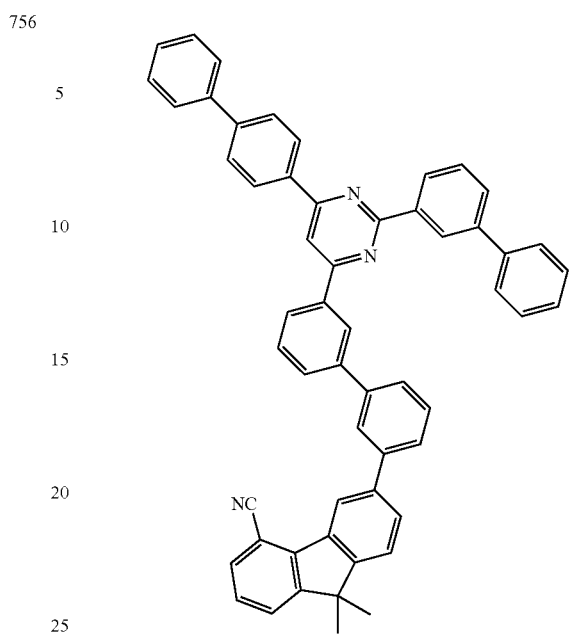
758
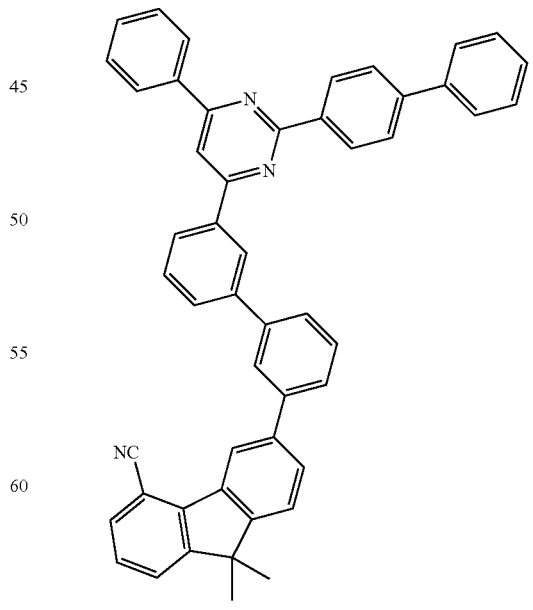
759

317
760
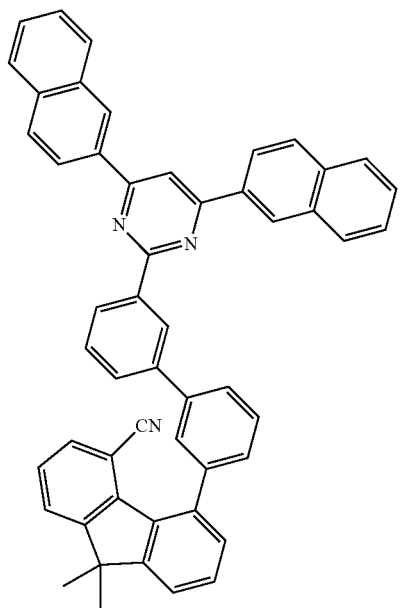
761
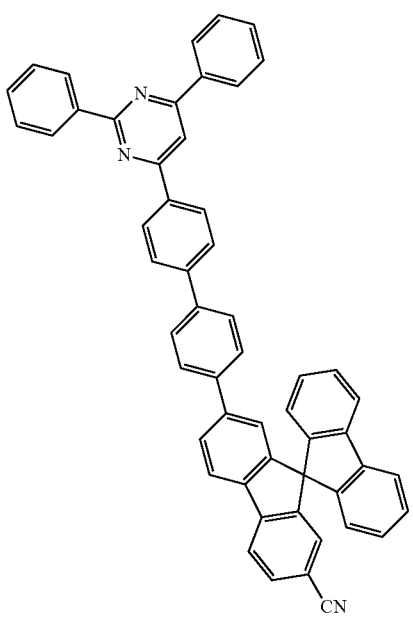
318
762
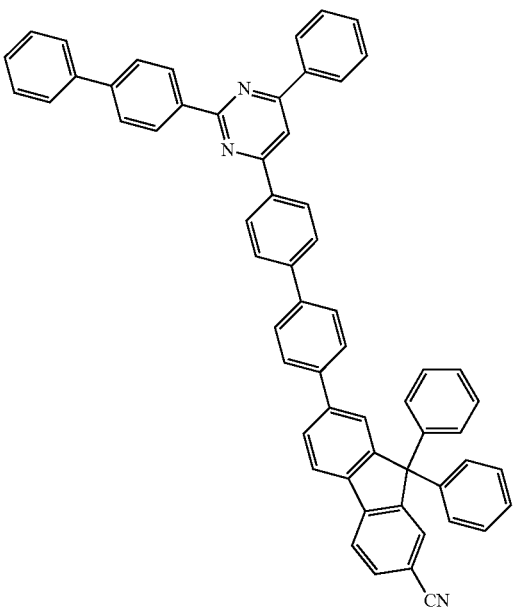
763
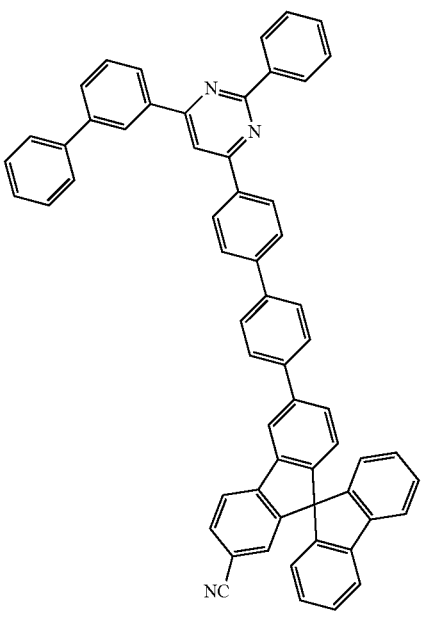

319
-continued
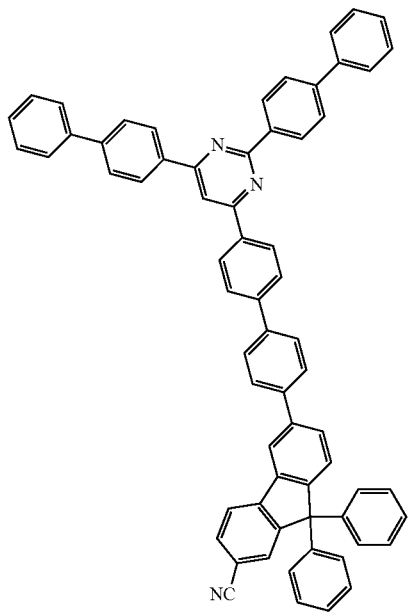
764
320
-continued
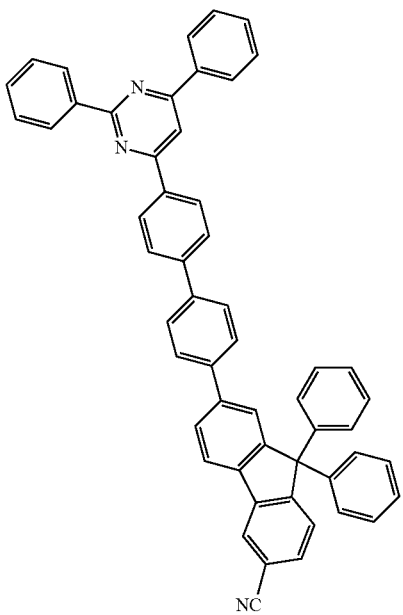
766
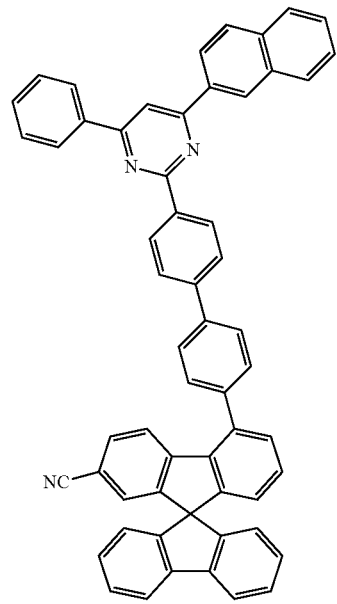
765
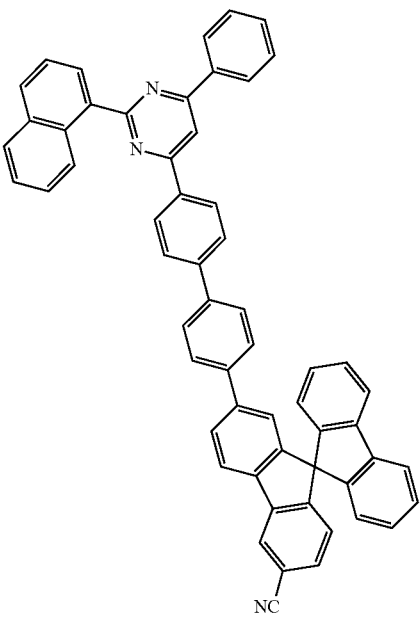
767

321
-continued
322
-continued
768
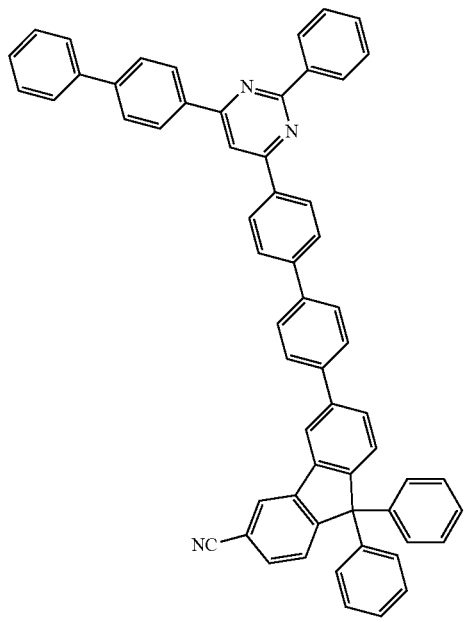
770
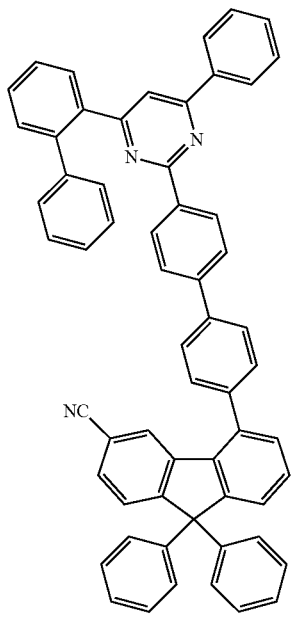
771
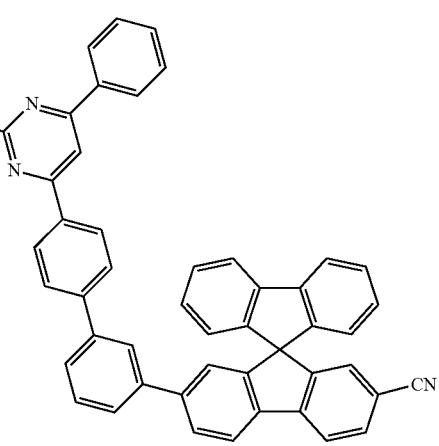
769
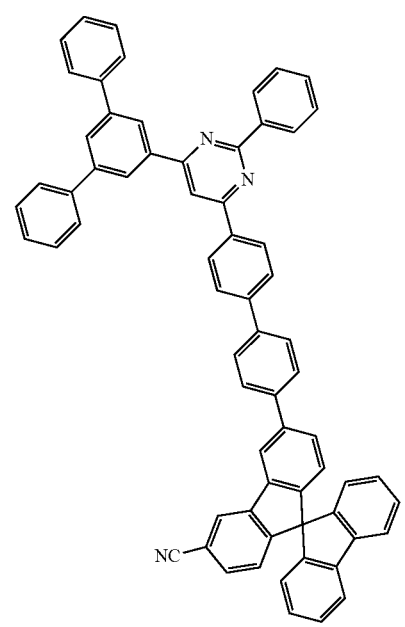
772
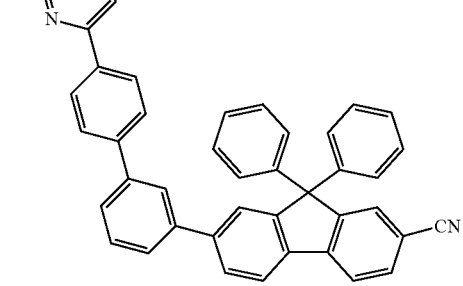

-continued
773
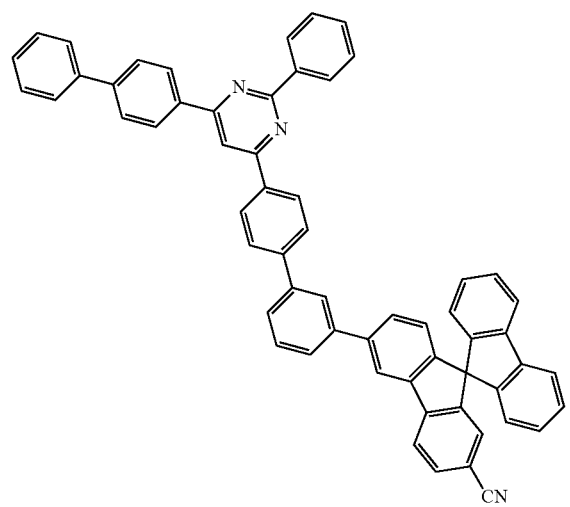
774
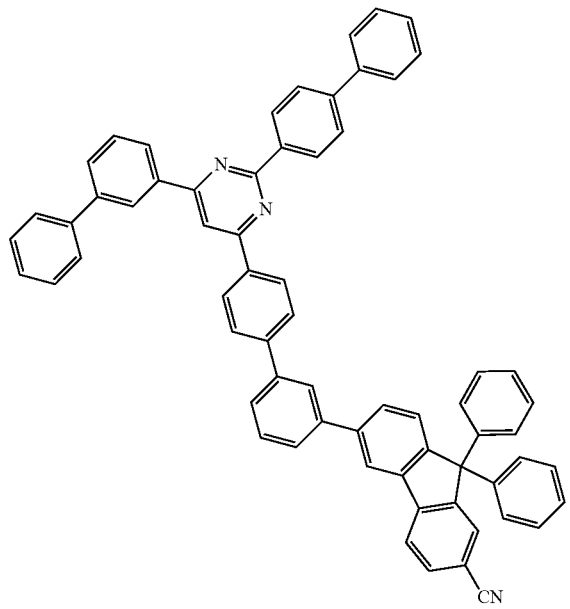
-continued
775
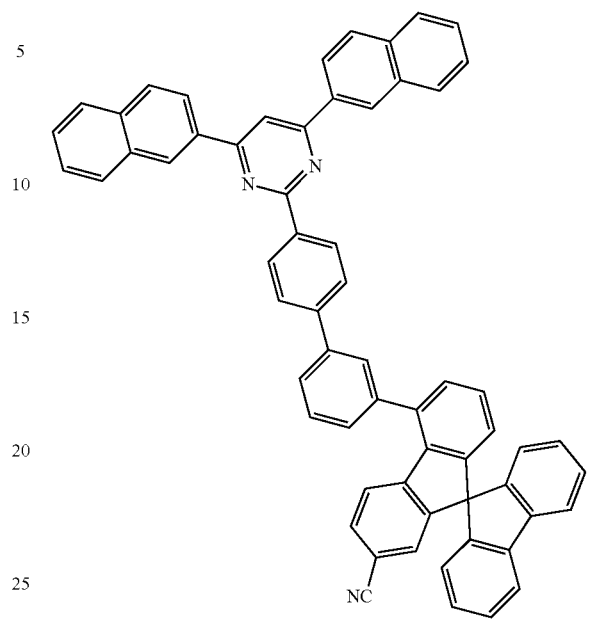
776
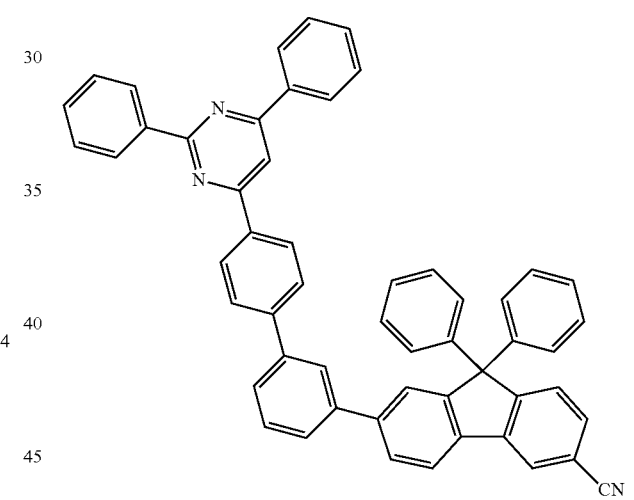
777
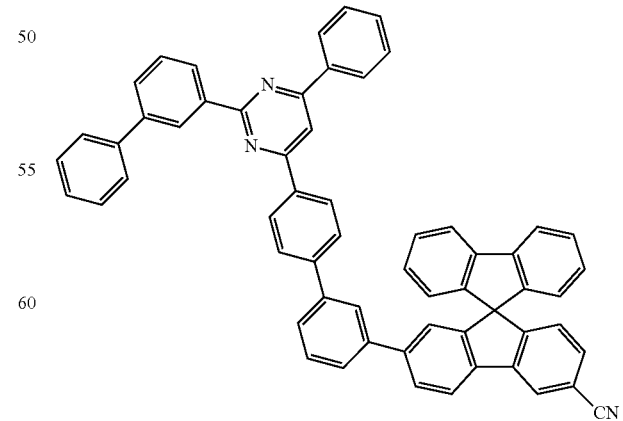

-continued
778
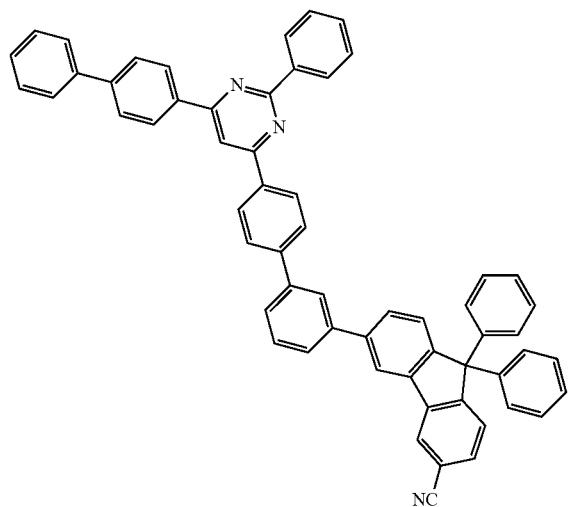
779
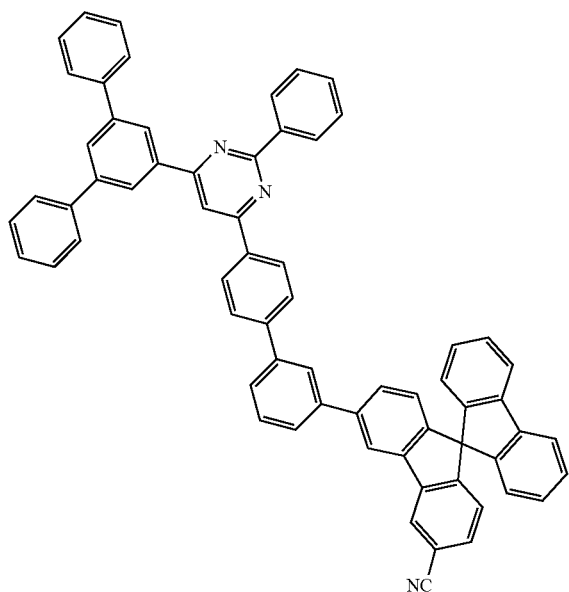
-continued
780
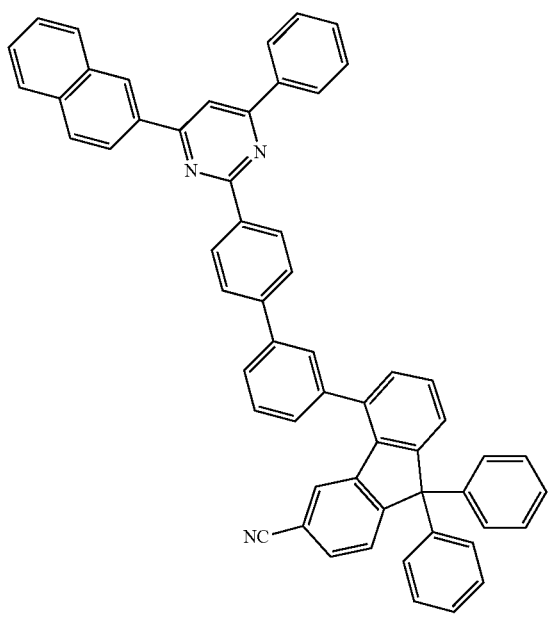
781
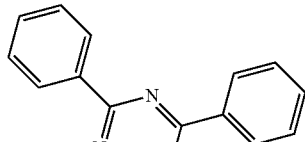
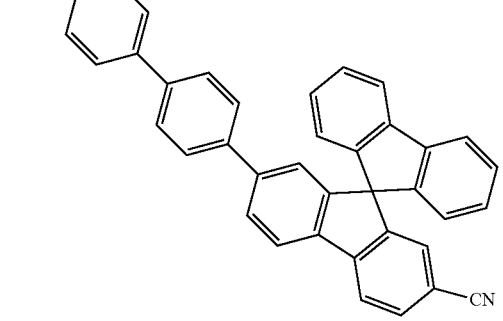

327
-continued
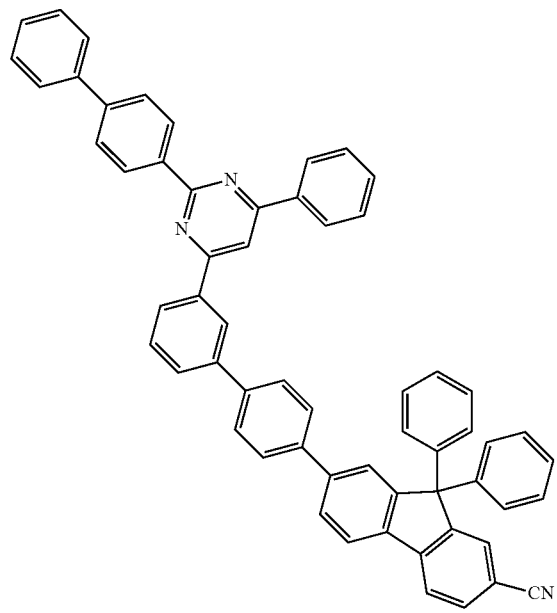
782
783
328
-continued
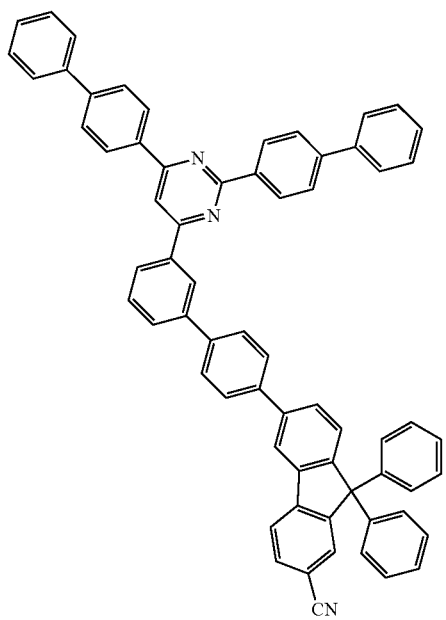
784
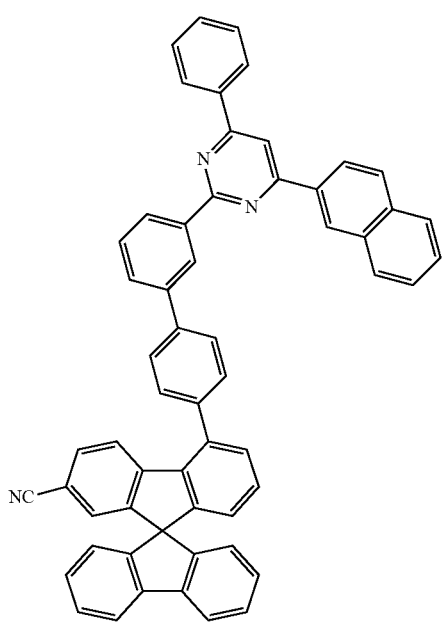
785

329
-continued
330
-continued
786
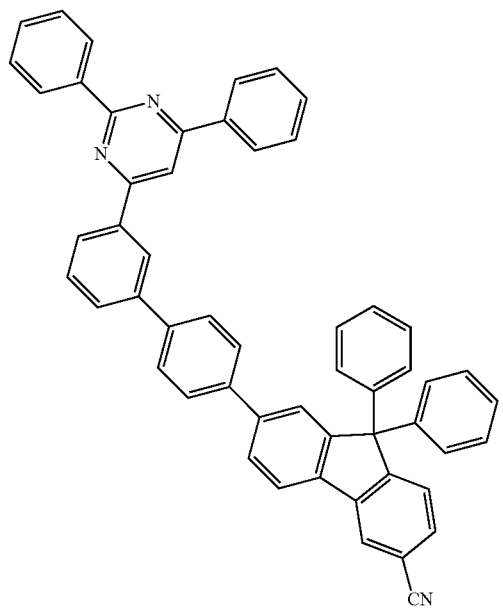
788
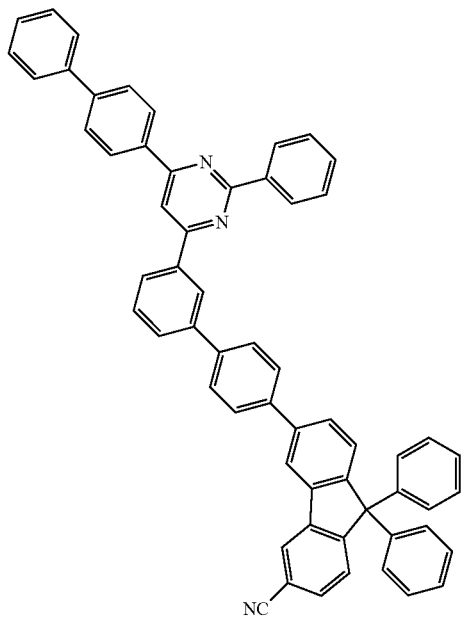
787
789
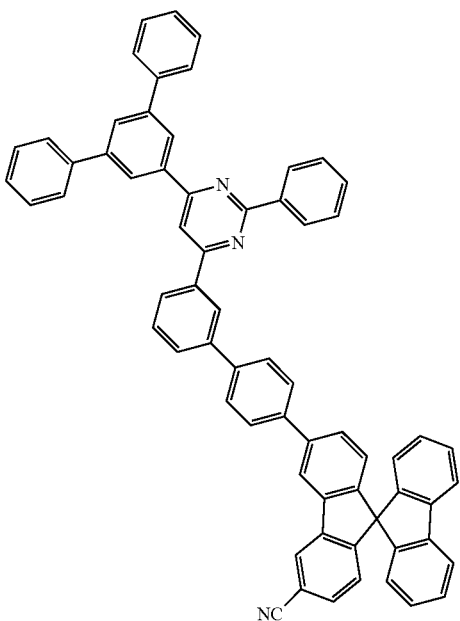

331
-continued
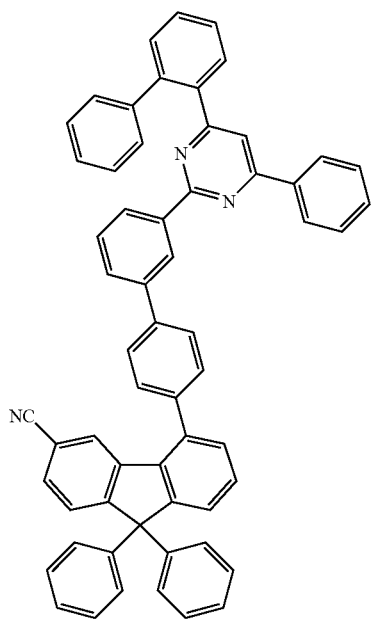
790
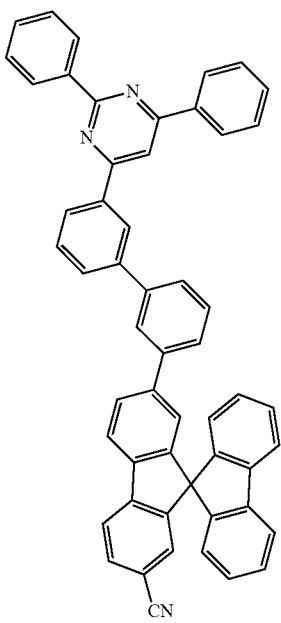
791
332
-continued
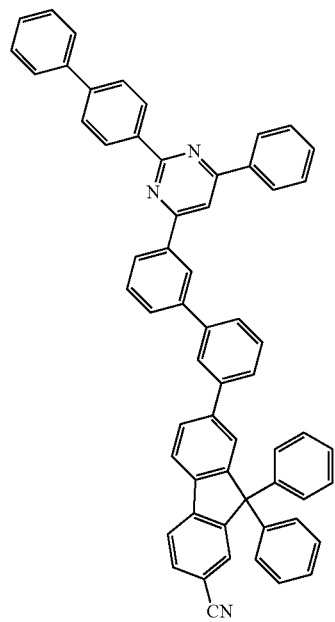
792
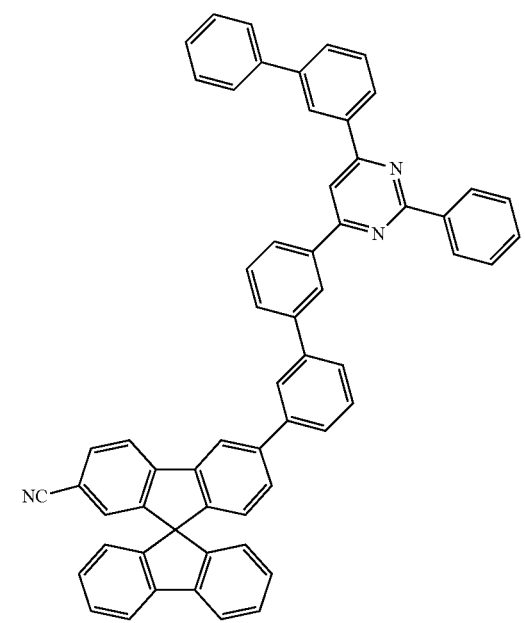
793

333
-continued
794
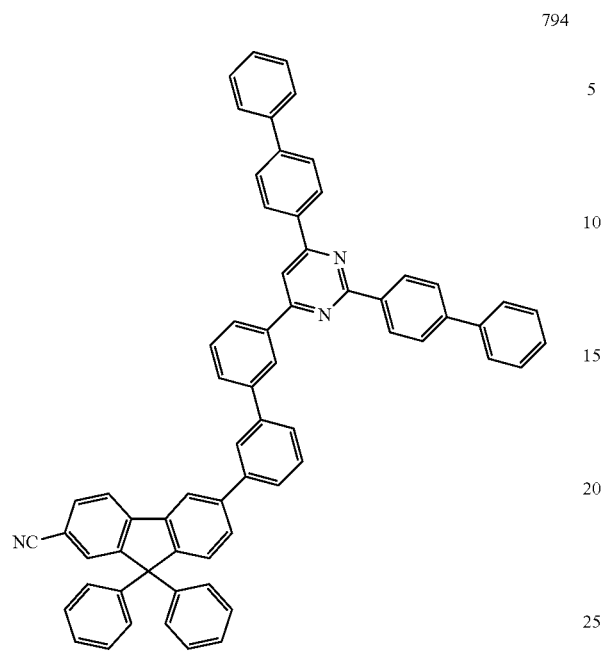
795
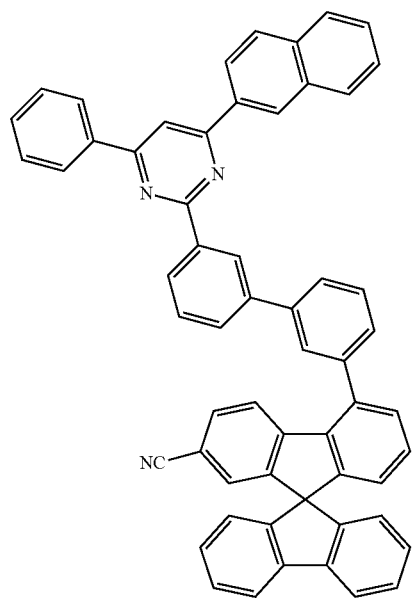
334
-continued
796
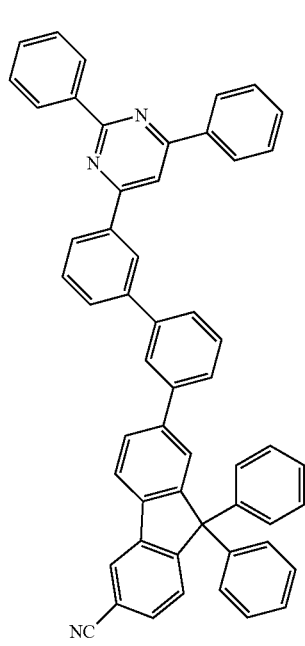
797
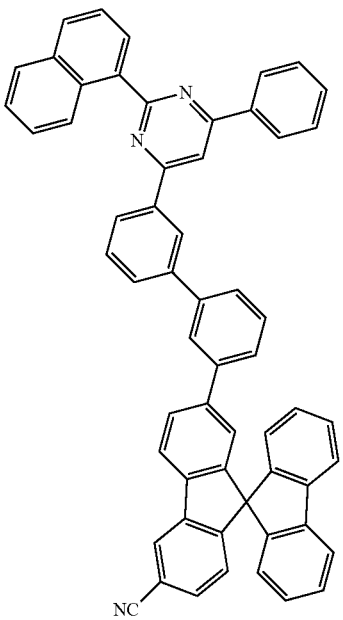

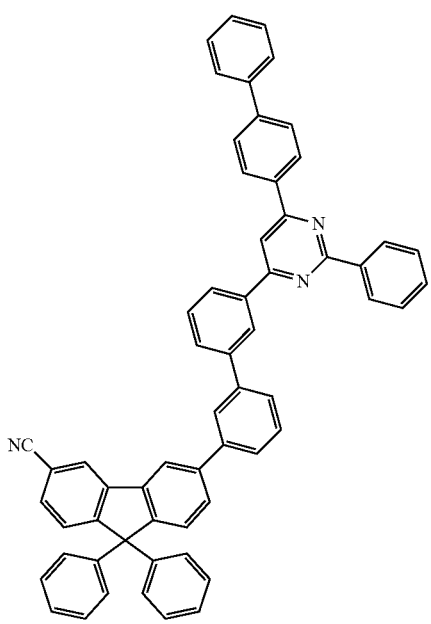

798

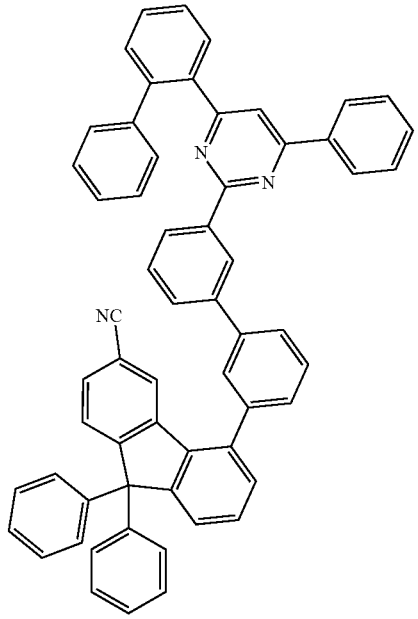

800

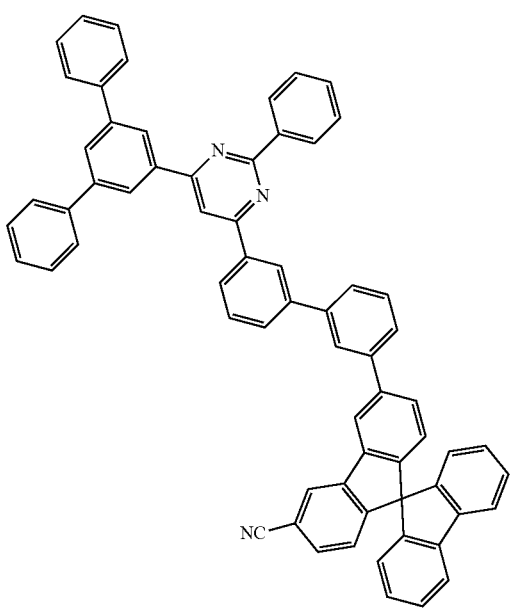

799

As used herein, "alkyl" refers to a monovalent substituent derived from a linear or branched chain saturated hydrocarbon having 1 to 40 carbon atoms. Examples of such alkyl may include, but are not limited to, methyl, ethyl, propyl, isobutyl, sec-butyl, pentyl, iso-amyl, hexyl or the like.

As used herein, "alkenyl" refers to a monovalent substituent derived from a linear or branched chain unsaturated hydrocarbon having 2 to 40 carbon atoms, having at least one carbon-carbon double bond. Examples of such alkenyl may include, but are not limited to, vinyl, allyl, isopropenyl, 2-butenyl or the like.

As used herein, "alkynyl" refers to a monovalent substituent derived from a linear or branched chain unsaturated hydrocarbon having 2 to 40 carbon atoms, having at least one carbon-carbon triple bond. Examples of such alkynyl may include, but are not limited to, ethynyl, 2-propynyl or the like.

As used herein, "aryl" refers to a monovalent substituent derived from a $C_6$ to $C_{40}$ aromatic hydrocarbon which is in a structure with a single ring or two or more rings combined with each other. In addition, a form in which two or more rings are pendant (e.g., simply attached) to or fused with each other may also be included. Examples of such aryl may include, but are not limited to, phenyl, naphthyl, phenanthryl, anthryl or the like.

As used herein, "heteroaryl" refers to a monovalent substituent derived from a monoheterocyclic or polyheterocyclic aromatic hydrocarbon having 5 to 40 nuclear atoms. In such an embodiment, one or more carbons in the ring, preferably one to three carbons, are substituted with a heteroatom such as N, O, S or Se. In addition, a form in which two or more rings are pendant to or fused with each other may be included and a form fused with an aryl group may be included. Examples of such heteroaryl may include, but are not limited to, a 6-membered monocyclic ring including, for example, pyridyl, pyrazinyl, pyrimidinyl, pyridazinyl and triazinyl; a polycyclic ring including, for example, phenoxathienyl, indolinzinyl, indolyl purinyl, quinolyl, benzothiazole, and carbazolyl; 2-furanyl; N-imidazolyl; 2-isoxazolyl; 2-pyridinyl; 2-pyrimidinyl or the like.

As used herein, "aryloxy" is a monovalent substituent represented by RO—, where R refers to aryl having 5 to 40 carbon atoms. Examples of such aryloxy may include, but are not limited to, phenyloxy, naphthyloxy, diphenyloxy or the like.

As used herein, "alkyloxy" refers to a monovalent substituent represented by R'O—, where R' refers to alkyl having 1 to 40 carbon atoms. Such alkyloxy may include a linear, branched or cyclic structure. Examples of such alkyloxy may include, but are not limited to, methoxy, ethoxy, n-propoxy, 1-propoxy, t-butoxy, n-butoxy, pentoxy or the like.

As used herein, "arylamine" refers to amine substituted with aryl having 6 to 40 carbon atoms.

As used herein, "cycloalkyl" refers to a monovalent substituent derived from a monocyclic or polycyclic non-aromatic hydrocarbon having 3 to 40 carbon atoms. Examples of such cycloalkyl may include, but are not limited to, cyclopropyl, cyclopentyl, cyclohexyl, norbornyl, adamantine or the like.

As used herein, "heterocycloalkyl" refers to a monovalent substituent derived from a non-aromatic hydrocarbon having 3 to 40 nuclear atoms, where one or more carbons in the ring, preferably one to three carbons, are substituted with a heteroatom such as N, O, S or Se. Examples of such heterocycloalkyl may include, but are not limited to, morpholine, piperazine or the like.

As used herein, "alkylsilyl" refers to silyl in which substitution with alkyl having 1 to 40 carbon atoms has been made, and "arylsilyl" refers to silyl in which substitution with aryl having 5 to 40 carbon atoms has been made.

As used herein, the term "fused ring (e.g., condensed ring)" refers to a fused aliphatic ring, a fused aromatic ring, a fused heteroaliphatic ring, a fused heteroaromatic ring, or a combination thereof.

<Electron Transport Layer Material>

The present invention provides an electron transport layer including the compound represented by Chemical Formula 1.

The electron transport layer (ETL) serves to move electrons injected from the cathode to an adjacent layer, specifically a light emitting layer.

The compound represented by Chemical Formula 1 may be used solely as an electron transport layer (ETL) material, or may be used in combination with an electron transport layer material known in the art. It may preferably be used solely.

The electron transport layer material that may be used in combination with the compound of Chemical Formula 1 includes an electron transport material commonly known in the art. Non-limiting examples of applicable electron transport materials may include oxazole-based compounds, isoxazole-based compounds, triazole-based compounds, isothiazole-based compounds, oxadiazole-based compounds, thiadiazole-based compounds, perylene-based compounds, aluminum complexes (e.g., tris(8-quinolinolato)-aluminium ($Alq_3$), BAlq, SAlq, $Almq_3$), gallium complexes (e.g., Gaq'2OPiv, Gag'2OAc, 2(Gaq'2)), etc. These may be used solely or two or more types may be used in combination.

In the present invention, when the compound of Chemical Formula 1 and the material for the electron transport layer are used in combination, a mixing ratio thereof is not particularly limited, and may be appropriately adjusted within a range known in the art.

<Electron Transport Auxiliary Layer Material>

In addition, the present invention provides an electron transport auxiliary layer including the compound represented by Chemical Formula 1.

The electron transport auxiliary layer is disposed between the light emitting layer and the electron transport layer and serves to substantially prevent diffusion of excitons or holes generated in the light emitting layer into the electron transport layer.

The compound represented by Chemical Formula 1 may be used solely as an electron transport auxiliary layer material, or may be combined with an electron transport layer material known in the art. It may preferably be used solely.

The electron transport auxiliary layer material that may be used in combination with the compound of Chemical Formula 1 includes an electron transport material commonly known in the art. For example, the electron transport auxiliary layer may include an oxadiazole derivative, a triazole derivative, a phenanthroline derivative (e.g., BCP), a heterocyclic derivative containing nitrogen, and the like.

In the present invention, when the compound of Chemical Formula 1 and the material for the electron transport auxiliary layer are used in combination, a mixing ratio thereof is not particularly limited, and may be appropriately adjusted within a range known in the art.

<Organic EL Device>

The present invention provides an organic EL device including the compound represented by Chemical Formula 1.

More specifically, the organic EL device according to the present invention includes an anode (e.g., a positive electrode), a cathode (e.g., a negative electrode), and one or more organic layers disposed between the anode and the cathode, and at least one of the one or more organic layers includes the compound represented by Chemical Formula 1. In such an embodiment, the compound may be used solely or as a combination of two or more kinds thereof.

The one or more organic layers may be any one or more of a hole injection layer, a hole transport layer, a light emitting layer, a light emitting auxiliary layer, a life improvement layer, an electron transport layer, an electron transport auxiliary layer, and an electron injection layer, and at least one of the organic layers thereof may include the compound represented by Chemical Formula 1. Specifically, the organic layer including the compound represented by Chemical Formula 1 preferably is a phosphorescent host material for the light emitting layer or an electron transport material for the electron transport layer or the electron transport auxiliary layer.

The light emitting layer of the organic EL device according to the present invention may include a host material and a dopant material, and in such a case, may include the compound of Chemical Formula 1 as the host material. In addition, the light emitting layer of the present invention may include a compound known in the art other than the compound represented by Chemical Formula 1 as a host.

When the compound represented by Chemical Formula 1 is included as a material for the light emitting layer of the organic EL device, preferably a phosphorescent host material of blue, green, and red colors, a bonding force between holes and electrons in the light emitting layer increases, so the efficiency (luminous efficiency and power efficiency), lifespan, luminance and driving voltage of the organic EL device may be improved. Specifically, the compound represented by Chemical Formula 1 may preferably be a green phosphorescent N-type host material of the light emitting layer having high efficiency.

The structure of the organic EL device of the present invention is not particularly limited, but a non-limiting example thereof may be a structure in which a substrate, an anode, a hole injection layer, a hole transport layer, a light emitting auxiliary layer, a light emitting layer, an electron transport auxiliary layer, an electron transport layer and a cathode are sequentially stacked. In such an embodiment, at least one of the hole injection layer, the hole transport layer, the light emitting auxiliary layer, the light emitting layer, the electron transport auxiliary layer and the electron transport layer may include the compound represented by Chemical Formula 1. Preferably, the light emitting layer, and more preferably, the phosphorescent host may include the compound represented by Chemical Formula 1. In such an embodiment, an electron injection layer may be further stacked on the electron transport layer.

In addition, the structure of the organic EL device of the present invention may have a structure in which an insulating layer or an adhesive layer is inserted at an interface between the electrode and the organic layer.

The organic EL device of the present invention may be prepared by materials and methods known in the art, except that the one or more organic layers include the compound represented by Chemical Formula 1.

The organic layer may be formed by a vacuum deposition (evaporation) method or a solution coating method. Examples of the solution coating method may include, but are not limited to, spin coating, dip coating, doctor blading, inkjet printing, thermal transfer or the like.

The substrate used in Preparation the organic EL device of the present invention is not particularly limited, but silicon wafers, quartz, glass plates, metal plates, plastic films, sheets or the like may be used.

In addition, any anode material known in the art may be used as a material of the anode without limitation. For example, examples thereof may include, but are not limited to, a metal such as vanadium, chromium, copper, zinc, and gold or an alloy thereof; metal oxides such as zinc oxide, indium oxide, indium tin oxide (ITO), or indium zinc oxide (IZO); combination of oxide with metal such as ZnO:Al or $SnO_2$:Sb; conductive polymers such as polythiophene, poly (3-methylthiophene), poly [3,4-(ethylene-1,2-dioxy) thiophene] (PEDT), polypyrrole or polyaniline; and carbon black or the like.

In addition, any cathode material known in the art may be used as a material of the cathode without limitation. For example, examples thereof may include, but are not limited to, a metal such as magnesium, calcium, sodium, potassium, titanium, indium, yttrium, lithium, gadolinium, aluminum, silver, tin, or lead or an alloy thereof; a multi-layered material such as LiF/Al or $LiO_2$/Al or the like.

In addition, a material of the hole injection layer, the hole transport layer, the electron injection layer, and the electron transport layer is not particularly limited and conventional materials known in the art may be used without limitation.

Hereinafter, the present invention will be described in detail with reference to the following embodiments. However, the following embodiments are merely to illustrate the invention, and the present invention is not limited to the following embodiments.

PREPARATION EXAMPLE

Preparation Example 1

Synthesis of FC-1

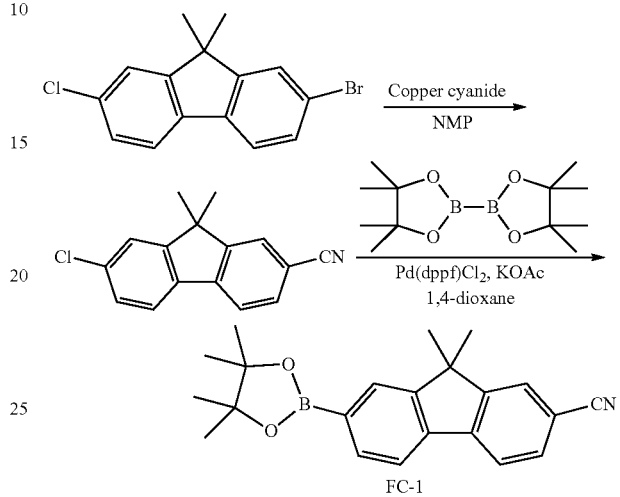

1.1 S:DMF, 20 h, reflux; reflux -> rt
1.2 R:HCl, R:FeCl3, S:H2O, rt, acidify; 0.5 h, 90° C.

<Step 1> Synthesis of 7-bromo-9,9-dimethyl-9H-fluorene-2-carbonitrile 50 g of 2-bromo-7-chloro-9,9-dimethyl-9H-fluorene and 18 g of copper cyanide were added to 250 ml of NMP, and the mixture was stirred under TLC monitoring at 120° C. After completion of the reaction, the mixture was cooled to room temperature, 300 ml of ice water was added thereto. A resultant solid was collected by filtration, neutralized with an aqueous ammonia solution, and extracted with chloroform. The extracted solution was concentrated under reduced pressure and recrystallized using ethanol, and thus a target compound 7-bromo-9,9-dimethyl-9H-fluorene-2-carbonitrile (32 g, yield 48%) was obtained.

1H-NMR: δ 8.08 (d, 1H), 7.80-7.79 (m, 2H), 7.72 (s, 1H), 7.63 (d, 1H), 7.55 (d, 1H), 1.69 (s, 6H)

<Step 2> Synthesis of FC-1

30 g of 7-bromo-9,9-dimethyl-9H-fluorene-2-carbonitrile, 26 g of 4,4,4',4',5,5,5',5'-octamethyl-2,2'-bi(1,3,2-dioxaborolane), 7.0 g of Pd(dppf)Cl$_2$, and 29 g of potassium acetate were added to 1000 ml of 1,4-dioxane and stirred at 110° C. for 8 hours. After completion of the reaction, extraction was performed with methylene chloride, a resultant organic layer was dried over magnesium sulfate, concentrated, and column chromatography was used to obtain a target compound FC-1 (26 g, yield 69%).

1H-NMR: δ 8.08 (d, 1H), 7.90 (d, 1H), 7.72 (s, 1H), 7.58 (d, 2H), 7.33 (s, 1H), 7.16 (d, 1H), 1.69 (s, 6H), 1.20 (s, 12H)

Preparation Example 2

Synthesis of FC-2

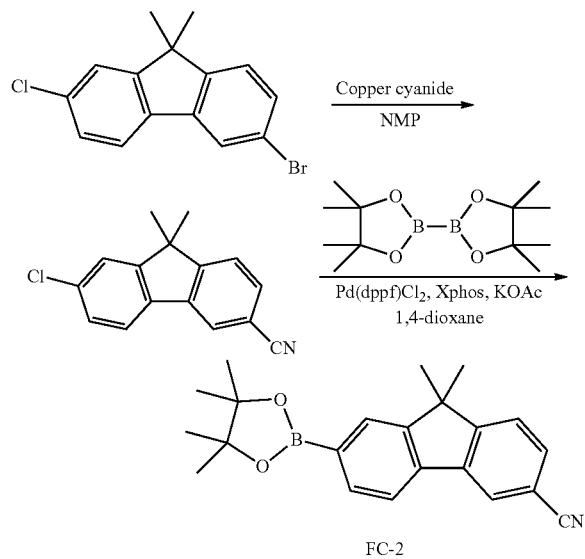

<Step 1> Synthesis of 7-chloro-9,9-dimethyl-9H-fluorene-3-carbonitrile 7-chloro-9,9-dimethyl-9H-fluorene-3-carbonitrile (31 g, yield 48%) was prepared in the same manner as in Preparation Example 1, except that 6-bromo-2-chloro-9,9-dimethyl-9H-fluorene was used instead of 2-bromo-7-chloro-9,9-dimethyl-9H-fluorene in step 1 of Preparation Example 1.

1H-NMR: δ 7.93 (d, 1H), 7.80 (d, 2H), 7.72 (s, 1H), 7.68 (d, 2H), 7.63 (d, 1H), 7.55 (d, 1H), 1.69 (s, 6H)

<Step 2> Synthesis of FC-2

FC-2 (23 g, yield 64%) was prepared in the same manner as in Preparation Example 1, except that 7-chloro-9,9-dimethyl-9H-fluorene-3-carbonitrile was used instead of 7-bromo-9,9-dimethyl-9H-fluorene-2-carbonitrile in step 2 of Preparation Example 1.

1H-NMR: δ 7.98 (d, 1H), 7.78-7.75 (m, 2H), 7.50-7.44 (m, 3H), 7.24 (d, 1H), 1.69 (s, 6H), 1.20 (s, 12H)

Preparation Example 3

Synthesis of FC-3

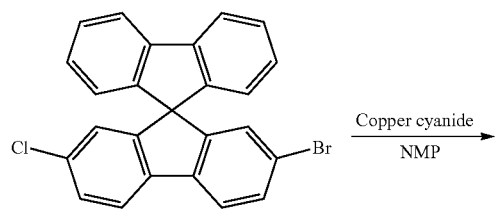

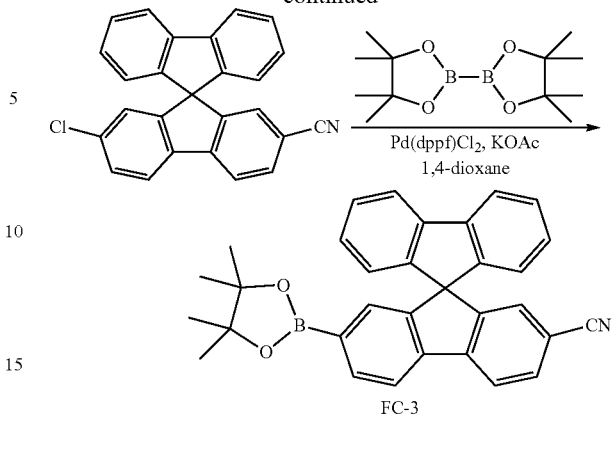

<Step 1> Synthesis of 2-bromo-9,9'-spirobi[fluorene]-7-carbonitrile 2-bromo-9,9'-spirobi[fluorene]-7-carbonitrile (34 g, yield 50%) was prepared in the same manner as in Preparation Example 1, except that 2,7-dibromo-9,9'-spirobi[fluorene] was used instead of 2-bromo-7-chloro-9,9-dimethyl-9H-fluorene in step 1 of Preparation Example 1.

1H-NMR: δ 8.08 (d, 1H), 7.89 (d, 2H), 7.79-7.72 (m, 3H), 7.63 (d, 1H), 7.55 (d, 1H), 7.45 (d, 1H), 7.28-7.25 (m, 4H)

<Step 2> Synthesis of FC-3

FC-3 (25 g, yield 63%) was prepared in the same manner as in Preparation Example 1, except that 2-bromo-9,9'-spirobi[fluorene]-7-carbonitrile was used instead of 7-bromo-9,9-dimethyl-9H-fluorene-2-carbonitrile in step 2 of Preparation Example 1.

1H-NMR: δ 8.07 (d, 1H), 7.87 (d, 2H), 7.79-7.72 (m, 3H), 7.62 (d, 1H), 7.53 (d, 1H), 7.44 (d, 1H), 7.28-7.25 (m, 4H), 1.20 (s, 12H)

Preparation Example 4

Synthesis of FC-4

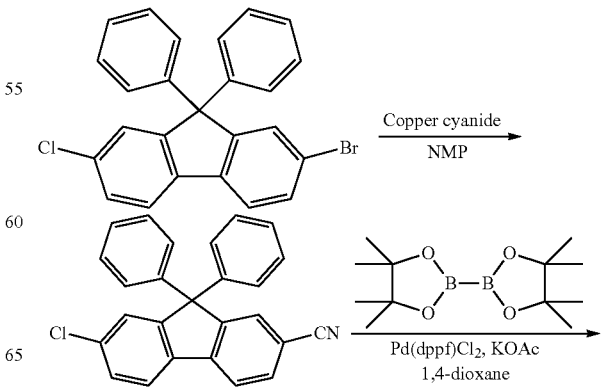

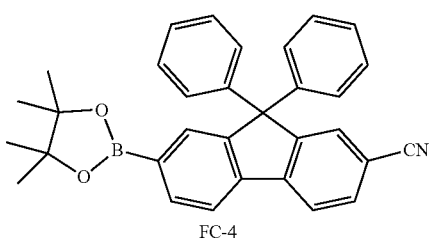

FC-4

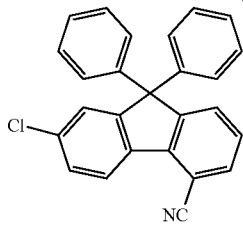

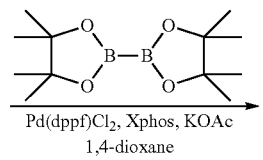

Pd(dppf)Cl₂, Xphos, KOAc
1,4-dioxane

FC-5

<Step 1> Synthesis of
7-bromo-9,9-diphenyl-9H-fluorene-2-carbonitrile 7-bromo-9,9-diphenyl-9H-fluorene-2-carbonitrile (32 g, yield 49%) was prepared in the same manner as in Preparation Example 1, except that 2,7-dibromo-9,9-diphenyl-9H-fluorene was used instead of 2-bromo-7-chloro-9,9-dimethyl-9H-fluorene in step 1 of Preparation Example 1.

1H-NMR: δ 8.07 (d, 1H), 7.86 (d, 2H), 7.81-7.72 (m, 3H), 7.63 (d, 1H), 7.50 (d, 1H), 7.43 (d, 1H), 7.28-7.25 (m, 4H), 7.10 (d, 2H)

<Step 2> Synthesis of FC-4

FC-4 (21 g, yield 57%) was prepared in the same manner as in Preparation Example 1, except that 7-bromo-9,9-diphenyl-9H-fluorene-2-carbonitrile was used instead of 7-bromo-9,9-dimethyl-9H-fluorene-2-carbonitrile in step 2 of Preparation Example 1.

1H-NMR: δ 8.06 (d, 1H), 7.87 (d, 2H), 7.80-7.71 (m, 3H), 7.62 (d, 1H), 7.54 (d, 1H), 7.43 (d, 1H), 7.28-7.25 (m, 4H), 7.10 (d, 2H), 1.20 (s, 12H)

Preparation Example 5

Synthesis of FC-5

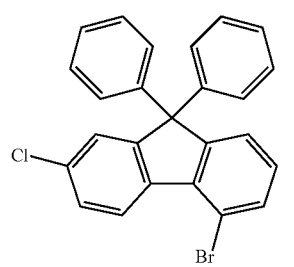

Copper cyanide
⎯⎯⎯⎯⎯→
NMP

<Step 1> Synthesis of
7-chloro-9,9-diphenyl-9H-fluorene-4-carbonitrile 7-chloro-9,9-diphenyl-9H-fluorene-4-carbonitrile (34 g, yield 50%) was prepared in the same manner as in Preparation Example 1, except that 5-bromo-2-chloro-9,9-diphenyl-9H-fluorene was used instead of 2-bromo-7-chloro-9,9-dimethyl-9H-fluorene in step 1 of Preparation Example 1.

1H-NMR: δ 7.84 (d, 2H), 7.64 (d, 1H), 7.56 (s, 1H), 7.46-7.39 (m, 2H), 7.26-7.18 (m, 10H)

<Step 2> Synthesis of FC-5

FC-5 (23 g, yield 58%) was prepared in the same manner as in Preparation Example 1, except that 7-chloro-9,9-diphenyl-9H-fluorene-4-carbonitrile was used instead of 7-bromo-9,9-dimethyl-9H-fluorene-2-carbonitrile in step 2 of Preparation Example 1.

1H-NMR: δ 7.83 (d, 2H), 7.64 (d, 1H), 7.46-7.39 (m, 2H), 7.38 (s, 1H), 7.26-7.18 (m, 10H), 1.20 (s, 12H)

Synthesis Example 1

Synthesis of Compound 1

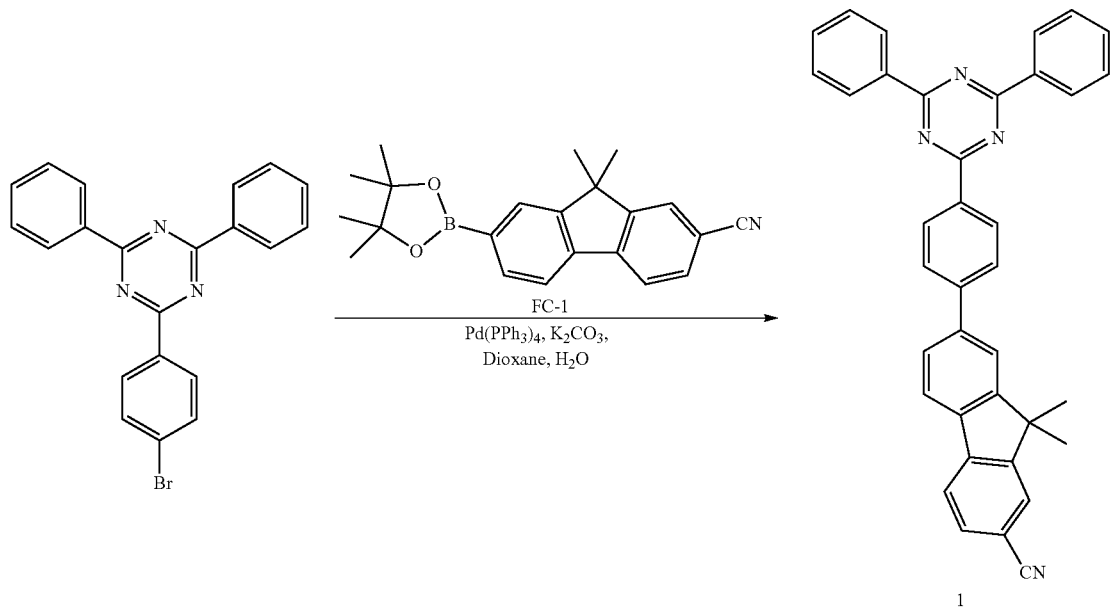

3.0 g of 2-(4-bromophenyl)-4,6-diphenyl-1,3,5-triazine, 2.6 g of FC-1, and 2.6 g of $K_2CO_3$ were mixed, 50 ml of dioxane and 10 ml of water were added thereto, and then 40 mg of $Pd(PPh_3)_4$ was further added thereto, and the mixture was heated and stirred for 2 hours. After completion of the reaction, the temperature was lowered to room temperature, and the reacted mixture was filtered. The filtrate was poured into water, extracted with ethyl acetate, and a resultant organic layer was dried over $MgSO_4$. The dried organic layer was concentrated under reduced pressure and then columned with EA:Hex=1:5, and thus Compound 1 (2.3 g, yield 51%) was prepared.

Mass: $[(M+H)^+]527$

Synthesis Example 2

Synthesis of Compound 2

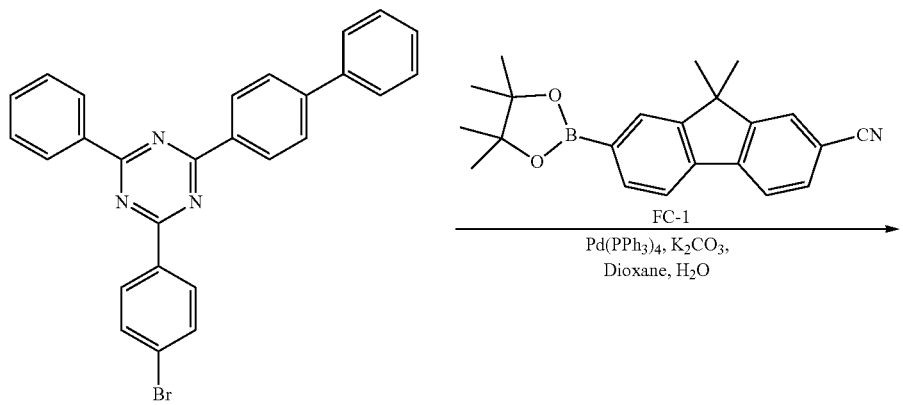

-continued

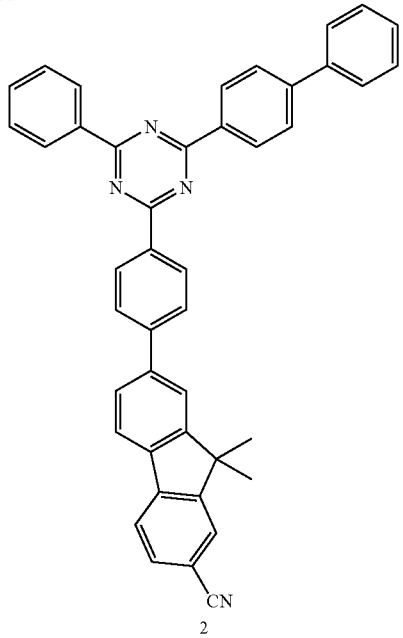

Compound 2 (2.4 g, yield 52%) was prepared in the same manner as in Synthesis Example 1, except that 2-([1,1'-biphenyl]-4-yl)-4-(4-bromophenyl)-6-phenyl-1,3,5-triazine was used instead of 2-(4-bromophenyl)-4,6-diphenyl-1,3,5-triazine.

Mass: [(M+H)+]:603

Synthesis Example 3

Synthesis of Compound 16

3.1 g of 2-(4-bromophenyl)-4,6-diphenyl-1,3,5-triazine, 2.7 g of FC-2, and 2.7 g of $K_2CO_3$ were mixed, 50 ml of dioxane and 10 ml of water were added thereto, and then 40 mg of $Pd(PPh_3)_4$ was further added thereto, and the mixture was heated and stirred for 2 hours. After completion of the reaction, the temperature was lowered to room temperature, and the reacted mixture was filtered. The filtrate was poured into water, extracted with ethyl acetate, and a resultant organic layer was dried over $MgSO_4$. The dried organic

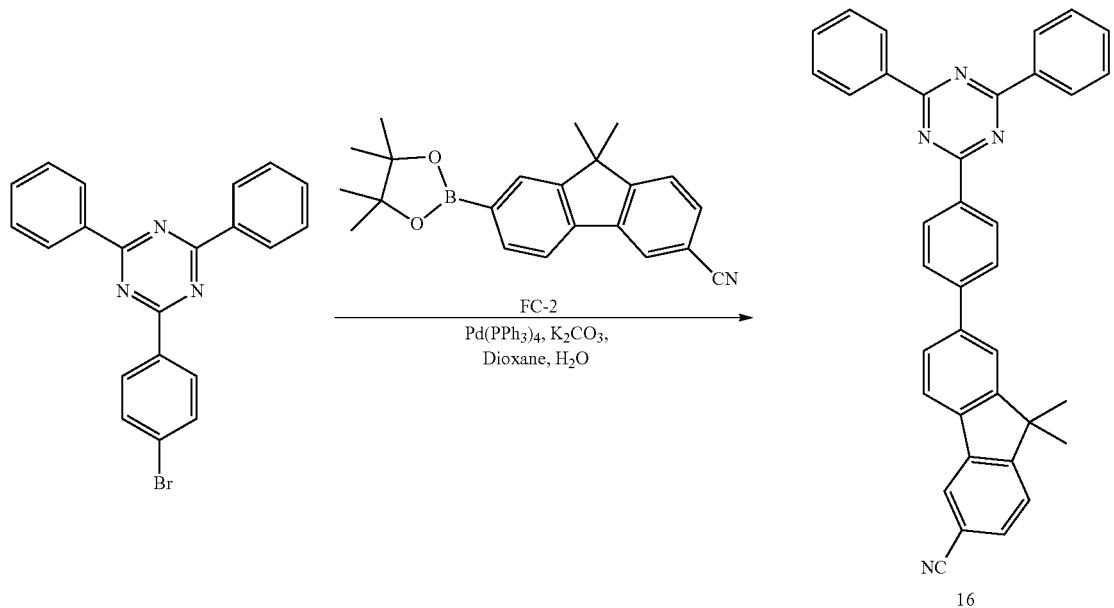

layer was concentrated under reduced pressure and then columned with MC:Hex=1:2, and thus Compound 16 (2.4 g, yield 52%) was prepared.

Mass: [(M+H)⁺]:527

Synthesis Example 4

Synthesis of Compound 19

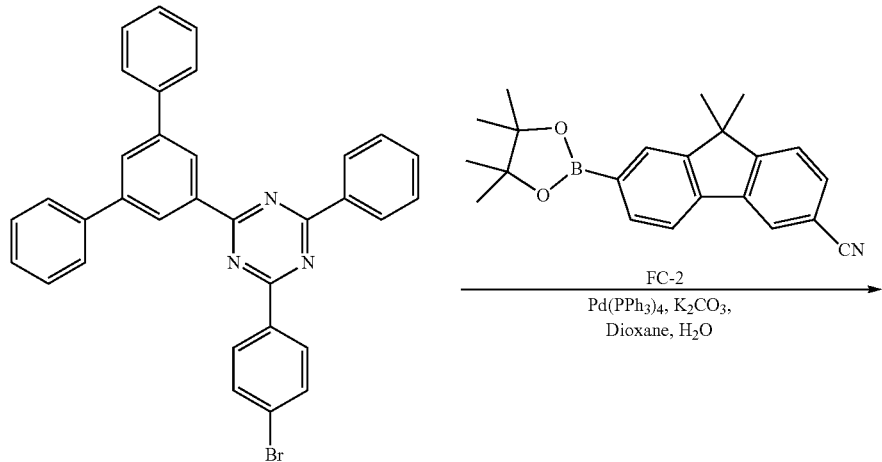

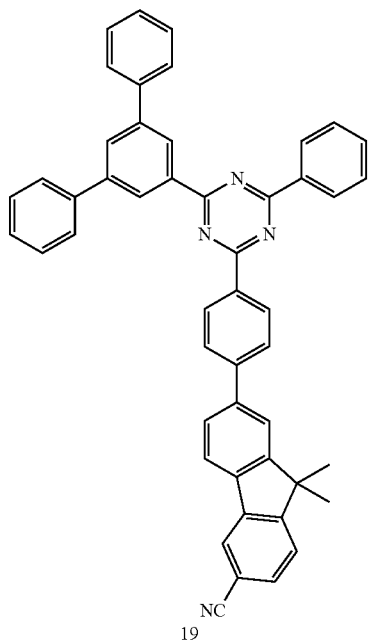

Compound 19 (2.1 g, yield 48%) was prepared in the same manner as in Synthesis Example 3, except that 2-([1,1':3',1''-terphenyl]-5'-yl)-4-(4-bromophenyl)-6-phenyl-1,3,5-triazine was used instead of 2-(4-bromophenyl)-4,6-diphenyl-1,3,5-triazine.

Mass: [(M+H)⁺]:680

Synthesis Example 5
Synthesis of Compound 48
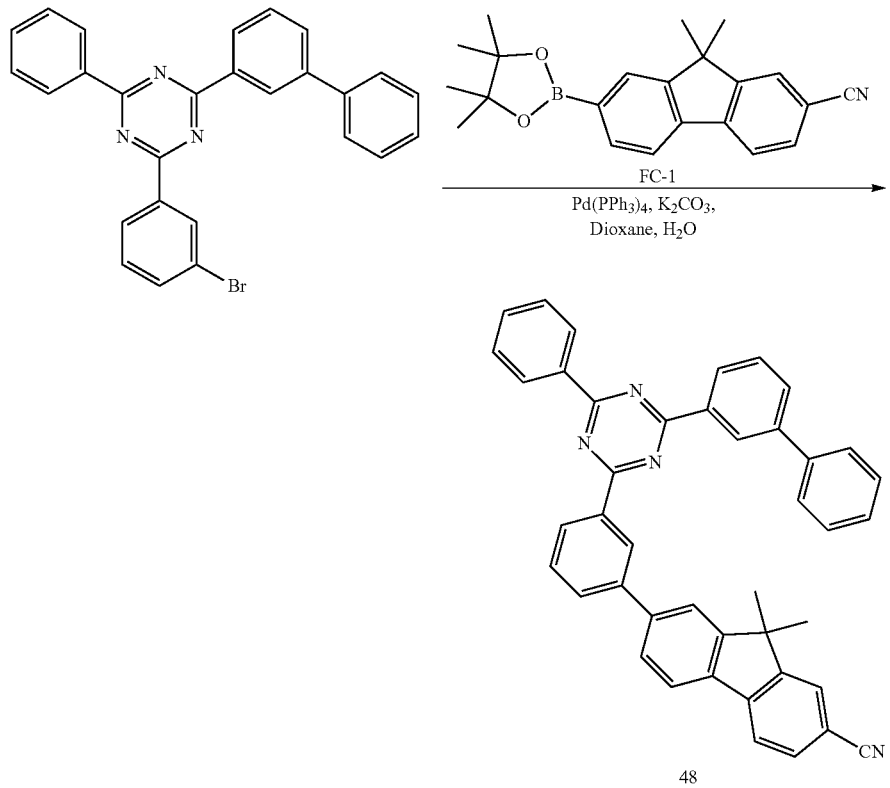
Compound 48 (2.4 g, yield 53%) was prepared in the same manner as in Synthesis Example 1, except that 2-([1,1'-biphenyl]-3-yl)-4-(3-bromophenyl)-6-phenyl-1,3,5-triazine was used instead of 2-(4-bromophenyl)-4,6-diphenyl-1,3,5-triazine.
Mass: $[(M+H)^+]$:604
Synthesis Example 6
Synthesis of Compound 102
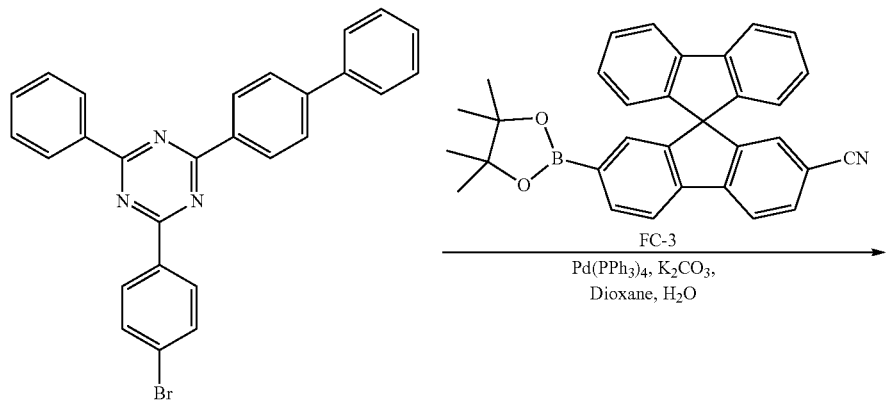

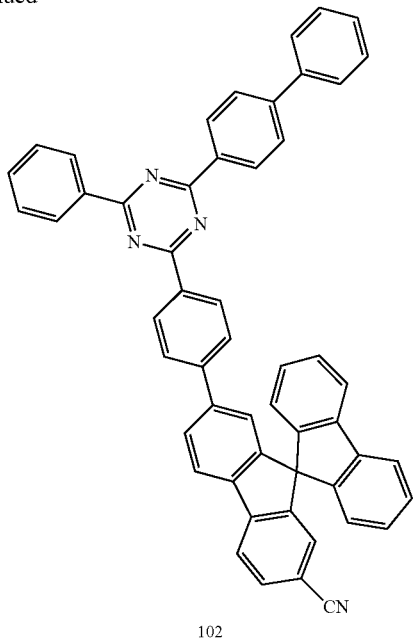

102

3.0 g of 2-([1,1'-biphenyl]-4-yl)-4-(4-bromophenyl)-6-phenyl-1,3,5-triazine, 3.1 g of FC-2, and 2.7 g of $K_2CO_3$ were mixed, 50 ml of dioxane and 10 ml of water were added thereto, and then 40 mg of $Pd(PPh_3)_4$ was further added thereto, and the mixture was heated and stirred for 2 hours. After completion of the reaction, the temperature was lowered to room temperature, and the reacted mixture was filtered. The filtrate was poured into water, extracted with ethyl acetate, and a resultant organic layer was dried over $MgSO_4$. The dried organic layer was concentrated under reduced pressure and then columned with THF:Hex=1:2, and thus Compound 102 (2.2 g, yield 46%) was prepared.

Mass: $[(M+H)^+]$:726

Synthesis Example 7

Synthesis of Compound 104

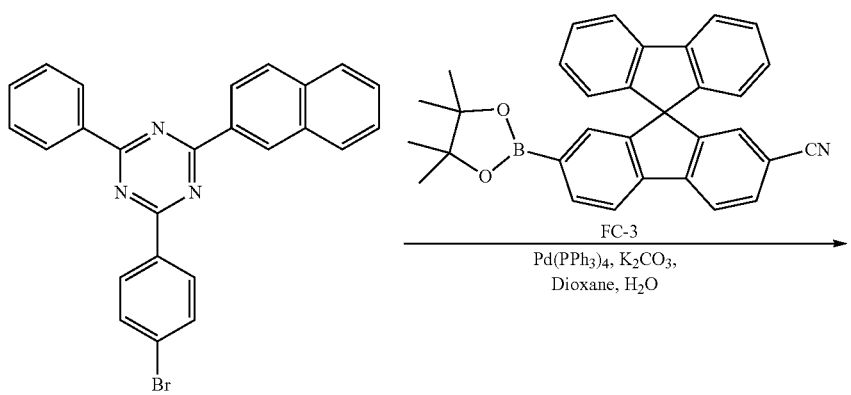

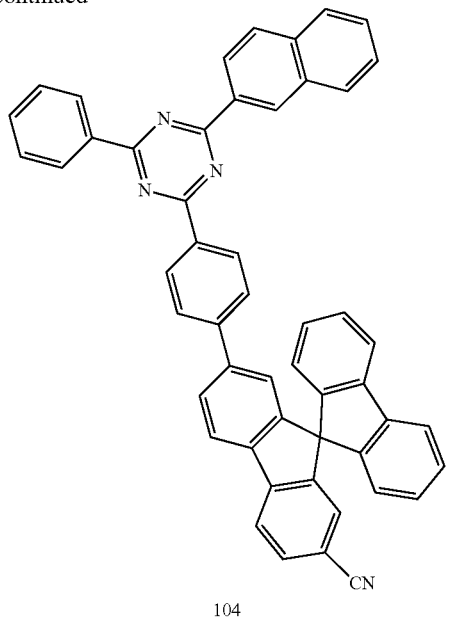
104
Compound 104 (2.3 g, yield 49%) was prepared in the same manner as in Synthesis Example 6, except that 2-(4-bromophenyl)-4-(naphthalen-2-yl)-6-phenyl-1,3,5-triazine was used instead of 2-([1,1'-biphenyl]-4-yl)-4-(4-bromophenyl)-6-phenyl-1,3,5-triazine.
Mass: [(M+H)$^+$]:700
Synthesis Example 8
Synthesis of Compound 232
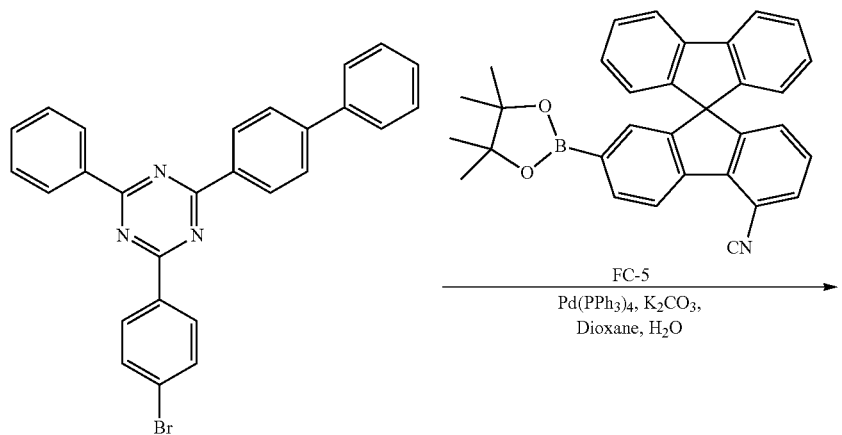

-continued

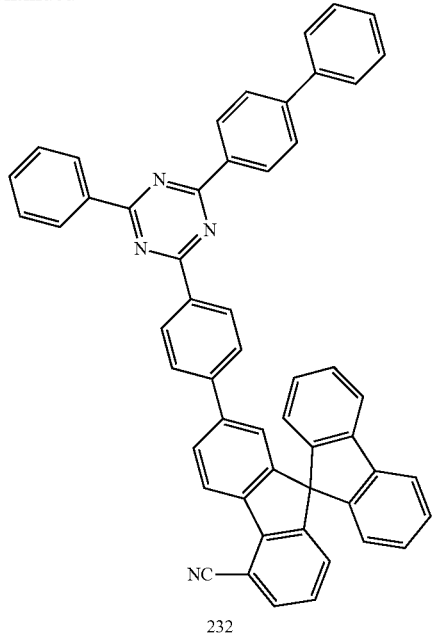

232

3.0 g of 2-([1,1'-biphenyl]-4-yl)-4-(4-bromophenyl)-6-phenyl-1,3,5-triazine, 3.1 g of FC-5, and 2.7 g of $K_2CO_3$ were mixed, 50 ml of dioxane and 10 ml of water were added thereto, and then 40 mg of $Pd(PPh_3)_4$ was further added thereto, and the mixture was heated and stirred for 2 hours. After completion of the reaction, the temperature was lowered to room temperature, and the reacted mixture was filtered. The filtrate was poured into water, extracted with ethyl acetate, and a resultant organic layer was dried over $MgSO_4$. The dried organic layer was concentrated under reduced pressure and then columned with THF:Hex=1:2, and thus Compound 232 (2.5 g, yield 52%) was prepared.

Mass: $[(M+H)^+]$:727

Synthesis Example 9

Synthesis of Compound 234

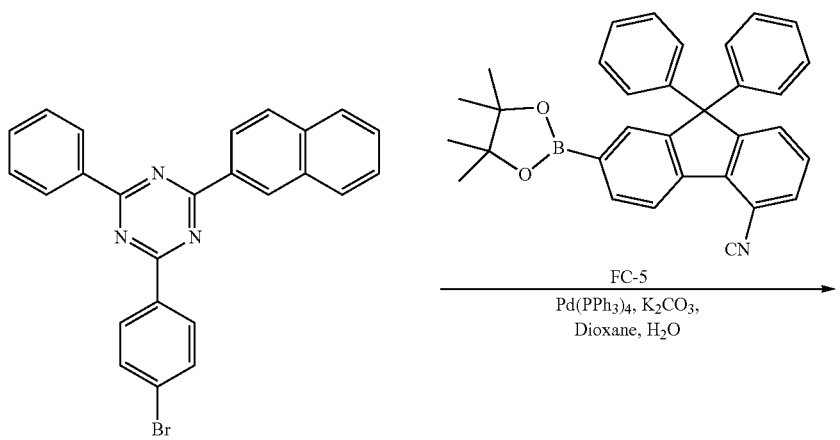

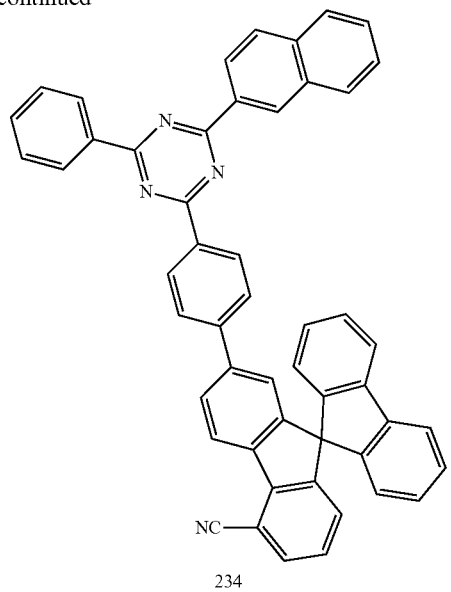
234
Compound 234 (2.6 g, yield 53%) was prepared in the same manner as in Synthesis Example 6, except that 2-(4-bromophenyl)-4-(naphthalen-2-yl)-6-phenyl-1,3,5-triazine was used instead of 2-([1,1'-biphenyl]-4-yl)-4-(4-bromophenyl)-6-phenyl-1,3,5-triazine.
Mass: [(M+H)$^+$]:701
Synthesis Example 10
Synthesis of Compound 301
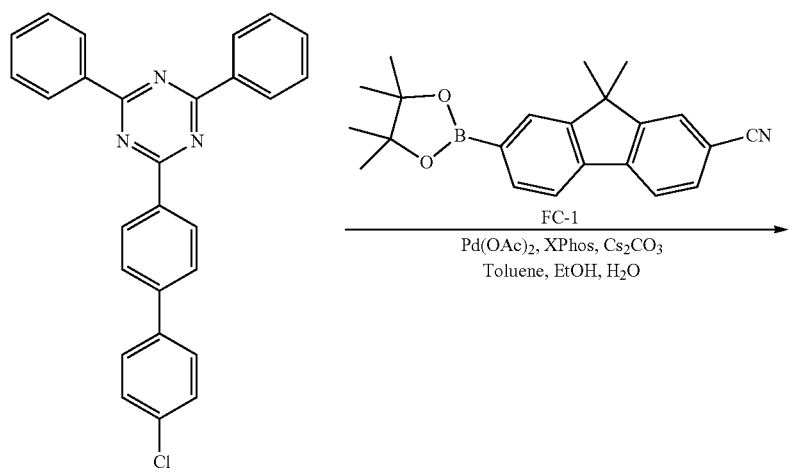

-continued

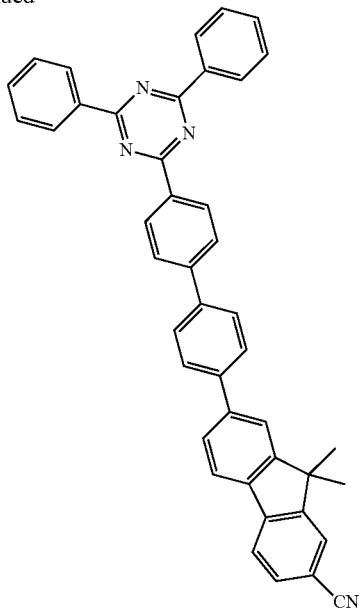

301

3.2 g of 2-(4'-chloro-[1,1'-biphenyl]-4-yl)-4,6-diphenyl-1,3,5-triazine, 2.2 g of FC-1, and 2.0 g of $Cs_2CO_3$ were mixed, 50 ml of toluene, 10 ml of ethanol, and 10 ml of water were added thereto, and then 50 mg of $Pd(OAc)_2$ and 250 mg of Xphos were further added thereto, followed by heating and stirring for 4 hours. After the reaction was completed, the temperature was lowered to room temperature and filtered. The filtrate was poured into water, a resultant solid was filtered to remove the solution and then dried in an oven. The dried solid was columned with THF:Hex=1:2, and thus compound 301 (2.7 g, yield 54%) was prepared.

Mass: [(M+H)$^+$]:604

Synthesis Example 11

Synthesis of Compound 307

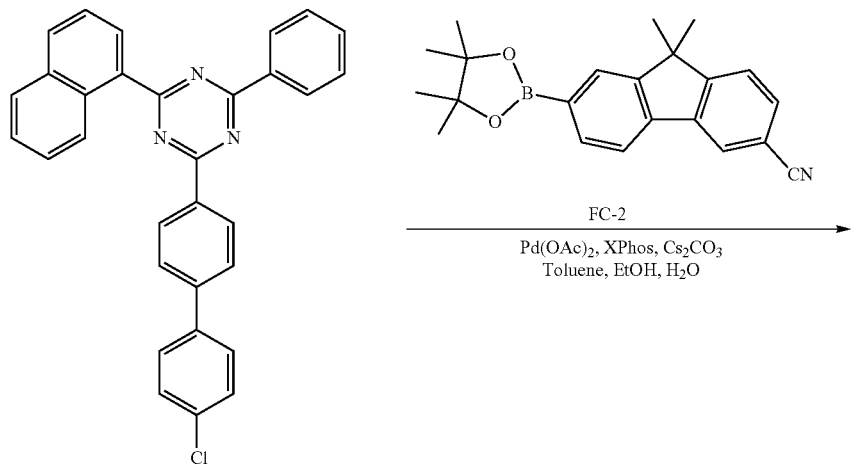

-continued

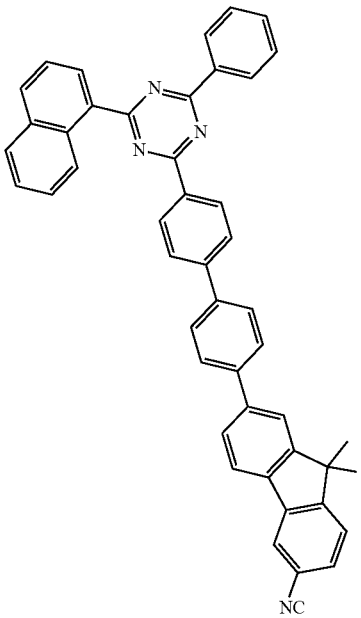

307

3.0 g of 2-(4'-chloro-[1,1'-biphenyl]-4-yl)-4-(naphthalen-1-yl)-6-phenyl-1,3,5-triazine, 2.5 g of FC-2, and 2.0 g of $Cs_2CO_3$ were mixed, 50 ml of toluene, 10 ml of ethanol, and 10 ml of water were added thereto, and then 50 mg of $Pd(OAc)_2$ and 250 mg of Xphos were further added thereto, followed by heating and stirring for 4 hours. After the reaction was completed, the temperature was lowered to room temperature and filtered. The filtrate was poured into water, extracted with methylene chloride, and a resultant organic layer was dried over $MgSO_4$. The dried organic layer was concentrated under reduced pressure and then columned with THF:Hex=1:3, and thus Compound 307 (2.1 g, yield 49%) was prepared.

Mass: [(M+H)$^+$]:654

Synthesis Example 12

Synthesis of Compound 316

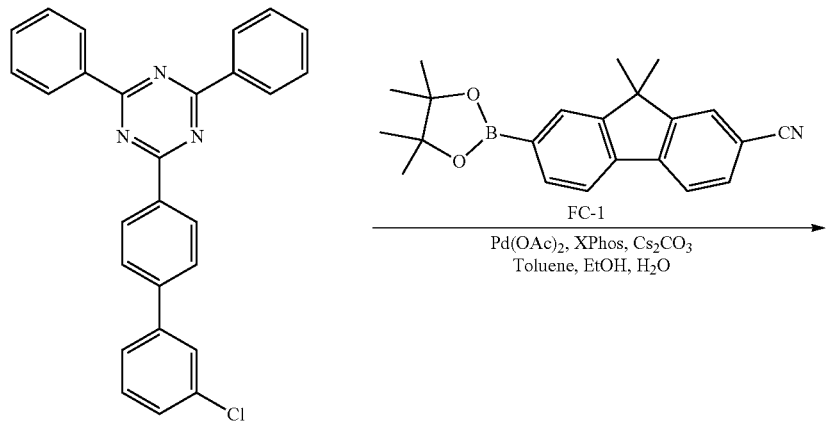

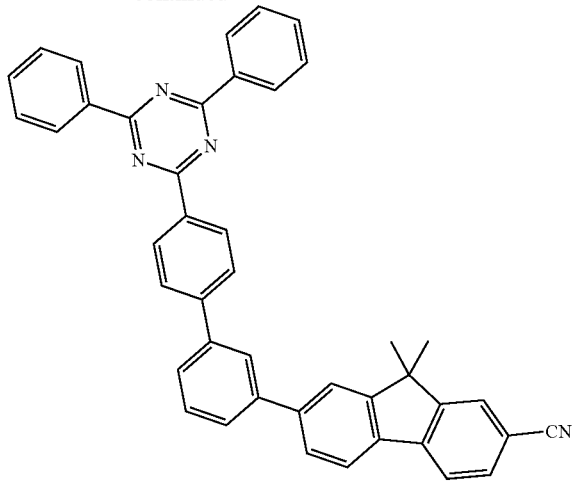

316

3.2 g of 2-(3'-chloro-[1,1'-biphenyl]-4-yl)-4,6-diphenyl-1,3,5-triazine, 2.3 g of FC-1, and 2.0 g of $Cs_2CO_3$ were mixed, 50 ml of toluene, 10 ml of ethanol, and 10 ml of water were added thereto, and then 50 mg of $Pd(OAc)_2$ and 250 mg of Xphos were further added thereto, followed by heating and stirring for 4 hours. After the reaction was completed, the temperature was lowered to room temperature and filtered. The filtrate was poured into water, a resultant solid was filtered to remove the solution and then dried in an oven. The dried solid was columned with THF:Hex=1:3, and thus compound 316 (2.6 g, yield 53%) was prepared.

Mass: $[(M+H)^+]$:604

Synthesis Example 13

Synthesis of Compound 322

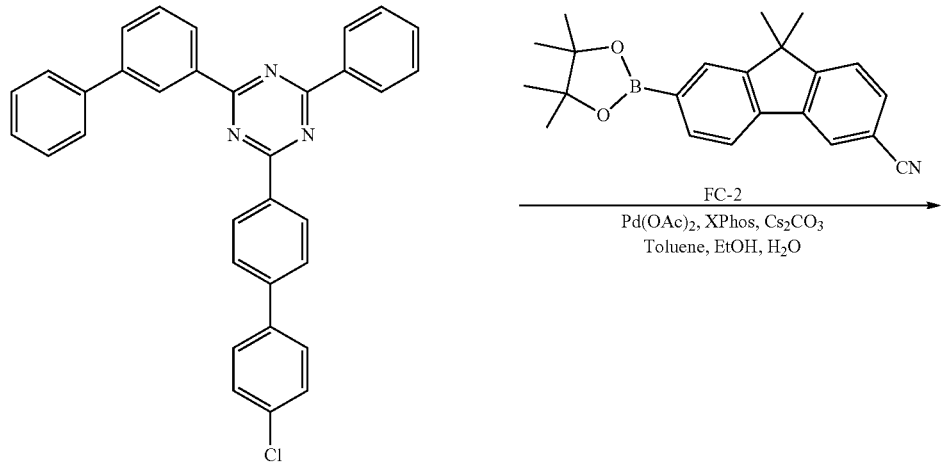

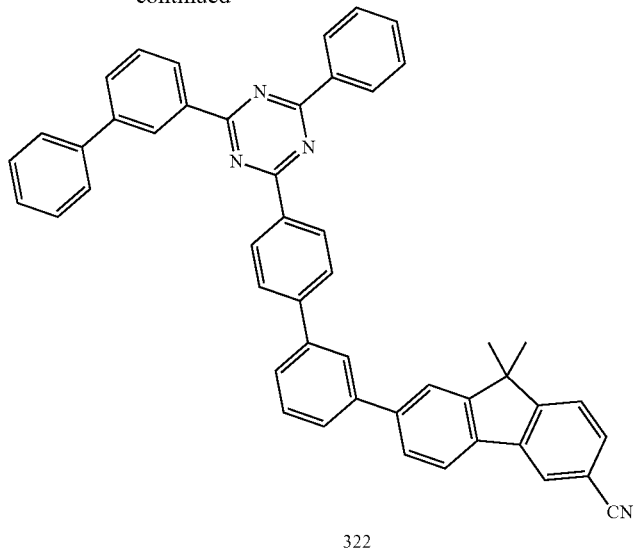
322
Compound 322 (3.1 g, yield 55%) was prepared in the same manner as in Synthesis Example 11, except that 2-([1,1'-biphenyl]-3-yl)-4-(3'-chloro-[1,1'-biphenyl]-4-yl)-6-phenyl-1,3,5-triazine was used instead of 2-(4'-chloro-[1,1'-biphenyl]-4-yl)-4-(naphthalen-1-yl)-6-phenyl-1,3,5-triazine.
Mass: [(M+H)$^+$]:680
Synthesis Example 14
Synthesis of Compound 331
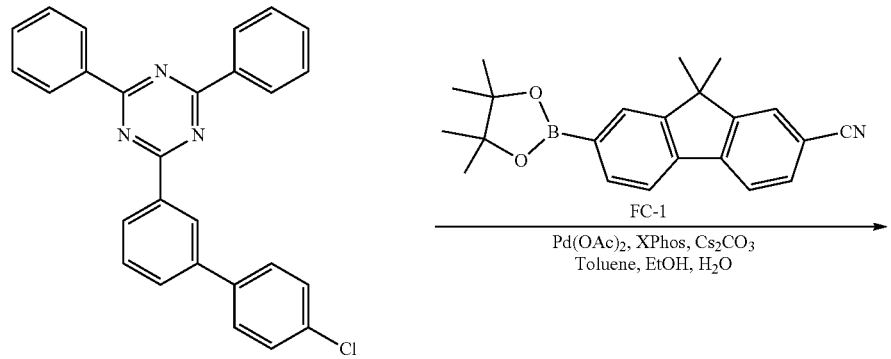

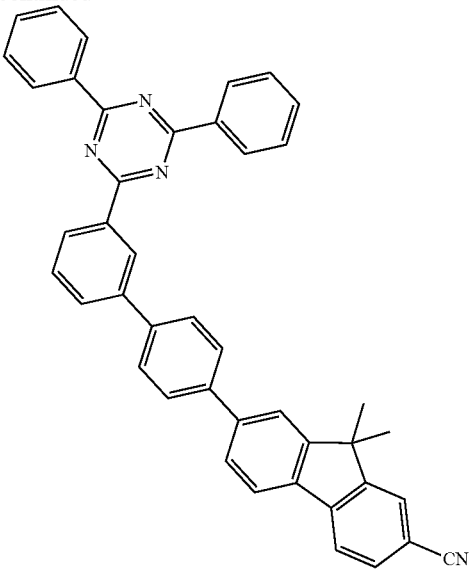
331
Compound 331 (3.2 g, yield 53%) was prepared in the same manner as in Synthesis Example 12, except that 2-(4'-chloro-[1,1'-biphenyl]-3-yl)-4,6-diphenyl-1,3,5-triazine was used instead of 2-(3'-chloro-[1,1'-biphenyl]-4-yl)-4,6-diphenyl-1,3,5-triazine.
Mass: [(M+H)$^+$]:604
Synthesis Example 15
Synthesis of Compound 346
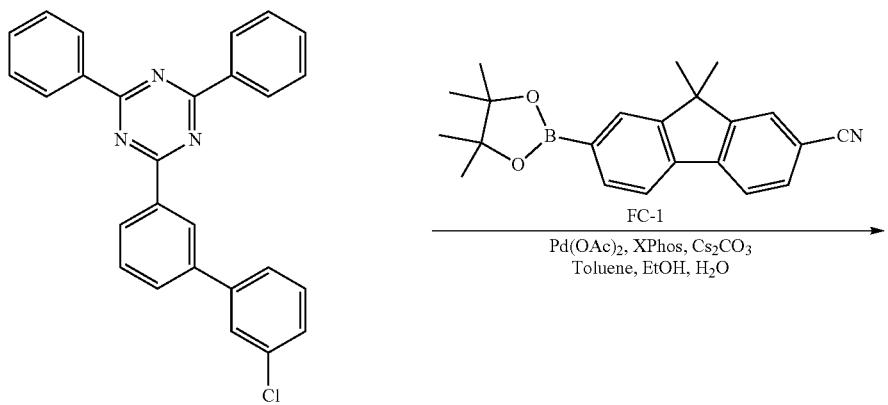

-continued
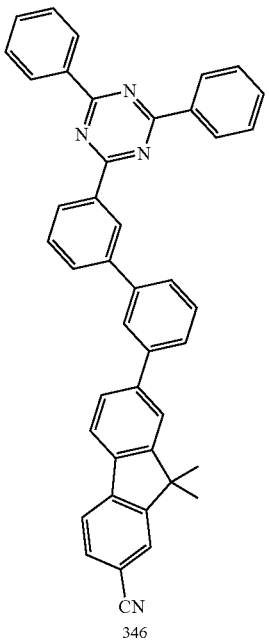
346
Compound 346 (3.1 g, yield 51%) was prepared in the same manner as in Synthesis Example 12, except that 2-(3'-chloro-[1,1'-biphenyl]-3-yl)-4,6-diphenyl-1,3,5-triazine was used instead of 2-(3'-chloro-[1,1'-biphenyl]-4-yl)-4,6-diphenyl-1,3,5-triazine.
Mass: $[(M+H)^+]$:604
Synthesis Example 16
Synthesis of Compound 371
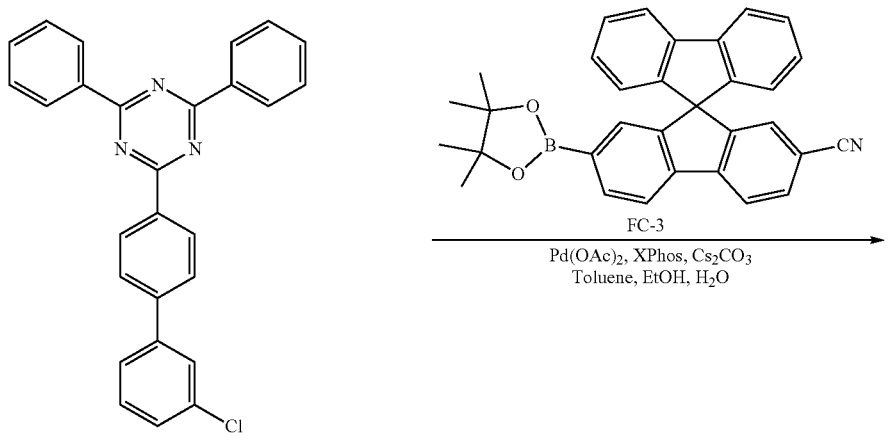

-continued

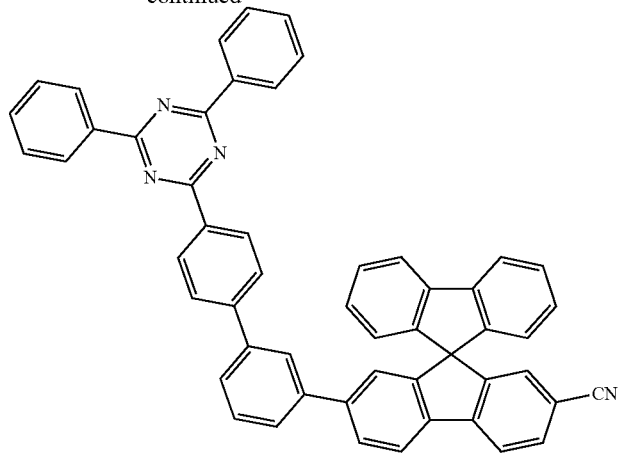

371

3.1 g of 2-(3'-chloro-[1,1'-biphenyl]-4-yl)-4,6-diphenyl-1,3,5-triazine, 2.8 g of FC-3, and 2.2 g of Cs$_2$CO$_3$ were mixed, 50 ml of toluene, 10 ml of ethanol, and 10 ml of water were added thereto, and then 55 mg of Pd(OAc)$_2$ and 260 mg of Xphos were further added thereto, followed by heating and stirring for 4 hours. After the reaction was completed, the temperature was lowered to room temperature and filtered. The filtrate was poured into water, a resultant solid was filtered to remove the solution and then dried in an oven. The dried solid was columned with THF:Hex=1:3, and thus compound 371 (2.5 g, yield 51%) was prepared.

Mass: [(M+H)$^+$]:726

Synthesis Example 17

Synthesis of Compound 382

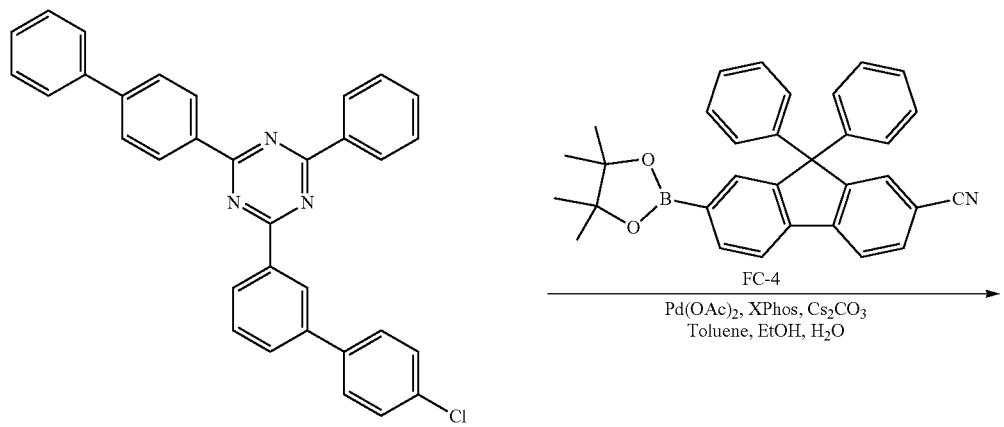

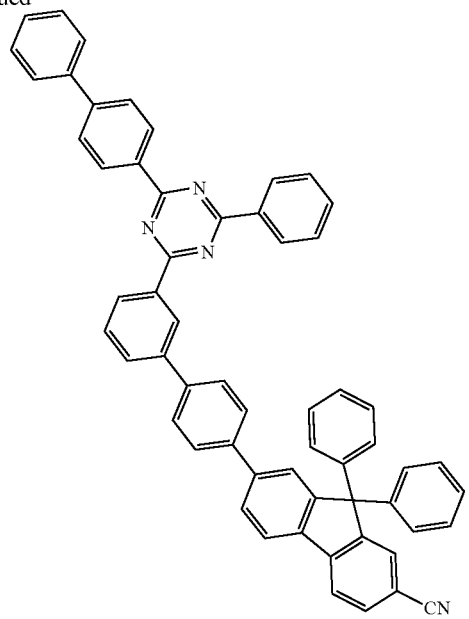
382
2-([1,1'-biphenyl]-4-yl)-4-(4'-chloro-[1,1'-biphenyl]-3-yl)-6-phenyl-1,3,5-triazine
Mass: [(M+H)⁺]:804
Synthesis Example 18
Synthesis of Compound 402
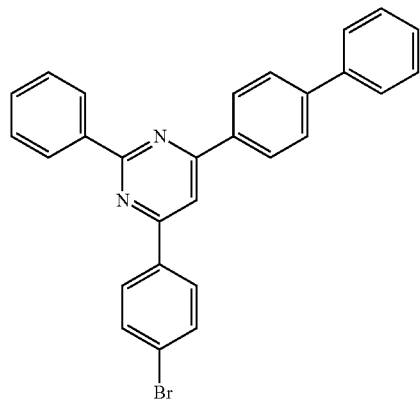 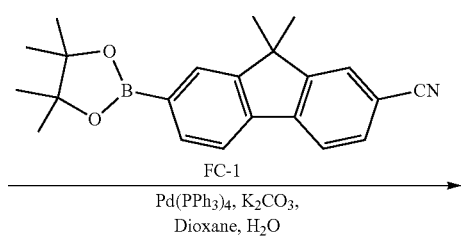

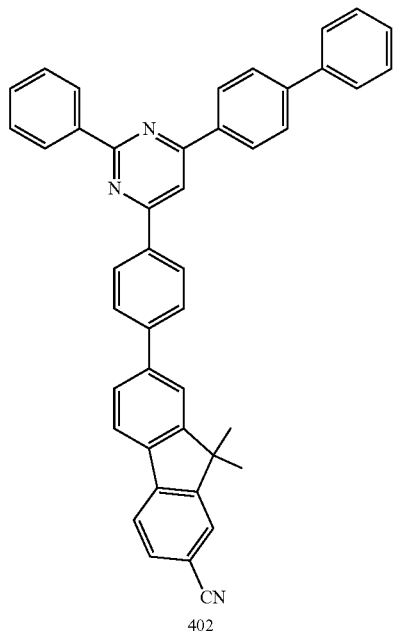
402
Compound 402 (1.8 g, yield 43%) was prepared in the same manner as in Synthesis Example 1, except that 4-([1,1'-biphenyl]-4-yl)-6-(4-bromophenyl)-2-phenylpyrimidine was used instead of 2-(4-bromophenyl)-4,6-diphenyl-1,3,5-triazine.
Mass: [(M+H)$^+$]:602
Synthesis Example 19
Synthesis of Compound 447
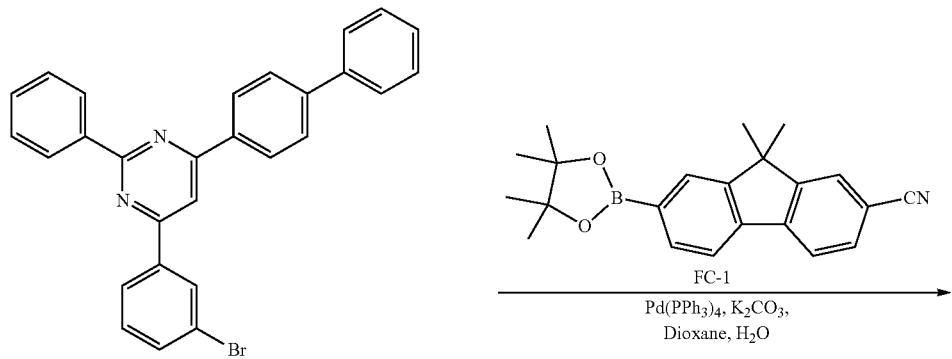

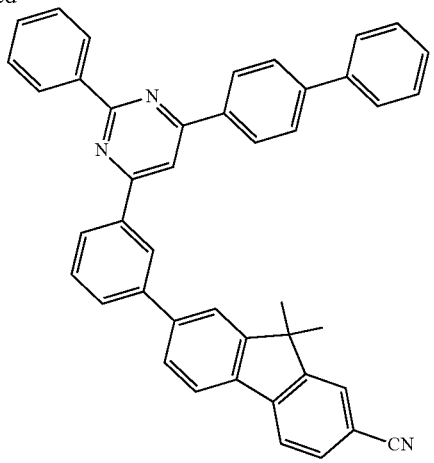
447
Compound 447 (2.1 g, yield 47%) was prepared in the same manner as in Synthesis Example 1, except that 4-([1,1'-biphenyl]-4-yl)-6-(3-bromophenyl)-2-phenylpyrimidine was used instead of 2-(4-bromophenyl)-4,6-diphenyl-1,3,5-triazine.
Mass: [(M+H)$^+$]:602
Synthesis Example 20
Synthesis of Compound 503
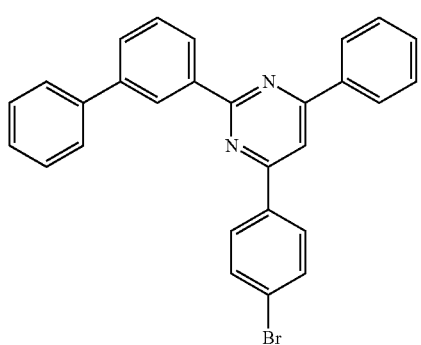 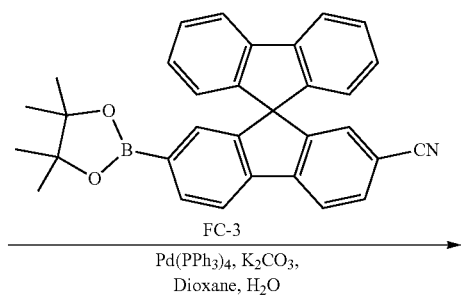
FC-3
Pd(PPh$_3$)$_4$, K$_2$CO$_3$,
Dioxane, H$_2$O

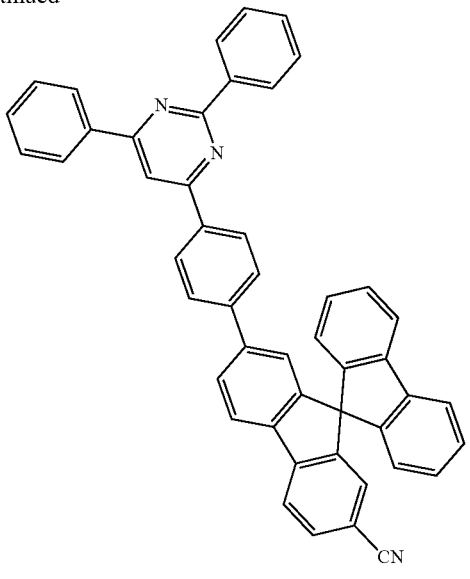
503
Compound 503 (2.2 g, yield 48%) was prepared in the same manner as in Synthesis Example 6, except that 2-([1,1'-biphenyl]-3-yl)-4-(4-bromophenyl)-6-phenylpyrimidine was used instead of 2-([1,1'-biphenyl]-4-yl)-4-(4-bromophenyl)-6-phenyl-1,3,5-triazine.
Mass: [(M+H)$^+$]:725
Synthesis Example 21
Synthesis of Compound 602
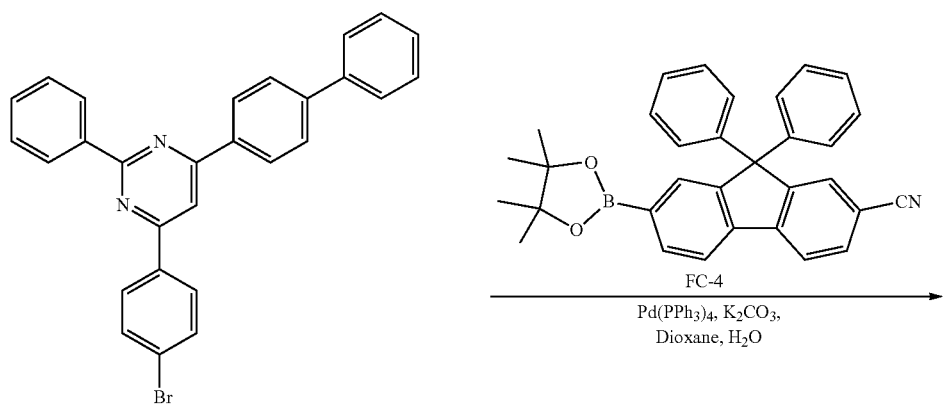

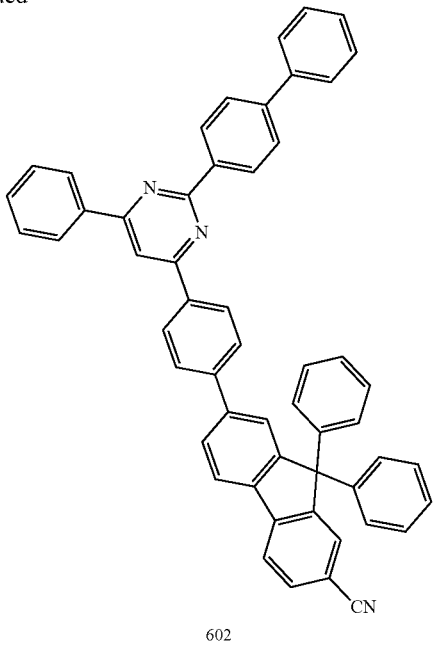

602

3.1 g of 4-([1,1'-biphenyl]-4-yl)-6-(4-bromophenyl)-2-phenylpyrimidine, 3.0 g of FC-4, and 2.5 g of $K_2CO_3$ were mixed, 50 ml of dioxane and 10 ml of water were added thereto, and then 40 mg of $Pd(PPh_3)_4$ was further added thereto, and the mixture was heated and stirred for 2 hours. After completion of the reaction, the temperature was lowered to room temperature, and the reacted mixture was filtered. The filtrate was poured into water, extracted with ethyl acetate, and a resultant organic layer was dried over $MgSO_4$. The dried organic layer was concentrated under reduced pressure and then columned with MC:Hex=1:1, and thus Compound 602 (2.1 g, yield 45%) was prepared.

Mass: $[(M+H)^+]$:726

Synthesis Example 22

Synthesis of Compound 631

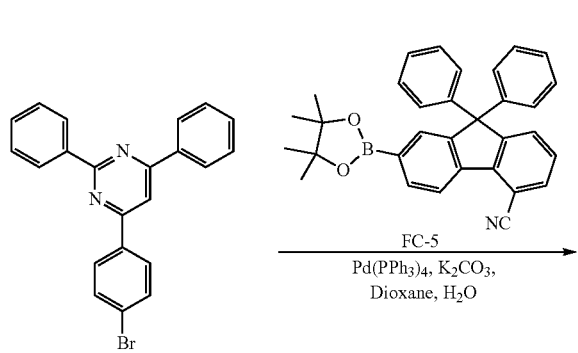

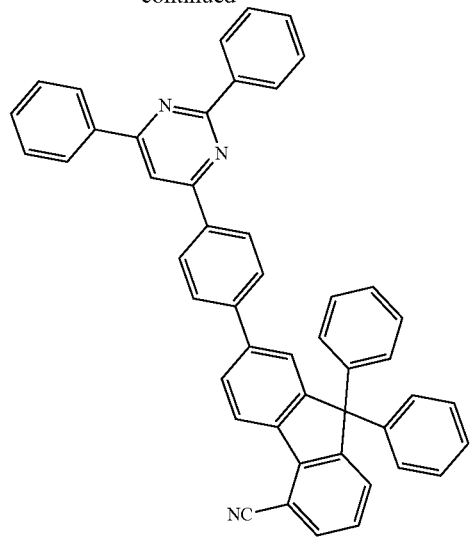

631

3.0 g of 4-(4-bromophenyl)-2,6-diphenylpyrimidine, 3.3 g of FC-4, and 2.5 g of $K_2CO_3$ were mixed, 50 ml of dioxane and 10 ml of water were added thereto, and then 40 mg of $Pd(PPh_3)_4$ was further added thereto, and the mixture was heated and stirred for 2 hours. After completion of the reaction, the temperature was lowered to room temperature, and the reacted mixture was filtered. The filtrate was poured into water, extracted with ethyl acetate, and a resultant organic layer was dried over $MgSO_4$. The dried organic layer was concentrated under reduced pressure and then columned with MC:Hex=1:2, and thus Compound 631 (2.4 g, yield 49%) was prepared.

Mass: $[(M+H)^+]$:650

Synthesis Example 23
Synthesis of Compound 647
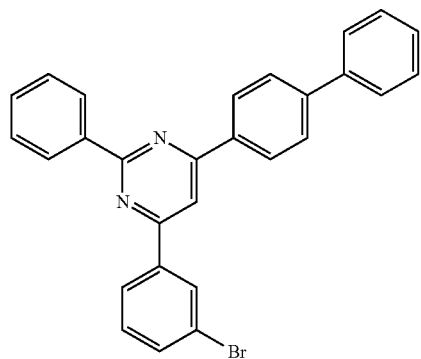
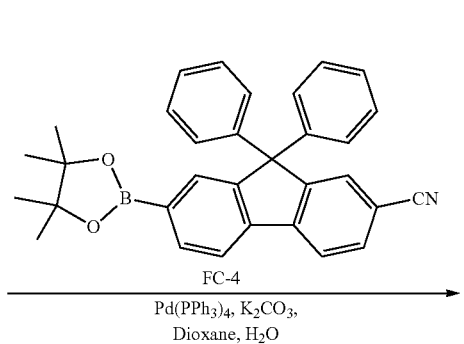
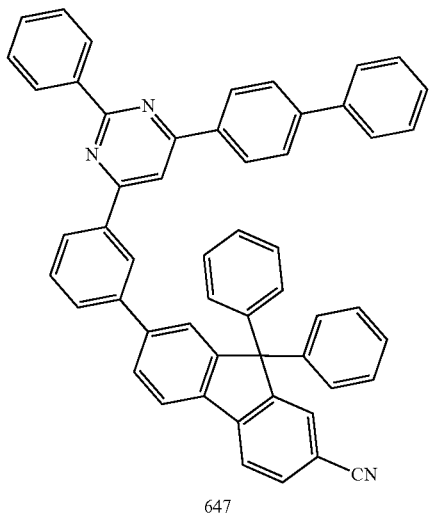
Compound 647 (2.1 g, yield 43%) was prepared in the same manner as in Synthesis Example 21, except that 4-([1,1'-biphenyl]-4-yl)-6-(3-bromophenyl)-2-phenylpyrimidine was used instead of 4-([1,1'-biphenyl]-4-yl)-6-(4-bromophenyl)-2-phenylpyrimidine.
Mass: [(M+H)$^+$]:727
Synthesis Example 24
Synthesis of Compound 716
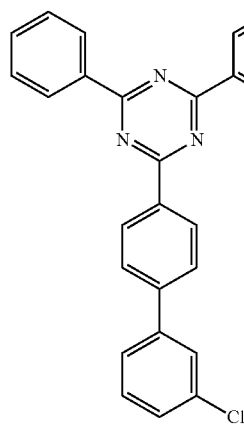
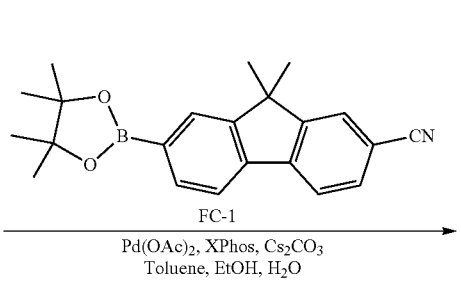

-continued
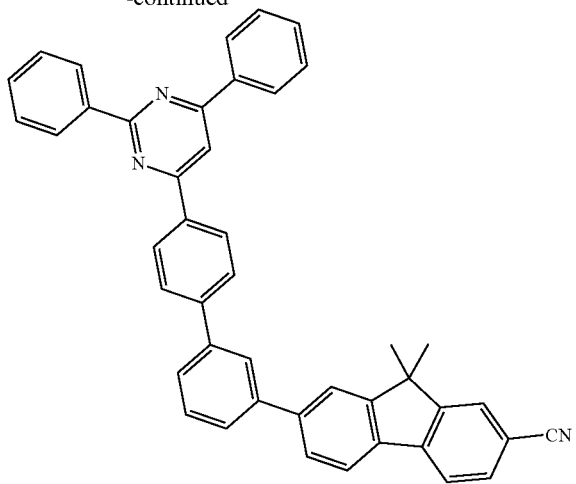
716
Compound 716 (3.0 g, yield 50%) was prepared in the same manner as in Synthesis Example 12, except that 4-(3'-chloro-[1,1'-biphenyl]-4-yl)-2,6-diphenylpyrimidine was used instead of 2-(3'-chloro-[1,1'-biphenyl]-4-yl)-4,6-diphenyl-1,3,5-triazine.
Mass: [(M+H)$^+$]:603
Synthesis Example 25
Synthesis of Compound 747
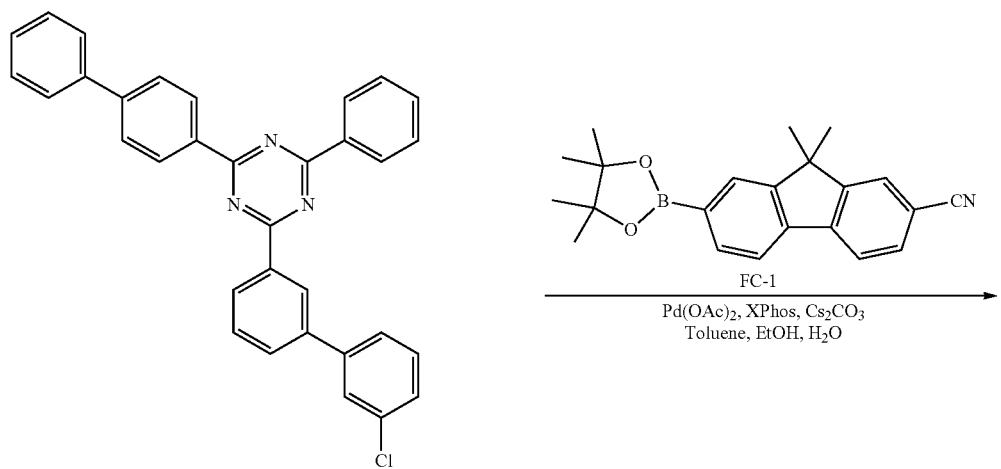

-continued

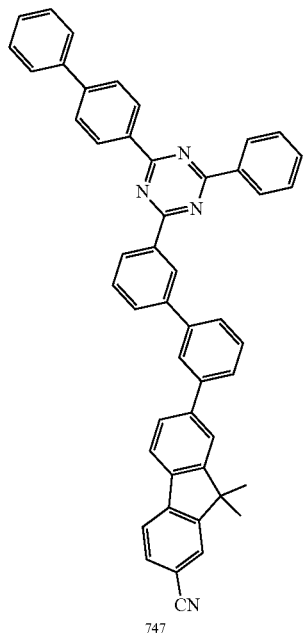
747

Compound 747 (3.0 g, yield 49%) was prepared in the same manner as in Synthesis Example 12, except that 2-([1,1'-biphenyl]-4-yl)-4-(3'-chloro-[1,1'-biphenyl]-3-yl)-6-phenylpyrimidine was used instead of 2-(3'-chloro-[1,1'-biphenyl]-4-yl)-4,6-diphenyl-1,3,5-triazine.

Mass: $[(M+H)^+]$:679

Embodiments 1 to 13

Preparation of Blue Organic EL Devices

Compounds 1, 2, 16, 19, 48, 102, 104, 232, 234, 301, 307, 316, and 322 synthesized in Synthesis Examples were subjected to high-purity sublimation purification in a conventionally known method, and then blue organic EL devices were prepared as follows.

First, a glass substrate thin-film-coated with indium tin oxide (ITO) to a thickness of 1500 Å was washed with distilled water ultrasonically. After washing with distilled water was completed, the glass substrate was ultrasonically cleaned with a solvent, such as isopropyl alcohol, acetone and methanol, dried, transferred to a UV OZONE cleaner (Power sonic 405, Hwasin Tech) cleaned for 5 minutes using UV, and then transferred to a vacuum evaporator.

On the ITO transparent electrode prepared as above, DS-205 (Doosan Electronics Co., Ltd., 80 nm)/NPB (15 nm)/ADN+5% DS-405 (Doosan Electronics Co., Ltd., 30 nm)/respective Compounds 1, 2, 16, 19, 48, 102, 104, 232, 234, 301, 307, 316, and 322 (30 nm)/LiF (1 nm)/Al (200 nm) were stacked in the order, so that organic EL devices were prepared (see the following Table 1).

TABLE 1

|  | Compound | Thickness (nm) |
| --- | --- | --- |
| Hole injection layer | DS-205 | 80 |

TABLE 1-continued

|  | Compound | Thickness (nm) |
| --- | --- | --- |
| Hole transport layer | NPB | 15 |
| Light emitting layer | ADN + 5% DS-405 | 30 |
| Electron transport layer | Compound 1, 2, 16, 19, 48, 102, 104, 232, 234, 301, 307, 316, 322 | 30 |
| Electron injection layer | LiF | 1 |
| Cathode | Al | 200 |

Comparative Example 1

Preparation of Blue Organic EL Device

A blue organic EL device was prepared in the same manner as in Embodiment 1, except that $Alq_3$ was used as an electron transport layer material instead of Compound 1.

Comparative Example 2

Preparation of Blue Organic EL Device

A blue organic EL device was prepared in the same manner as in Embodiment 1, except that Compound 1 was not used as an electron transport layer material.

Comparative Example 3

Preparation of Blue Organic EL Device

A blue organic EL device was prepared in the same manner as in Embodiment 1, except that Compound T-1 was used as an electron transport layer material instead of Compound 1.

Comparative Example 4

Preparation of Blue Organic EL Device

A blue organic EL device was prepared in the same manner as in Embodiment 1, except that Compound T-2 was used as an electron transport layer material instead of Compound 1.

Comparative Example 5

Preparation of Blue Organic EL Device

A blue organic EL device was prepared in the same manner as in Embodiment 1, except that Compound T-3 was used as an electron transport layer material instead of Compound 1.

For example, structures of NPB, ADN, Alq$_3$, Compounds T1 to T3 used in Embodiments 1 to 13 and Comparative Examples 1 to 5 are as follows.

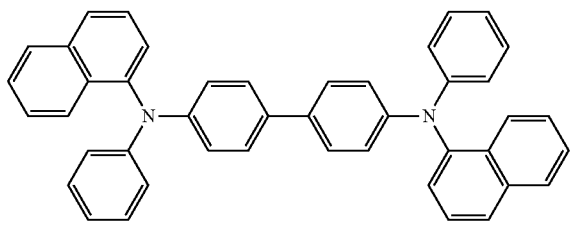

NPB

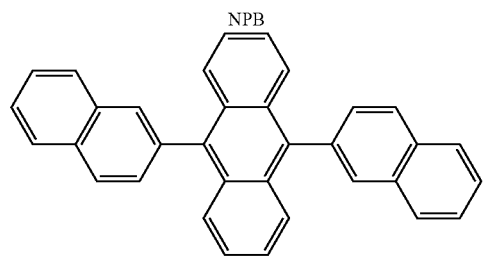

ADN

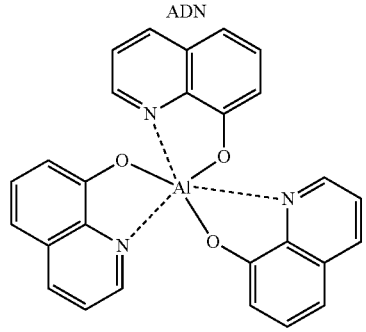

Alq$_3$

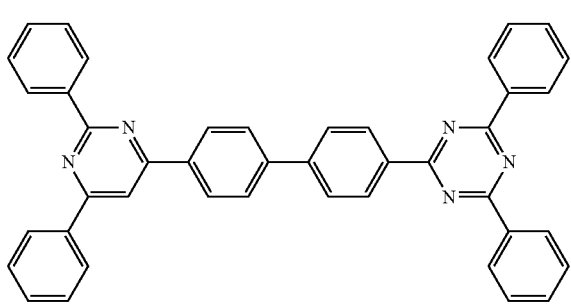

T-1

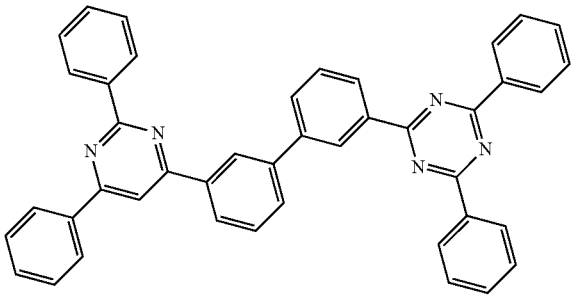

T-2

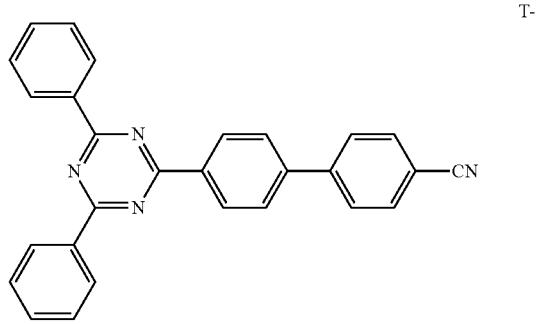

T-3

Experimental Example 1

For each of the blue organic EL devices prepared in Embodiments 1 to 13 and Comparative Examples 1 to 5, a driving voltage, a current efficiency and an emission peak at a current density of 10 mA/cm$^2$ were measured and the results are shown in Table 2 below.

TABLE 2

| Sample | Electron transport layer | Driving voltage (V) | Luminous efficiency (nm) | Current efficiency (cd/A) |
|---|---|---|---|---|
| Embodiment 1 | Compound 1 | 3.2 | 455 | 7.8 |
| Embodiment 2 | Compound 2 | 3.1 | 453 | 8.1 |
| Embodiment 3 | Compound 16 | 3.2 | 456 | 7.6 |
| Embodiment 4 | Compound 19 | 3.0 | 454 | 7.9 |
| Embodiment 5 | Compound 48 | 3.1 | 455 | 7.7 |
| Embodiment 6 | Compound 102 | 3.0 | 454 | 7.4 |
| Embodiment 7 | Compound 104 | 3.2 | 453 | 7.8 |
| Embodiment 8 | Compound 232 | 3.1 | 454 | 8.0 |
| Embodiment 9 | Compound 234 | 3.0 | 455 | 7.1 |
| Embodiment 10 | Compound 301 | 3.1 | 453 | 7.6 |
| Embodiment 11 | Compound 307 | 3.1 | 455 | 7.4 |
| Embodiment 12 | Compound 316 | 3.3 | 454 | 7.7 |
| Embodiment 13 | Compound 322 | 3.4 | 456 | 8.0 |
| Comp. Example 1 | Alq$_3$ | 4.8 | 457 | 5.6 |
| Comp. Example 2 | — | 4.7 | 459 | 6.1 |
| Comp. Example 3 | T-1 | 4.5 | 459 | 5.9 |
| Comp. Example 4 | T-2 | 3.8 | 456 | 7.2 |
| Comp. Example 5 | T-3 | 4.1 | 455 | 6.5 |

As shown in Table 2, it was appreciated that the blue organic EL devices of Embodiments 1 to 13 in which the compounds of the present invention were used in the electron transport layer exhibited excellent performance in terms of the driving voltage, the emission peak and the current efficiency, as compared to the blue organic EL device (Comparative Example 1) in which conventional Alq₃ was used in the electron transport layer and the blue organic EL device (Comparative Example 2) in which the electron transport layer is not included.

In addition, it was appreciated that the blue organic EL devices of Embodiments 1 to 13 including the electron transport layer material according to the present invention having a biphenylene linker (e.g., p,m-biphenylene) bonded in a para-meta position between triazine and the fluorene group exhibited superior performance in terms of driving voltage, emission peak, and current efficiency, as compared to blue organic EL devices in Comparative Examples 3 and 4 including an electron transport layer (Compounds T-1 and T-2) having a conventional p,p-biphenylene or m,m-biphenylene linker and a blue organic EL device in Comparative Example 5 including an electron transport layer (Compound T-3) having a biphenylene linker between triazine and a cyano group. In particular, it was confirmed that the driving voltage of the device has a remarkable improvement in a range of about 0.4 to 1.5 v.

Embodiments 14 to 25

Preparation of Blue Organic EL Devices

Compounds 331, 346, 371, 382, 402, 447, 503, 602, 631, 647, 716, and 747 synthesized in Synthesis Examples were subjected to high-purity sublimation purification in a conventionally known method, and then blue organic EL devices were prepared as follows.

First, a glass substrate thin-film-coated with indium tin oxide (ITO) to a thickness of 1500 Å was washed with distilled water ultrasonically. After washing with distilled water was completed, the glass substrate was ultrasonically cleaned with a solvent, such as isopropyl alcohol, acetone and methanol, dried, transferred to a UV OZONE cleaner (Power sonic 405, Hwasin Tech) cleaned for 5 minutes using UV, and then transferred to a vacuum evaporator.

On the ITO transparent electrode prepared as above, DS-205 (Doosan Electronics Co., Ltd., 80 nm)/NPB (15 nm)/ADN+5% DS-405 (Doosan Electronics Co., Ltd., 30 nm)/respective Compounds 331, 346, 371, 382, 402, 447, 503, 602, 631, 647, 716, and 747 (5 nm)/Alq₃ (25 nm)/LiF (1 nm)/Al (200 nm) were stacked in the order, so that organic EL devices were prepared (see the following Table 3).

TABLE 3

| | Compound | Thickness (nm) |
|---|---|---|
| Hole injection layer | DS-205 | 80 |
| Hole transport layer | NPB | 15 |
| Light emitting layer | ADN + 5% DS-405 | 30 |
| Electron transport auxiliary layer | Compound 331, 346, 371, 382, 402, 447, 503, 602, 631, 647, 716, 747 | 5 |
| Electron transport layer | Alq₃ | 25 |
| Electron injection layer | LiF | 1 |
| Cathode | Al | 200 |

Comparative Example 6

Preparation of Blue Organic EL Device

A blue organic EL device was prepared in the same manner as in Embodiment 14, except that Compound 331 was not used as the electron transport auxiliary layer material, and Alq₃, which is an electron transport layer material, was deposited to 30 nm instead of 25 nm.

Comparative Example 7

Preparation of a Blue Organic EL Device

A blue organic EL device was prepared in the same manner as in Embodiment 14, except that Compound T-1 was used instead of Compound 331 as the electron transport auxiliary layer material.

Comparative Example 8

Preparation of a Blue Organic EL Device

A blue organic EL device was prepared in the same manner as in Embodiment 14, except that Compound T-2 was used instead of Compound 331 as the electron transport auxiliary layer material.

Comparative Example 9

Preparation of a Blue Organic EL Device

A blue organic EL device was prepared in the same manner as in Embodiment 14, except that Compound T-3 was used instead of Compound 331 as the electron transport auxiliary layer material.

Experimental Example 2

For each of the blue organic EL devices prepared in Embodiments 14 to 25 and Comparative Examples 6 to 9, a driving voltage, a current efficiency and an emission peak at a current density of 10 mA/cm² were measured and the results are shown in Table 4 below.

TABLE 4

| Sample | Electron transport auxiliary layer | Driving voltage (V) | Luminous efficiency (nm) | Current efficiency (cd/A) |
|---|---|---|---|---|
| Embodiment 14 | Compound 331 | 3.1 | 454 | 7.9 |
| Embodiment 15 | Compound 346 | 3.2 | 453 | 7.6 |
| Embodiment 16 | Compound 371 | 3.1 | 455 | 7.4 |
| Embodiment 17 | Compound 382 | 3.2 | 455 | 7.8 |
| Embodiment 18 | Compound 402 | 3.4 | 453 | 8.1 |
| Embodiment 19 | Compound 447 | 3.3 | 456 | 7.9 |
| Embodiment 20 | Compound 503 | 3.3 | 455 | 7.7 |
| Embodiment 21 | Compound 602 | 3.2 | 455 | 8.1 |
| Embodiment 22 | Compound 631 | 3.3 | 453 | 8.0 |
| Embodiment 23 | Compound 647 | 3.4 | 454 | 7.9 |
| Embodiment 24 | Compound 716 | 3.3 | 455 | 7.8 |
| Embodiment 25 | Compound 747 | 3.4 | 454 | 7.2 |
| Comp. Example 6 | — | 4.7 | 459 | 6.1 |
| Comp. Example 7 | T-1 | 4.5 | 459 | 5.9 |
| Comp. Example 8 | T-2 | 3.9 | 455 | 7.8 |
| Comp. Example 9 | T-3 | 4.2 | 455 | 6.7 |

As shown in Table 4, it was appreciated that the blue organic EL devices of Embodiments 14 to 25 in which the compounds of the present invention were used in the electron transport auxiliary layer exhibited excellent performance in terms of the current efficiency and the emission peak, particularly showing remarkable improvement in the driving voltage, as compared to the blue organic EL device (Comparative Example 6) which does not include an electron transport auxiliary layer.

Specifically, it was appreciated that the blue organic EL devices of Embodiments 14 to 25 including the electron transport auxiliary layer according to the present invention having a biphenylene linker (e.g., p,m-biphenylene) bonded in a para-meta position between triazine and the fluorene group exhibited superior performance in terms of driving voltage, emission peak, and current efficiency, as compared to blue organic EL devices in Comparative Examples 7 and 8 including an electron transport auxiliary layer (Compounds T-1 and T-2) having a p,p-biphenylene or m,m-biphenylene linker and a blue organic EL device in Comparative Example 9 including an electron transport auxiliary layer (compound T-3) having a biphenylene linker between triazine and a cyano group. In particular, it was confirmed that the driving voltage of the device has a remarkable improvement in a range of about 0.5 to 1.4 V.

The invention claimed is:

1. A compound of the following Chemical Formula 1:

Chemical Formula 1

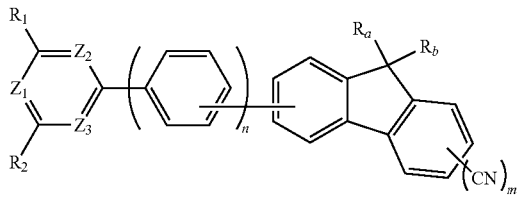

wherein in Chemical Formula 1, $R_a$ and $R_b$ are the same as or different from each other, and are each independently a methyl group or a phenyl group, or combine with each other to form a fused ring, m is 1, and n is an integer of 1 or 2, wherein the cyano group (CN)-substituted ring is selected from the group of the following structural formulas:

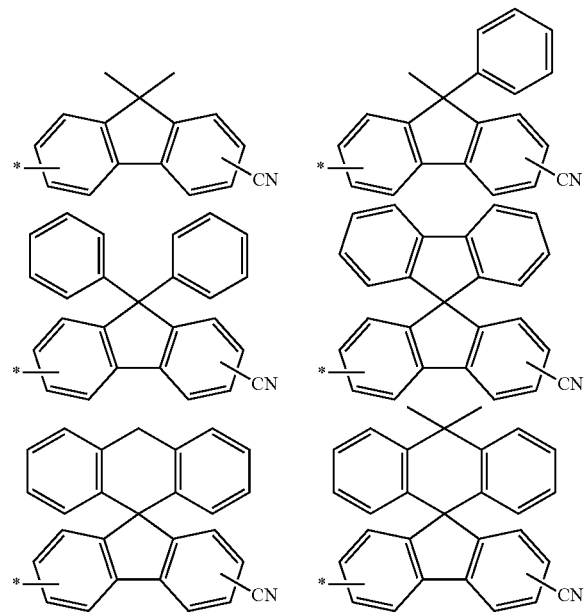

wherein in the above structural formulas,
* represents a site where a bond is made with the compound of Chemical Formula 1, $Z_1$ to $Z_3$ are the same as or different from each other, and are each independently N or $C(R_3)$, provided that $Z_1$ to $Z_3$ include at least one N, $R_1$ to $R_3$ are the same as or different from each other, each independently being selected from the group consisting of: hydrogen, deuterium, a halogen group, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and with the proviso that:

(i) when $Z_1$ to $Z_3$ are all N, and n is 1, $R_1$ and $R_2$ are each a $C_6$ to $C_{60}$ aryl group, (ii) when $Z_1$ to $Z_3$ are all N, n is 1, and $R_1$ and $R_2$ are each a $C_6$ to $C_{60}$ aryl group, $R_1$ and $R_2$ are different from each other, and (iii) when $Z_1$ to $Z_3$ are all N, and n is 2, the compound of Chemical Formula 1 is selected from the group consisting of the compounds of the following Chemical Formula 4 to Chemical Formula 6:

Chemical Formula 4

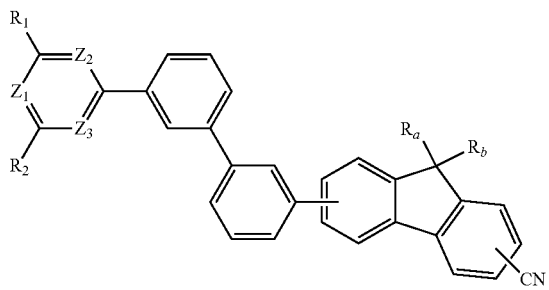

Chemical Formula 5

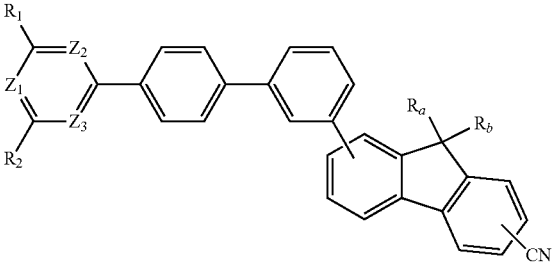

Chemical Formula 6

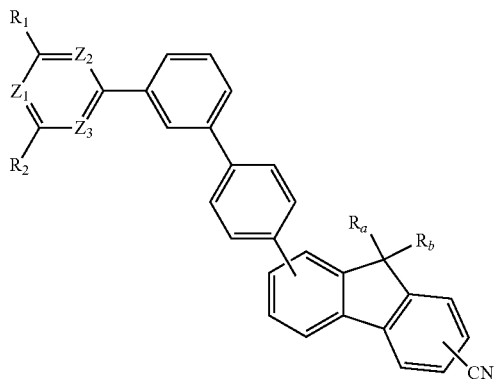

wherein in Chemical Formulas 4 to 6, $Z_1$ to $Z_3$, $R_a$ and $R_b$, and $R_1$ and $R_2$ are as defined above, respectively, the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_1$ to $R_3$ are each independently substituted or unsubstituted with one or more substituents selected from the group consisting of deuterium, a halogen group, a cyano group, a nitro group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_1$ to $C_{40}$ alkyl group, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other.

2. The compound of claim 1, wherein the compound of Chemical Formula 1 is selected from the group consisting of the compounds of the following Chemical Formula 2a to 2c and Chemical Formula 4 to Chemical Formula 6:

Chemical Formula 2a

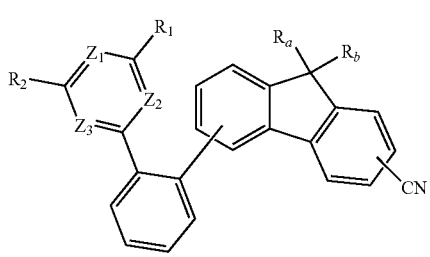

Chemical Formula 2b

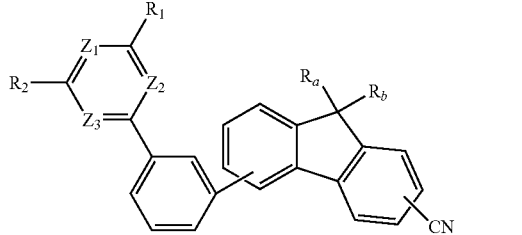

Chemical Formula 2c

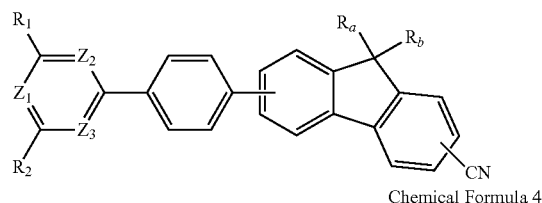

Chemical Formula 4

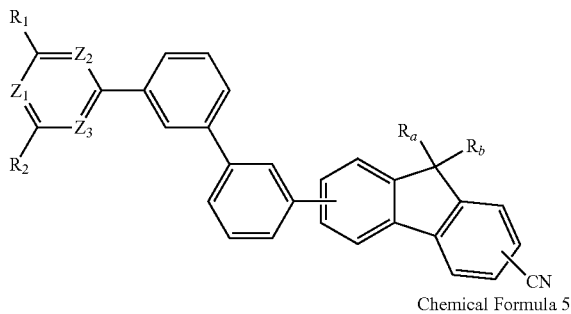

Chemical Formula 5

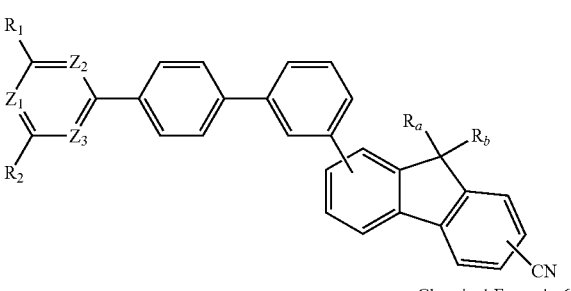

Chemical Formula 6

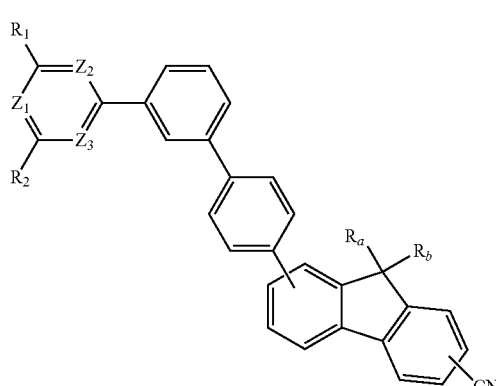

wherein in Chemical Formulas 2a to 2c and 4 to 6, $Z_1$ to $Z_3$, $R_a$ and $R_b$, and $R_1$ and $R_2$ are as defined in claim 1, respectively.

3. The compound of claim 1, wherein the compound of Chemical Formula 1 is selected from the group consisting of the compounds of the following Chemical Formula 7 to Chemical Formula 10:

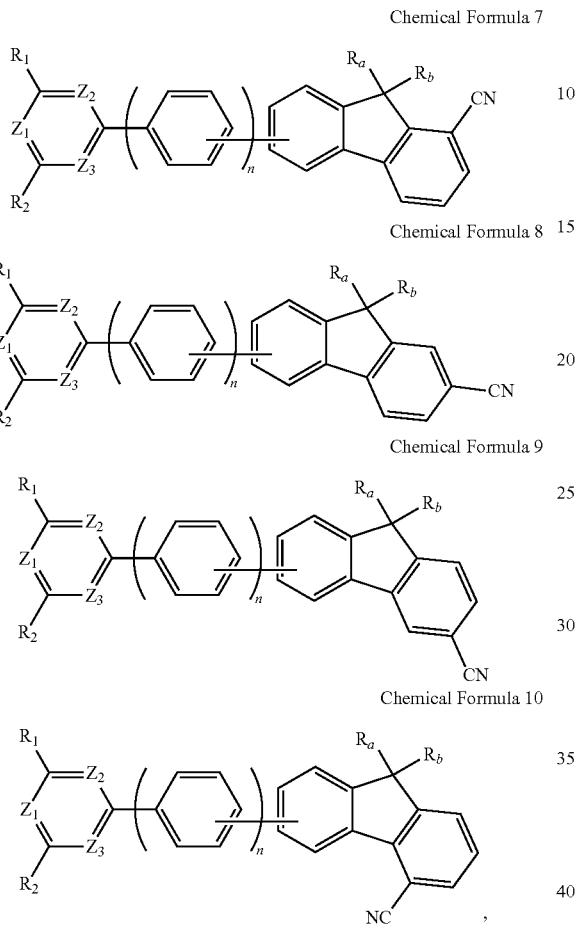

wherein in Chemical Formulas 7 to 10,
$Z_1$ to $Z_3$, $R_a$ and $R_b$, $R_1$ and $R_2$, and n are as defined in claim 1, respectively.

4. The compound of claim 1, wherein $Z_1$ to $Z_3$ include two or three nitrogens (N).

5. The compound of claim 1,
wherein $R_1$ and $R_2$ are the same as or different from each other, each independently being a $C_6$ to $C_{60}$ aryl group or a heteroaryl group having 5 to 60 nuclear atoms,
$R_3$ is selected from the group consisting of: hydrogen, a $C_1$ to $C_{40}$ alkyl group, a $C_6$ to $C_{60}$ aryl group, and a heteroaryl group having 5 to 60 nuclear atoms, and
the aryl group and the heteroaryl group of $R_1$ and $R_2$ and the alkyl group, the aryl group, and the heteroaryl group of $R_3$ are each independently substituted or unsubstituted with one or more substituents selected from the group consisting of: deuterium, a halogen group, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other.

6. The compound of claim 1,
wherein the compound of Chemical Formula 1 is an electron transport layer material or an electron transport auxiliary layer material.

7. An electroluminescent device comprising:
an anode,
a cathode, and
at least one organic layer disposed between the anode and the cathode,
wherein at least one of the organic layer comprises the compound of the following formula 1:

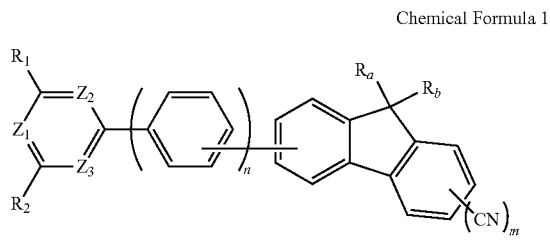

wherein in Chemical Formula 1,
$R_a$ and $R_b$ are the same as or different from each other, and are each independently a methyl group or a phenyl group, or combine with each other to form a fused ring,
m is 1, and n is an integer of 1 or 2,
wherein the cyano group (CN)-substituted ring is selected from the group of substituents of the following structural formulas:

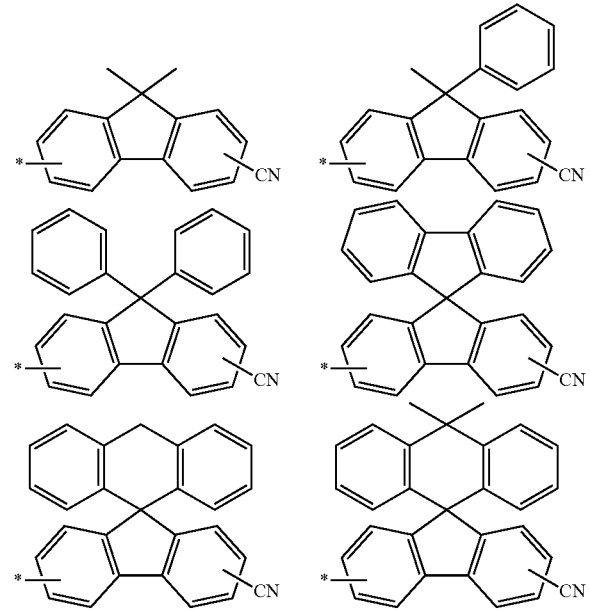

wherein in the above structural formulas,
* represents a site where a bond is made with the compound of Chemical Formula 1, $Z_1$ to $Z_3$ are the same as or different from each other, and are each independently N or $C(R_3)$, provided that $Z_1$ to $Z_3$ include at least one N, $R_1$ to $R_3$ are the same as or different from each other, each independently being selected from the group consisting of: hydrogen, deuterium, a halogen group, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and with the proviso that:

(i) when $Z_1$ to $Z_3$ are all N, and n is 1, $R_1$ and $R_2$ are each a $C_6$ to $C_{60}$ aryl group, (ii) when $Z_1$ to $Z_3$ are all N, n is 1, and $R_1$ and $R_2$ are each a $C_6$ to $C_{60}$ aryl group, $R_1$ and $R_2$ are different from each other, and (iii) when $Z_1$ to $Z_3$ are all N, and n is 2, the compound of Chemical Formula 1 is selected from the group consisting of the compounds of the following Chemical Formula 4 to Chemical Formula 6:

Chemical Formula 4

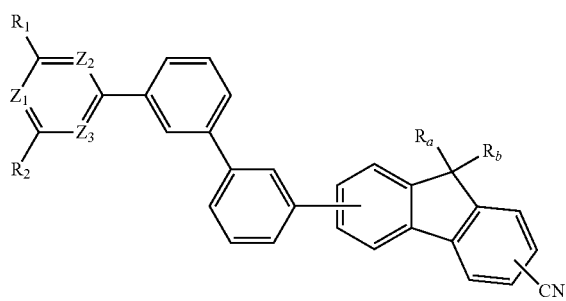

Chemical Formula 5

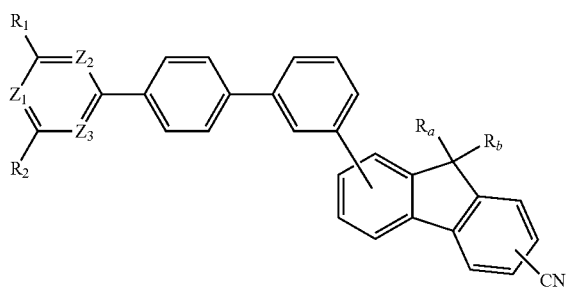

Chemical Formula 6

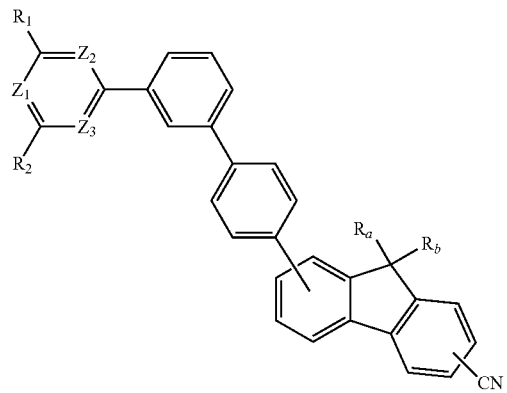

wherein in Chemical Formulas 4 to 6, $Z_1$ to $Z_3$, $R_a$ and $R_b$, and $R_1$ and $R_2$ are as defined above, respectively, the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_1$ to $R_3$ are each independently substituted or unsubstituted with one or more substituents selected from the group consisting of deuterium, a halogen group, a cyano group, a nitro group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_1$ to $C_{40}$ alkyl group, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other.

8. The electroluminescent device of claim 7, wherein the compound of Chemical Formula 1 is selected from the group consisting of the compounds of the following Chemical Formula 2a to 2c and Chemical Formula 4 to Chemical Formula 6:

Chemical Formula 2a

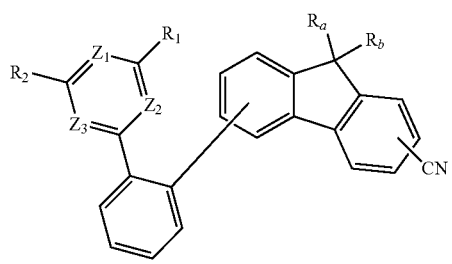

-continued

Chemical Formula 2b

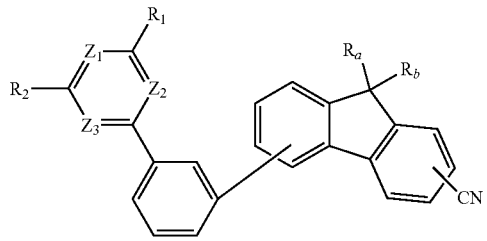

Chemical Formula 2c

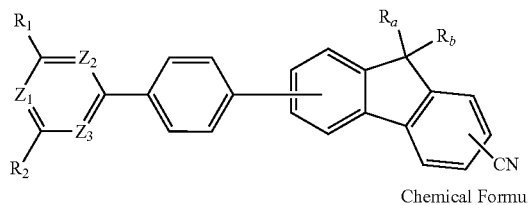

Chemical Formula 4

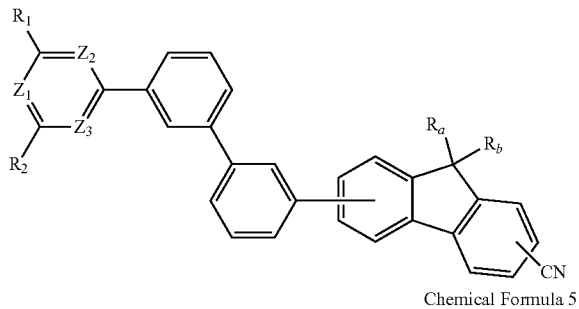

Chemical Formula 5

Chemical Formula 6

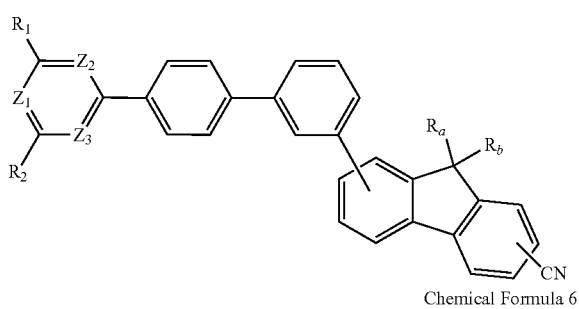

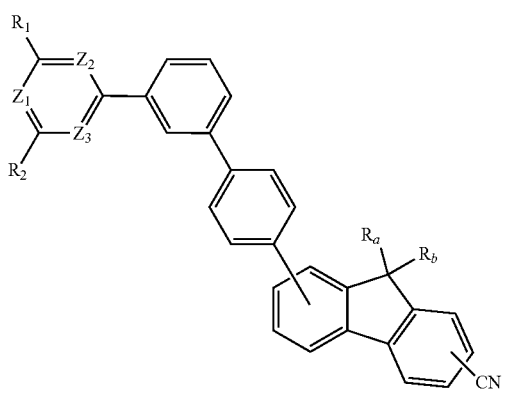

wherein in Chemical Formulas 2a to 2c and 4 to 6, $Z_1$ to $Z_3$, $R_a$ and $R_b$, and $R_1$ and $R_2$ are as defined in claim 7, respectively.

9. The electroluminescent device of claim 7, wherein the compound of Chemical Formula 1 is selected from the group consisting of the compounds of the following Chemical Formula 7 to Chemical Formula 10:

Chemical Formula 7

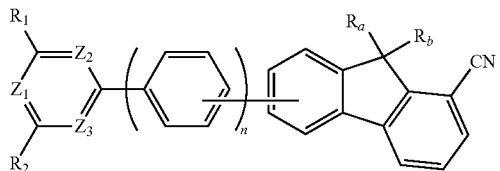

Chemical Formula 8

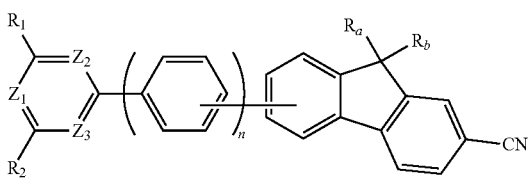

Chemical Formula 9

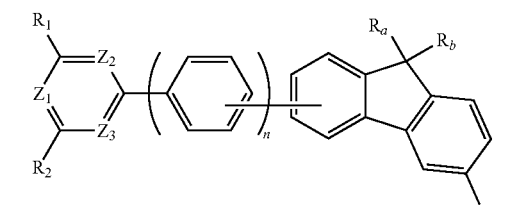

Chemical Formula 10

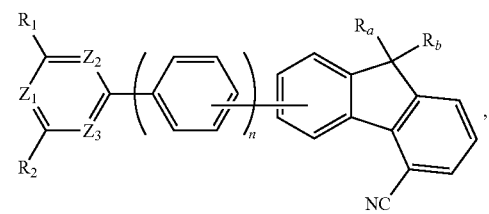

wherein in Chemical Formulas 7 to 10, $Z_1$ to $Z_3$, $R_a$ and $R_b$, $R_1$ and $R_2$, and n are as defined in claim 7, respectively.

10. The electroluminescent device of claim 7, wherein $Z_1$ to $Z_3$ include two or three nitrogens (N).

11. The electroluminescent device of claim 7, wherein $R_1$ and $R_2$ are the same as or different from each other, each independently being a $C_6$ to $C_{60}$ aryl group or a heteroaryl group having 5 to 60 nuclear atoms, $R_3$ is selected from the group consisting of: hydrogen, a $C_1$ to $C_{40}$ alkyl group, a $C_6$ to $C_{60}$ aryl group, and a heteroaryl group having 5 to 60 nuclear atoms, and the aryl group and the heteroaryl group of $R_1$ and $R_2$ and the alkyl group, the aryl group, and the heteroaryl group of $R_3$ are each independently substituted or unsubstituted with one or more substituents selected from the group consisting of: hydrogen, deuterium, a halogen group, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other.

12. The electroluminescent device of claim 7, wherein the organic layer comprising the compound is selected from the group consisting of: a light emitting layer, a light emitting auxiliary layer, a hole injection layer, a hole transport layer, an electron injection layer, an electron transport layer, and an electron transport auxiliary layer.

* * * * *